US010510964B2

(12) United States Patent
Mizutani et al.

(10) Patent No.: US 10,510,964 B2
(45) Date of Patent: Dec. 17, 2019

(54) COMPOUND, ORGANIC ELECTROLUMINESCENCE DEVICE MATERIAL, ORGANIC ELECTROLUMINESCENCE DEVICE AND ELECTRONIC DEVICE

(71) Applicant: IDEMITSU KOSAN CO., LTD., Tokyo (JP)

(72) Inventors: Sayaka Mizutani, Sodegaura (JP); Takayasu Sado, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 15/834,156

(22) Filed: Dec. 7, 2017

(65) Prior Publication Data

US 2018/0102484 A1 Apr. 12, 2018

Related U.S. Application Data

(63) Continuation of application No. 14/024,637, filed on Sep. 12, 2013, now Pat. No. 9,871,206.

(30) Foreign Application Priority Data

Sep. 12, 2012 (JP) ................................. 2012-201028

(51) Int. Cl.

*H01L 51/50* (2006.01)
*H01L 51/00* (2006.01)
*C07D 471/04* (2006.01)
*C07D 519/00* (2006.01)

(52) U.S. Cl.

CPC ........ *H01L 51/0067* (2013.01); *C07D 471/04* (2013.01); *C07D 519/00* (2013.01); *H01L 51/0072* (2013.01); *H01L 51/0073* (2013.01); *H01L 51/0074* (2013.01); *H01L 51/5076* (2013.01)

(58) Field of Classification Search

None
See application file for complete search history.

(56) References Cited

U.S. PATENT DOCUMENTS

| | | | |
|---|---|---|---|
| 5,645,948 | A | 7/1997 | Shi et al. |
| 7,265,378 | B2 | 9/2007 | Lecloux et al. |
| 7,750,340 | B2 | 7/2010 | Hasegawa et al. |
| 7,820,478 | B2 | 10/2010 | Hasegawa et al. |
| 7,906,228 | B2 | 3/2011 | Lee et al. |
| 7,989,644 | B2 | 8/2011 | Tanabe et al. |
| 2004/0066135 | A1 | 4/2004 | Lecloux et al. |
| 2006/0017050 | A1 | 1/2006 | Hasegawa et al. |
| 2007/0190355 | A1 | 8/2007 | Ikeda |
| 2007/0267968 | A1 | 11/2007 | Lecloux et al. |
| 2008/0138654 | A1 | 6/2008 | Kathirgamanathan et al. |
| 2008/0233387 | A1 | 9/2008 | Kambe et al. |
| 2009/0131673 | A1 | 5/2009 | Tanabe et al. |
| 2009/0134384 | A1 | 5/2009 | Stoessel et al. |
| 2009/0230852 | A1 | 9/2009 | Lee et al. |
| 2009/0288707 | A1 | 11/2009 | Lee et al. |
| 2010/0032658 | A1 | 2/2010 | Lee et al. |
| 2010/0033083 | A1 | 2/2010 | Eum et al. |
| 2010/0041171 | A1 | 2/2010 | Hasegawa et al. |
| 2010/0045170 | A1 | 2/2010 | Lee et al. |
| 2010/0051106 | A1 | 3/2010 | Kim et al. |
| 2010/0327270 | A1 | 12/2010 | Buesing et al. |
| 2011/0101310 | A1 | 5/2011 | Meng et al. |
| 2011/0121268 | A1 | 5/2011 | Nagao et al. |
| 2011/0127513 | A1 | 6/2011 | Lee et al. |
| 2011/0168992 | A1 | 7/2011 | Bae et al. |
| 2011/0204339 | A1 | 8/2011 | Dobbs et al. |
| 2011/0248217 | A1 | 10/2011 | Tanabe et al. |

FOREIGN PATENT DOCUMENTS

| | | |
|---|---|---|
| CA | 2425797 | 10/2004 |
| EP | 2 182 040 | 5/2010 |
| EP | 2 256 176 | 12/2010 |
| JP | 2003-338377 | 11/2003 |
| JP | 2004-107263 | 4/2004 |
| JP | 2005-063938 | 3/2005 |
| JP | 2007/77094 | 3/2007 |
| JP | 2007-138228 | 6/2007 |
| JP | 2007-238500 | 9/2007 |
| JP | 2008-141217 | 6/2008 |
| JP | 2008-222624 | 9/2008 |
| JP | 2008-545729 | 12/2008 |
| JP | 2009-179585 | 8/2009 |

(Continued)

OTHER PUBLICATIONS

International Search Report for corresponding International Application No. PCT/JP2013/074431 (dated Oct. 29, 2013).

(Continued)

*Primary Examiner* — Gregory D Clark
(74) *Attorney, Agent, or Firm* — Oblon, McClelland, Maier & Neustadt, L.L.P.

(57) ABSTRACT

A compound is represented by a formula (1) below. In the formula (1), $X^1$ to $X^8$ each independently represent a carbon atom to be bonded to a group represented by the following formula (20), $CR^X$ or a nitrogen atom. At least one of $X^1$ to $X^8$ is a carbon atom to be bonded to the group represented by the following formula (2). $R^X$ is each independently a hydrogen atom, a substituted or unsubstituted alkyl group having 1 to 30 carbon atoms, or the like.

(1)

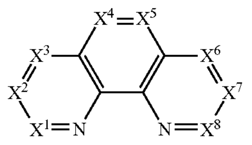

(2)

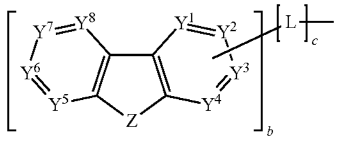

20 Claims, No Drawings

(56) References Cited

FOREIGN PATENT DOCUMENTS

| | | | | |
|---|---|---|---|---|
| JP | 2010-034548 | * | 2/2010 | ............. H01L 51/50 |
| JP | 2010-118591 | | 5/2010 | |
| JP | 2010-199296 | | 9/2010 | |
| JP | 2011-093931 | | 5/2011 | |
| JP | 2011-134810 | | 7/2011 | |
| JP | 2011-142096 | | 7/2011 | |
| JP | 2011-204843 | | 10/2011 | |
| JP | 2012-510988 | | 5/2012 | |
| JP | 2012-513680 | | 6/2012 | |
| JP | 2013-065722 | | 4/2013 | |
| JP | 2013-110224 | | 6/2013 | |
| JP | 2013-183113 | | 9/2013 | |
| KR | 2009065201 | | 6/2009 | |
| KR | 936400 | | 9/2009 | |
| KR | 2010082676 | | 7/2010 | |
| KR | 2010097797 | | 9/2010 | |
| KR | 2010112903 | | 10/2010 | |
| KR | 2010119077 | | 11/2010 | |
| KR | 2011002156 | | 1/2011 | |
| KR | 10-2012-0072785 A | | 7/2012 | |
| KR | 2012072785 | * | 7/2012 | ............. H01L 51/54 |
| KR | 10-2012-0096383 | | 8/2012 | |
| WO | WO 2004/026870 | | 4/2004 | |
| WO | WO 2006/128800 | | 12/2006 | |
| WO | 2010/064871 | | 6/2010 | |
| WO | 2010/075411 | | 7/2010 | |
| WO | 2010/085087 | | 7/2010 | |
| WO | 2010/114256 | | 10/2010 | |
| WO | 2010/114263 | | 10/2010 | |
| WO | 2011/105700 | | 9/2011 | |
| WO | 2012/111462 | | 8/2012 | |
| WO | WO 2012/115034 | | 8/2012 | |
| WO | 2012/176674 | | 12/2012 | |
| WO | 2013/145666 | | 10/2013 | |
| WO | 2013/145667 | | 10/2013 | |

OTHER PUBLICATIONS

Written Opinion for corresponding International Application No. PCT/JP2013/074431 (dated Oct. 29, 2013).
Office Action dated Feb. 7, 2017, in corresponding Japanese Patent Application No. 2014-535558 (with English-language Translation).
Office Action dated Dec. 2, 2016, in corresponding Chinese Patent Application No. 201380046637.8 (with English-language Translation).
Extended European Search Report dated Jan. 28, 2016 in Patent Application No. 13837441.8.

* cited by examiner

COMPOUND, ORGANIC ELECTROLUMINESCENCE DEVICE MATERIAL, ORGANIC ELECTROLUMINESCENCE DEVICE AND ELECTRONIC DEVICE

CROSS-REFERENCE TO A RELATED APPLICATION

The application is a Continuation of U.S. patent application Ser. No. 14/024,637, filed Sep. 12, 2013, now allowed, and the entire disclosure of Japanese Patent Application No. 2012-201028, filed Sep. 12, 2012, is expressly incorporated by reference herein.

FIELD

Embodiment(s) described herein relate generally to a new compound, an organic-electroluminescence-device material, an organic electroluminescence device and an electronic device.

BACKGROUND

An organic electroluminescence device (hereinafter, occasionally abbreviated as an organic EL device) using an organic substance is highly expected to be used as a device for a full color display having a large area in a form of a low-cost solid-emitting device, so that the organic electroluminescence device has been variously developed.

A typical organic EL device is configured to include a pair of opposing electrodes and an emitting layer interposed between the pair of opposing electrodes. When an electric field is applied between both of the electrodes, electrons are injected from the cathode and holes are injected from the anode. The injected electrons and holes are recombined in the emitting layer to form excitons. When the excited state is returned to the ground state, energy is radiated as light. The organic EL device emits light according to this principle.

A typical organic EL device requires a drive voltage higher than that for an inorganic light-emitting diode. Properties of the typical organic EL device are also significantly deteriorated, so that the typical organic EL device is in no practical use. Although organic EL devices have been gradually improved recently, further lowering of the voltage is demanded.

Patent Literature 1 (U.S. Pat. No. 5,645,948) discloses an organic EL device including a benzazole compound. Moreover, Patent Literature 2 (JP-A-2010-34548) and Patent Literature 3 (International Publication No. 2006/128800) also disclose organic EL devices.

However, demanded is an organic EL device driven by a voltage further lower than that of the organic EL device using a nitrogen-containing heterocyclic derivative disclosed in Patent Literature 1.

BRIEF SUMMARY OF THE INVENTION

A compound according to an exemplary embodiment of the invention is represented by the following formula (1).

(1)

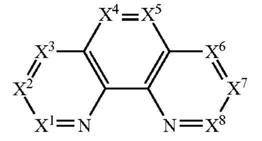

In the formula (1), $X^1$ to $X^8$ each independently represent a carbon atom to be bonded to a group represented by the following formula (2), $CR^X$ or a nitrogen atom. At least one of $X^1$ to $X^8$ is a carbon atom to be bonded to the group represented by the following formula (2).

$R^X$ is each independently selected from the group consisting of a hydrogen atom, a halogen atom, a cyano group, a nitro group, a substituted or unsubstituted hydroxyl group, a substituted or unsubstituted carboxyl group, a substituted or unsubstituted sulfonyl group, a substituted or unsubstituted boryl group, a substituted or unsubstituted phosphino group, a substituted or unsubstituted mercapto group, a substituted or unsubstituted acyl group, a substituted or unsubstituted amino group, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aralkyl group having 6 to 30 carbon atoms, a substituted or unsubstituted aryl group having 6 to 40 ring carbon atoms, and a substituted or unsubstituted heteroaryl group having 5 to 40 ring atoms.

Among $X^1$ to $X^8$, adjacent $R^X$ of $CR^X$ are bonded to each other to form a cyclic structure, or are not bonded to each other.

(2)

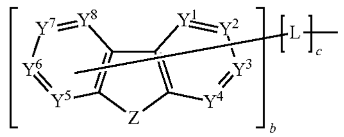

In the formula (2): b is an integer of 1 to 5; c is an integer of 1 to 8; and Z is an oxygen atom, a sulfur atom or a silicon atom. When b is 2 to 5, Z are mutually the same or different. When Z is a silicon atom, $R^9$ and $R^{10}$ are bonded to the silicon atom. $R^9$ and $R^{10}$ each independently represent the same as $R^X$ in the formula (1). $R^9$ and $R^{10}$ may be bonded to the structure represented by the formula (1). However, when Z is a silicon atom, $R^9$ and $R^{10}$ are not bonded to each other to form a cyclic structure.

L is selected from a single bond or a linking group.

The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms.

The polyvalent heteroaryl group having 5 to 40 ring atoms for L in the formula (2) includes a substituted or unsubstituted polyvalent group derived from a phenanthroline ring represented by the formula (1). When c is 2 to 8, L are mutually the same or different.

$Y^1$ to $Y^8$ each independently represent a nitrogen atom, $CR^Y$ or a carbon atom bonded to L.

$R^Y$ represents the same as $R^X$ in the formula (1). The heteroaryl group having 5 to 40 ring atoms for $R^Y$ includes a substituted or unsubstituted phenanthrolyl group derived from the phenanthroline ring represented by the formula (1). Adjacent $R^Y$ are bonded to each other to form a cyclic structure, or are not bonded to each other.

When $X^1$ or $X^8$ is a carbon atom bonded to the group represented by the formula (2), b is 1, Z is an oxygen atom, $Y^4$ or $Y^5$ is a carbon atom bonded to L, and c is 2, L closer to the phenanthroline ring represented by the formula (1) among two L is a divalent group other than an anthracene group.

When two of $X^1$ to $X^8$ are carbon atoms bonded to the group represented by the formula (2), b and c are 1, both of Z are sulfur atoms, $Y^4$ or $Y^5$ is a carbon atom bonded to L, and L is a p-phenylene group, L is bonded to any one of $X^1$, $X^2$, $X^4$, $X^5$, $X^7$ and $X^8$.

When $X^1$ or $X^8$ is a carbon atom bonded to the group represented by the formula (2), b and c are 1, Z is an oxygen atom or a sulfur atom, $Y^3$ is a carbon atom bonded to L, and L is a p-phenylene group, $R^Y$ for $Y^4$ is a group other than a phenyl group.

When $X^1$ or $X^8$ is a carbon atom bonded to the group represented by the formula (2), b and c are 1, Z is an oxygen atom or a sulfur atom, $Y^6$ is a carbon atom bonded to L, and L is a p-phenylene group, $R^Y$ for $Y^5$ is a group other than a phenyl group.

When $X^1$ or $X^8$is a carbon atom bonded to the group represented by the formula (2), Z is a silicon atom, $Y^3$ is a carbon atom bonded to L, L is a single bond, $R^Y$ for $Y^6$ is bonded to the phenanthrolyl group (heteroaryl group having 5 to 40 ring atoms) with a single bond, the phenanthrolyl group is bonded to $R^Y$ for $Y^6$ at a position other than a position 2

When $X^4$ or $X^5$ is a carbon atom bonded to the group represented by the formula (2), $Y^2$ is a carbon atom bonded to L, L is a single bond, and Z is an oxygen atom, $R^Y$ for $Y^7$ is a group other than a pyrenyl group.

When $X^4$ or $X^5$ is a carbon atom bonded to the group represented by the formula (2), $Y^7$ is a carbon atom bonded to L, L is a single bond, and Z is an oxygen atom, $R^Y$ for $Y^2$ is a group other than a pyrenyl group.

An organic electroluminescence device according to another aspect of the invention includes: an anode; a cathode opposed to the anode; and an organic compound layer provided between the anode and the cathode, in which the organic compound layer includes an emitting layer and an electron transporting layer provided to the emitting layer closer to the cathode, and the electron transporting layer comprises a compound represented by the following formula (10).

(10)

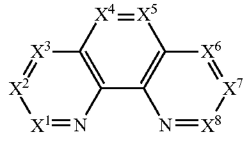

In the formula (10), $X^1$ to $X^8$ each independently represent a carbon atom to be bonded to a group represented by the following formula (20), $CR^X$ or a nitrogen atom. At least one of $X^1$ to $X^8$ is a carbon atom to be bonded to the group represented by the following formula (2).

$R^X$ is each independently selected from the group consisting of a hydrogen atom, a halogen atom, a cyano group, a nitro group; a substituted or unsubstituted hydroxyl group, a substituted or unsubstituted carboxyl group, a substituted or unsubstituted sulfonyl group, a substituted or unsubstituted boryl group, a substituted or unsubstituted phosphino group, a substituted or unsubstituted mercapto group, a substituted or unsubstituted acyl group, a substituted or unsubstituted amino group, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aralkyl group having 6 to 30 carbon atoms, a substituted or unsubstituted aryl group having 6 to 40 ring carbon atoms, and a substituted or unsubstituted heteroaryl group having 5 to 40 ring atoms.

Among $X^1$ to $X^8$, adjacent $R^X$ of $CR^X$ are bonded to each other to form a cyclic structure, or are not bonded to each other.]

(20)

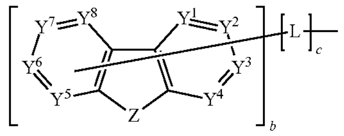

In the formula (20): b is an integer of 1 to 5; c is an integer of 1 to 8; and Z is an oxygen atom, a sulfur atom or a silicon atom. When b is 2 to 5, Z are mutually the same or different. When Z is a silicon atom, $R^9$ and $R^{10}$ are bonded to the silicon atom, $R^9$ and $R^{10}$ each independently represent the same as $R^X$ in the formula (10), and $R^9$ and $R^{10}$ are optionally bonded to the structure represented by the formula (10).

L is selected from a single bond or a linking group.

The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms.

The polyvalent heteroaryl group having 5 to 40 ring atoms for L in the formula (20) comprises a substituted or unsubstituted polyvalent group derived from a phenanthroline ring represented by the formula (10). When c is 2 to 8, L are mutually the same or different.

$Y^1$ to $Y^8$ each independently represent a nitrogen atom, $CR^Y$ or a carbon atom bonded to L.

$R^Y$ represents the same as $R^X$ in the formula (10), and the heteroaryl group having 5 to 40 ring atoms for $R^Y$ comprises a substituted or unsubstituted phenanthrolyl group derived from the phenanthroline ring represented by the formula (10). Adjacent $R^Y$ are bonded to each other to form a cyclic structure, or are not bonded to each other.

DETAILED DESCRIPTION OF THE INVENTION

An exemplary embodiment of the invention will be described below in detail.

Compound

A compound according to the exemplary embodiment is represented by the following formula (1).

(1)

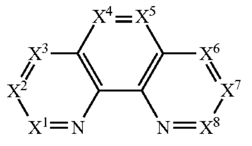

In the formula (1), $X^1$ to $X^8$ each independently represent a carbon atom to be bonded to a group represented by the following formula(2), $CR^X$ or a nitrogen atom. In the formula (1), at least one of $X^1$ to $X^8$ is a carbon atom to be bonded to the group represented by the following formula (2). In the formula (1): $R^X$ is each independently selected from the group consisting of a hydrogen atom, halogen atom, cyano group, nitro group, substituted or unsubstituted hydroxyl group, substituted or unsubstituted carboxyl group, substituted or unsubstituted sulfonyl group, substituted or unsubstituted boryl group, substituted or unsubstituted phosphino group, substituted or unsubstituted mercapto group, substituted or unsubstituted acyl group, substituted or unsubstituted amino group, substituted or unsubstituted silyl group, substituted or unsubstituted alkyl group having 1 to 30 carbon atom, substituted or unsubstituted alkenyl group having 2 to 30 carbon atoms, substituted or unsubstituted alkynyl group having 2 to 30 carbon atoms, substituted or unsubstituted aralkyl group having 6 to 30 carbon atoms, substituted or unsubstituted aryl group having 6 to 40 ring carbon atoms, and substituted or unsubstituted heteroaryl group having 5 to 40 ring atoms. Among $X^1$ to $X^8$ in the formula (1), adjacent $R^X$ of $CR^X$ are bonded to each other to form a cyclic structure, or are not bonded to each other. For instance, $R^X$ of $CR^X$ for $X^1$ may be bonded to $R^X$ of $CR^X$ for $X^2$ adjacent to $X^1$ to form a saturated or unsaturated cyclic structure.

(2)

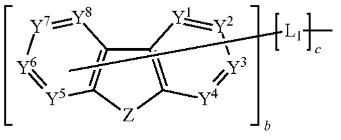

In the formula (2), b is an integer of 1 to 5, preferably 1 to 3, more preferably 1 to 2.

In the formula (2), c is an integer of 1 to 8, preferably 1 to 5, more preferably 1 to 3.

In the formula (2), Z is an oxygen atom, a sulfur atom or a silicon atom. In the formula (2), when b is 2 to 5, Z are mutually the same or different. In the formula (2), when Z is a silicon atom, $R^9$ and $R^{10}$ are bonded to the silicon atom. $R^9$ and $R^{10}$ each independently represent the same as $R^X$ in the formula (1). $R^9$ and $R^{10}$ may be bonded to the structure represented by the formula (1). However, when Z is a silicon atom in the formula (2), $R^9$ and $R^{10}$ are not bonded to each other to form a cyclic structure.

In the formula (2), L is selected from a single bond or a linking group. The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms. The polyvalent heteroaryl group having 5 to 40 ring atoms for L in the formula (2) includes a substituted or unsubstituted polyvalent group derived from a phenanthroline ring represented by the formula (1). "Polyvalent" means having valence of 2 or more. In the formula (2), when c is 2 to 8, Z are mutually the same or different. L is preferably a single bond or phenylene, more preferably phenylene rather than a single bond.

In the formula (2), $Y^1$ to $Y^8$ each independently represent a nitrogen atom, $CR^Y$ or a carbon atom bonded to L. $Y^4$ and $Y^5$ are preferably a carbon atom bonded to L. Alternatively, $Y^2$ and $Y^7$ are preferably a carbon atom bonded to L.

$R^Y$ represents the same as $R^X$ in the formula (1). The heteroaryl group having 5 to 40 ring atoms for $R^Y$ includes a substituted or unsubstituted phenanthrolyl group derived from the phenanthroline ring represented by the formula (1). In the formula (2), adjacent $R^Y$ are bonded to each other to form a cyclic structure, or are not bonded to each other.

An instance where a substituted or unsubstituted polyvalent group derived from the phenanthroline ring represented by the formula (1) is included in L of the formula (2) is represented by the following formula (2-1). In the following formula (2-1), A1 schematically shows the structure represented by the formula (1).

(2-1)

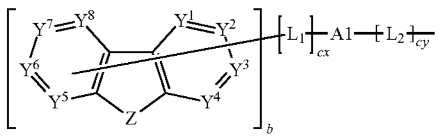

In the above formula (2-1), cx is an integer of 0 to 7, cy is an integer of 0 to 7, and $0 \leq cx+cy \leq 7$. In the formula (2-1), $L_1$ and $L_2$ each independently represent the same as L in the formula (2). In the formula (2-1), $Y^1$ to $Y^8$, Z, b and $X^1$ to $X^8$ in A1 each represent the same as $X^1$ to $X^8$, $Y^1$ to $Y^8$, Z and b in the formulae (1) and (2).

For instance, the following formula (1-1) represents a case where $R^Y$ of $CR^Y$ in the formula (2) is a substituted or unsubstituted phenanthrolyl group derived from the phenanthroline ring represented by the formula (1). In the following formula (1-1), A2 and A3 each independently schematically show the structure represented by the formula (1).

(1-1)

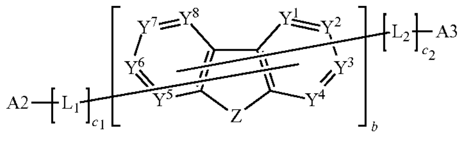

In the formula (1-1), $c_1$ is an integer of 1 to 8 and $c_2$ is an integer of 1 to 8. In the formula (1-1), $L_1$ and $L_2$ each independently represent the same as L in the formula (2). In the formula (1-1), $Y^1$ to $Y^8$, Z, b and $X^1$ to $X^8$ in A2 and A3 each represent the same as $X^1$ to $X^8$, $Y^1$ to $Y^8$, Z and b in the formulae (1) and (2).

Moreover, an instance where a substituted or unsubstituted polyvalent group derived from the phenanthroline ring represented by the formula (1) is included in L of the formula (2) and $R^Y$ of $CR^Y$ in the formula (2) is a substituted or unsubstituted phenanthrolyl group derived from the phenanthroline ring represented by the formula (1) is represented, for instance, by the following formula (1-2). In the following formula (1-2), A1, A2 and A3 each independently schematically show the structure represented by the formula (1).

(1-2)

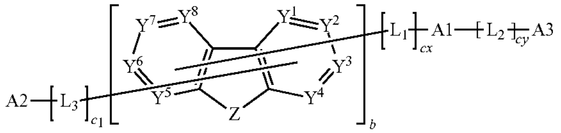

In the formula (1-2), $Y^1$ to $Y^8$, Z, $L_1$ to $L_3$, b, cx, cy, $c_1$ and $X^1$ to $X^8$ in A1, A2 and A3 each represent the same as $X^1$ to $X^8$, $Y^1$ to $Y^8$, Z, $L_1$ to $L_3$, b, cx, cy and $c_1$ in the formulae (1), (2), (1-1) and (2-1).

In the formula (1), as an example of a case where two or more carbon atoms of $X^1$ to $X^8$ are bonded to the group represented by the formula (2), an instance where two carbon atoms of $X^1$ to $X^8$ are bonded to the the group represented by the formula (2) is represented by the following formula (1-3). In the following formula (1-3), A1 schematically shows the structure represented by the formula (1).

(1-3)

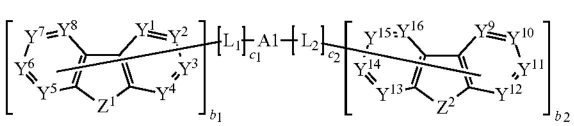

In the formula (1-3), $Y^9$ to $Y^{16}$ each independently represent the same as $Y^1$ to $Y^8$ in the formula (2). In the formula (1-3), $L_1$ and $L_2$ each independently represent the same as L in the formula (2). In the formula (1-3), $b_1$ and $b_2$ are each independently an integer of 1 to 5, and $c_1$ and $c_2$ are each independently an integer of 1 to 8. In the formula (1-3), $Z^1$ and $Z^2$ each independently represent the same as Z in the formula (2). In the formula (1-3), $Y^1$ to $Y^8$ and $X^1$ to $X^8$ in A1 each represent the same as $X^1$ to $X^8$ and $Y^1$ to $Y^8$ in the formulae (1) and (2).

When $X^1$ or $X^8$ in the formula (1) is a carbon atom bonded to the group represented by the formula (2) and, in the formula (2), b is 1, Z is an oxygen atom, $Y^4$ or $Y^5$ is a carbon atom bonded to L, and c is 2, L closer to the phenanthroline ring represented by the formula (1) among two L is a divalent group other than an anthracene group. Specifically, when the compound represented by the formula (1) is represented by the following formula (1-x) in which two L are defined as $L_1$ and $L_2$, $X^1$ or $X^8$ is a carbon atom bonded to $L_2$, $Y^4$ or $Y^5$ is a carbon atom bonded to $L_1$, $L_2$ closer to the phenanthrorine ring is selected from a single bond or a linking group. The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms (other than a divalent anthracene group), or a substituted or unsubstituted polyvalent heteroaryl group having 5 to 40 ring atoms. In the following formula (1-x), $L_1$ represents the same as L in the formula (2). In the following formula (1-x), $X^1$ to $X^8$ and $Y^1$ to $Y^8$ each represent the same as $X^1$ to $X^8$ and $Y^1$ to $Y^8$ in the formulae (1) and (2).

(1-x)

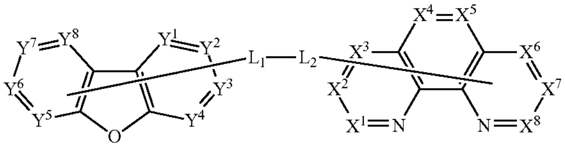

When two of $X^1$ to $X^8$ are carbon atoms bonded to the group represented by the formula (1), b and c are 1, both of Z are sulfur atoms, $Y^4$ or $Y^5$ is a carbon atom bonded to L, and L is a p-phenylene group, L is bonded to any one of $X^1$, $X^2$, $X^4$, $X^5$, $X^7$ and $X^8$.

In other words, when the compound represented by the formula (1) is represented by the following formula (1-4), A1 in the following formula (1-4) schematically shows the structure represented by the formula (1). In the following formula (1-4), $X^1$, $X^2$, $X^4$, $X^5$, $X^7$ and $X^8$ and $Y^1$ to $Y^8$ in A1 each represent the same as $X^1$, $X^2$, $X^4$, $X^5$, $X^7$ and $X^8$ and $Y^1$ to $Y^8$ in the formulae (1) and (2). In the following formula (1-4), $Y^9$ to $Y^{16}$ each independently represent a nitrogen atom, $CR^Y$ or a carbon atom bonded to L. In the following formula (1-4), $R^Y$ represents the same as $R^Y$ in the formula (2). In the following formula (1-4), when $Y^4$ or $Y^5$ is a carbon atom bonded to a p-phenylene group as L and $Y^{12}$ or $Y^{13}$ is a carbon atom bonded to a p-phenylene group as the other L, $X^3$ and $X^6$ in A1 is a nitrogen atom or $CR^X$.

(1-4)

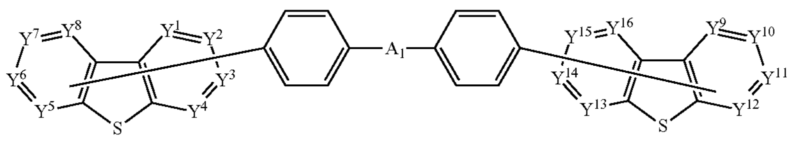

When $X^1$ or $X^8$ in the formula (1) is a carbon atom bonded to the group represented by the formula (2) and, in the formula (2), b and c are 1, Z is an oxygen atom or a sulfur atom, $Y^3$ is a carbon atom bonded to L, and L is a p-phenylene group, $R^Y$ for $Y^4$ is a group other than a phenyl group.

When $X^1$ or $X^8$ in the formula (1) is a carbon atom bonded to the group represented by the formula (2) and, in the formula (2), b and c are 1, Z is an oxygen atom or a sulfur atom, $Y^6$ is a carbon atom bonded to L, and L is a p-phenylene group, $R^Y$ for $Y^5$ is a group other than a phenyl group.

In other words, when the compound represented by the formula (1) is represented by the following formula (1-5-1), $Y^3$ is a carbon atom bonded to a p-phenylene group as L, and $Y^4$ is $CR^Y$ in the formula (2), in which $R^Y$ represents the same as $R^Y$ in the formula (2). However, $R^Y$ is a group other than a phenyl group. In the following formula (1-5-1), Z is an oxygen atom or a sulfur atom. In the following formula (1-5-1), $Y^1$ to $Y^2$, $Y^3$ to $Y^8$ and $X^1$ to $X^8$ each independently represent the same as $X^1$ to $X^8$, $Y^1$ to $Y^2$ and $Y^3$ to $Y^8$ in the formulae (1) and (2).

When the compound represented by the formula (1) is represented by the following formula (1-5-2), $Y^6$ is a carbon atom bonded to a p-phenylene group as L and $Y^5$ is $CR^Y$ in the formula (2), in which $R^Y$ represents the same as $R^Y$ in the formula (2). However, $R^Y$ is a group other than a phenyl group. In the following formula (1-5-2), Z is an oxygen atom or a sulfur atom. In the following formula (1-5-2), $Y^1$ to $Y^4$, $Y^7$ to $Y^8$ and $X^1$ to $X^8$ each independently represent the same as $X^1$ to $X^8$, $Y^1$ to $Y^4$ and $Y^7$ to $Y^8$ in the formulae (1) and (2).

(1-5-1)

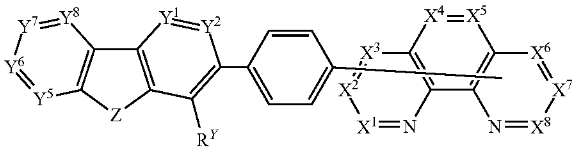

(1-5-2)

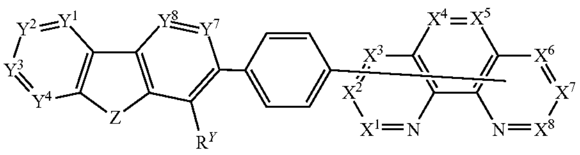

In the formula (1), when $X^1$ or $X^8$ is a carbon atom bonded to the group represented by the formula (2) and, in the formula (2), Z is a silicon atom, $Y^3$ is a carbon atom bonded to L, L is a single bond, $R^Y$ for $Y^6$ is bonded to the phenanthrolyl group (heteroaryl group having 5 to 40 ring atoms) with a single bond, the phenanthrolyl group is bonded to $R^Y$ for $Y^6$ at a position other than a position 2.

In other words, when the compound represented by the formula (1) is represented by the following formula (1-6), $Y^3$ is a carbon atom bonded to $X^1$ or $X^8$, $Y^6$ is $CR^Y$ in the formula (2), in which $R^Y$ is the phenanthrolyl group (phenanthrolyl group shown on the left in the following formula (1-6)) as a heteroaryl group having 5 to 40 ring atoms, and any one of $X^{10}$ to $X^{15}$ is bonded to a carbon atom (C) of $Y^6$. In the following formula (1-6), the rest of $X^1$ to $X^{16}$ being a carbon atom bonded to the group represented by the formula (2) is $CR^X$ or a nitrogen atom, in which $R^X$ represents the same as $R^X$ in the formula (1). In the following formula (1-6), $Y^1$, $Y^2$, $Y^4$, $Y^5$, $Y^7$, $Y^8$, $R^9$ and $R^{10}$ each independently represent the same as $Y^1$, $Y^2$, $Y^4$, $Y^5$, $Y^7$, $Y^8$, $R^9$ and $R^{10}$ in the formula (2).

However, $R^Y$ is a group other than a pyrenyl group. In the following formula (1-xx-2), $Y^1$, $Y^3$ to $Y^4$, $Y^5$, $Y^8$ and $X^1$ to $X^8$ each independently represent the same as $X^1$ to $X^8$, $Y^1$, $Y^3$ to $Y^4$, $Y^5$ and $Y^8$ in the formulae (1) and (2).

(1-xx-1)

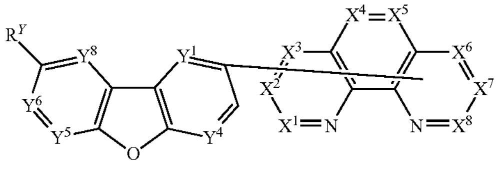

(1-xx-2)

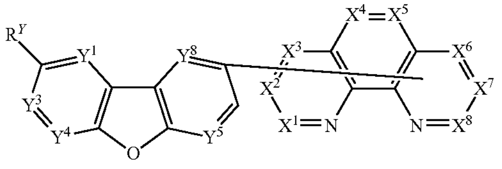

In the compound of the exemplary embodiment, $X^1$ or $X^8$ in the formula (1) is preferably a carbon atom to be bonded to a group represented by the formula (2). Specifically, the compound of the exemplary embodiment is preferably a compound represented by the following formula (1-7).

In the following formula (1-7), $Y^1$ to $Y^8$, Z, L, b and c each represent the same as $Y^1$ to $Y^8$, Z, L, b and c in the formula (2). In the following formula (1-7), $X^2$ to $X^8$ each independently represent $CR^X$ or a nitrogen atom, in which $R^X$ represents the same as $R^X$ in the formula (1).

(1-6)

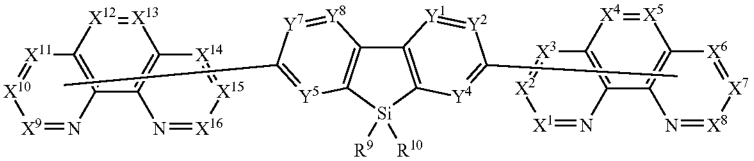

In the formula (1), when $X^4$ or $X^5$ is a carbon atom bonded to the group represented by the formula (2), $Y^2$ is a carbon atom bonded to L, L is a single bond, and Z is an oxygen atom, $R^Y$ for $Y^7$ is a group other than a pyrenyl group.

Alternatively, in the formula (1), when $X^4$ or $X^5$ is a carbon atom bonded to the group represented by the formula (2), $Y^7$ is a carbon atom bonded to L, L is a single bond, and Z is an oxygen atom, $R^Y$ for $Y^2$ is a group other than a pyrenyl group.

In other words, when the compound represented by the formula (1) is represented by the following formula (1-xx-1), $Y^2$ of the formula (2) is a carbon atom bonded to $X^4$ or $X^5$, $Y^7$ is $CR^Y$ in which $R^Y$ represents the same as $R^Y$ in the formula (2). However, $R^Y$ is a group other than a pyrenyl group. In the following formula (1-xx-1), $Y^1$, $Y^4$ to $Y^6$, $Y^8$ and $X^1$ to $X^8$ each independently represent the same as $X^1$ to $X^8$, $Y^1$, $Y^4$ to $Y^6$ and $Y^8$ in the formulae (1) and (2).

When the compound represented by the formula (1) is represented by the following formula (1-xx-2), $Y^7$ of the formula (2) is a carbon atom bonded to $X^4$ or $X^5$, $Y^2$ is $CR^Y$ in which $R^Y$ represents the same as $R^Y$ in the formula (2).

(1-7)

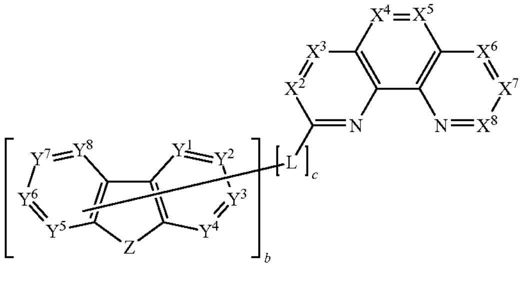

Unlike in the formula (1-7), not $X^1$ but $X^8$ may be a carbon atom to be bonded to the group represented by the formula (2).

In the compound of the exemplary embodiment, $X^1$ and $X^8$ in the formula (1) are preferably carbon atoms to be bonded to the group represented by the formula (2). Specifically, the compound of the exemplary embodiment is preferably a compound represented by the following formula (1-8).

In the following formula (1-8), $X^2$ to $X^7$ each independently represent $CR^X$ or a nitrogen atom, in which $R^X$ represents the same as $R^X$ in the formula (1). In the following formula (1-8), $Y^1$ to $Y^{16}$ each independently represent a nitrogen atom, $CR^Y$ or a carbon atom bonded to L, in which $R^Y$ represents the same as $R^Y$ in the formula (2). In the following formula (1-8), $Z^1$ and $Z^2$ each independently represent the same as Z in the formula (2). In the following formula (1-8), $L^1$ and $L^2$ each independently represent the same as L in the formula (2). In the following formula (1-8), $b_1$ and $b_2$ are each independently an integer of 1 to 5, and $c_1$ and $c_2$ are each independently an integer of 1 to 8.

(1-10)

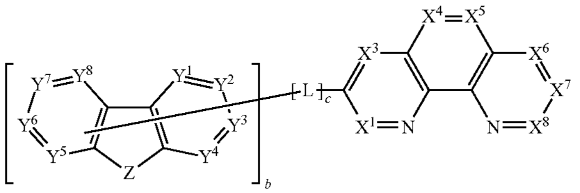

Unlike in the formula (1-10), not $X^2$ but $X^7$ may be a carbon atom to be bonded to the group represented by the formula (2).

In the compound of the exemplary embodiment, $X^3$ or $X^6$ in the formula (1) is preferably a carbon atom to be bonded (1-8)

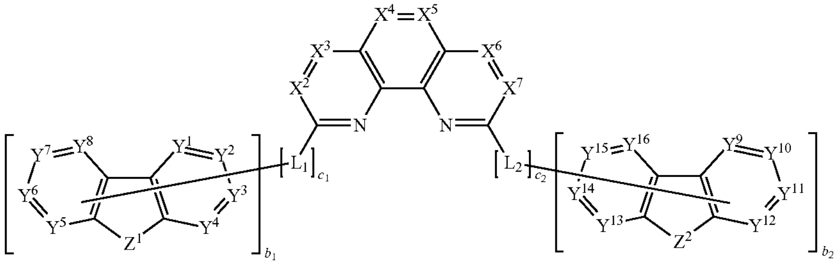

In the compound of the exemplary embodiment, $X^3$ and $X^8$ in the formula (1) are preferably carbon atoms to be bonded to the group represented by the formula (2). Specifically, the compound of the exemplary embodiment is preferably a compound represented by the following formula (1-9).

In the following formula (1-9), $X^1$, $X^2$, $X^4$, $X^5$, $X^7$ and $X^8$ each independently represent $CR^X$ or a nitrogen atom, in which $R^X$ represents the same as $R^X$ in the formula (1). In the following formula (1-9), $Y^1$ to $Y^{16}$, $Z^1$, $Z^2$, $L_1$, $L_2$, $b_1$, $b_2$, $c_1$ and $c_2$ each represent the same as $Y^1$ to $Y^{16}$, $Z^1$, $Z^2$, $L_1$, $L_2$, $b_1$, $b_2$, $c_1$ and $c_2$ in the formula (1-8).

to a group represented by the formula (2). Specifically, the compound of the exemplary embodiment is preferably a compound represented by the following formula (1-11).

In the following formula (1-11), $X^1$, $X^2$ and $X^4$ to $X^8$ each independently represent $CR^X$ or a nitrogen atom, in which $R^X$ represents the same as $R^X$ in the formula (1). In the following formula (1-11), $Y^1$ to $Y^8$, Z, L, b and c each represent the same as $Y^1$ to $Y^8$, Z, L, b and c in the formula (2).

(1-9)

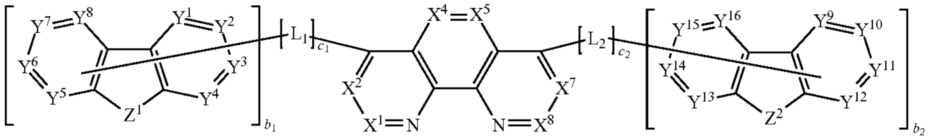

In the compound of the exemplary embodiment, $X^2$ or $X^7$ in the formula (1) is preferably a carbon atom to be bonded to a group represented by the formula (2). Specifically, the compound of the exemplary embodiment is preferably a compound represented by the following formula (1-10).

In the following formula (1-10), $X^1$ and $X^3$ to $X^8$ each independently represent $CR^X$ or a nitrogen atom, in which $R^X$ represents the same as $R^X$ in the formula (1). In the following formula (1-10), $Y^1$ to $Y^8$, Z, L, b and c each represent the same as $Y^1$ to $Y^8$, Z, L, b and c in the formula (2).

(1-11)

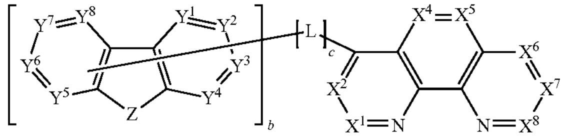

Unlike in the formula (1-11), not $X^3$ but $X^6$ may be a carbon atom to be bonded to the group represented by the formula (2).

In the compound of the exemplary embodiment, $X^4$ or $X^5$ in the formula (1) is preferably a carbon atom to be bonded to a group represented by the formula (2). Specifically, the compound of the exemplary embodiment is preferably a compound represented by the following formula (1-12).

In the following formula (1-12), $X^1$ to $X^3$ and $X^5$ to $X^8$ each independently represent $CR^X$ or a nitrogen atom, in which $R^X$ represents the same as $R^X$ in the formula (1). In the following formula (1-12), $Y^1$ to $Y^8$, Z, L, b and c each represent the same as $Y^1$ to $Y^8$, Z, L, b and c in the formula (2).

(1-12)

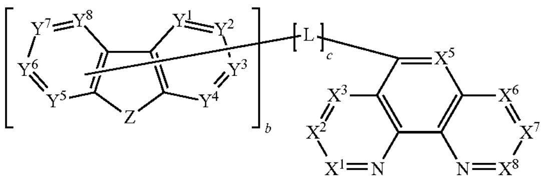

Unlike in the formula (1-12), not $X^4$ but $X^5$ may be a carbon atom to be bonded to the group represented by the formula (2).

In the compound of the exemplary embodiment, $X^1$ and $X^7$ in the formula (1) are preferably carbon atoms to be bonded to a group represented by the formula (2). Specifically, the compound of the exemplary embodiment is preferably a compound represented by the following formula (1-13).

In the following formula (1-13), $X^2$ to $X^6$ and $X^8$ each independently represent $CR^X$ or a nitrogen atom, in which $R^X$ represents the same as $R^X$ in the formula (1). In the following formula (1-13), $Y^1$ to $Y^{16}$, $Z^1$, $Z^2$, $L_1$, $L_2$, $b_1$, $b_2$, $c_1$ and $c_2$ each represent the same as $Y^1$ to $Y^{16}$, $Z^1$, $Z^2$, $L_1$, $L_2$, $b_1$, $b_2$, $c_1$ and $c_2$ in the formula (1-8).

(1-13)

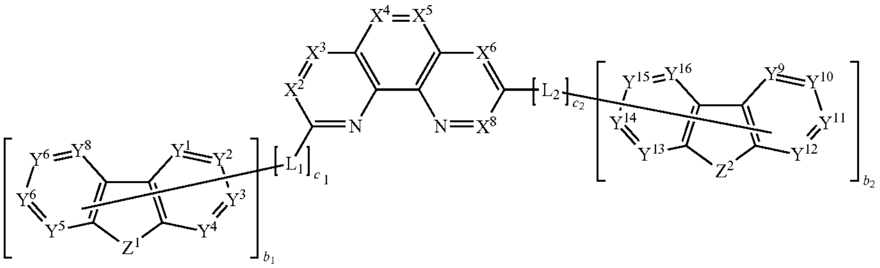

In the compound of the exemplary embodiment, $X^2$ and $X^7$ in the formula (1) are preferably carbon atoms to be bonded to a group represented by the formula (2). Specifically, the compound of the exemplary embodiment is preferably a compound represented by the following formula (1-14).

In the following formula (1-14), $X^1$, $X^3$ to $X^6$ and $X^8$ each independently represent $CR^X$ or a nitrogen atom, in which $R^X$ represents the same as $R^X$ in the formula (1). In the following formula (1-14), $Y^1$ to $Y^{16}$, $Z^1$, $Z^2$, $L_1$, $L_2$, $b_1$, $b_2$, $c_1$ and $c_2$ each represent the same as $Y^1$ to $Y^{16}$, $Z^1$, $Z^2$, $L_1$, $L_2$, $b_1$, $b_2$, $c_1$ and $c_2$ in the formula (1-8).

(1-14)

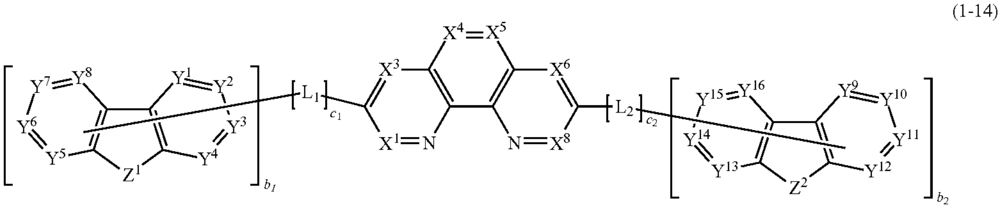

In the compound of the exemplary embodiment, $X^1$, $X^2$, $X^7$ and $X^8$ are preferably carbon atoms to be bonded to a group represented by the formula (2). Specifically, the compound of the exemplary embodiment is preferably a compound represented by the following formula (1-15).

In the following formula (1-15), $X^3$ to $X^6$ each independently represent $CR^X$ or a nitrogen atom, in which $R^X$ represents the same as $R^X$ in the formula (1). In the following formula (1-15), $Y^1$ to $Y^{32}$ each independently represent a nitrogen atom, $CR^Y$ or a carbon atom bonded to L, in which $R^Y$ represents the same as $R^Y$ in the formula (2). In the following formula (1-15), $Z^1$ to $Z^4$ each independently represent the same as Z in the formula (2). In the following formula (1-15), $L^1$ to $L^4$ each independently represent the same as L in the formula (2). In the following formula (1-15), $b_1$ to $b_4$ are each independently an integer of 1 to 5, and $c_1$ to $c_4$ are each independently an integer of 1 to 8.

(2-2)

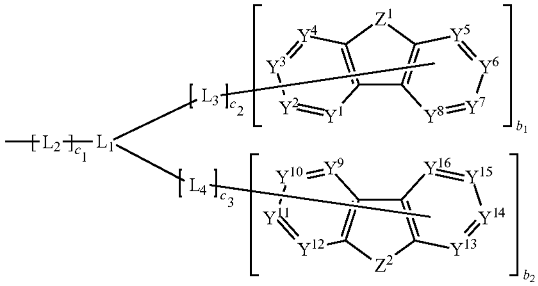

In the formula (2-2), $b_1$ and $b_2$ each independently represent an integer of 1 to 5.

(1-15)

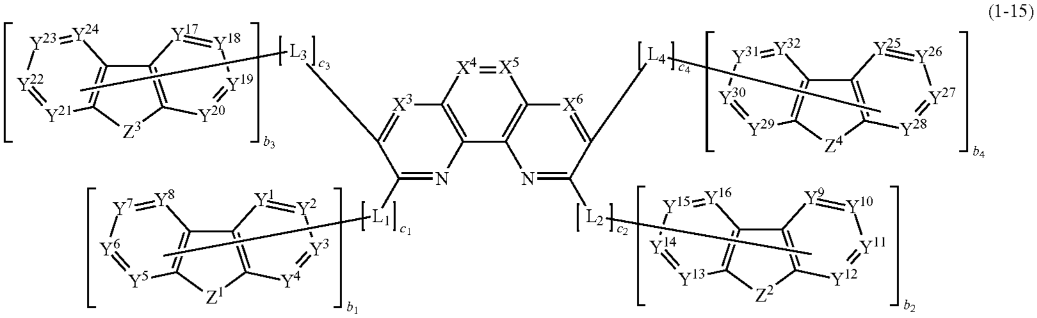

In the compound of the exemplary embodiment, $X^1$, $X^3$, $X^6$ and $X^8$ in the formula (1) are preferably carbon atoms to be bonded to a group represented by the formula (2). Specifically, the compound of the exemplary embodiment is preferably a compound represented by the following formula (1-16).

In the following formula (1-16), $X^2$, $X^4$, $X^5$ and $X^7$ each independently represent $CR^X$ or a nitrogen atom, in which $R^X$ represents the same as $R^X$ in the formula (1). In the following formula (1-16), $Y^1$ to $Y^{32}$ each independently represent a nitrogen atom, $CR^Y$ or a carbon atom bonded to L, in which $R^Y$ represents the same as $R^Y$ in the formula (2). In the following formula (1-16), $Z^1$ to $Z^4$ each independently represent the same as Z in the formula (2). In the following formula (1-16), $L^1$ to $L^4$ each independently represent the same as L in the formula (2). In the following formula (1-16), $b_1$ to $b_4$ are each independently an integer of 1 to 5, and $c_1$ to $c_4$ are each independently an integer of 1 to 8.

$c_1$, $c_2$ and $c_3$ are each independently an integer of 0 to 7 while $c_1+c_2+c_3$ is an integer of 7 or less.

Z is an oxygen atom, a sulfur atom or a silicon atom. When b is 2 to 5, Z are mutually the same or different. When Z is a silicon atom, $R^9$ and $R^{10}$ are bonded to the silicon atom. $R^9$ and $R^{10}$ each independently represent the same as $R^X$ in the formula (10). $R^9$ and $R^{10}$ may be bonded to the structure represented by the formula (10).

$L_1$ is a linking group representing a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms.

$L_2$, $L_3$ and $L_4$ are each independently selected from a single bond and a linking group. The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms.

(1-16)

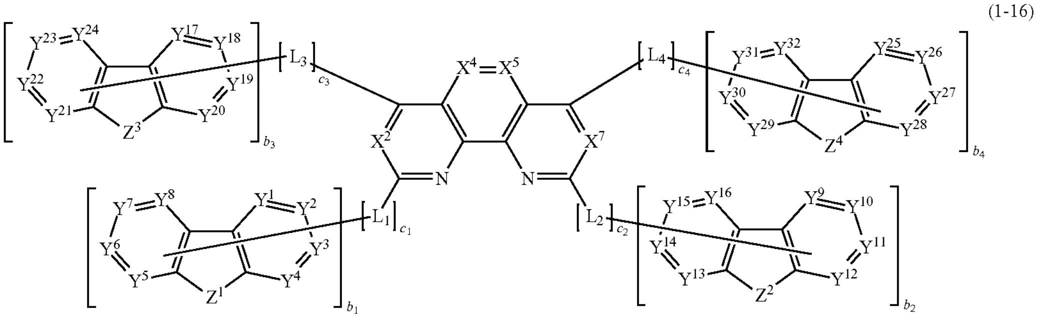

In the compound of the exemplary embodiment, the group represented by the formula (2) is preferably represented by the following formula (2-2). At least one of $X^1$ to $X^8$ is a carbon atom to be bonded to the group represented by the following formula (2-2).

The polyvalent heteroaryl group having 5 to 40 ring atoms for $L_1$ to $L_4$ in the formula (2-2) includes a substituted or unsubstituted polyvalent group derived from the phenanthroline ring represented by the formula (10). When $c_1$ is an integer of 2 or more, $L_2$ are mutually the same or different. When $c_2$ is an integer of 2 or more, $L_3$ are mutually the same or different. When $c_3$ is an integer of 2 or more, $L_4$ are mutually the same or different.

$Y^1$ to $Y^8$ each independently represent a nitrogen atom, $CR^Y$ or a carbon atom bonded to $L_3$.

$Y^9$ to $Y^{16}$ each independently represent a nitrogen atom, $CR^Z$ or a carbon atom bonded to $L_4$.

$R^Y$ and $R^Z$ each independently represent the same as $R^X$ in the formula (10). The heteroaryl group having 5 to 40 ring atoms for $R^Y$ and $R^Z$ includes a substituted or unsubstituted phenanthrolyl group derived from the phenanthroline ring represented by the formula (10). Adjacent $R^Y$ are bonded to each other to form a cyclic structure, or are not bonded to each other, In the exemplary embodiment, it is preferable that $X^1$ or $X^8$ is a carbon atom and is bonded to the group represented by the formula (2-2).

In the exemplary embodiment, $L_1$ in the formula (2-2) is preferably a substituted or unsubstituted polyvalent aryl group having 6 to 40 ring carbon atoms, more preferably a substituted or unsubstituted polyvalent aryl group having 6 ring carbon atoms.

In the exemplary embodiment, $L_2$ in the formula (2-2) is preferably a substituted or unsubstituted polyvalent heteroaryl group having 5 to 40 ring atoms. In the formula (2-2), $L_2$ directly bonded to $L_1$ is preferably a substituted or unsubstituted polyvalent heteroaryl group having 5 to 40 ring atoms.

In the exemplary embodiment, it is preferable that $c_1$ in the formula (2-2) is 2 or more and a plurality of $L_2$ include a substituted or unsubstituted polyvalent heteroaryl group having 5 to 40 ring atoms and a substituted or unsubstituted polyvalent aryl group having 6 to 40 ring carbon atoms. In this case, in the formula (2-2), $L_2$ directly bonded to $L_1$ is preferably a substituted or unsubstituted polyvalent heteroaryl group having 5 to 40 ring atoms.

In the exemplary embodiment, it is preferable that $L_3$ and $L_4$ in the formula (2-2) are each independently a substituted or unsubstituted polyvalent aryl group having 6 to 40 ring carbon atoms, more preferably a single bond or a substituted or unsubstituted polyvalent aryl group having 6 ring carbon atoms.

In the exemplary embodiment, $c_2$ and $c_3$ are preferably 1. In this case, $L_3$ and $L_4$ are preferably a substituted or unsubstituted polyvalent aryl group having 6 to 40 ring carbon atoms, more preferably a single bond or a substituted or unsubstituted polyvalent aryl group having 6 ring carbon atoms.

Among the compounds represented by the formulae (1-7) to (1-16), the compounds represented by the formulae (1-7) and (1-8) are preferable.

The compound represented by the formula (1-1) is also preferable.

In the compounds according to the exemplary embodiment, Z and $Z^1$ to $Z^4$ in the formulae (2), (2-1), (1-1) to (1-3), (1-5), and (1-7) to (1-16) are preferably an oxygen atom or a sulfur atom, more preferably an oxygen atom.

In the formulae (1), (1-1) to (1-16), (2-1), (1-x), (1-xx-1) and (1-xx-2), other than $X^1$ to $X^{16}$ being a carbon atom bonded to the group represented by the formula (2), $X^1$ to $X^{16}$ are preferably $CR^X$, in which $R^X$ is more preferably any one of a hydrogen atom, an alkyl group and an aryl group, further preferably a hydrogen atom or a phenyl group.

Next, substituents in the formulae (1), (1-1) to (1-16), (2), (2-1), (1-x), (1-xx-1) and (1-xx-2) will be described. Specific examples of the substituents in the formulae (1), (1-1) to (1-16), (2), (2-1), (1-x), (1-xx-1) and (1-xx-2) include a halogen atom, cyano group, nitro group, substituted or unsubstituted hydroxyl group, substituted or unsubstituted carboxyl group, substituted or unsubstituted sulfonyl group, substituted or unsubstituted boryl group, substituted or unsubstituted phosphino group, substituted or unsubstituted mercapto group, substituted or unsubstituted acyl group, substituted or unsubstituted amino group, substituted or unsubstituted silyl group, substituted or unsubstituted alkyl group having 1 to 30 carbon atom, substituted or unsubstituted alkenyl group having 2 to 30 carbon atoms, substituted or unsubstituted alkynyl group having 2 to 30 carbon atoms, substituted or unsubstituted aralkyl group having 6 to 30 carbon atoms, substituted or unsubstituted aryl group having 6 to 40 ring carbon atoms, and substituted or unsubstituted heteroaryl group having 5 to 40 ring atoms.

Examples of the halogen atom in the formulae (1), (1-1) to (1-16), (2), (2-1), (1-x), (1-xx-1) and (1-xx-2) include fluorine, chlorine, bromine and iodine, among which fluorine is preferable.

Examples of the substituted or unsubstituted hydroxyl group in the formulae (1), (1-1) to (1-16), (2), (2-1), (1-x), (1-xx-1) and (1-xx-2) include not only a hydroxyl group (—OH) but also a group represented by $-OR^A$ that is provided by substituting H of a hydroxyl group (—OH) with $R^A$.

Herein, when $R^A$ is an alkyl group, the group represented by $—OR^A$ becomes an alkoxy group, among which a substituted or unsubstituted alkoxy group having 1 to 30 carbon atoms is preferable. The alkyl group as $R^A$ is preferably the following alkyl group having 1 to 30 carbon atoms. Examples of the alkoxy group are a methoxy group, ethoxy group, propoxy group, butoxy group, pentyloxy group and hexyloxy group. Among the alkoxy group, an alkoxy group having 1 to 10 carbon atoms is preferable and an alkoxy group having 1 to 8 carbon atoms is more preferable. An alkoxy group having 1 to 4 carbon atoms is particularly preferable, The substituted or unsubstituted alkoxy group herein includes a haloalkoxy group provided by substituting the alkyl group as $R^A$ with one or more of the halogen atoms.

When $R^A$ is an aryl group, the group represented by $—OR^A$ becomes an aryloxy group, among which a substituted or unsubstituted aryloxy group having 6 to 40 ring carbon atoms is preferable. The aryl group as $R^A$ is preferably the following aryl group having 6 to 40 ring carbon atoms. The aryloxy group is exemplified by a phenoxy group.

The substituted or unsubstituted aryloxy group herein includes a haloaryloxy group provided by substituting the aryl group as $R^A$ with one or more of the halogen atoms.

When $R^A$ is a heteroaryl group, the group represented by $—OR^A$ becomes a heteroaryloxy group, among which a substituted or unsubstituted heteroaryloxy group having 5 to 40 ring atoms is preferable. The heteroaryl group as $R^A$ is preferably the following heteroaryl group having 5 to 40 ring atoms.

Examples of the substituted or unsubstituted carboxyl group in the formulae (1), (1-1) to (1-16), (2), (2-1), (1-x), (1-xx-1) and (1-xx-2) include not only a carboxyl group (—COOH) but also a group represented by —COOR$^B$ that is provided by substituting H of a carboxyl group (—COOH) with R$^B$.

Herein, when R$^B$ is an alkyl group, the group represented by —COOR$^B$ becomes an alkoxycarbonyl group, among which a substituted or unsubstituted alkoxycarbonyl group having 2 to 30 carbon atoms is preferable. The alkyl group as R$^B$ is preferably the following alkyl group having 1 to 30 carbon atoms.

When R$^B$ is an aryl group, the group represented by —COOR$^B$ becomes an aryloxycarbonyl group, among which a substituted or unsubstituted aryloxycarbonyl group having 7 to 40 carbon atoms is preferable. The aryl group as R$^B$ is preferably the following aryl group having 6 to 40 ring carbon atoms.

When R$^B$ is a heteroaryl group, the group represented by —COOR$^B$ becomes a heteroaryloxycarbonyl group, among which a substituted or unsubstituted heteroaryloxycarbonyl group having 5 to 40 ring atoms is preferable. The heteroaryl group as R$^B$ is preferably the following heteroaryl group having 5 to 40 ring atoms.

Examples of the substituted or unsubstituted boryl group in the formulae (1), (1-1) to (1-16), (2), (2-1), (1-x), (1-xx-1) and (1-xx-2) include not only a boryl group (—$BH_2$) but also a group represented by —BR$^E$R$^E$ that is provided by substituting H of a boryl group (—$BH_2$) with R$^E$ and R$^E$.

Herein, when R$^E$ is an alkyl group, the group represented by —BR$^E$R$^E$ becomes an alkylboryl group, among which a substituted or unsubstituted alkylboryl group is preferable. The alkyl group as R$^E$ is preferably the following alkyl group having 1 to 30 carbon atoms.

Herein, when R$^E$ is an aryl group, the group represented by —BR$^E$R$^E$ becomes an arylboryl group, among which a substituted or unsubstituted arylboryl group is preferable. The aryl group as R$^E$ is preferably the following aryl group having 6 to 40 ring carbon atoms.

When R$^E$ is a heteroaryl group, the group represented by —BR$^E$R$^E$ becomes a heteroarylboryl group, among which a substituted or unsubstituted a heteroarylboryl group is preferable. The heteroaryl group as R$^E$ is preferably the following heteroaryl group having 5 to 40 ring atoms.

In addition, a dihydroxyboryl group (—$B(OH)_2$) is also usable.

Examples of the substituted or unsubstituted phosphino group in the formulae (1), (1-1) to (1-16), (2), (2-1), (1-x), (1-xx-1) and (1-xx-2) include not only a phosphino group (—$PH_2$) but also a group represented by —PR$^F$R$^F$ that is provided by substituting H of a phosphino group (—$PH_2$) with R$^F$ and R$^F$, and a group represented by —P(O)R$^F$R$^F$.

Herein, when R$^F$ is an alkyl group, the group represented by —PR$^F$R$^F$ or the group represented by —P(O)R$^F$R$^F$ becomes an alkylphosphino group, among which a substituted or unsubstituted alkylphosphino group is preferable. The alkyl group as R$^F$ is preferably the following alkyl group having 1 to 30 carbon atoms.

Herein, when R$^F$ is an aryl group, the group represented by —PR$^F$R$^F$ or the group represented by —P(O)R$^F$R$^F$ becomes an arylphosphino group, among which a substituted or unsubstituted arylphosphino group is preferable. The aryl group as R$^F$ is preferably the following aryl group having 6 to 40 ring carbon atoms.

Herein, when R$^F$ is a heteroaryl group, the group represented by —PR$^F$R$^F$ or the group represented by —P(O)R$^F$R$^F$ becomes a heteroarylphosphino group, among which a substituted or unsubstituted heteroarylphosphino group is preferable. The heteroaryl group as R$^F$ is preferably the following heteroaryl group having 5 to 40 ring atoms.

Examples of the substituted or unsubstituted mercapto group in the formulae (1), (1-1) to (1-16), (2), (2-1), (1-x), (1-xx-1) and (1-xx-2) include not only a mercapto group (—SH) but also a group represented by —SR$^C$ that is provided by substituting H of a mercapto group (—SH) with R$^C$.

Herein, when R$^C$ is an alkyl group, the group represented by —SR$^C$ becomes an alkoxythio group, among which a substituted or unsubstituted alkoxythio group having 1 to 30 carbon atoms is preferable. The alkyl group as R$^C$ is preferably the following alkyl group having 1 to 30 carbon atoms.

When R$^C$ is an aryl group, the group represented by —SR$^C$ becomes an arylthio group, among which a substituted or unsubstituted arylthio group having 6 to 40 ring carbon atoms is preferable. The aryl group as R$^C$ is preferably the following aryl group having 6 to 40 ring carbon atoms.

When R$^C$ is a heteroaryl group, the group represented by —SR$^C$ becomes a heteroarylthio group, among which a substituted or unsubstituted heteroarylthio group having 5 to 40 ring atoms is preferable. The heteroaryl group as R$^C$ is preferably the following heteroaryl group having 5 to 40 ring atoms.

The substituted or unsubstituted acyl group in the formulae (1), (1-1) to (1-16), (2), (2-1), (1-x), (1-xx-1) and (1-xx-2) is represented by —CO—R$^D$.

Herein, when R$^D$ is an alkyl group, the group represented by —CO—R$^D$ becomes an alkylcarbonyl group, among which a substituted or unsubstituted alkylcarbonyl group having 2 to 30 carbon atoms is preferable. The alkyl group as R$^D$ is preferably the following alkyl group having 1 to 30 carbon atoms. Specific examples of the alkylcarbonyl group are an acetyl group, propyonyl group, butyryl group, valeryl group, pivaloyl group, palmitoyl group, stearoyl group and oleoyl group.

When R$^D$ is an aryl group, the group represented by —CO—R$^D$ becomes an arylcarbonyl group (occasionally referred to as an aroyl group), among which a substituted or unsubstituted arylcarbonyl group having 6 to 40 ring carbon atoms is preferable. The aryl group as R$^D$ is preferably the following aryl group having 6 to 40 ring carbon atoms. Specific examples of the arylcarbonyl group are a benzoyl group, toluoyl group, salicyloyl group, cinnamoyl group, naphthoyl group and phthaloyl group.

When R$^D$ is a heteroaryl group, the group represented by —CO—R$^D$ becomes a heteroarylcarbonyl group, among which a substituted or unsubstituted heteroarylcarbonyl group having 5 to 40 ring atoms is preferable. The heteroaryl group as R$^D$ is preferably the following heteroaryl group having 5 to 40 ring atoms. Specific examples of the heteroarylcarbonyl group are a furoyl group, pyrrolylcarbonyl group, pyridylcarbonyl group and thienylcarbonyl group.

It should be noted that a formyl group (—CO—H) provided when R$^D$ is a hydrogen atom is also included in the acyl group.

Examples of the substituted or unsubstituted amino group in the formulae (1), (1-1) to (1-16), (2), (2-1), (1-x), (1-xx-1) and (1-xx-2) include not only an amino group (—$NH_2$) but also a group provided by substituting H of an amino group (—$NH_2$) with substituents. Examples of the group that is provided by substituting H of an amino group (—$NH_2$) with substituents include an alkylamino group provided by substituting the amino group with a substituted or unsubstituted alkyl group having 1 to 30 carbon atoms, an arylamino group provided by substituting the amino group with a substituted or unsubstituted aryl group having 6 to 40 ring carbon atoms, a heteroarylamino group provided by substituting the amino group with a substituted or unsubstituted heteroaryl group having 5 to 40 ring atoms, and an acylamino group provided by substituting the amino group with a substituted or unsubstituted acyl group having 2 to 30 carbon atoms.

The alkyl group having 1 to 30 carbon atoms in the alkylamino group is preferably the following alkyl group having 1 to 30 carbon atoms. When the amino group is substituted by two alkyl groups, the two alkyl groups may be mutually the same or different.

The aryl group having 6 to 40 ring carbon atoms in the arylamino group is preferably the following aryl group having 6 to 40 ring carbon atoms. The arylamino group is preferably an amino group substituted by a phenyl group. When the amino group is substituted by two aryl groups, the two aryl groups may be mutually the same or different.

The heteroaryl group having 5 to 40 ring atoms in the heteroarylamino group is preferably the following heteroaryl group having 5 to 40 ring atoms. When the amino group is substituted by two heteroaryl groups, the two heteroaryl groups may be mutually the same or different.

The acyl group having 2 to 30 carbon atoms in the acylamino group is preferably selected from the aforementioned acyl group.

A substituted amino group may be an amino group substituted by two selected from a hydrogen atom, alkyl group, aryl group, heteroaryl group and acyl group.

The substituted amino group may be provided by the amino group substituted by an alkyl group and an aryl group. Examples of the substituted amino group include an alkylarylamino group, alkylheteroarylamino group, arylheteroarylamino group, alkylacylamino group and arylacylamino group.

Examples of the substituted or unsubstituted silyl group in the formulae (1), (1-1) to (1-16), (2), (2-1), (1-x), (1-xx-1) and (1-xx-2) include not only an unsubstituted silyl group but also an alkylsilyl group substituted by a substituted or unsubstituted alkyl group having 1 to 30 carbon atoms, an arylsilyl group substituted by a substituted or unsubstituted aryl group having 6 to 40 ring carbon atoms, and a heteroarylsilyl group substituted by a substituted or unsubstituted heteroaryl group having 5 to 40 ring atoms.

The alkylsilyl group is exemplified by a trialkylsilyl group including the aforementioned alkyl group having 1 to 30 carbon atoms, specific examples of which are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propyosilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups may be mutually the same or different.

The arylsilyl group is exemplified by a triarylsilyl group having the following three aryl groups each having 6 to 40 ring carbon atoms. The triarylsilyl group preferably has 18 to 30 carbon atoms. Three aryl groups may be mutually the same or different.

The heteroarylsilyl group is exemplified by a triheteroarylsilyl group including the following three heteroaryl groups each having 5 to 40 ring atoms. Three heteroaryl groups may be mutually the same or different.

A substituted silyl group may be a silyl group substituted by at least two selected from an alkyl group, aryl group and heteroaryl group.

The substituted silyl group may be provided by substituting the silyl group with an alkyl group and an aryl group. Examples of the substituted silyl group include an alkylarylsilyl group, dialkylarylsilyl group, diarylsilyl group, alkyldiarylsilyl group and triarylsilyl group. A plurality of aryl groups may be the same or different, or a plurality of alkyl groups may be the same or different The dialkylarylsilyl group is exemplified by a dialkylarylsilyl group including two of the above-exemplified alkyl groups having 1 to 30 carbon atoms and one of the following aryl group having 6 to 40 ring carbon atoms. The dialkylarylsilyl group preferably has 8 to 30 carbon atoms. The two alkyl groups may be mutually the same or different.

The alkyldiarylsilyl group is exemplified by an alkyldiarylsilyl group including one of the above-exemplified alkyl group having 1 to 30 carbon atoms and two of the above aryl group having 6 to 40 ring carbon atoms. The alkyldiarylsilyl group preferably has 13 to 30 carbon atoms. The two aryl groups may be mutually the same or different.

Examples of the arylsilyl group include a phenyldimethylsilyl group, diphenylmethylsilyl group, diphenyl-t-butylsilyl group and triphenylsilyl group.

A silyl group substituted with alkyl group and heteroaryl group, a silyl group with substituted aryl group and heteroaryl group, and a silyl group with substituted alkyl group, aryl group and heteroaryl group may be used.

The substituted or unsubstituted alkyl group having 1 to 30 carbon atoms in the formulae (1), (1-1) to (1-16), (2), (2-1), (1-x), (1-xx-1) and (1-xx-2) may be linear, branched or cyclic. The substituted alkyl group having 1 to 30 carbon atoms includes a haloalkyl group. The haloalkyl group is exemplified by a haloalkyl group provided by substituting the alkyl group having 1 to 30 carbon atoms with one or more halogen atoms. Examples of the substituted or unsubstituted, linear or branched alkyl group include a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, 1,2,3-trinitropropyl group, fluoromethyl group, difluoromethyl group, trifluoromethyl group, fluoroethyl group, 2,2,2-trifluoroethyl group and 1,1,1,3,3,3-hexafluoro-2-propyl group.

The substituted or unsubstituted cyclic alkyl group (cycloalkyl group) is preferably a substituted or unsubstituted cycloalkyl group having 3 to 30 carbon atoms, examples of which include a cyclopropyl group, cyclobutyl group, cyclopentyl group, cyclohexyl group, cyclooctyl group, 4-methylcyclohexyl group, 3,5-tetramethylcyclohexyl group, 1-adamantyl group, 2-adamantyl group, 1-norbornyl group and 2-norbornyl group.

Among the aforementioned alkyl group, an alkyl group having 1 to 10 carbon atoms is preferable, an alkyl group having 1 to 8 carbon atoms is more preferable, and an alkyl group having 1 to 6 carbon atoms is particularly preferable. Among the above, a methyl group, isopropyl group, t-butyl group and cyclohexyl group are preferable.

The substituted or unsubstituted alkenyl group having 2 to 30 carbon atoms in the formulae (1), (1-1) to (1-16), (2), (2-1), (1-x), (1-xx-1) and (1-xx-2) may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group, among which a vinyl group is preferable.

Examples of the substituted or unsubstituted alkynyl group having 2 to 30 carbon atoms in the formulae (1), (1-1) to (1-16), (2), (2-1), (1-x), (1-xx-1) and (1-xx-2) include ethynyl propynyl and 2-phenylethynyl, among which an ethynyl group is preferable.

The substituted or unsubstituted aralkyl group having 7 to 40 carbon atoms in the formulae (1), (1-1) to (1-16), (2), (2-1), (1-x), (1-xx-1) and (1-xx-2) is represented by —$R^E$—$R^F$. $R^E$ is exemplified by an alkylene group that is a divalent group formed from the above alkyl group having 1 to 30 carbon atoms. $R^F$ is exemplified by the examples of the following aryl group having 6 to 40 ring carbon atoms. In the aralkyl group, an aryl group moiety has 6 to 40 carbon atoms, preferably 6 to 20 carbon atoms, more preferably 6 to 12 carbon atoms. In the aralkyl group, an alkyl group moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryl group having 6 to 40 ring carbon atoms in the formulae (1), (1-1) to (1-16), (2), (2-1), (1-x), (1-xx-1) and (1-xx-2) is exemplified by a non-fused aryl group and a fused aryl group. Specific examples of the aryl group include a phenyl group, naphthyl group, anthryl group, phenanthryl group, biphenyl group, terphenyl group, quaterphenyl group, fluoranthenyl group, pyrenyl group, triphenylenyl group, phenanthrenyl group, fluorenyl group, 9,9-dimethylfluorenyl group, spirofluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group and benzo[b]fluoranthenyl group. Among the aforementioned aryl group, an aryl group having 6 to 30 ring carbon atoms is more preferable, an aryl group having 6 to 20 ring carbon atoms is further preferable, and an aryl group having 6 to 12 ring carbon atoms is particularly preferable.

Moreover, since a higher triplet energy level is desirable in use as an electron transporting material, an aryl group having triplet energy T1 exceeding 2.1 eV is preferable. Examples of the aryl group include a phenyl group, naphthyl group, phenanthryl group, biphenyl group, terphenyl group, quaterphenyl group, fluoranthenyl group, triphenylenyl group, phenanthrenyl group, fluorenyl group, 9,9-dimethylfluorenyl group, spirofluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group and benzo[b]fluoranthenyl group.

The heteroaryl group having 5 to 40 ring atoms in the formulae (1), (1-1) to (1-16), (2), (2-1), (1-x), (1-xx-1) and (1-xx-2) are exemplified by non-fused heteroaryl and fused heteroaryl. Examples of the heteroaryl group include a pyrrolyl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenanthrydinyl group, acridinyl group, phenanthrolinyl group, thienyl group, and group formed based on a pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyrane ring, dibenzofuran ring, benzo[c]dibenzofuran ring and silafluorene ring. Among the aforementioned heteroaryl group, a heteroaryl group having 5 to 40 ring atoms is more preferable, a heteroaryl group having 5 to 20 ring atoms is further preferable, and a heteroaryl group having 5 to 12 ring atoms is particularly preferable.

When L and $L_1$ to $L_{12}$ in the formulae (1-1) to (1-16), (2), (2-1), (1-x), (1-xx-1) and (1-xx-2) are linking groups, the linear, branched or cyclic polyvalent aliphatic hydrocarbon group having 1 to 30 carbon atoms is exemplified by a polyvalent group formed from the aforementioned linear, branched or cyclic polyvalent alkyl group having 1 to 30 carbon atoms; linear, branched or cyclic polyvalent alkenyl group having 1 to 30 carbon atoms; linear, branched or cyclic polyvalent alkynyl group having 1 to 30 carbon atoms, among which a divalent group or trivalent group is preferable and a divalent group is more preferable. The divalent group may have the aforementioned substituents. The substituents are specifically a methylene group, ethylene group, acethylenylene group and vinylidene group.

When L and $L_1$ to $L_{12}$ in the formulae (1-1) to (1-16), (2), (2-1), (1-x), (1-xx-1) and (1-xx-2) are linking groups, the polyvalent aryl group having 6 to 40 ring carbon atoms is exemplified by a polyvalent group formed from the aforementioned aryl group having 6 to 40 ring carbon atoms, among which a divalent group or trivalent group is preferable and a divalent group is more preferable. Specifically, a divalent group formed from a phenyl group, biphenyl group, naphthyl group and 9,9-dimethylfluorenyl group is preferable and may have the aforementioned substitutents.

When L and $L_1$ to $L_{12}$ in the formulae (1-1) to (1-16), (2), (2-1), (1-x), (1-xx-1) and (1-xx-2) are linking groups, the polyvalent heteroaryl group having 5 to 40 ring atoms is exemplified by a polyvalent group formed from the aforementioned heteroaryl group having 5 to 40 ring atoms, among which a divalent group or trivalent group is preferable and a divalent group is more preferable. Specifically, a divalent group formed from a pyridyl group, pyrimidyl group, dibenzofuranyl group, dibenzothiophenyl group, silafluorenyl group and carbazolyl group is preferable and may have the aforementioned substitutents.

In the formulae (1-1) to (1-16), (2), (2-1), (1-x), (1-xx-1) and (1-xx-2), other than $Y^1$ to $Y^{16}$ that are a carbon atom bonded to L and $L_1$ to $L_{12}$, $Y^1$ to $Y^{16}$ are preferably $CR^Y$, in which $R^Y$ is more preferably a hydrogen atom or an alkyl group, particularly preferably a hydrogen atom.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

In the invention, a "hydrogen atom" means isotopes having different neutron numbers and specifically encompasses protium, deuterium and tritium.

Examples of the substituent meant by "substituted or unsubstituted" are the aforementioned aryl group, heteroaryl group, alkyl group (linear or branched alkyl group, cycloalkyl group and haloalkyl group), alkoxy group, aryloxy group, aralkyl group, haloalkoxy group, alkylsilyl group, dialkylarylsilyl group, alkyldiarylsilyl group, triarylsilyl group, halogen atom, cyano group, hydroxyl group, nitro group and carboxy group. In addition, an alkenyl group and an alkynyl group are also usable.

In the aforementioned substituents, the aryl group, heteroaryl group, alkyl group, halogen atom, alkylsilyl group, arylsilyl group and cyano group are preferable. Preferable ones of the specific examples of each substituent are further preferable.

"Unsubstituted" in "substituted or unsubstituted" means that a group is not substituted by the above-described substituents but bonded with a hydrogen atom.

Herein, "a to b carbon atoms" in the description of "substituted or unsubstituted XX group having a to b carbon atoms" represent carbon atoms of an unsubstituted XX group and does not include carbon atoms of a substituted XX group.

In a later-described compound or a partial structure thereof, the same applies to the above description of "substituted or unsubstituted."

Specific examples of the compound represented by the formula (1) are shown below, but the invention is not limited to the examples.

Examples of the compound represented by the formula (1-7) are as follows.

ET1

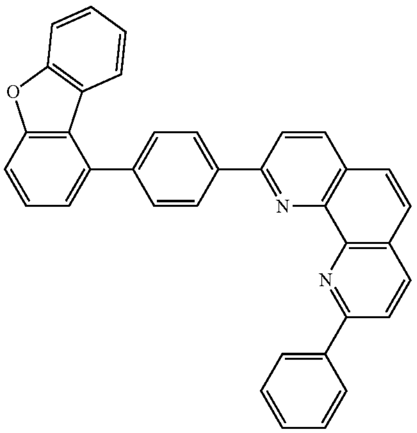

ET2

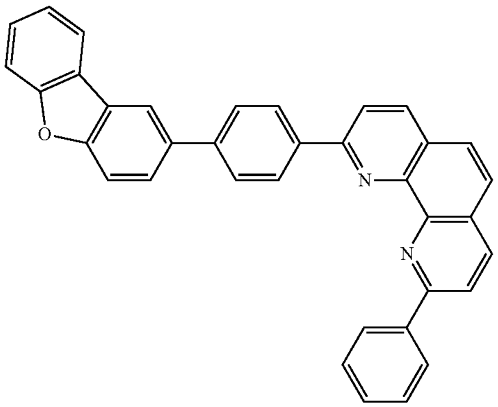

ET3

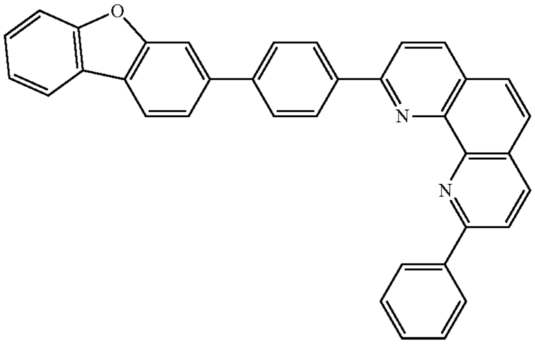

ET4

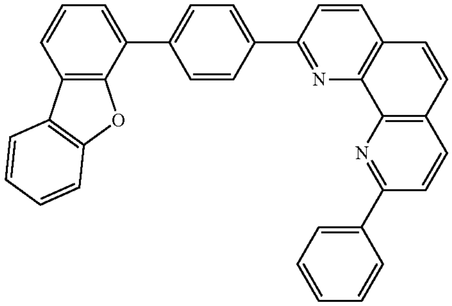

-continued
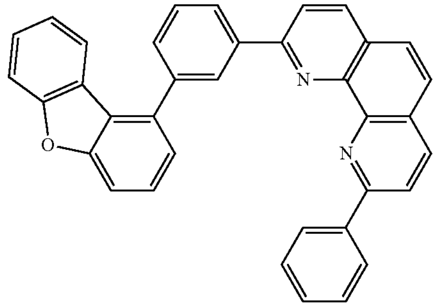
ET5
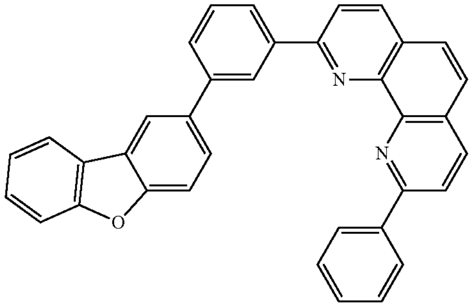
ET6
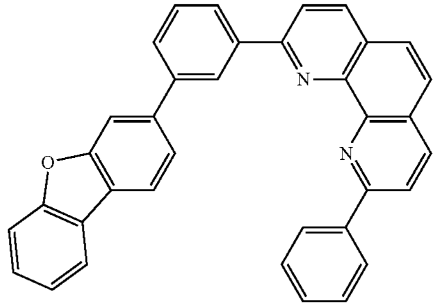
ET7
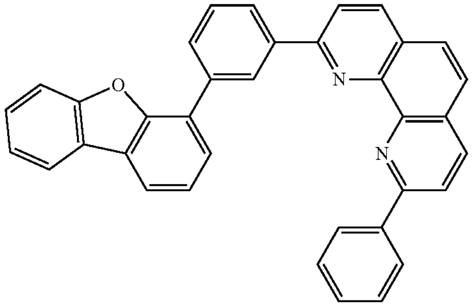
ET8
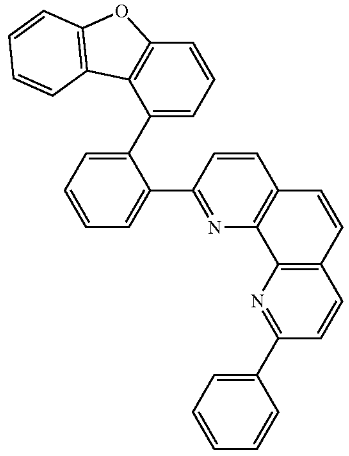
ET9
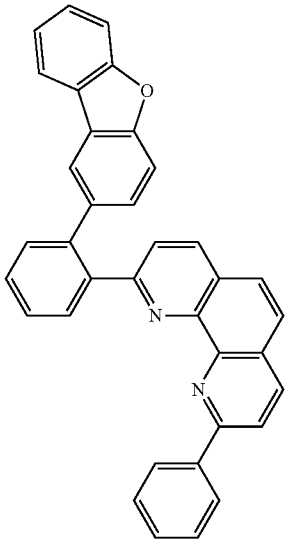
ET10

-continued
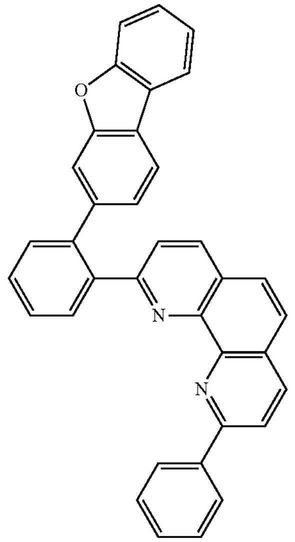
ET11
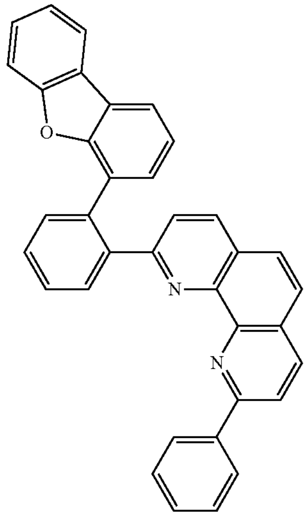
ET12
ET13
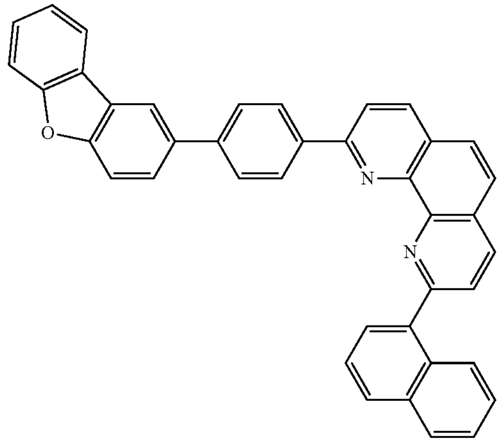
ET14
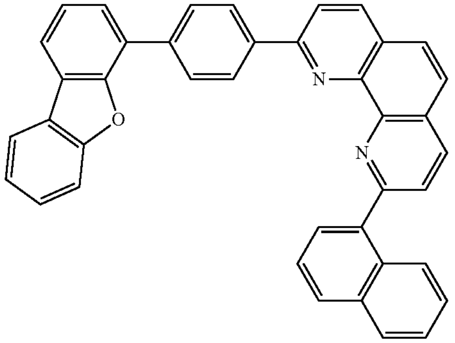
ET15
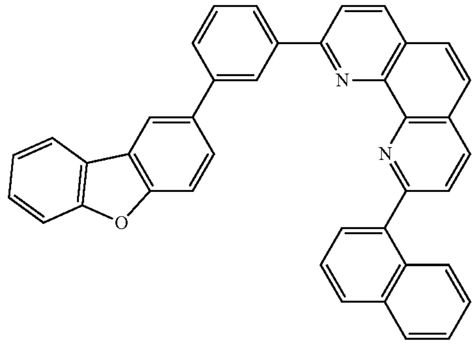
ET16
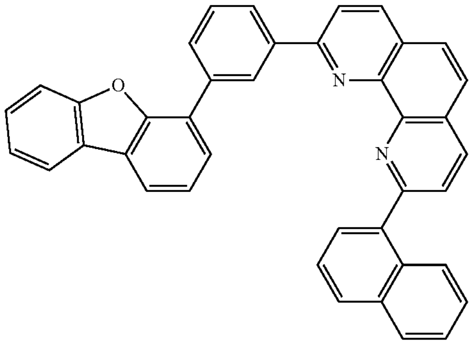

-continued
ET17
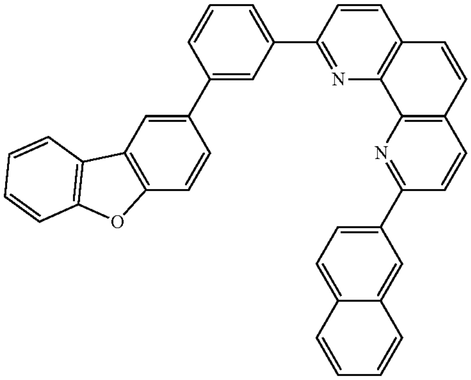
ET18
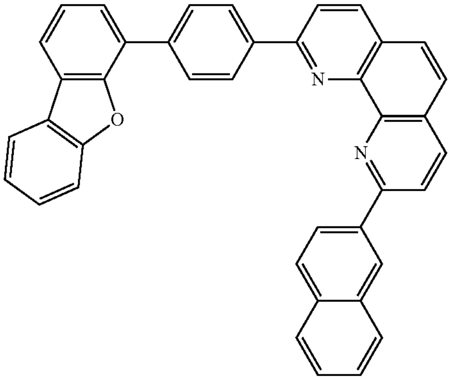
ET19
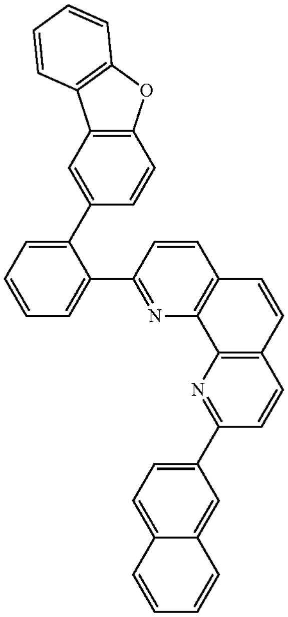
ET20
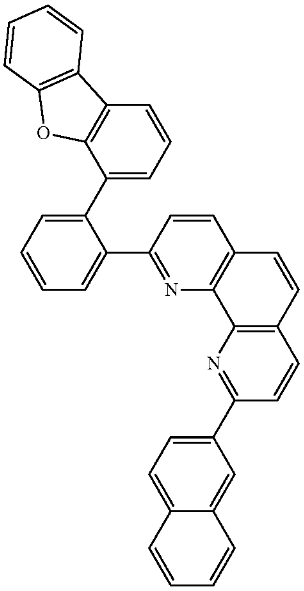
ET21
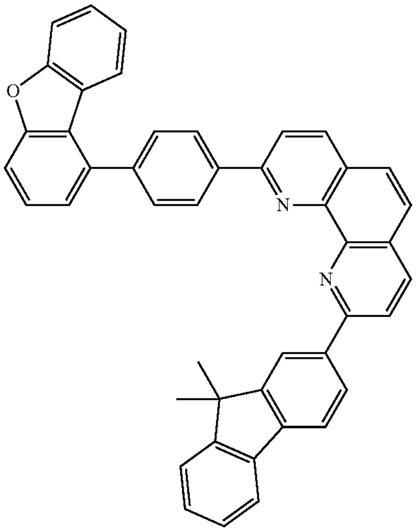
ET22
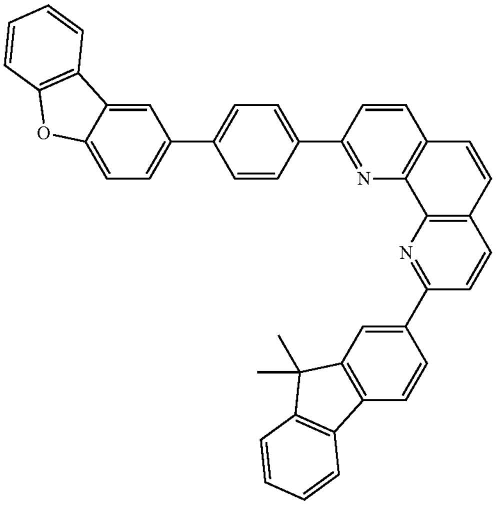

-continued
ET23
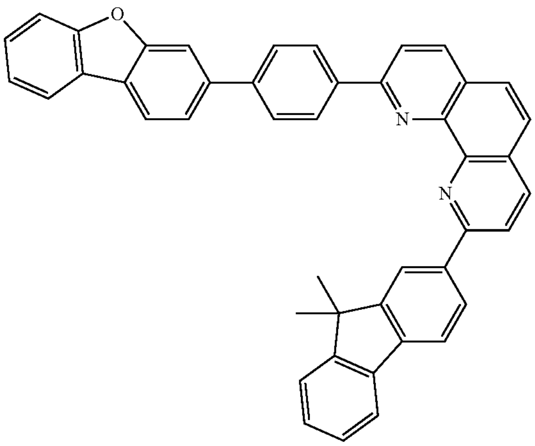
ET24
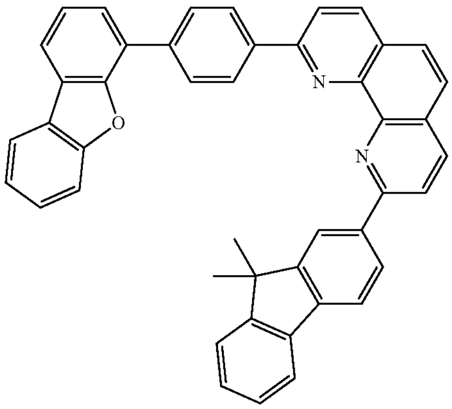
ET25
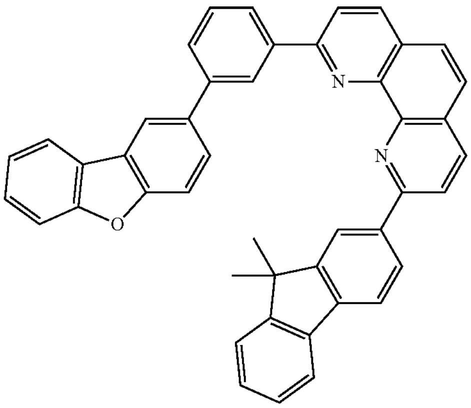
ET26
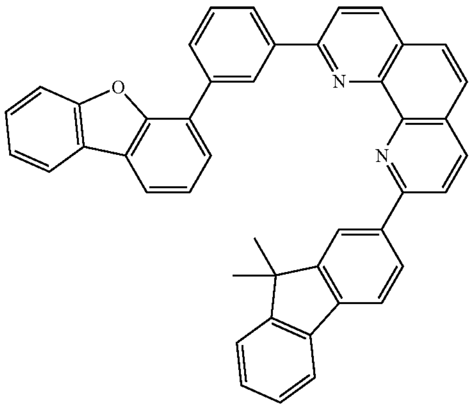
ET27
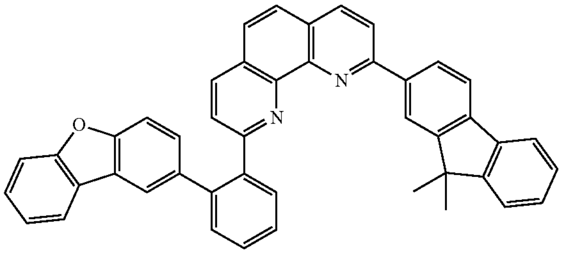
ET28
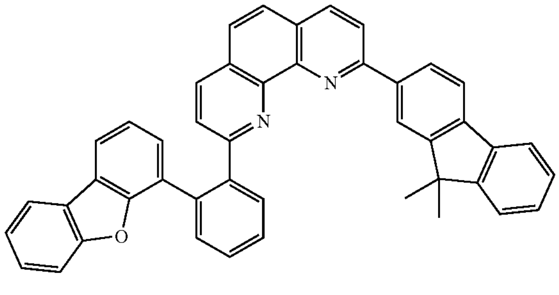

-continued
ET29
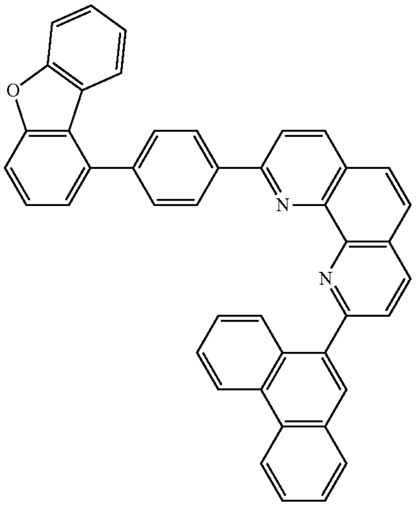
ET30
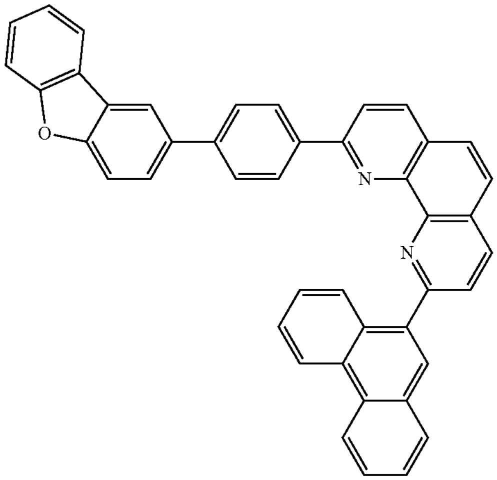
ET31
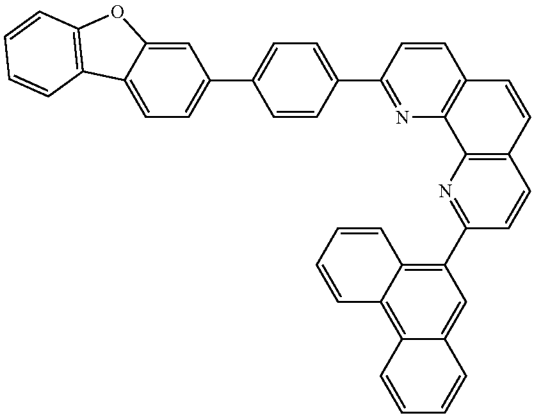
ET32
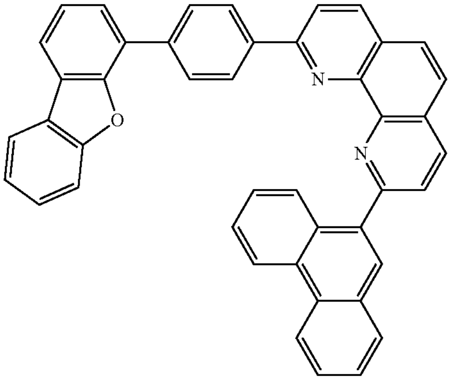
ET33
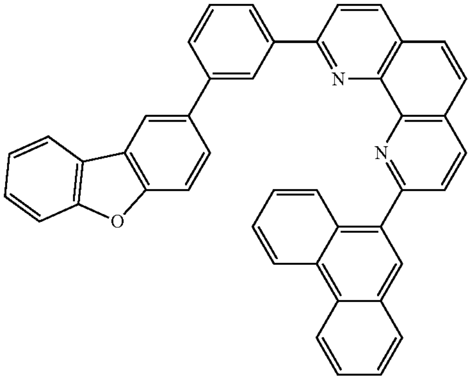
ET34
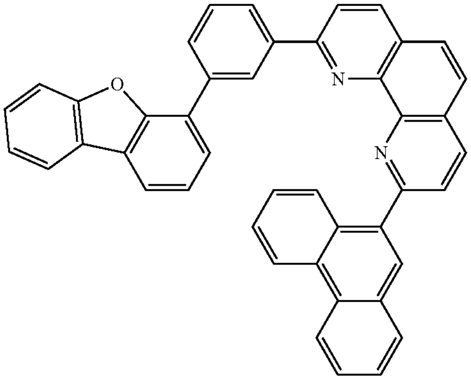
ET35
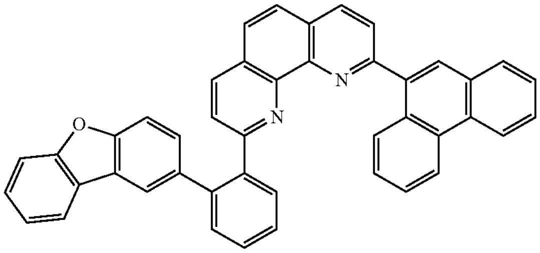
ET36
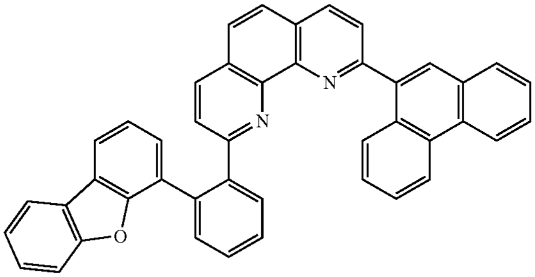

-continued
ET37
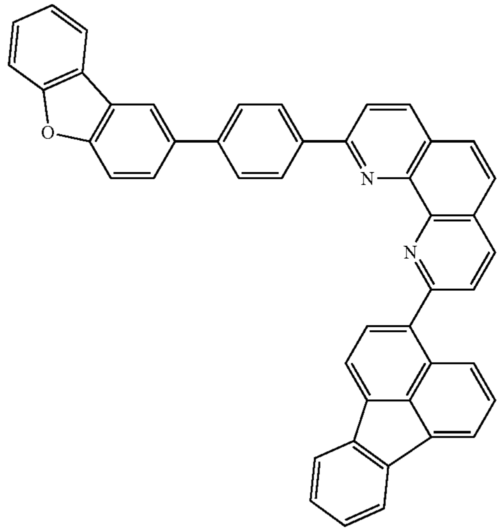
ET38
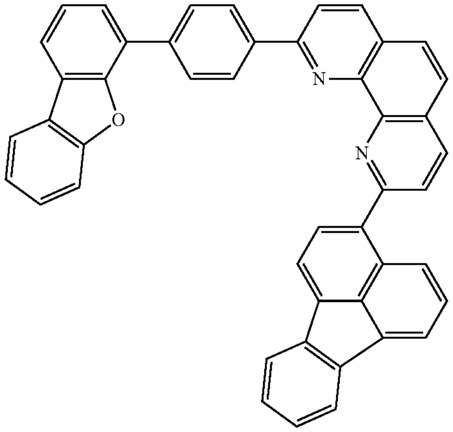
ET39
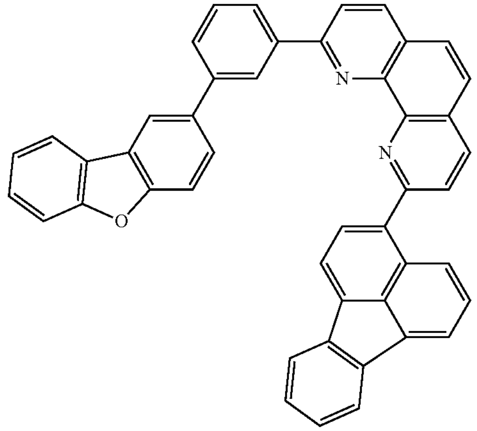
ET40
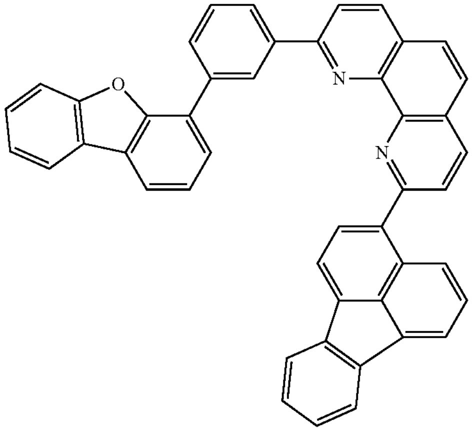
ET41
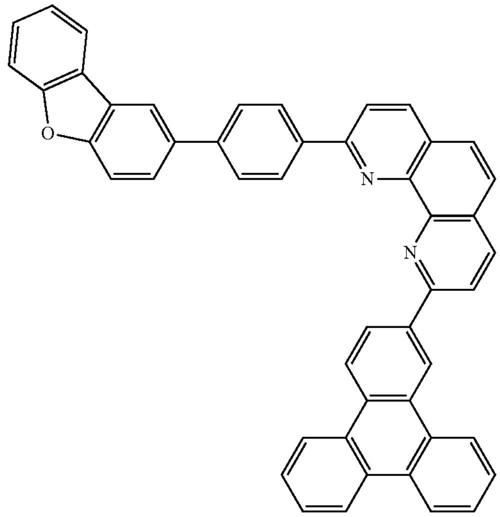
ET42
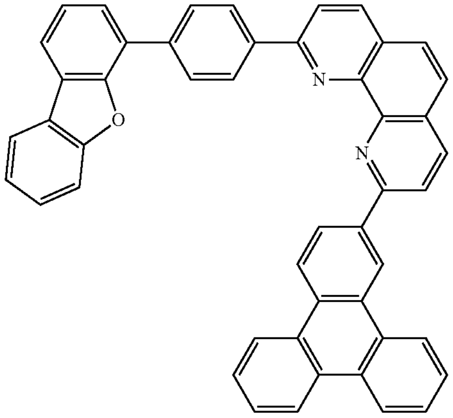

-continued
ET43
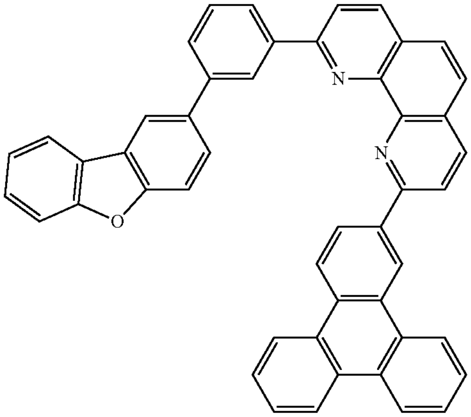
ET44
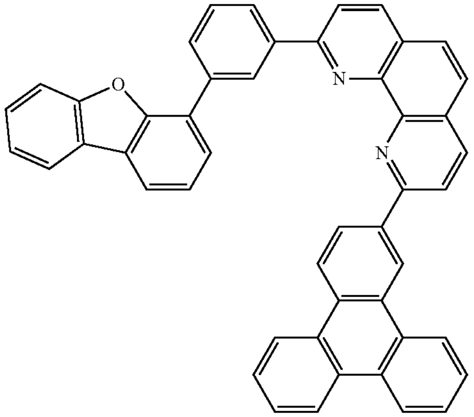
ET45
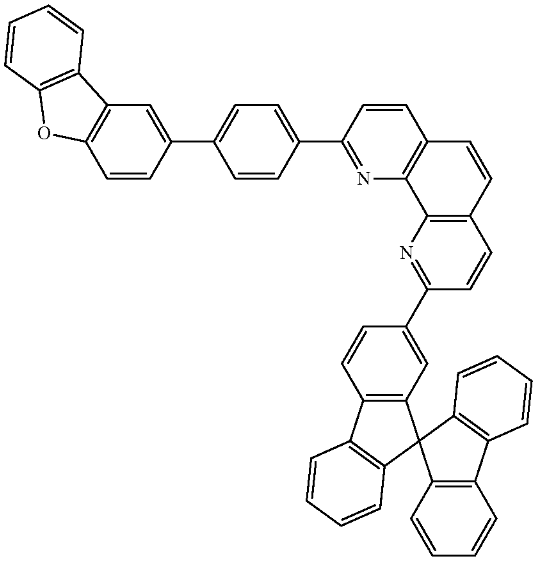
ET46
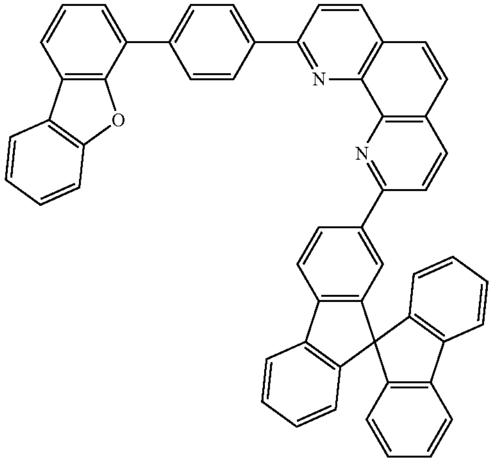
ET47
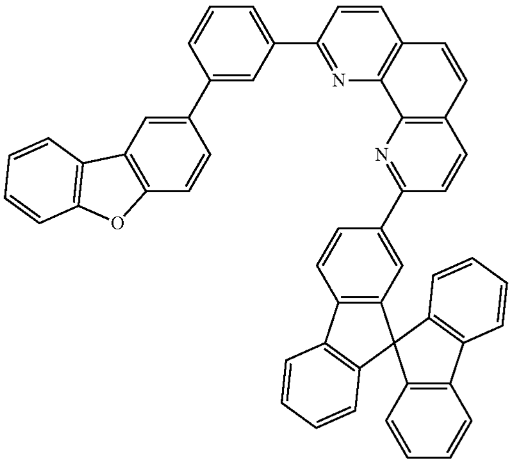
ET48
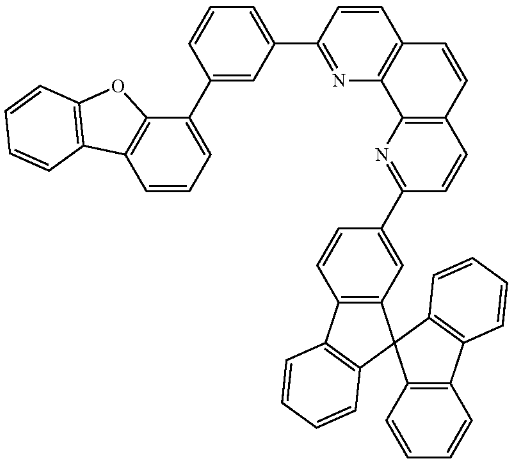

-continued
ET49
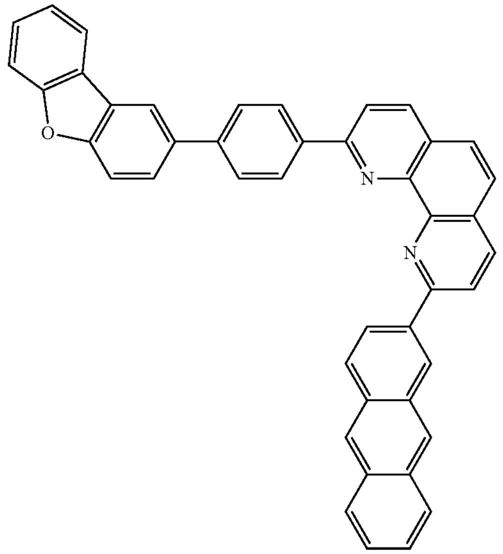
ET50
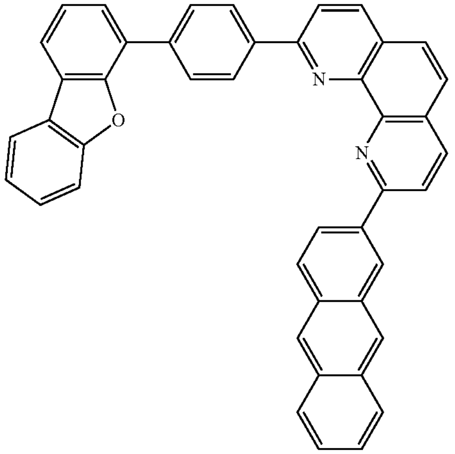
ET51
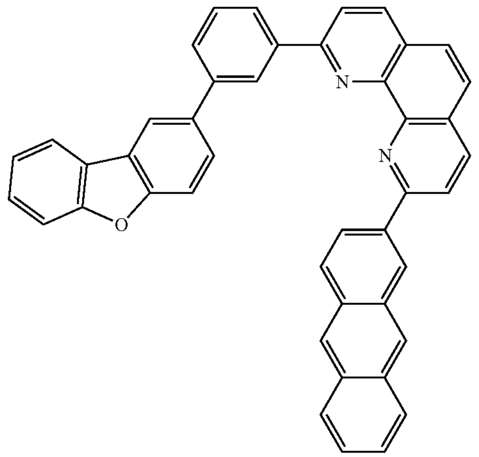
ET52
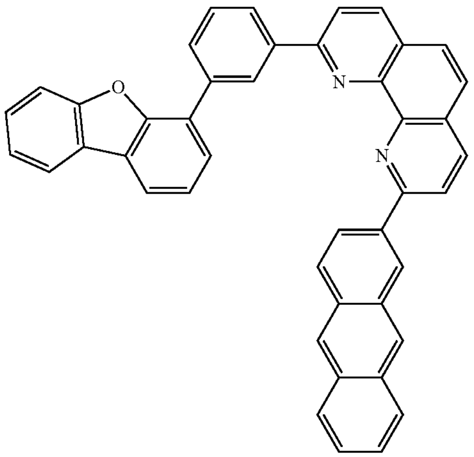
ET53
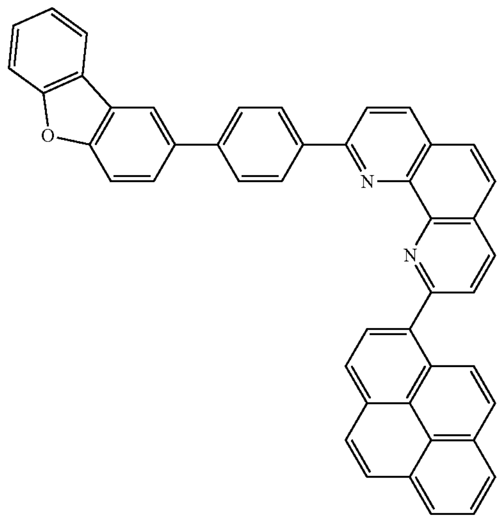
ET54
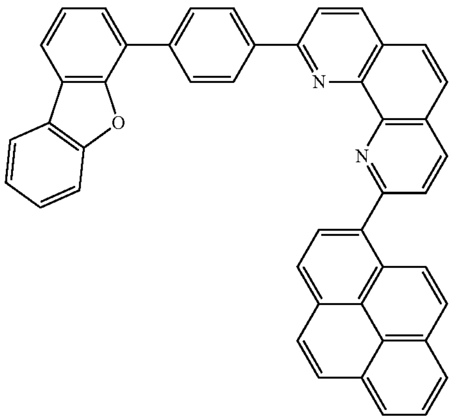

-continued
ET55
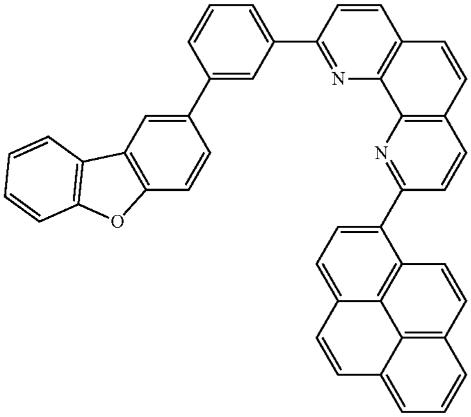
ET56
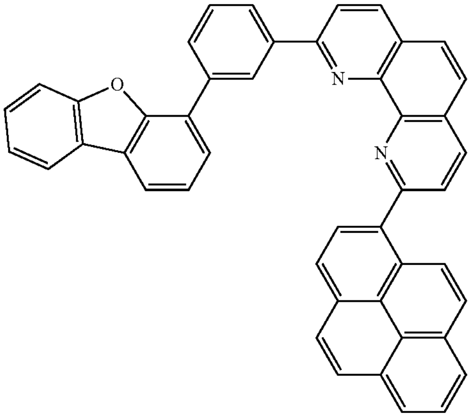
ET57
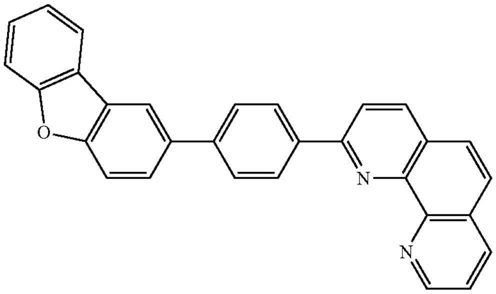
ET58
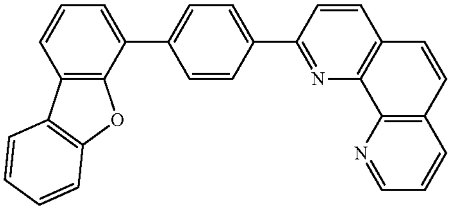
ET59
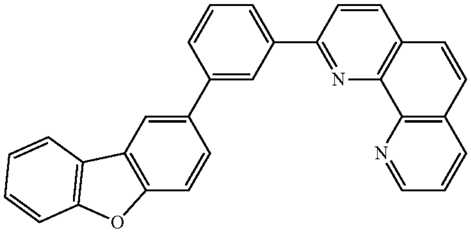
ET60
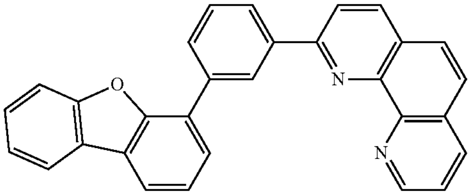
ET61
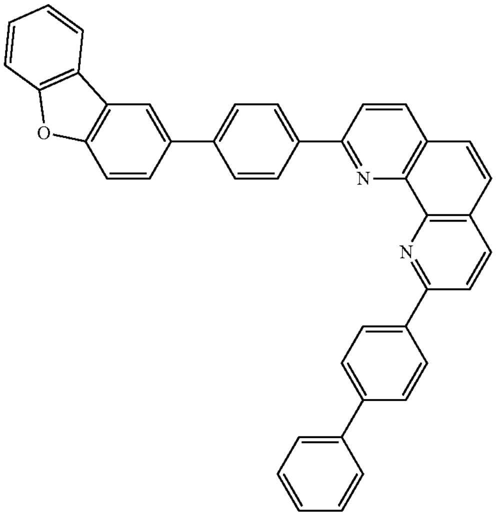
ET62
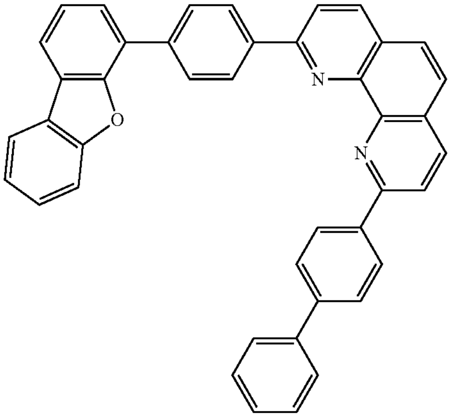

-continued
ET63
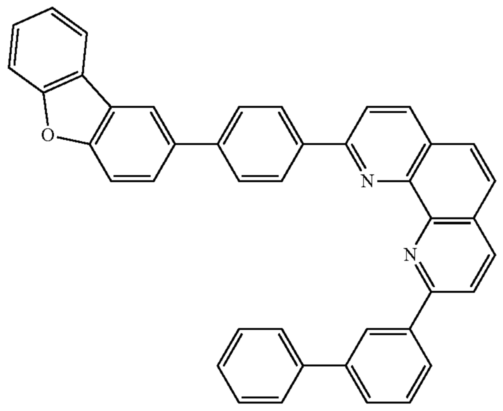
ET64
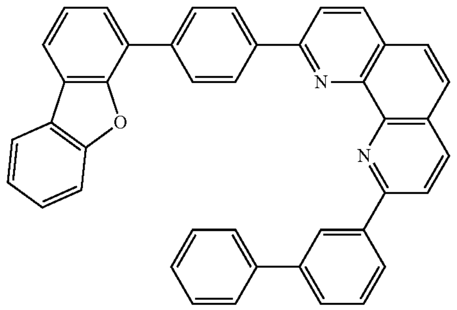
ET65
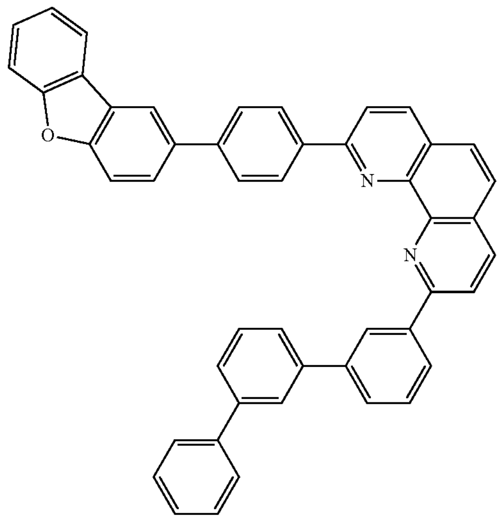
ET66
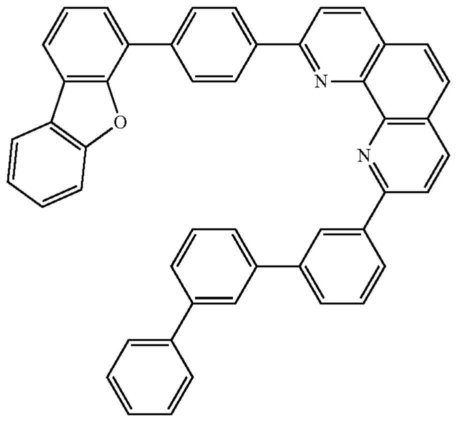
ET67
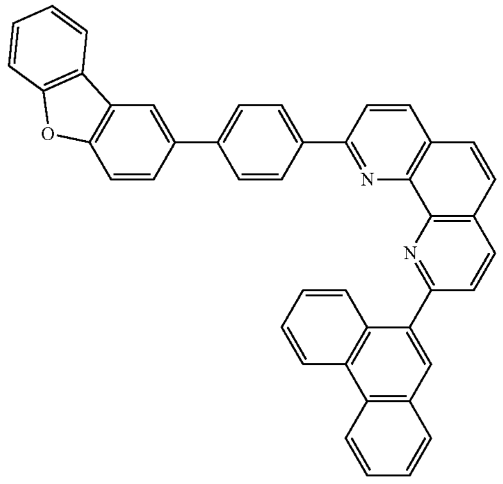
ET68
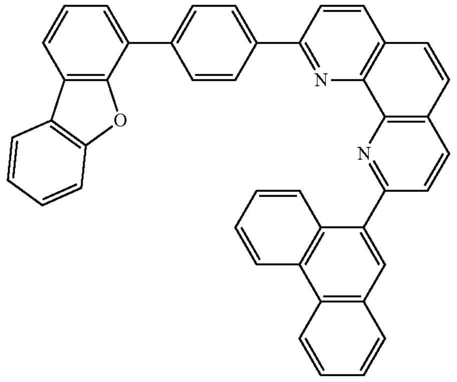

-continued
ET69
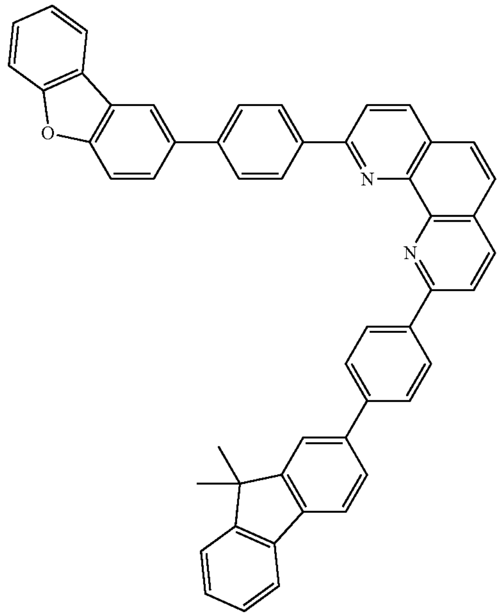
ET70
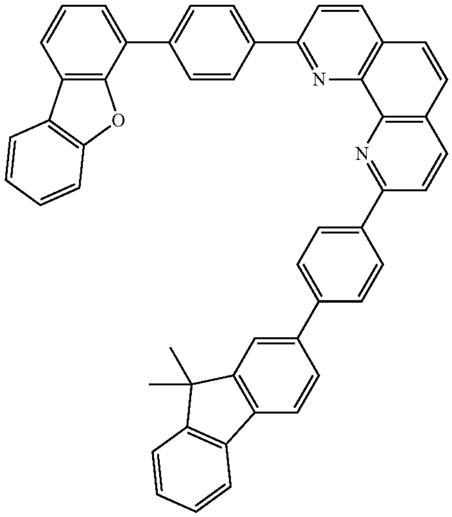
ET71
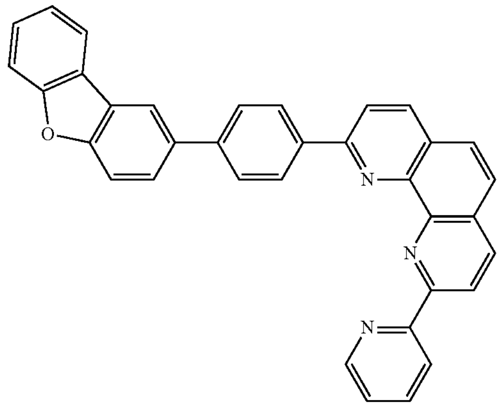
ET72
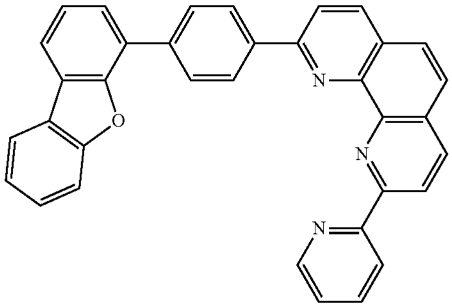
ET73
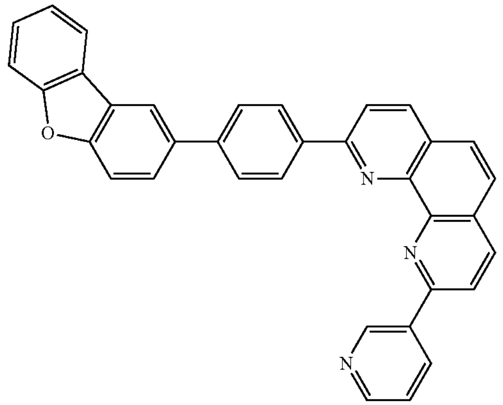
ET74
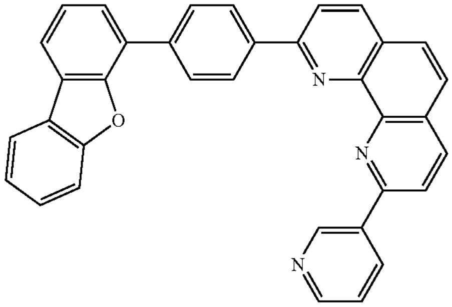

-continued
ET75
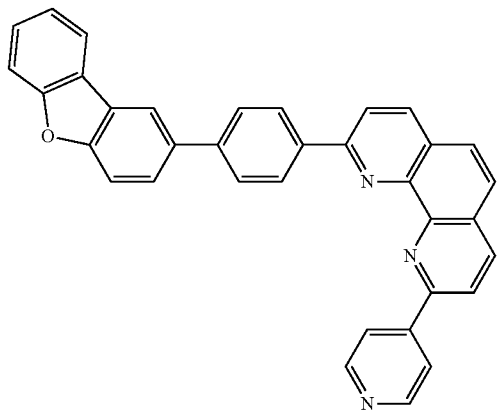
ET76
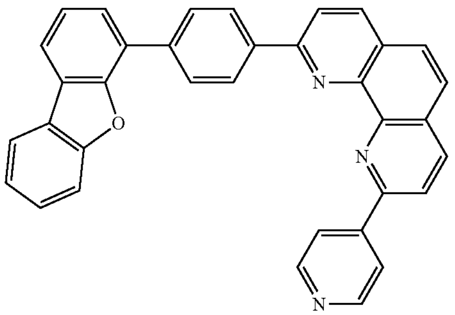
ET77
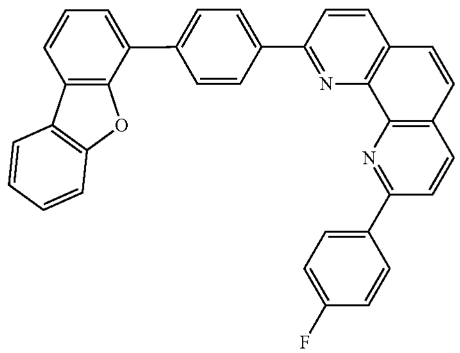
ET78
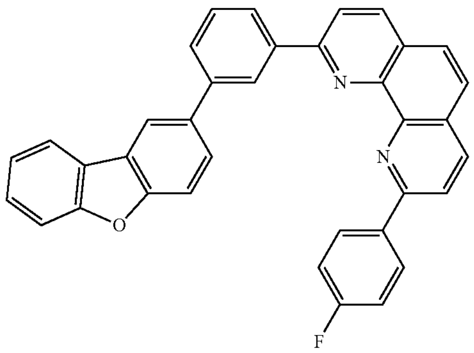
ET79
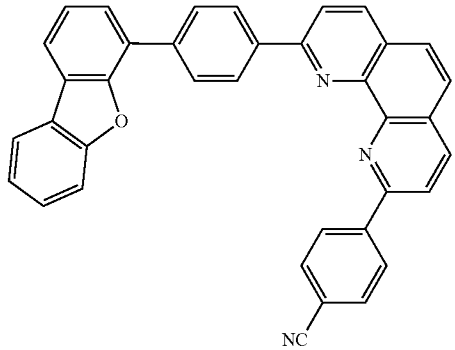
ET80
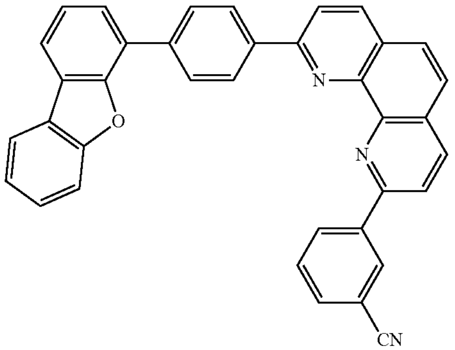

-continued
ET81
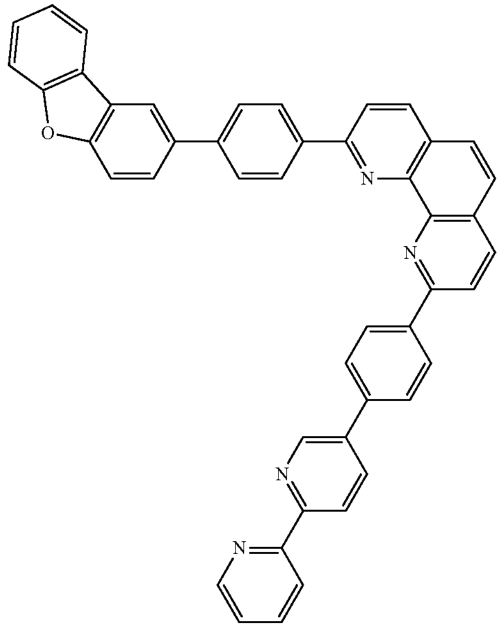
ET82
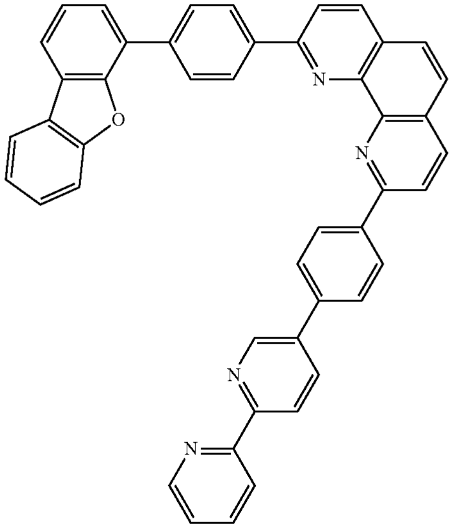
ET83
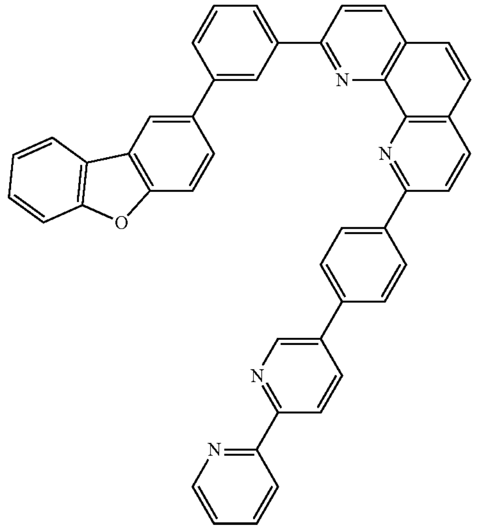
ET84
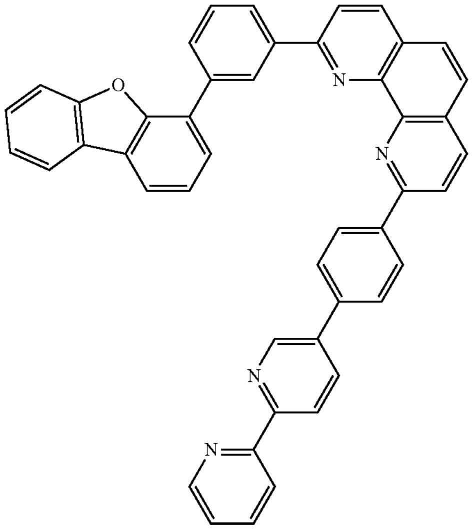

-continued
ET85
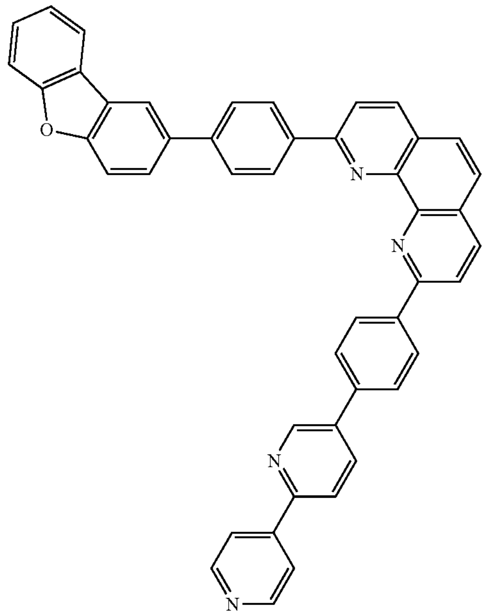
ET86
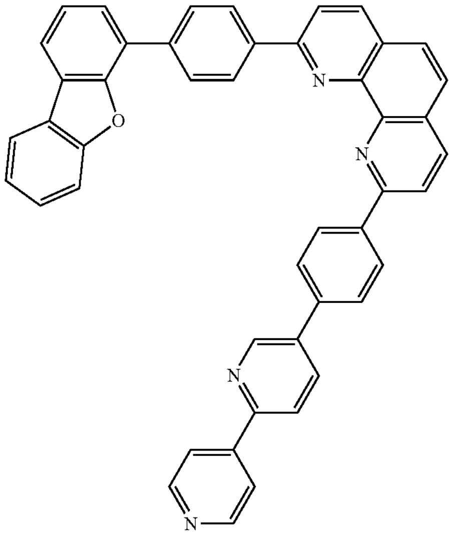
ET87
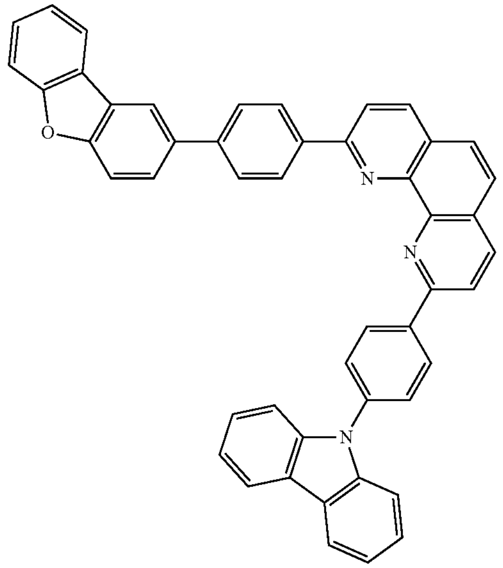
ET88
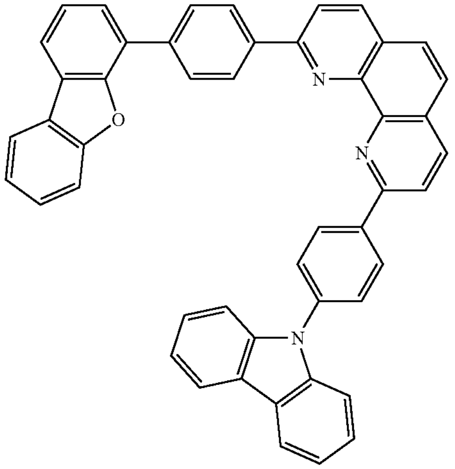
ET89
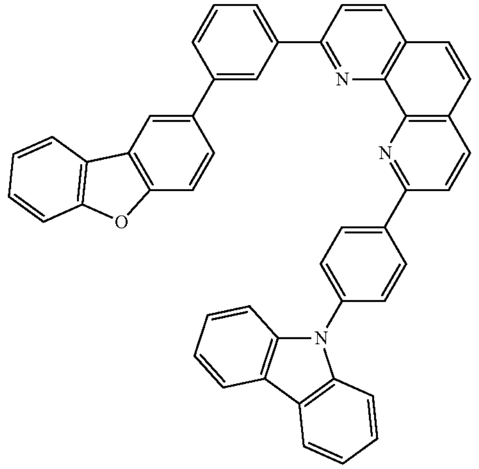
ET90
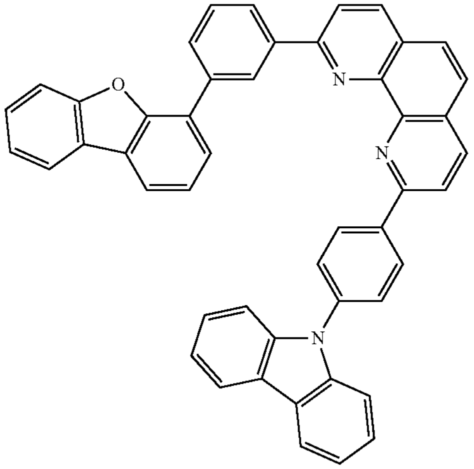

-continued
ET91
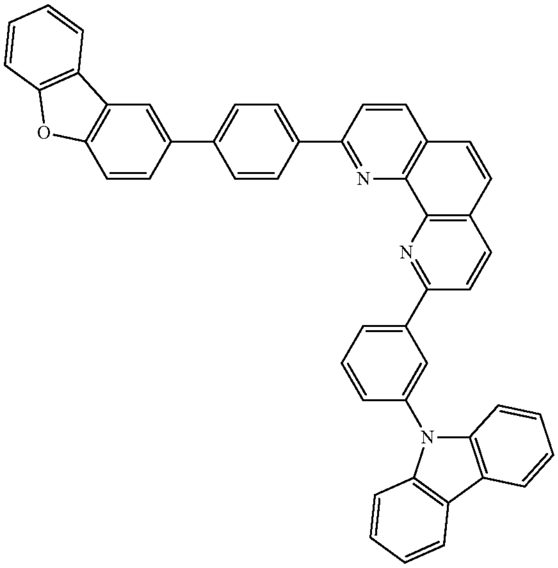
ET92
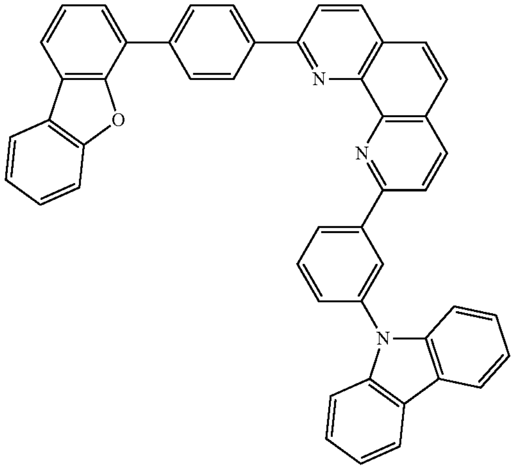
ET93
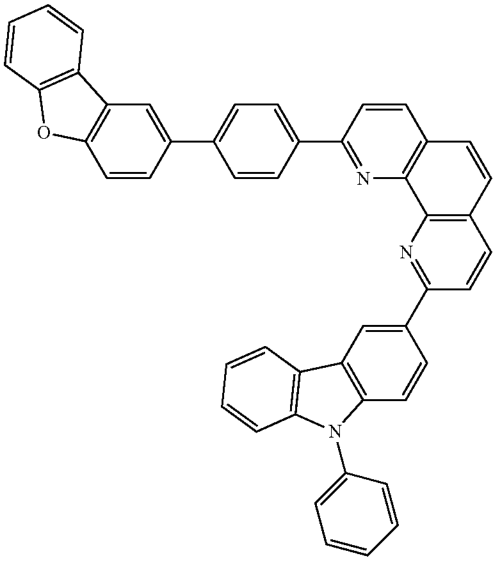
ET94
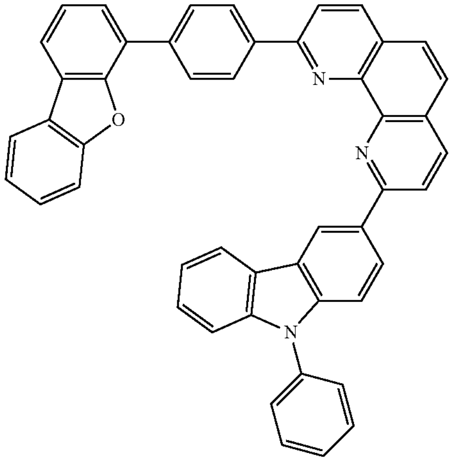

-continued
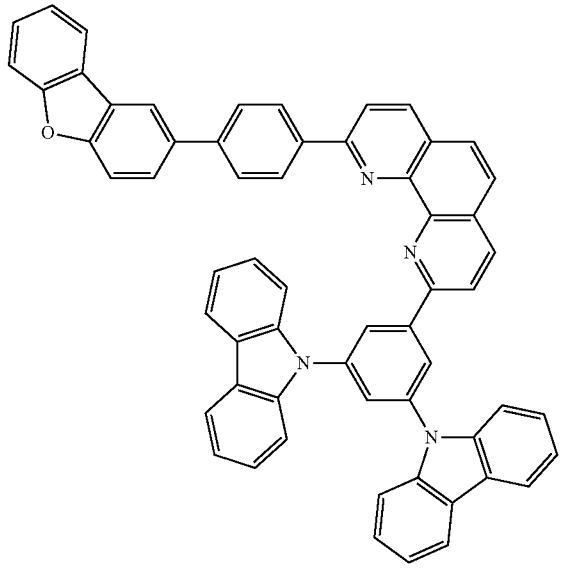
ET95
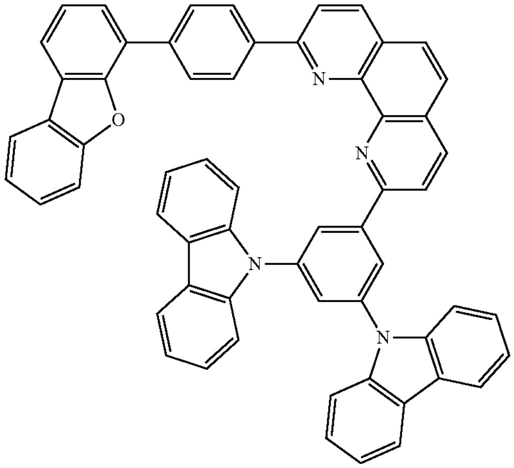
ET96
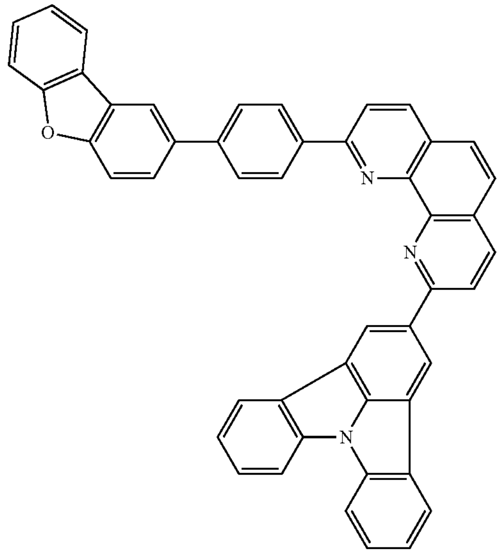
ET97
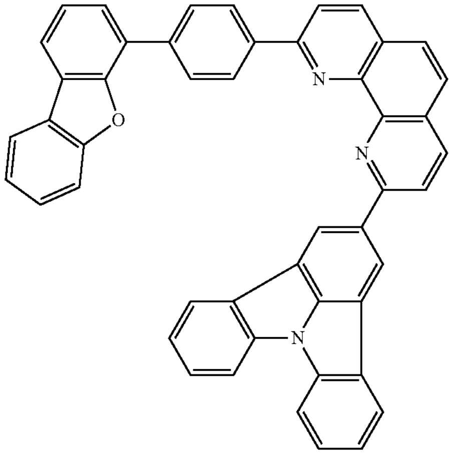
ET98

-continued
ET99
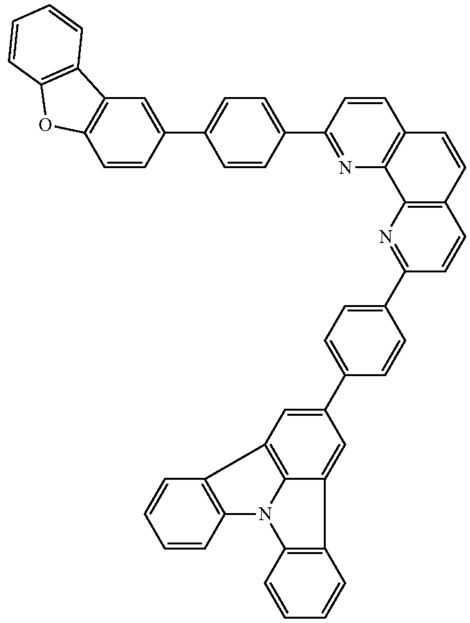
ET100
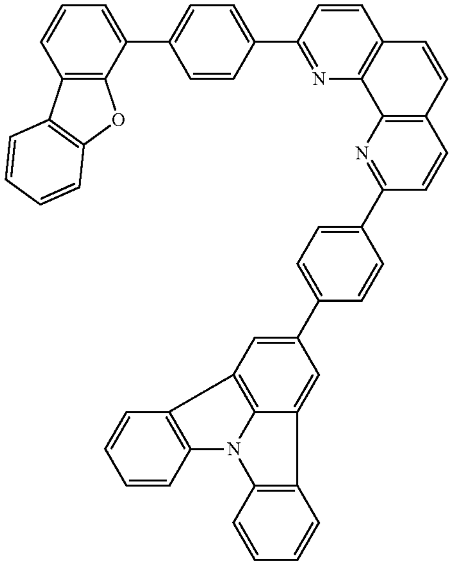
ET101
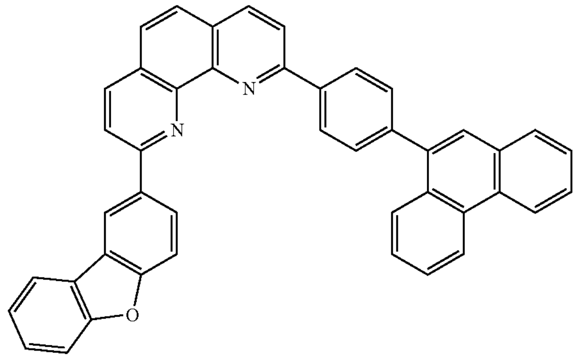
ET102
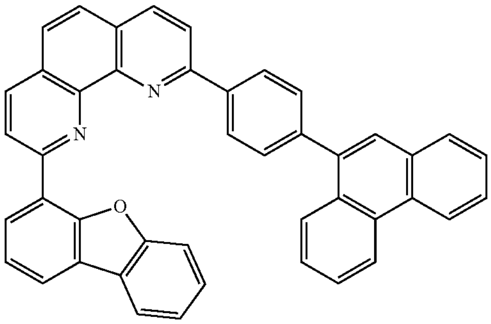
ET103
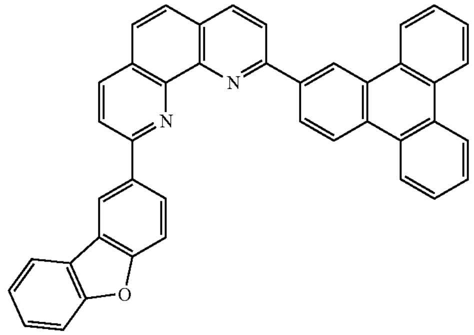
ET104
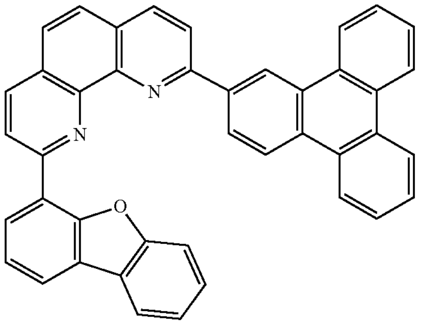

-continued
ET105
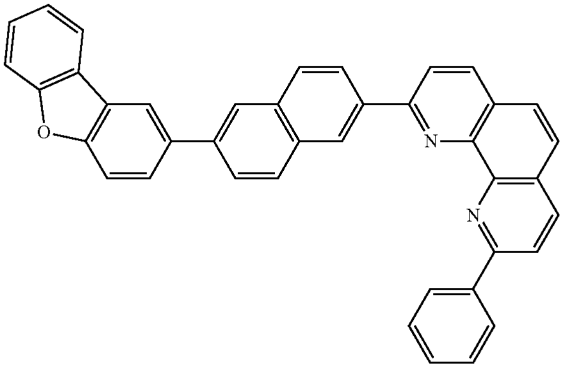
ET106
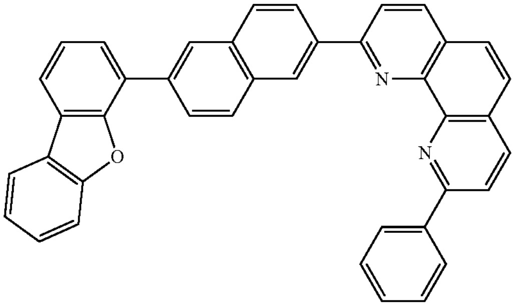
ET107
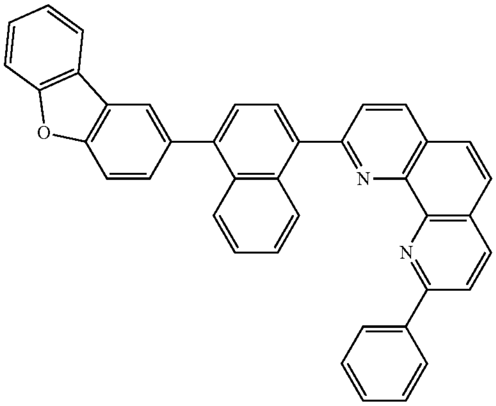
ET108
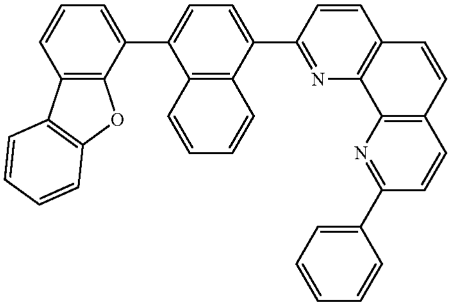
ET109
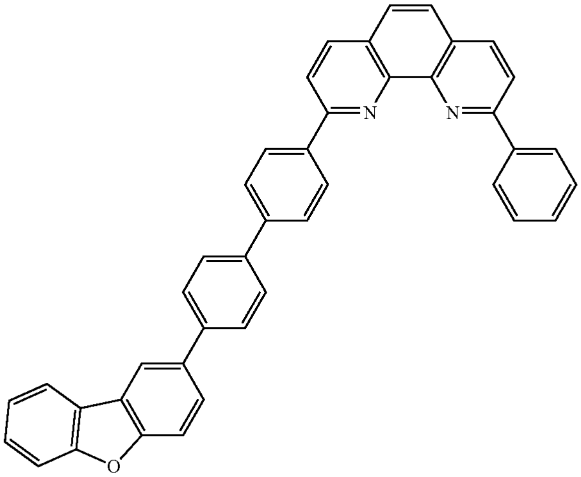
ET110
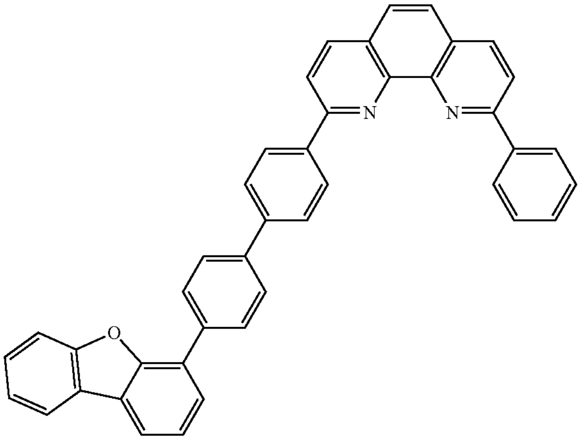

-continued
ET111
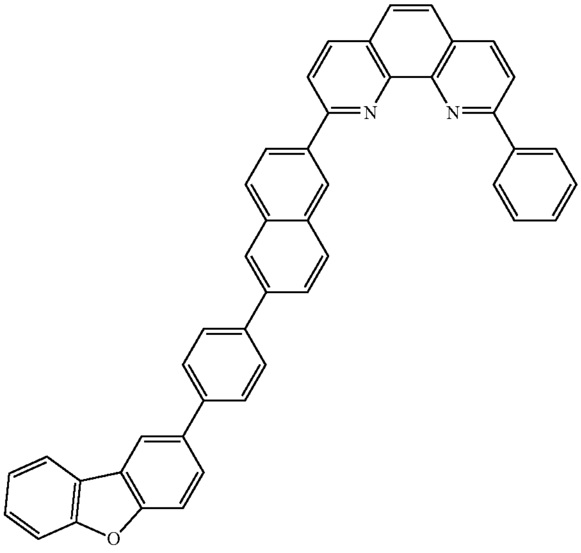
ET112
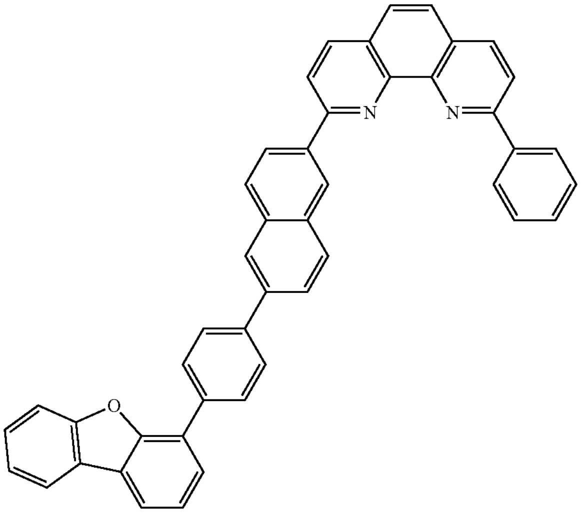
ET113
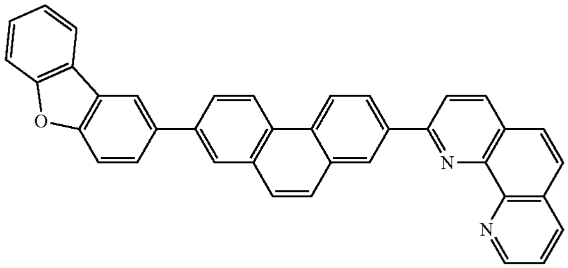
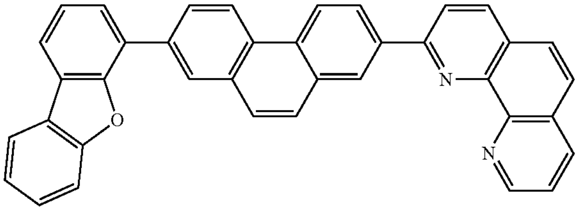
ET115
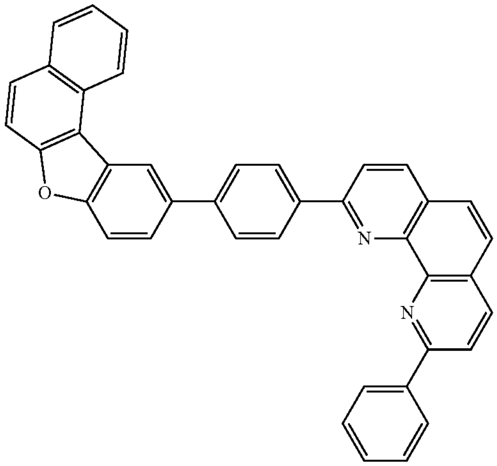
ET116
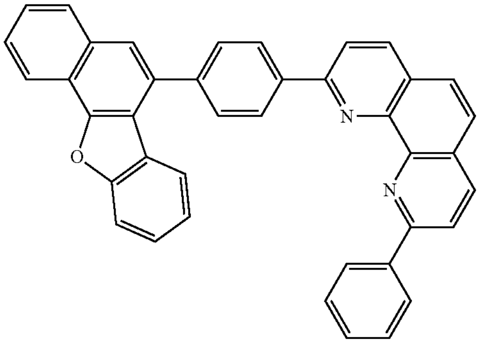

-continued
ET117
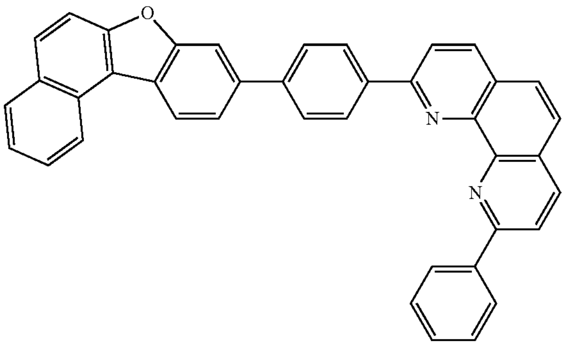
ET118
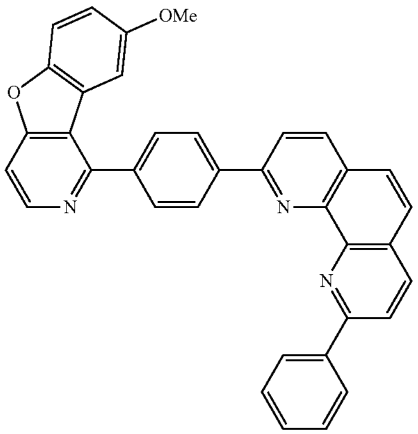
ET119
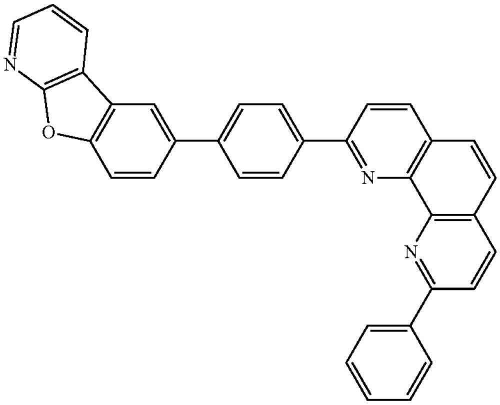
ET120
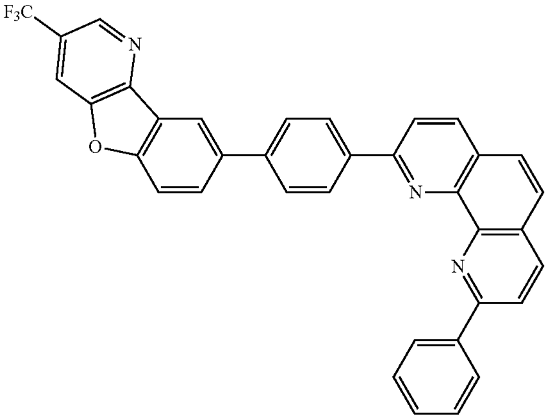
ET121
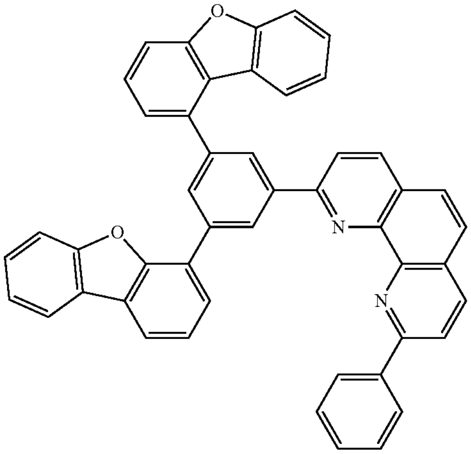
ET122
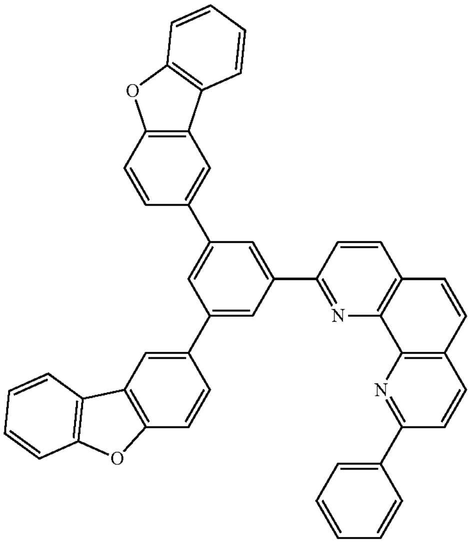

-continued
ET123
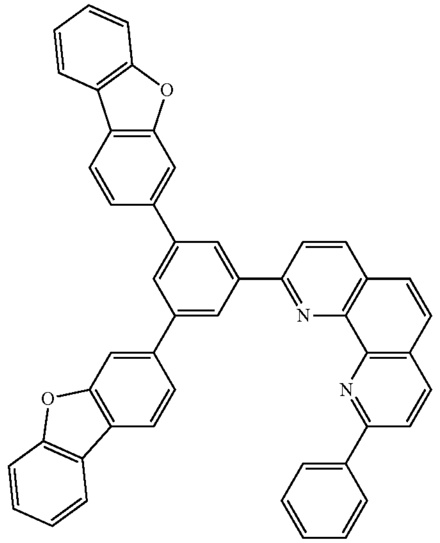
ET124
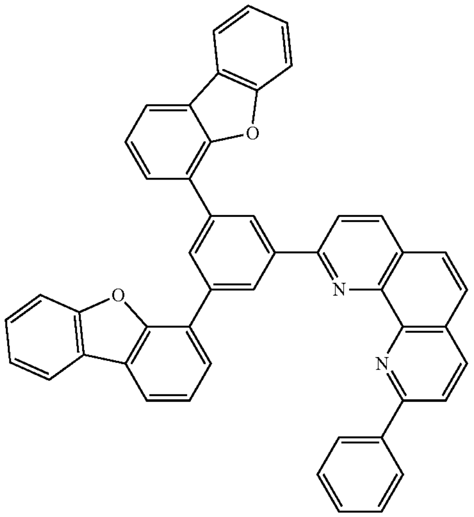
ET125
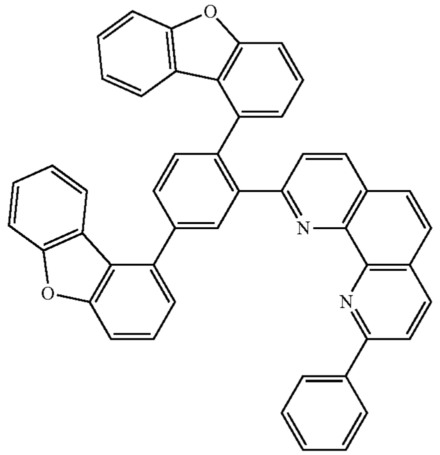
ET126
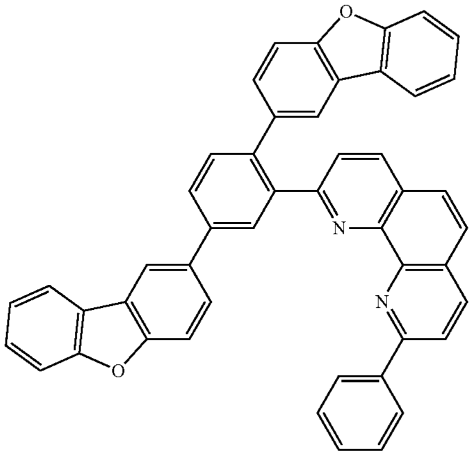
ET127
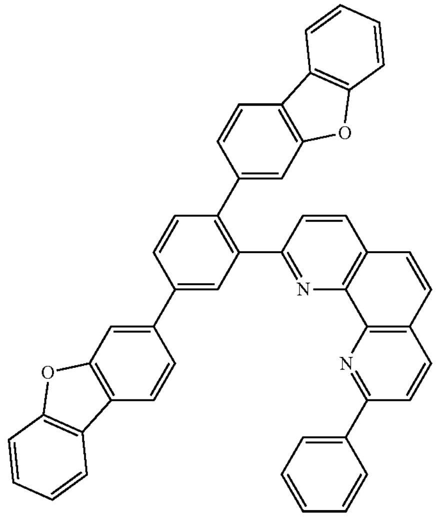
ET128
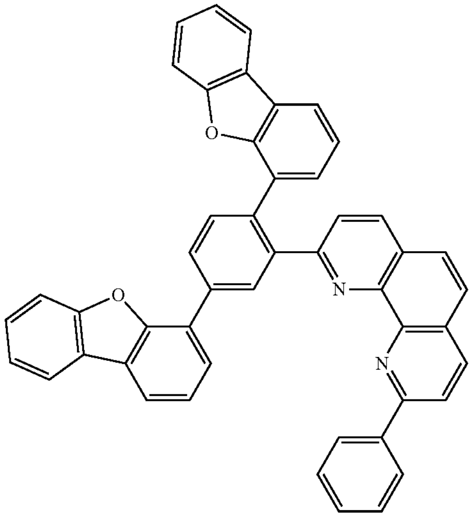

-continued
ET129
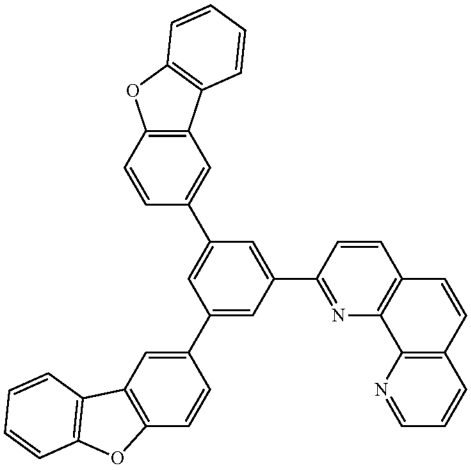
ET130
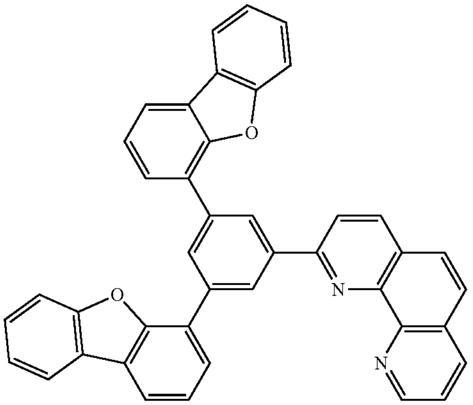
ET131
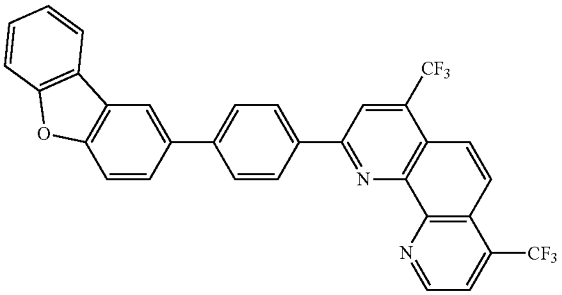
ET132
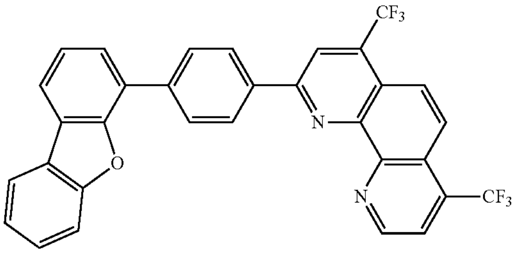
ET133
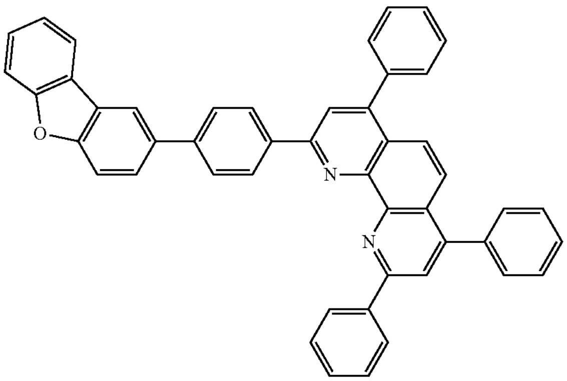
ET134
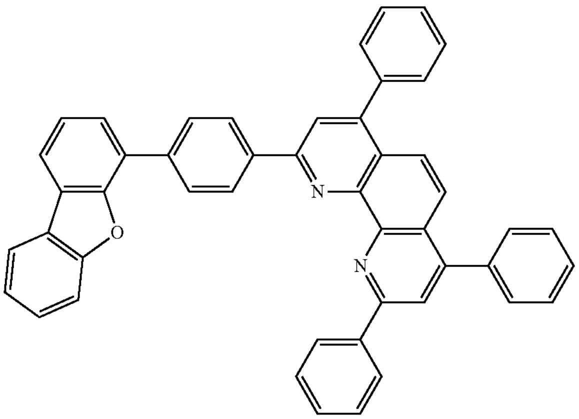

-continued
ET135
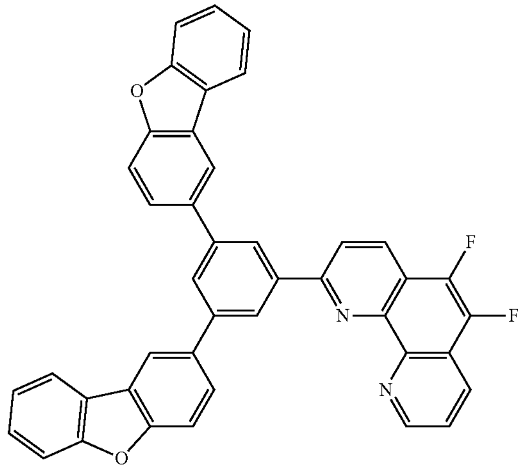
ET136
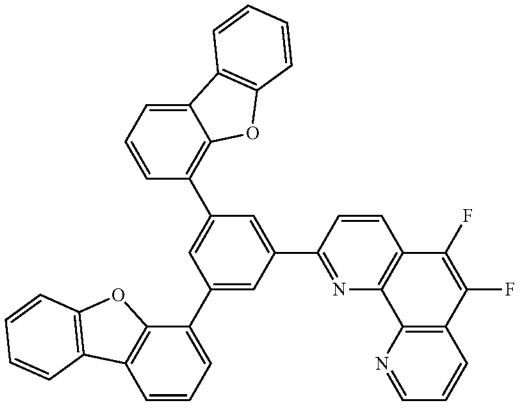
ET137
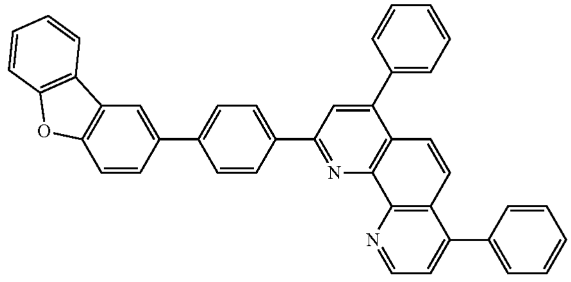
ET138
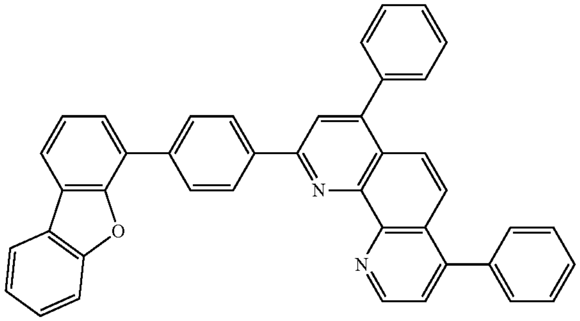
ET139
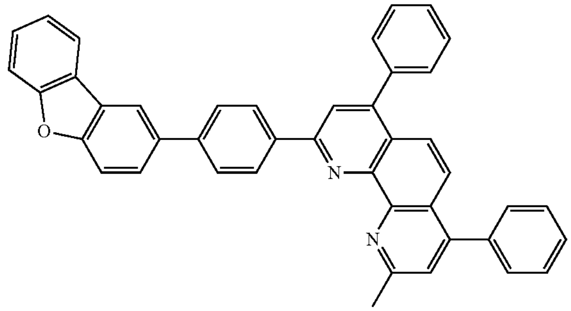
ET140
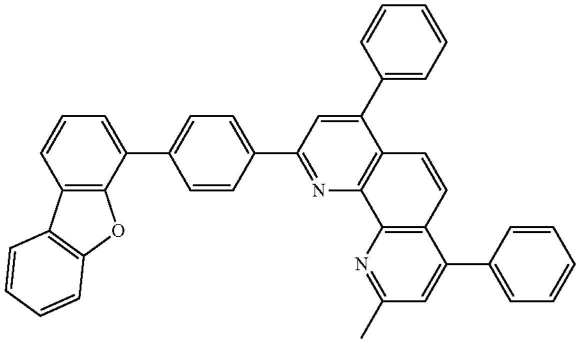
ET141
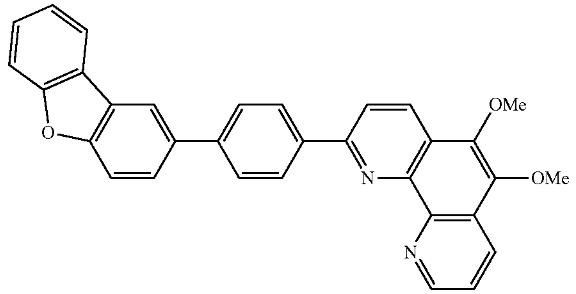
ET142
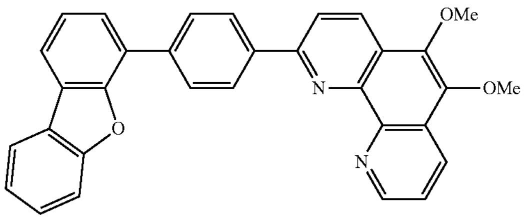

-continued
ET143
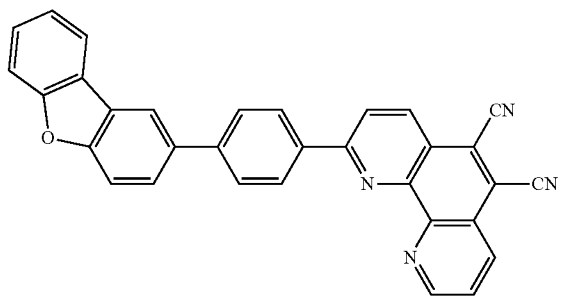
ET144
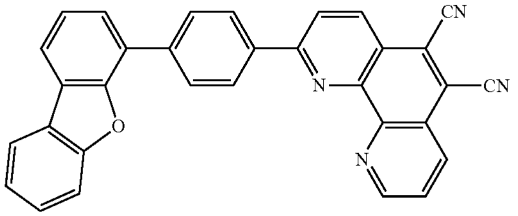
ET145
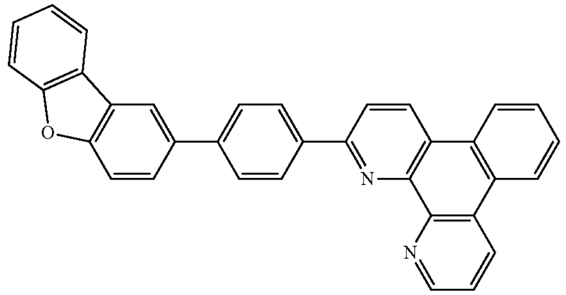
ET146
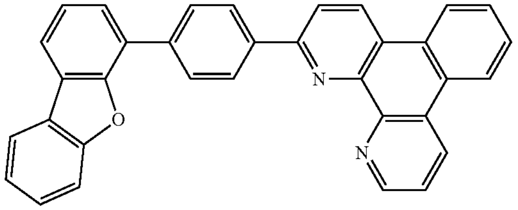
ET147
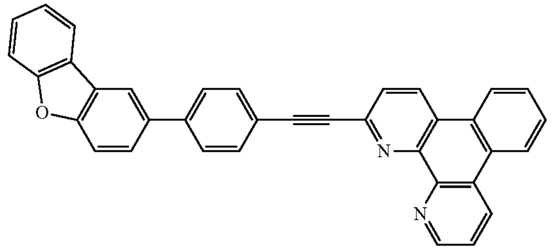
ET148
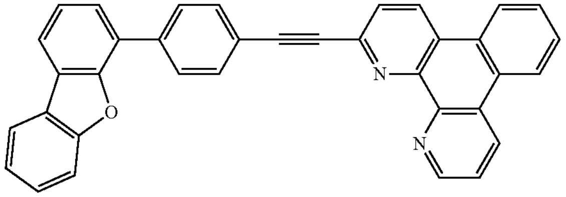
ET149
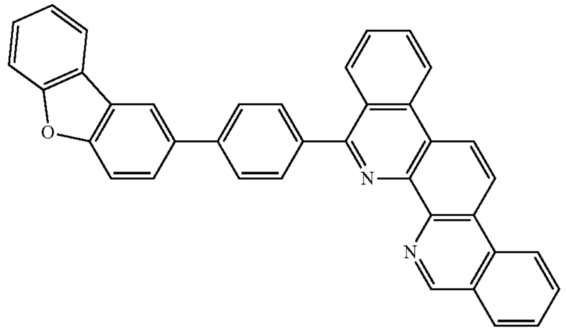
ET150
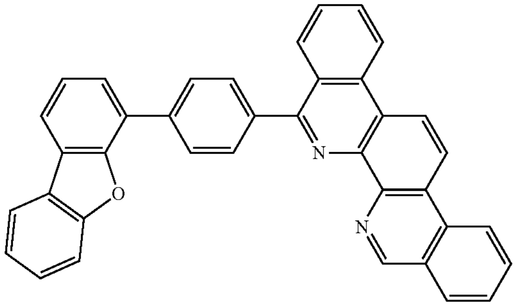
ET151
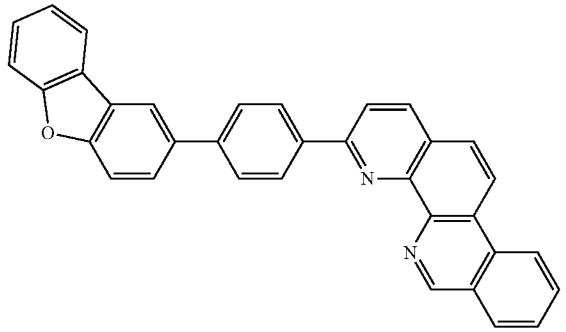
ET152
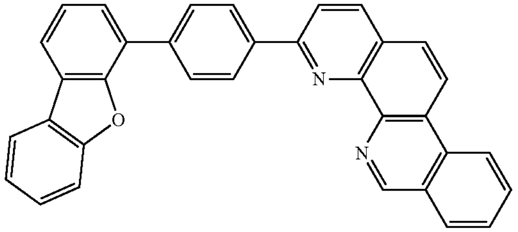

-continued
ET153
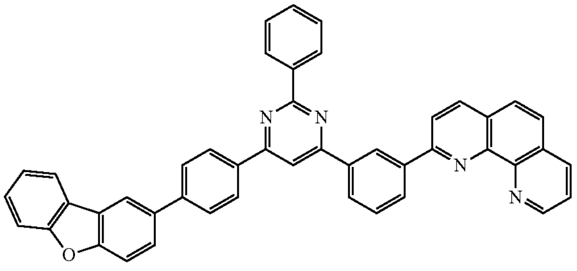
ET154
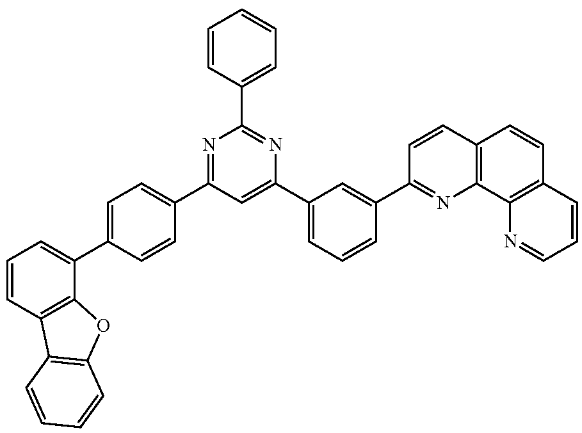
ET155
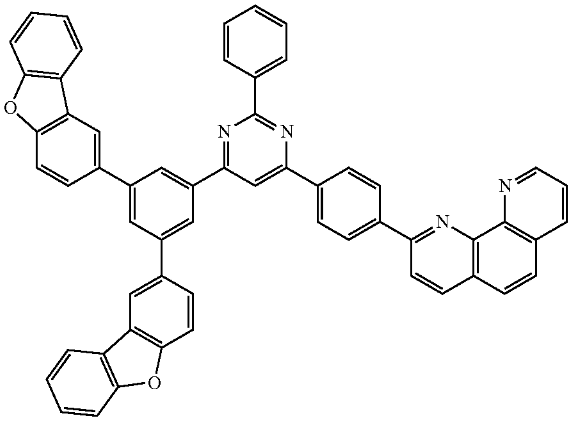
ET156
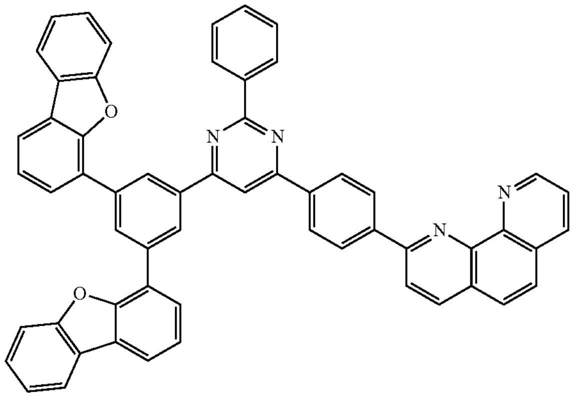
ET160
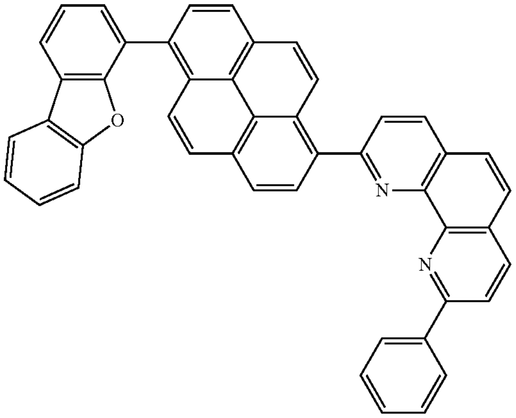
ET161
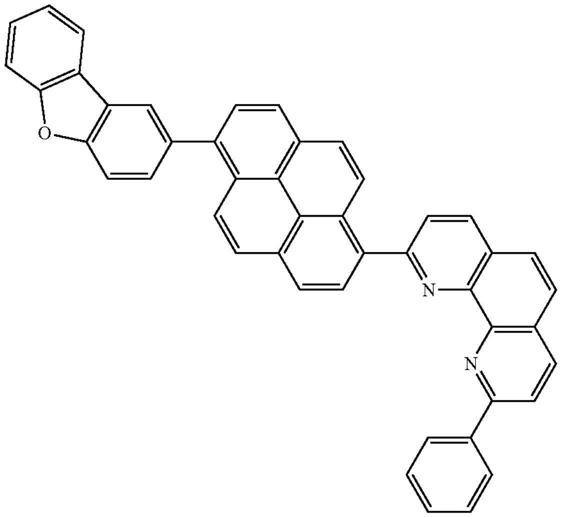

-continued
ET162
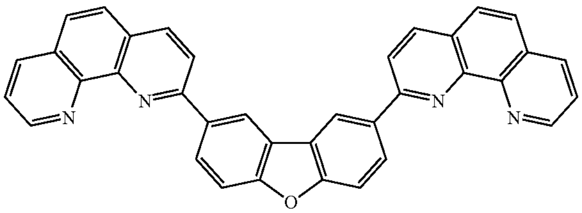
ET163
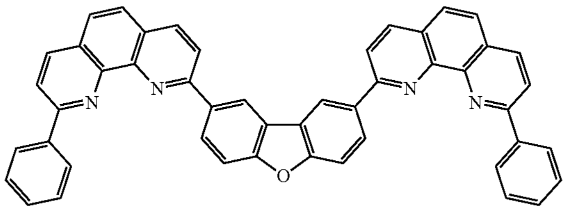
ET164
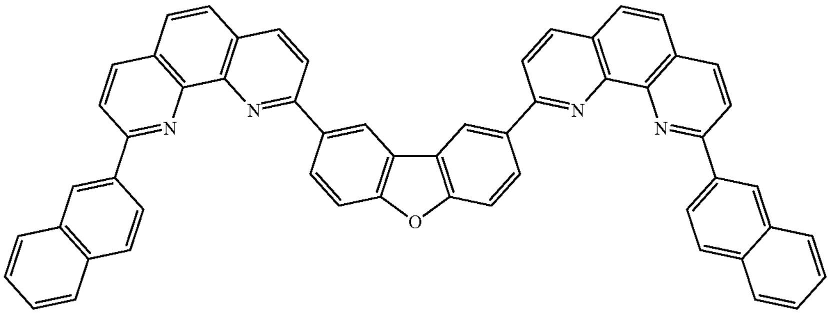
ET165
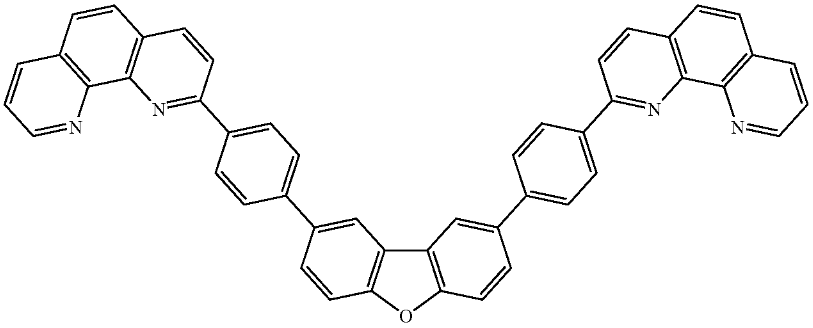
ET166
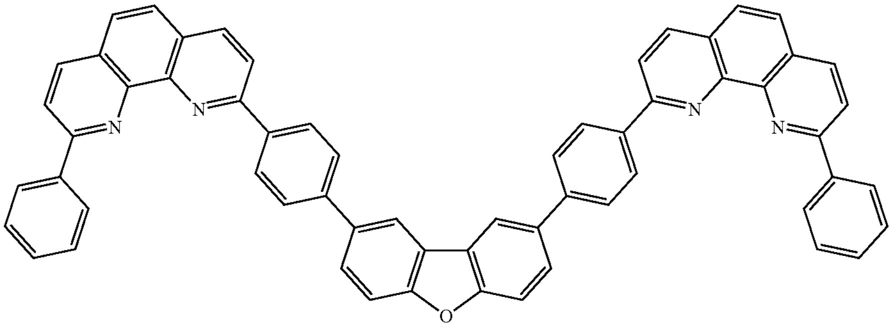
ET167
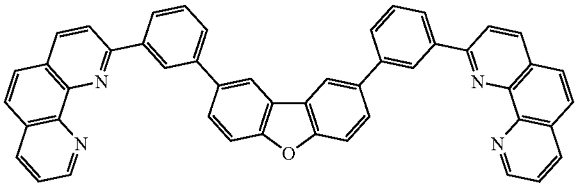
ET168
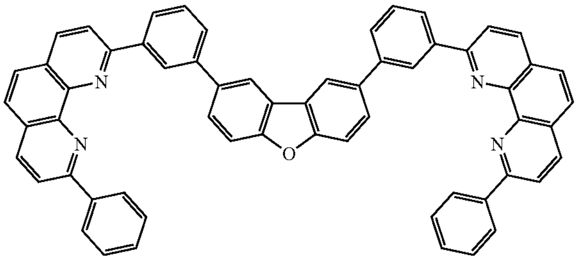

-continued
ET169
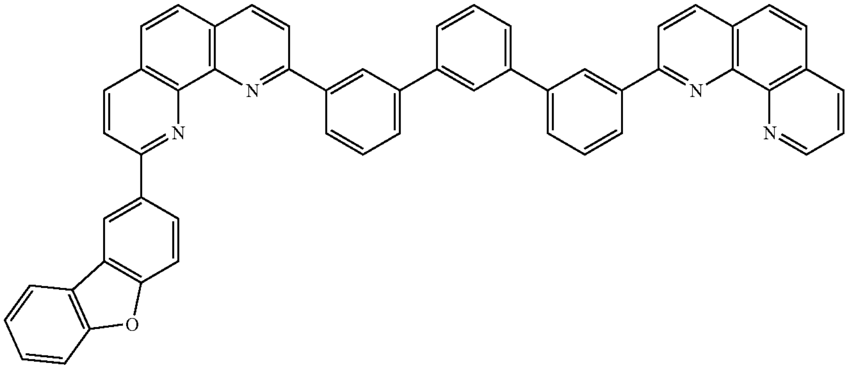
ET170
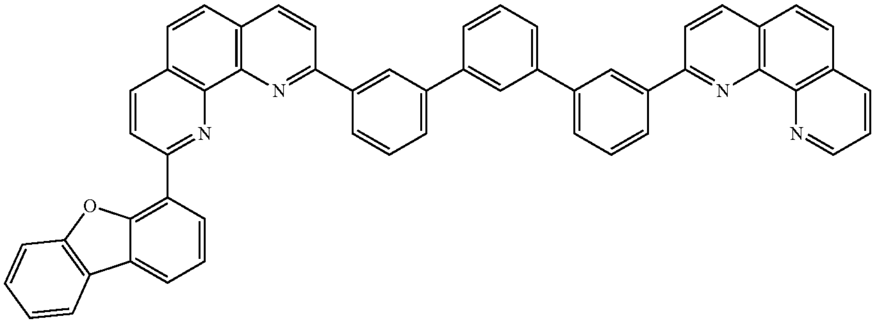
ET171
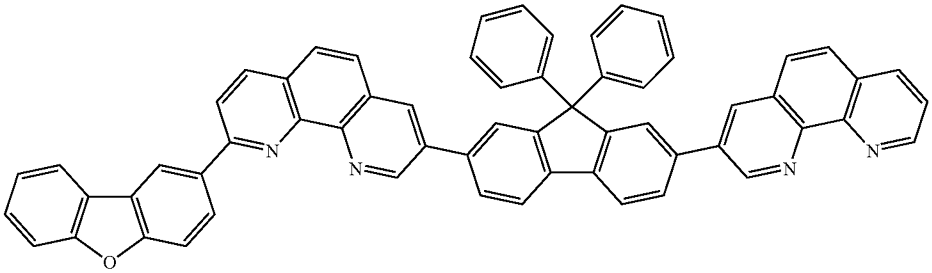
ET172
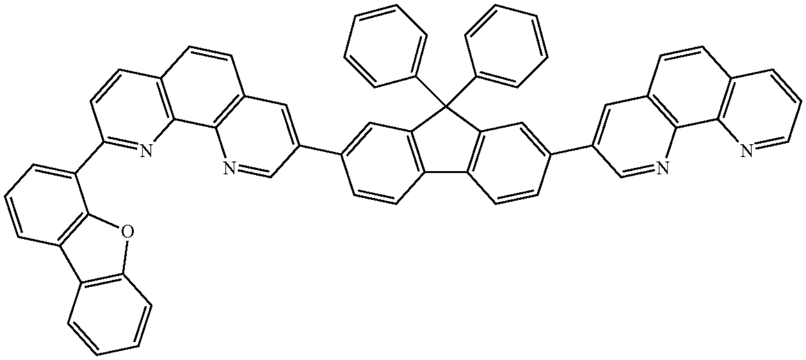

-continued
ET1001
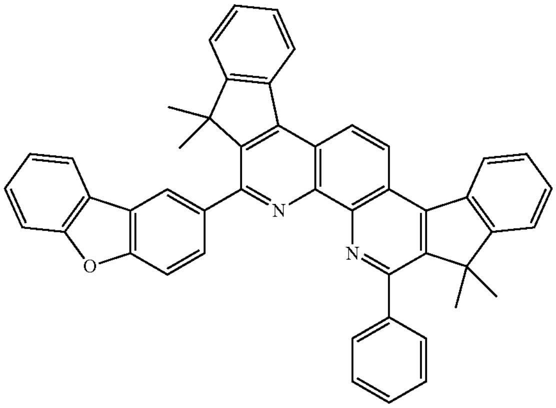
ET1002
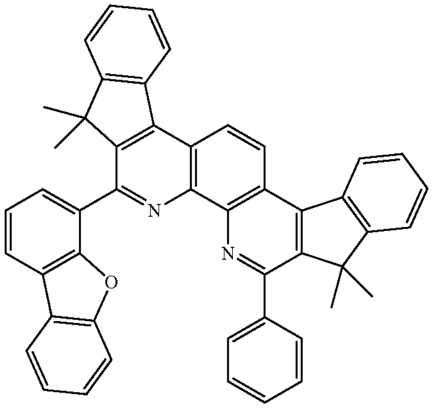
ET1003
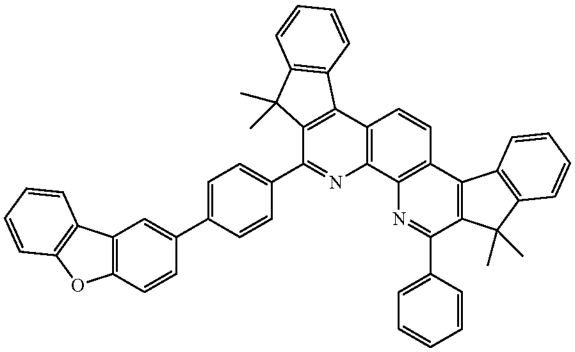
ET1004
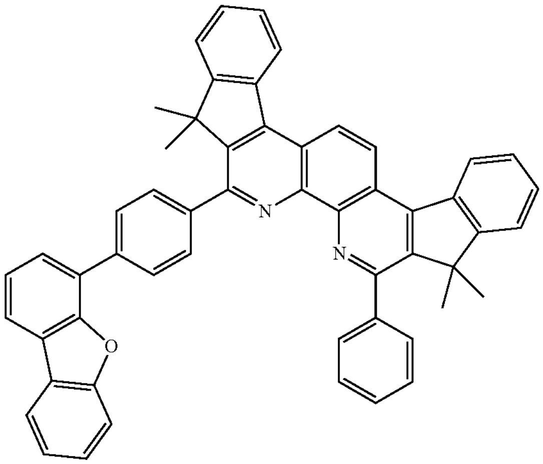
ET1005
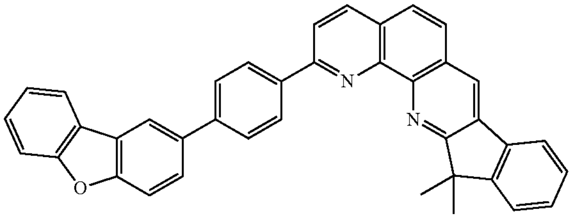
ET1006
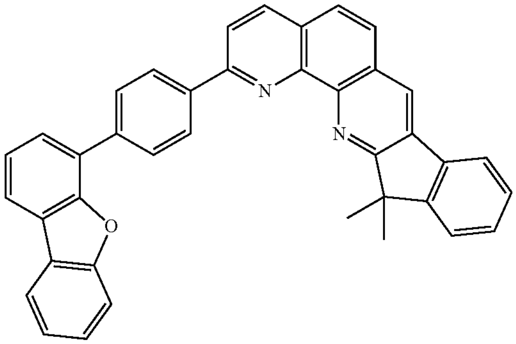

-continued
ET173
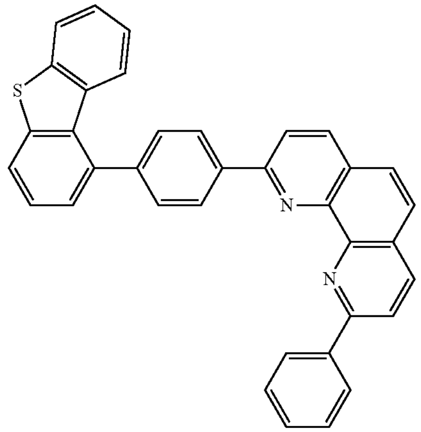
ET174
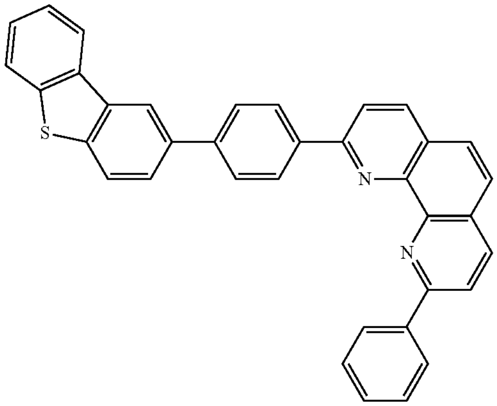
T175
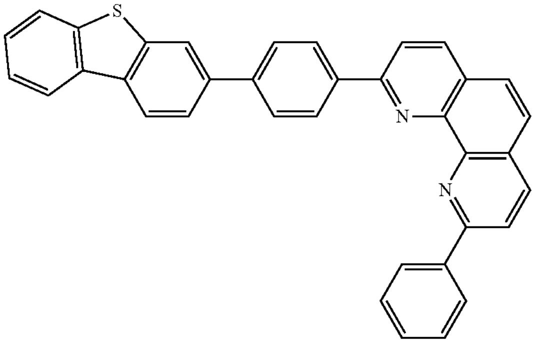
ET176
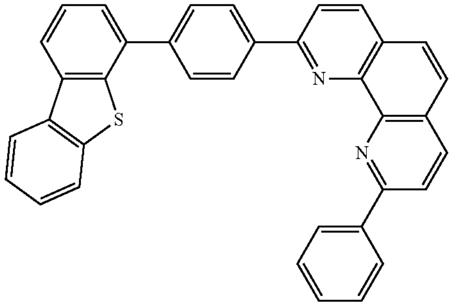
ET177
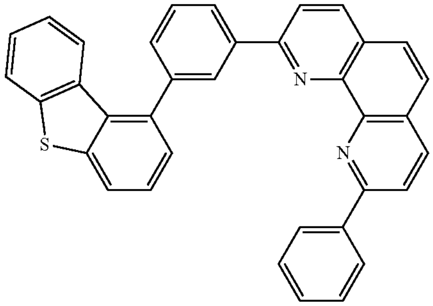
ET178
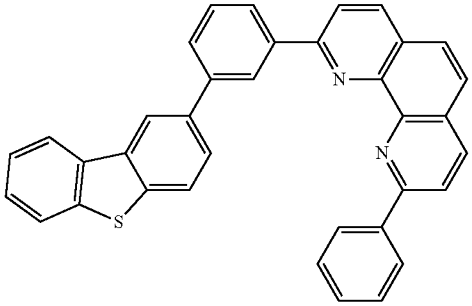
ET179
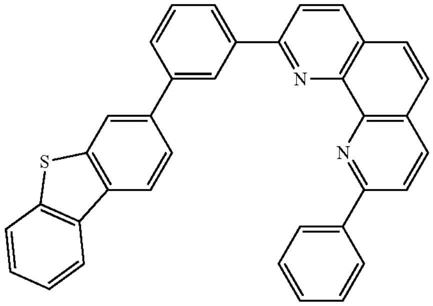
ET180
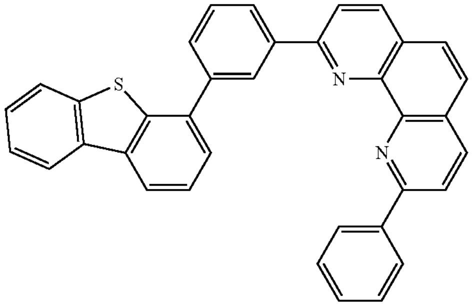

-continued
ET181
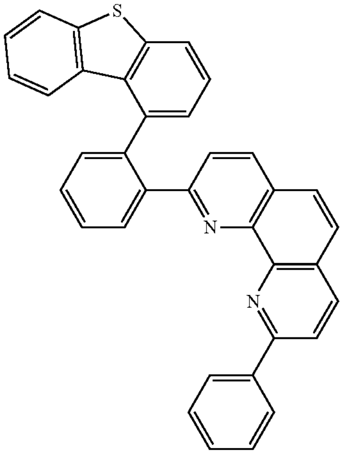
ET182
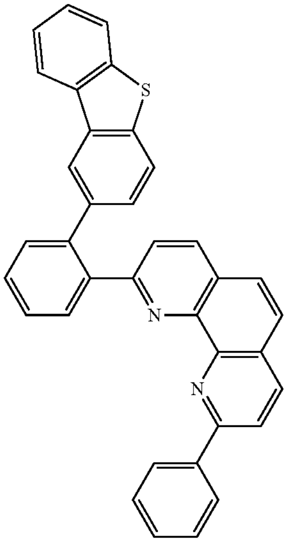
ET183
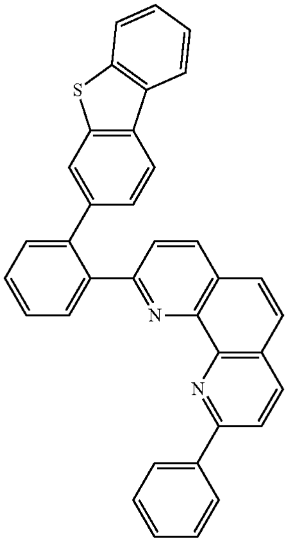
ET184
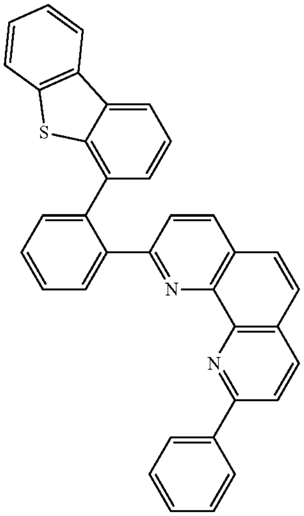
ET185
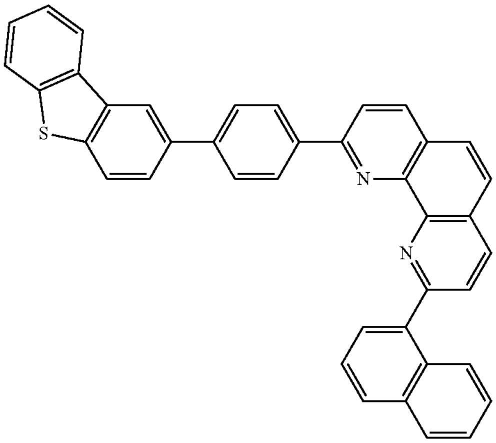
ET186
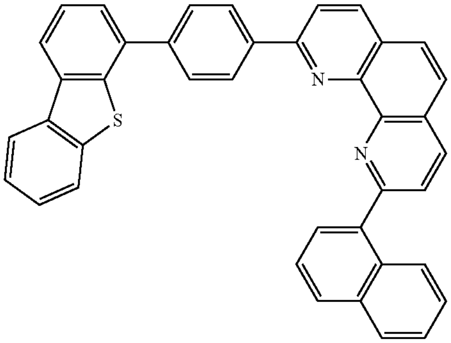

-continued
ET187
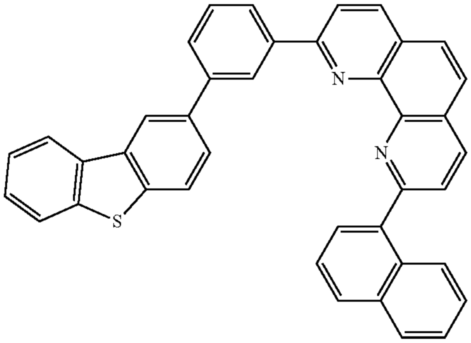
ET188
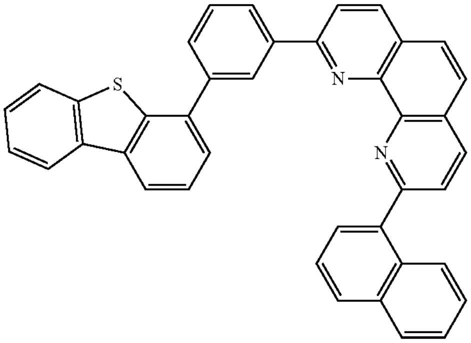
ET189
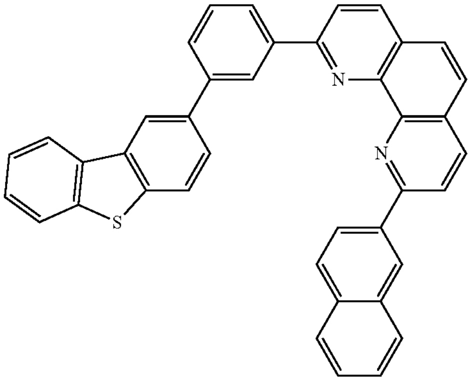
ET190
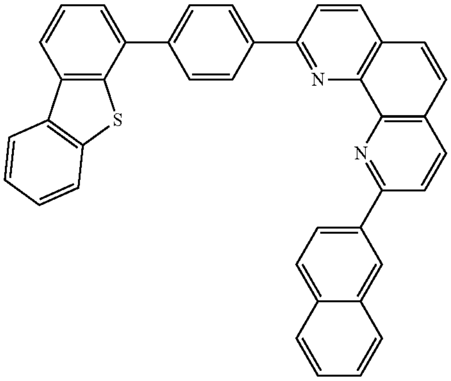
ET191
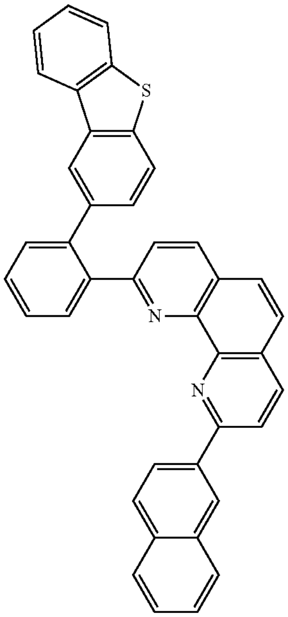
ET192
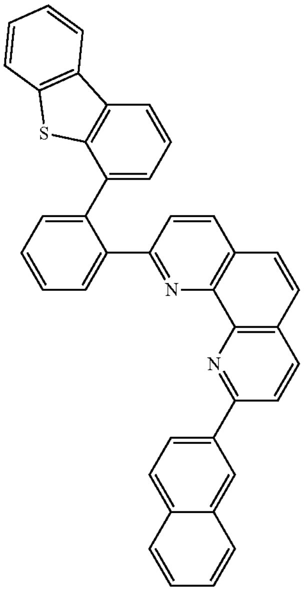

-continued
ET193
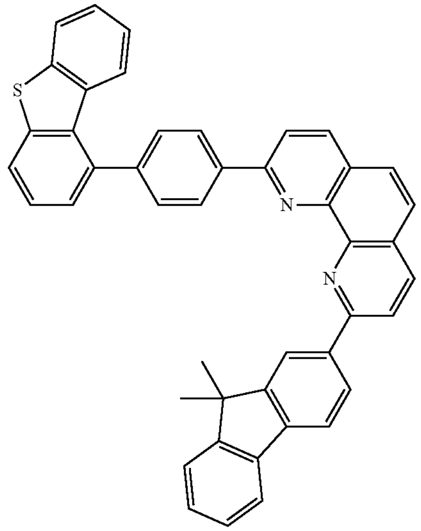
ET194
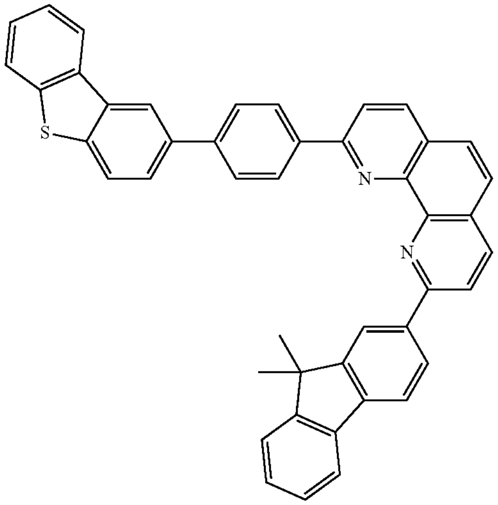
ET195
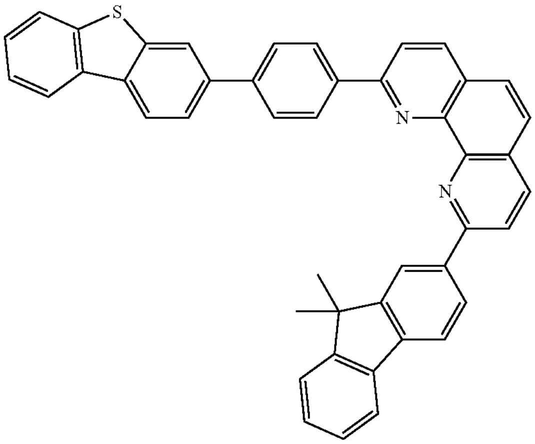
ET196
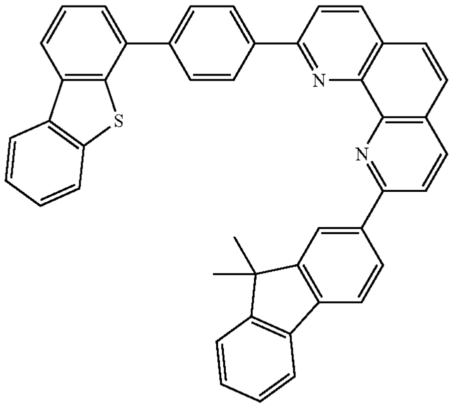
ET197
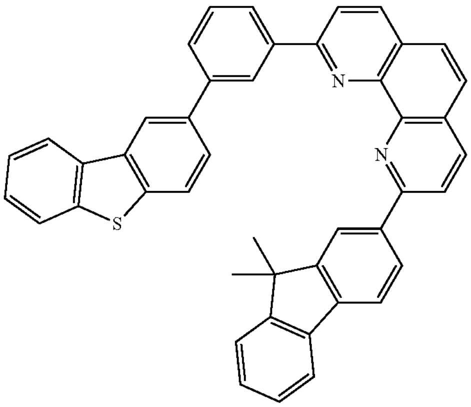
ET198
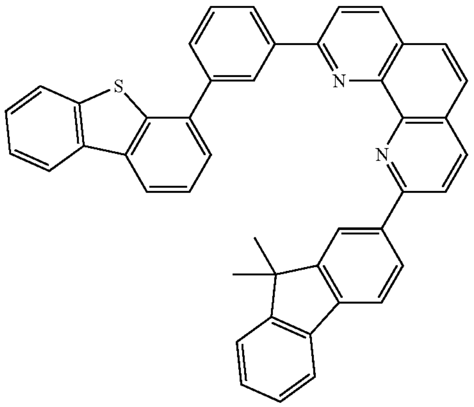

-continued
ET199
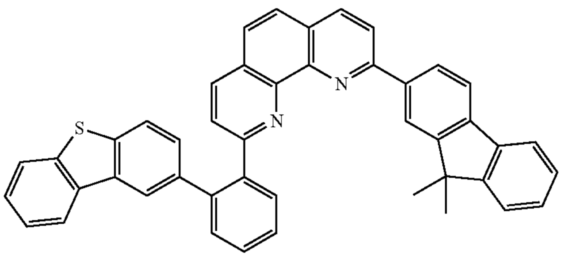
ET200
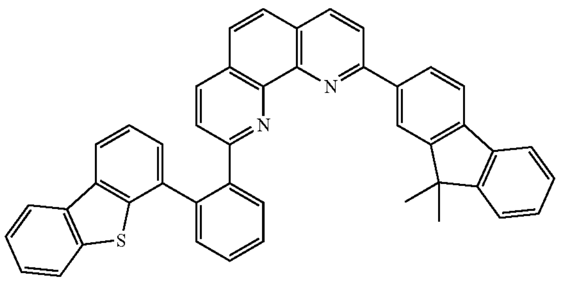
ET201
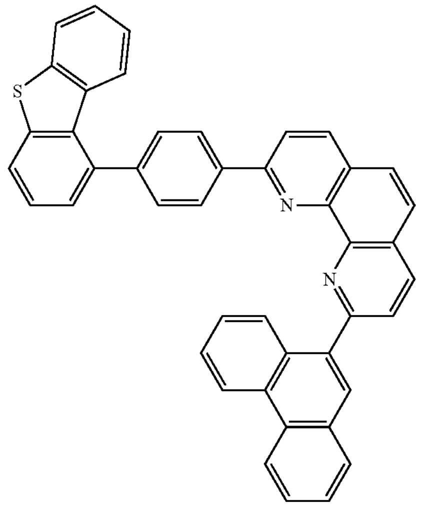
ET202
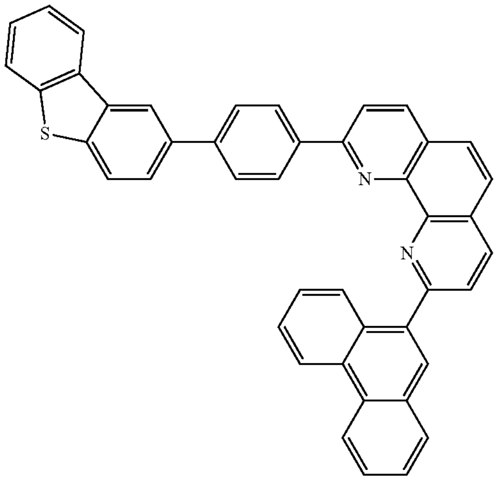
ET203
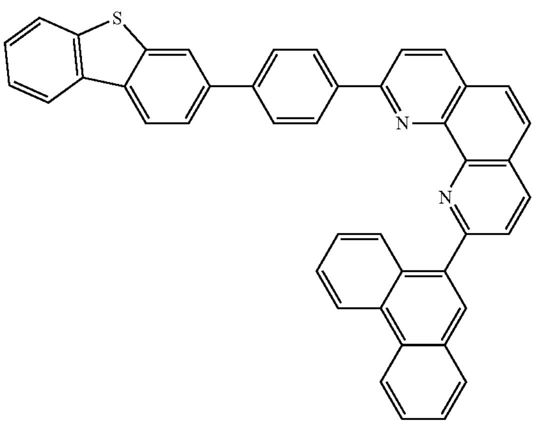
ET204
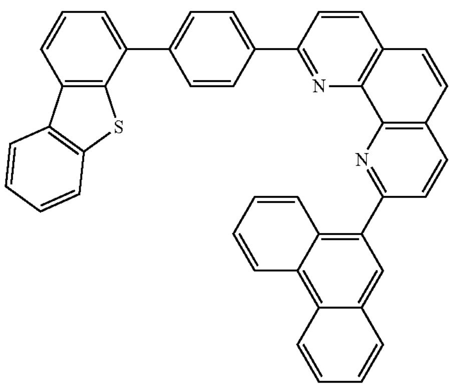
ET205
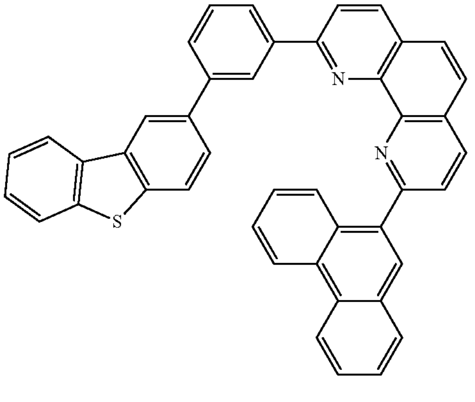
ET206
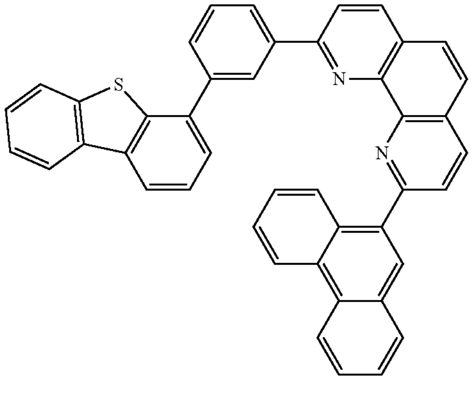

-continued
ET207
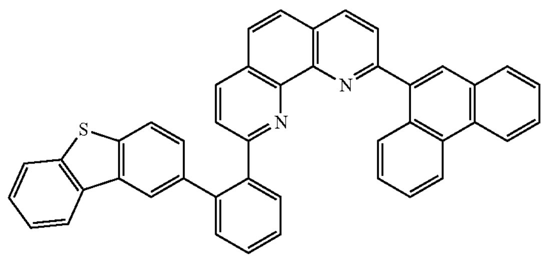
ET208
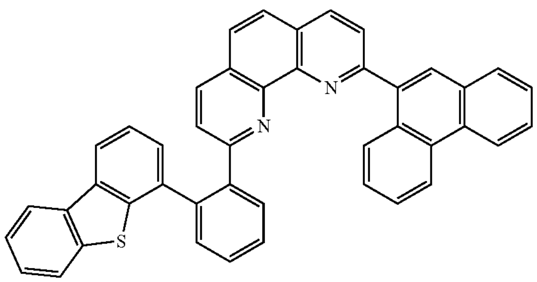
ET209
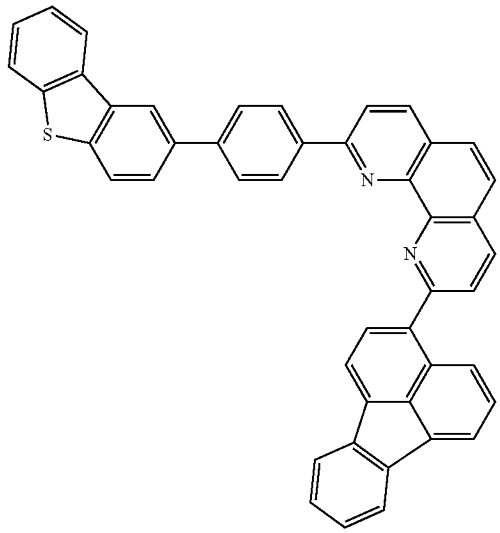
ET210
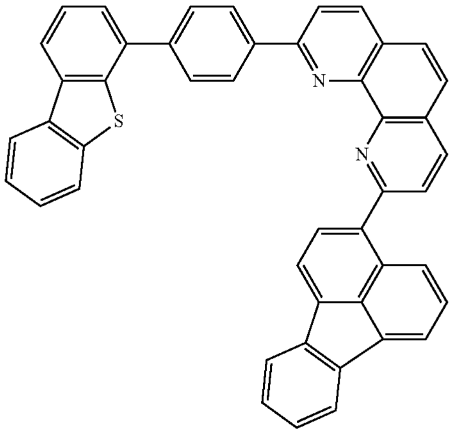
ET211
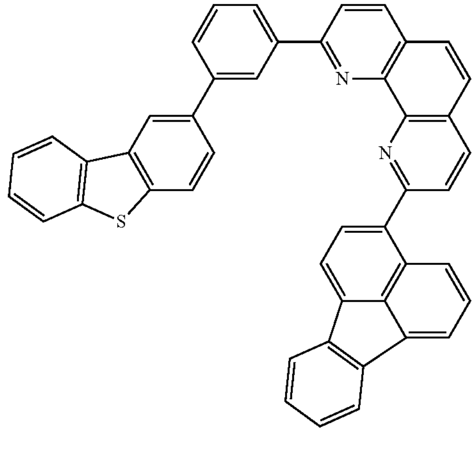
ET212
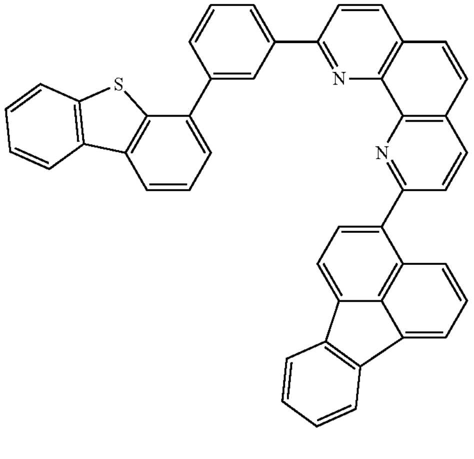

-continued
ET213
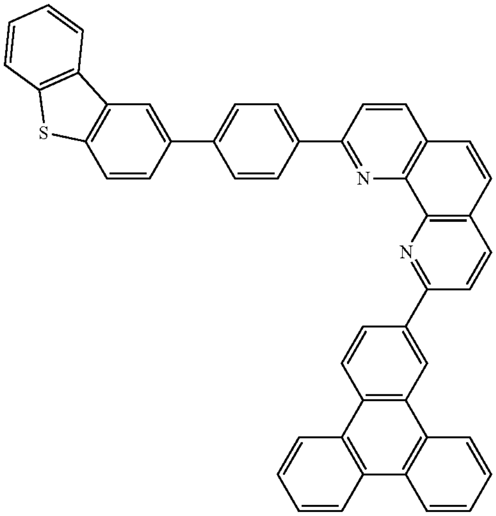
ET214
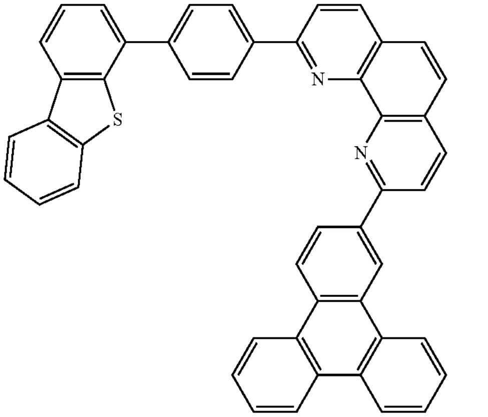
ET215
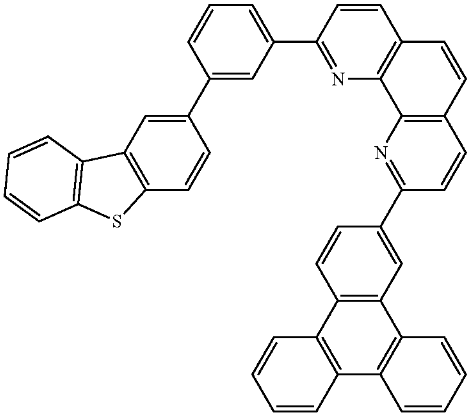
ET216
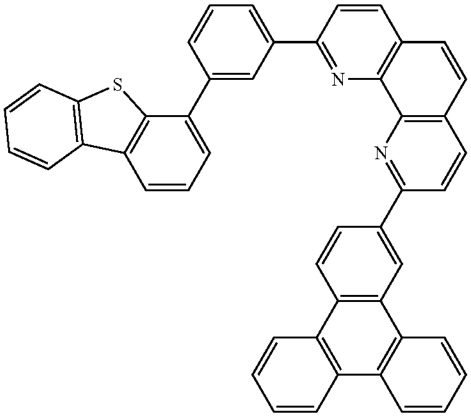
ET217
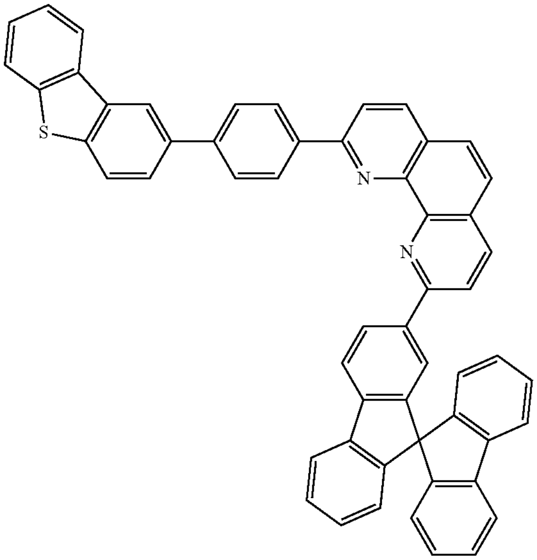
ET218
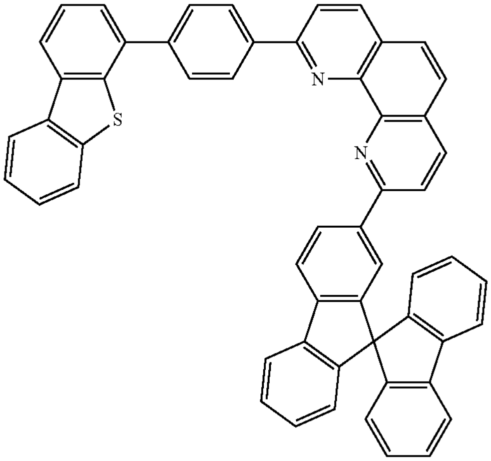

-continued
ET219
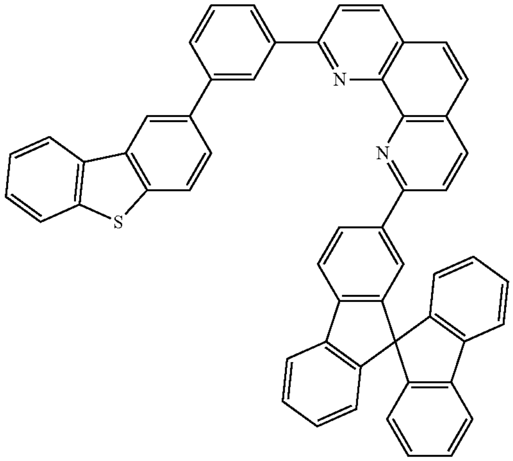
ET220
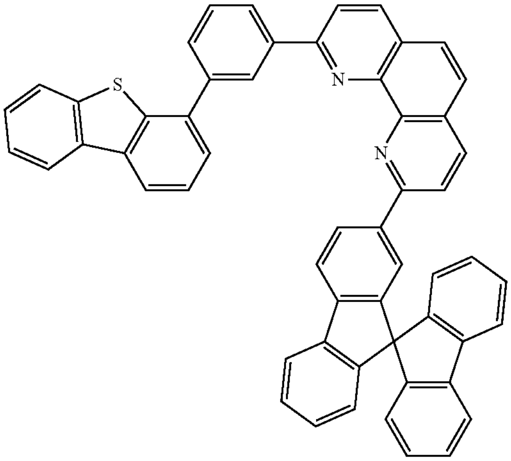
ET221
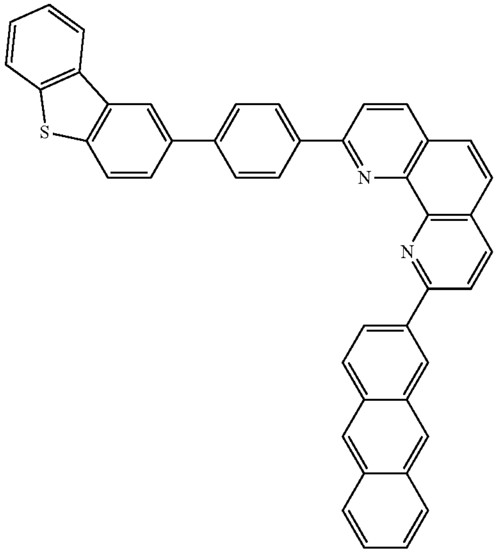
ET222
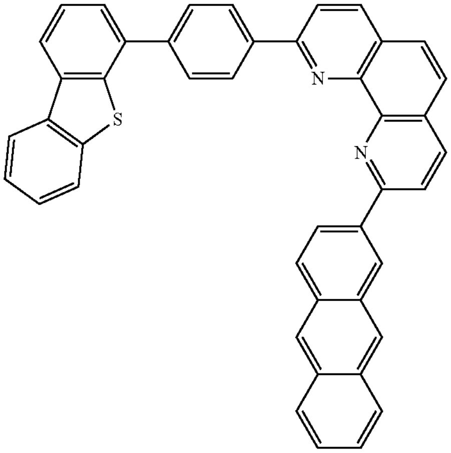
ET223
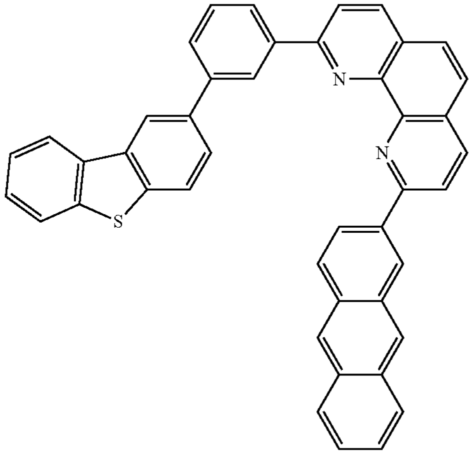
ET224
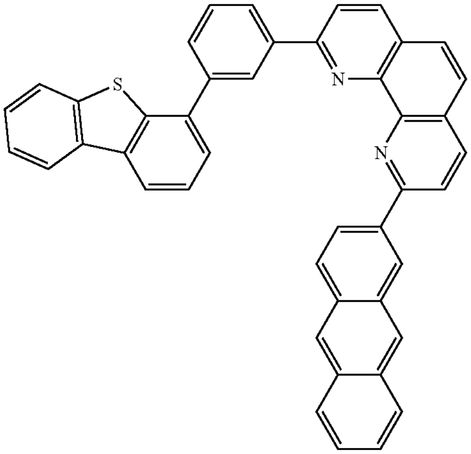

-continued
ET225
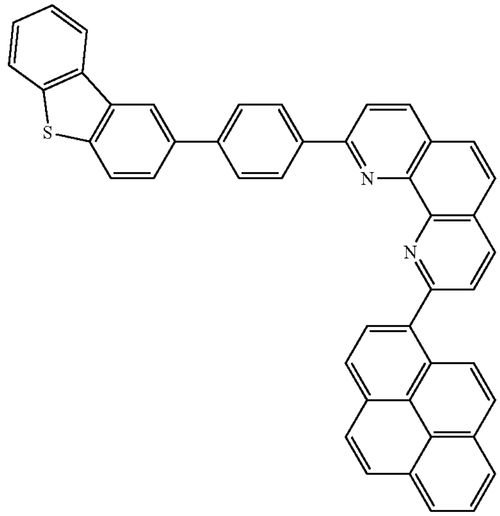
ET226
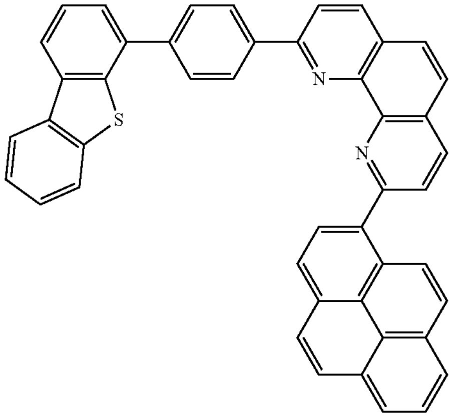
ET227
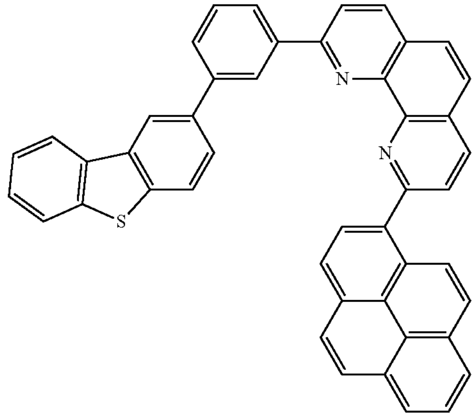
ET228
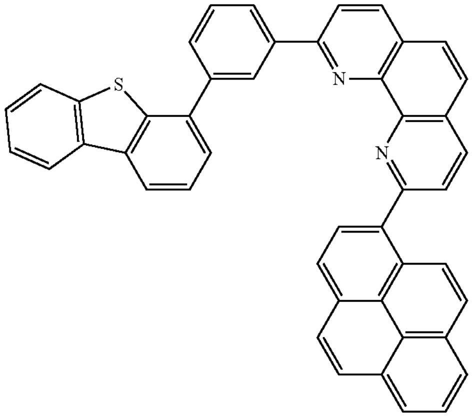
ET229
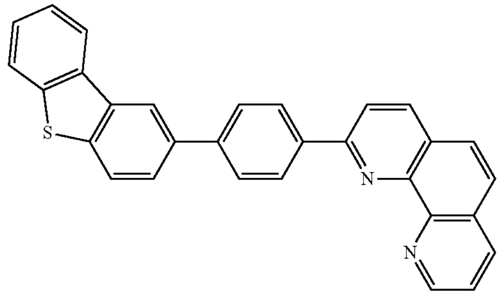
ET230
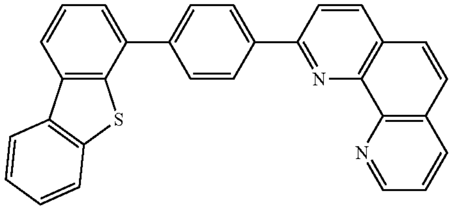
ET231
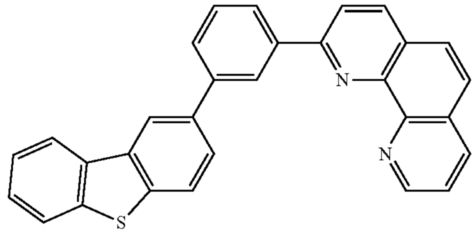
ET232
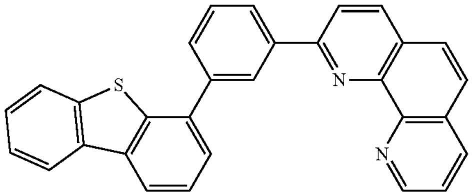

-continued
ET233
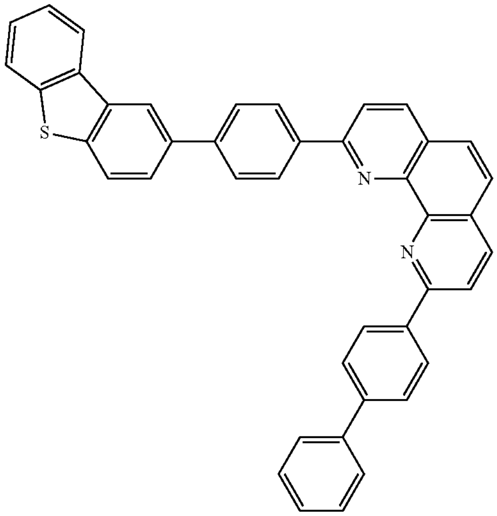
ET234
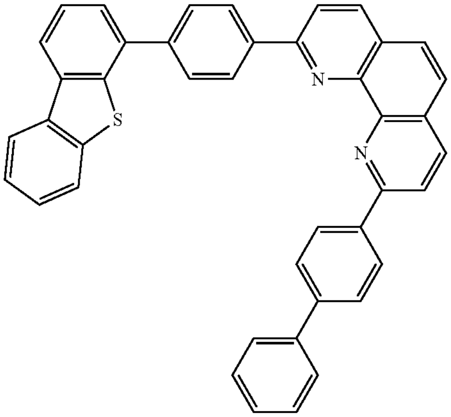
ET235
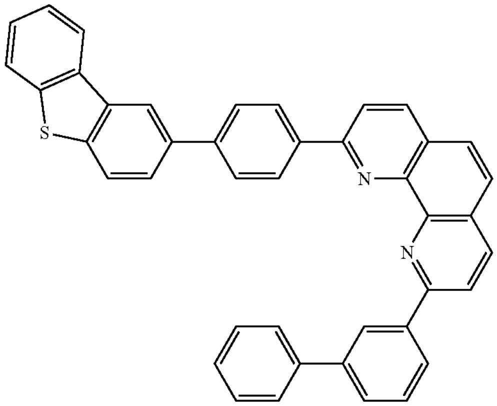
ET236
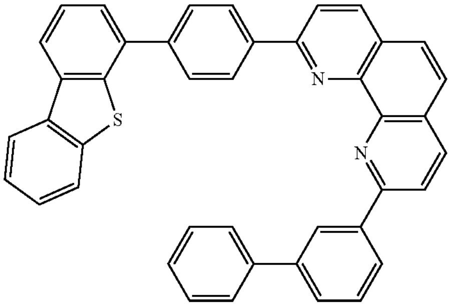
ET237
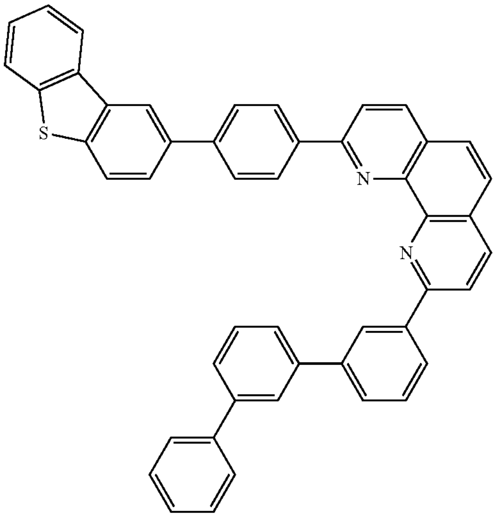
ET238
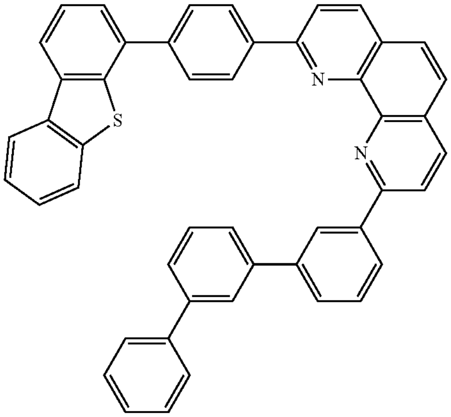

-continued
ET239
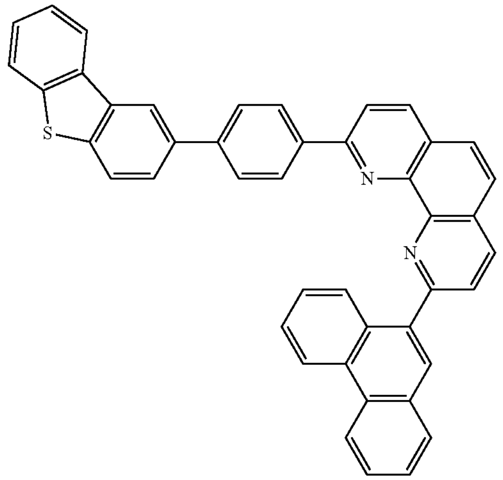
ET240
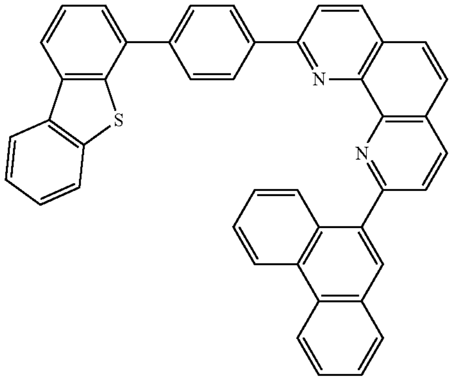
ET241
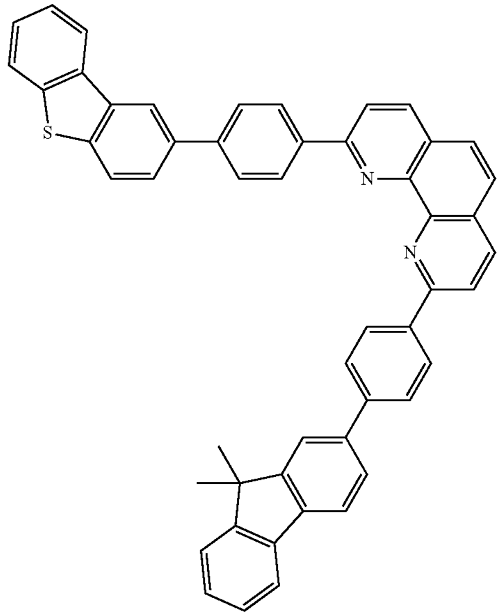
ET242
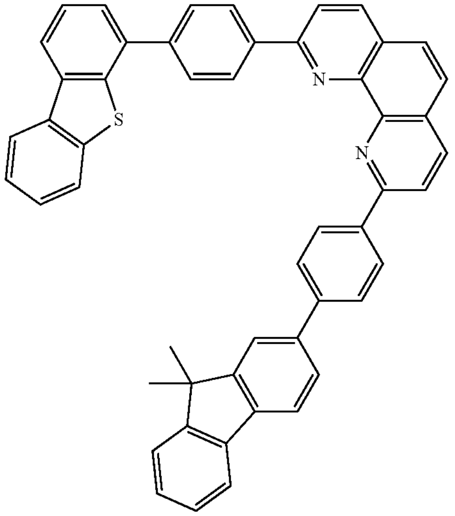
ET243
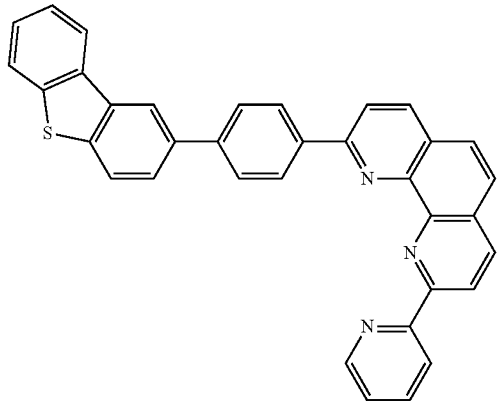
ET244
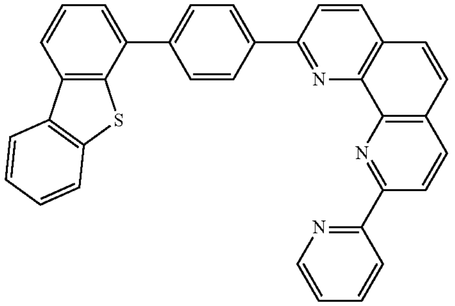

-continued
ET245
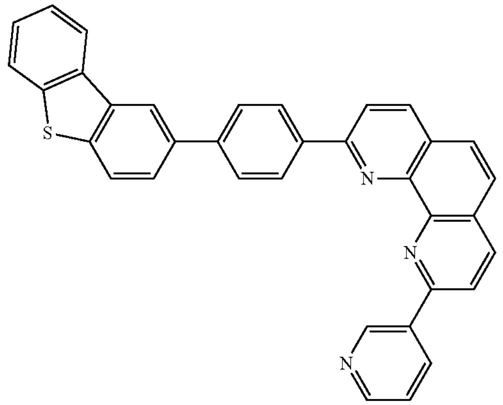
ET246
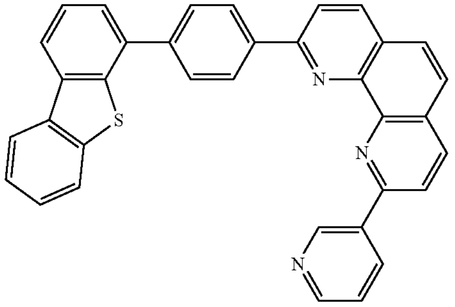
ET247
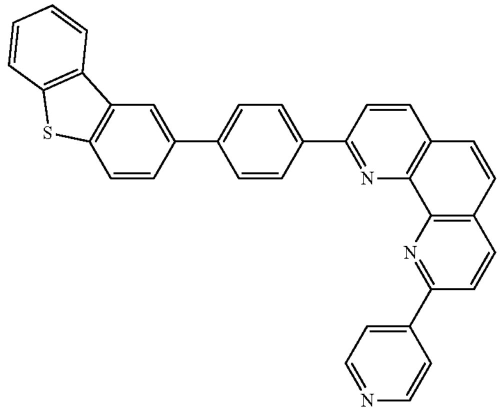
ET248
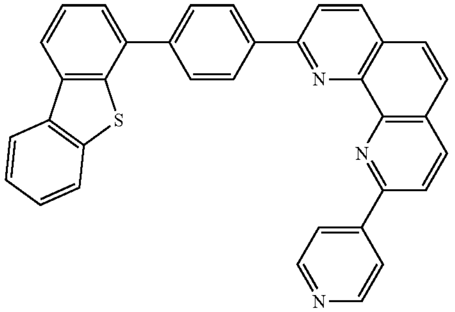
ET249
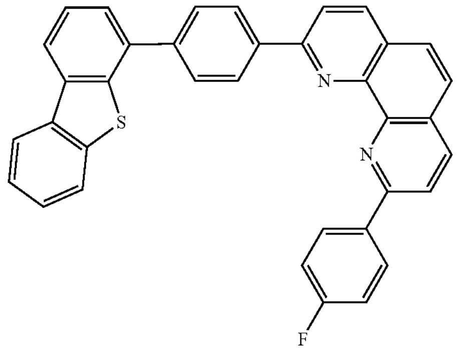
ET250
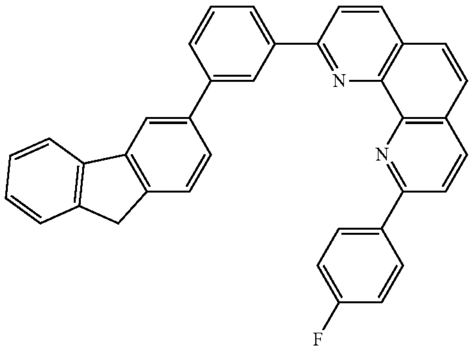
ET251
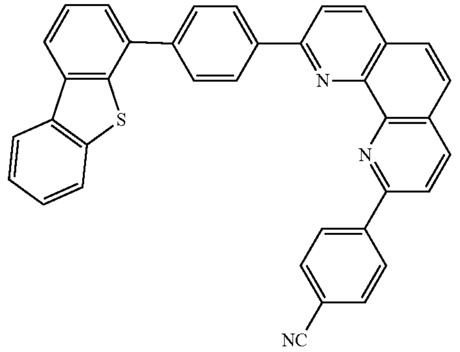
ET252
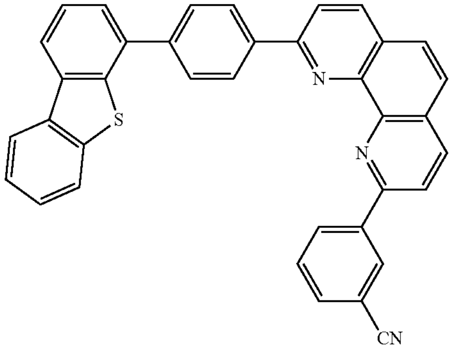

-continued
ET253
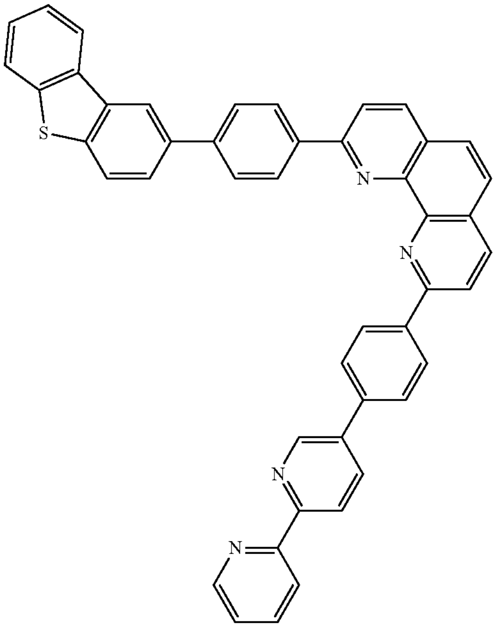
ET254
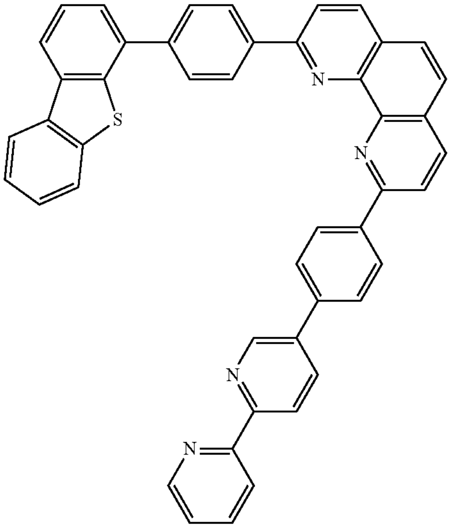
ET255
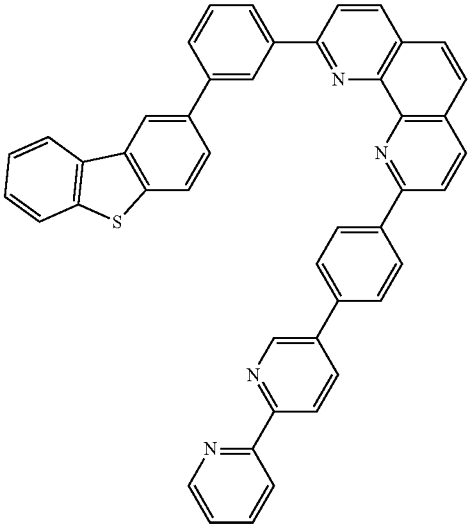
ET256
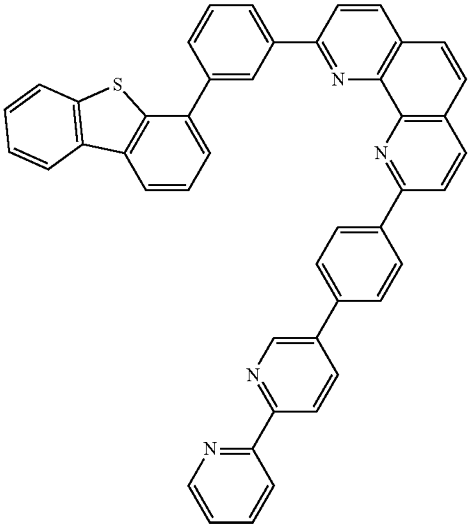

-continued
ET257
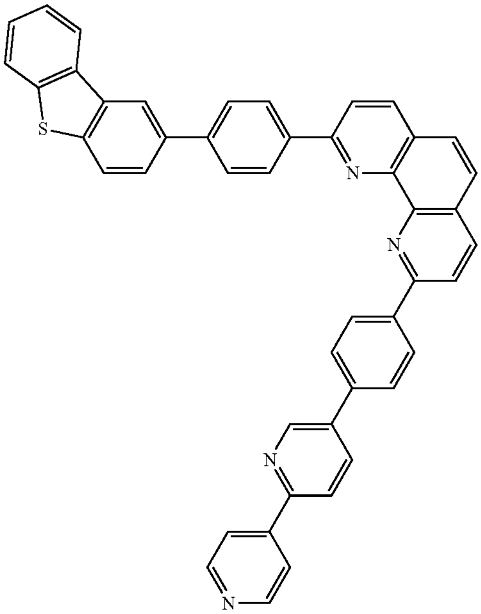
ET258
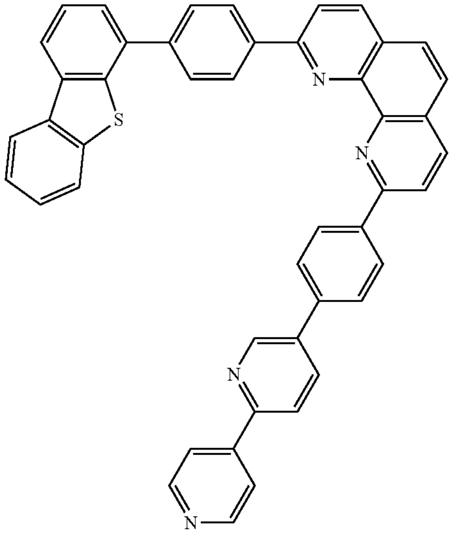
ET259
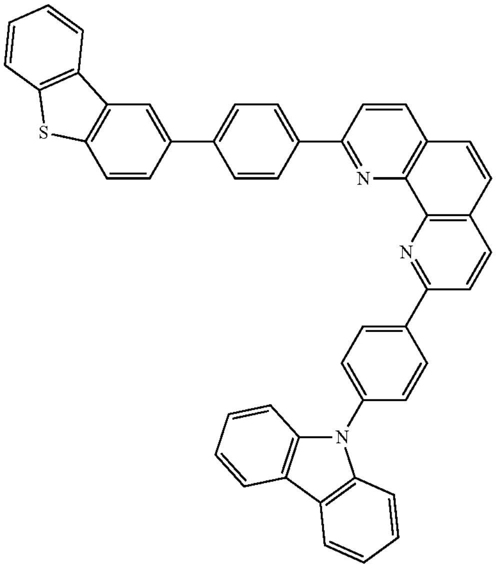
ET260
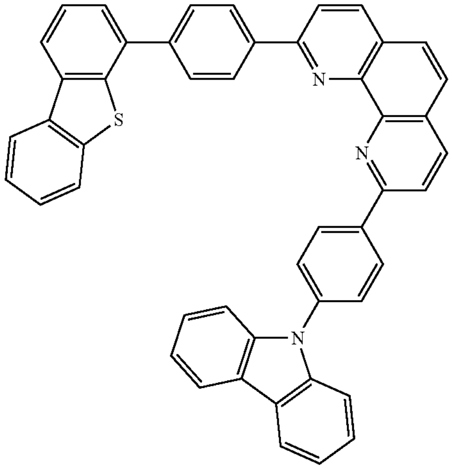
ET261
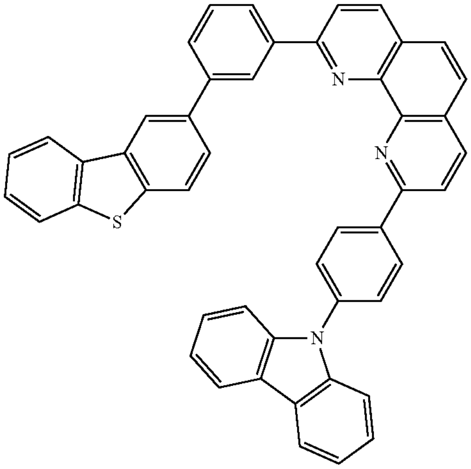
ET262
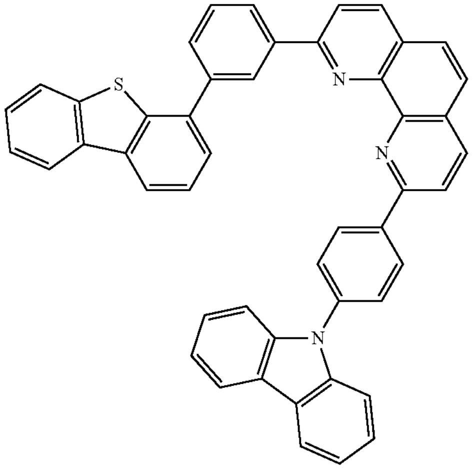

-continued
ET263
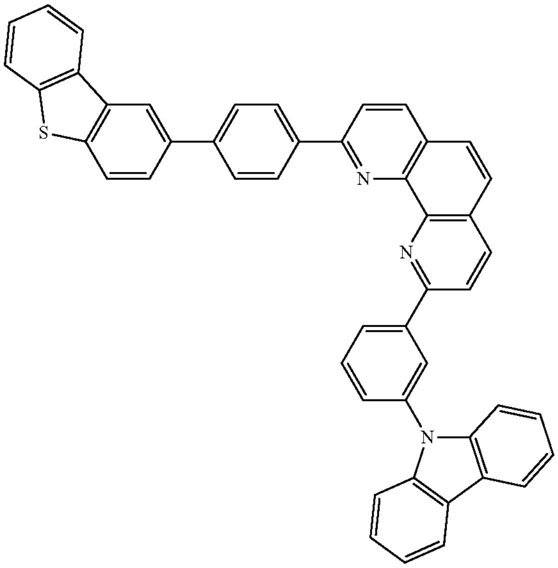
ET264
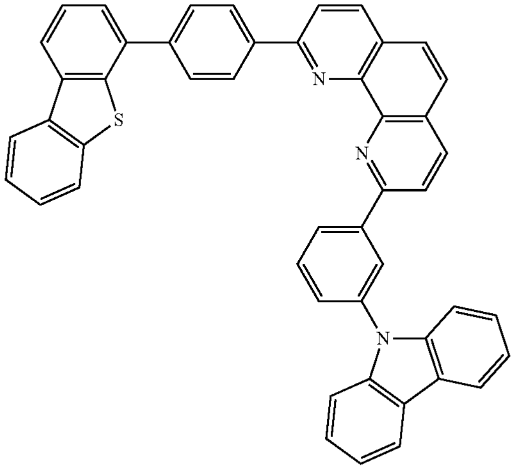
ET265
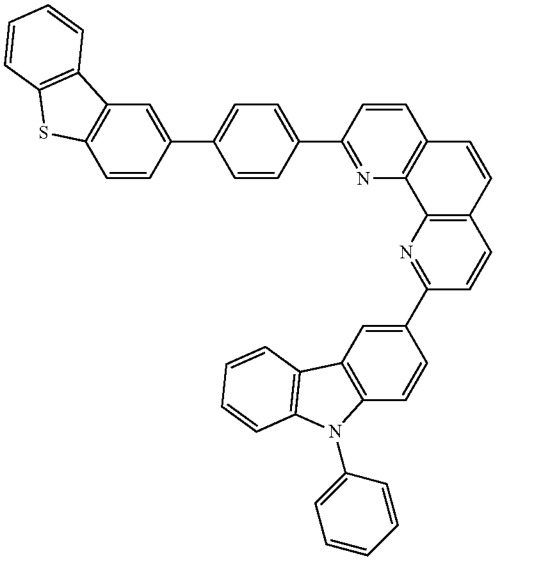
ET266
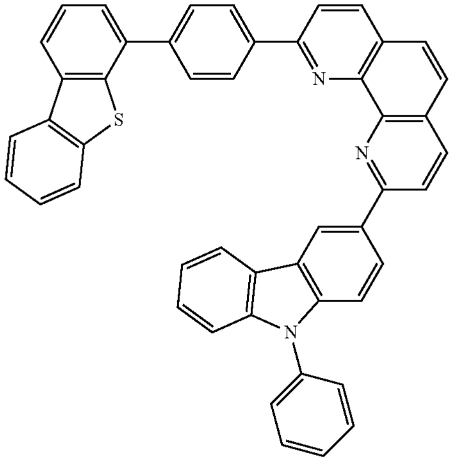

-continued
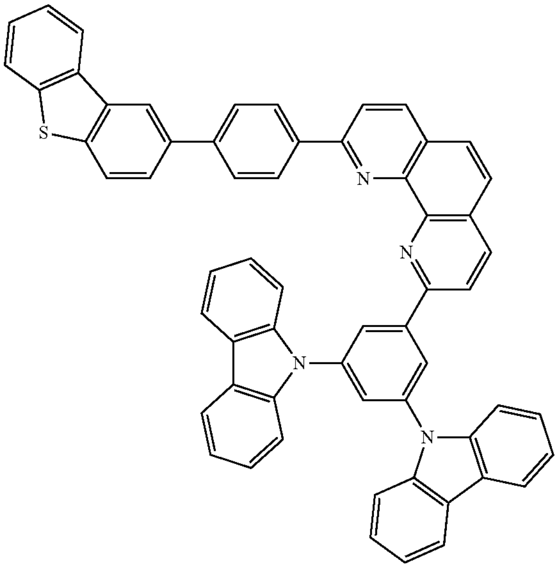
ET267
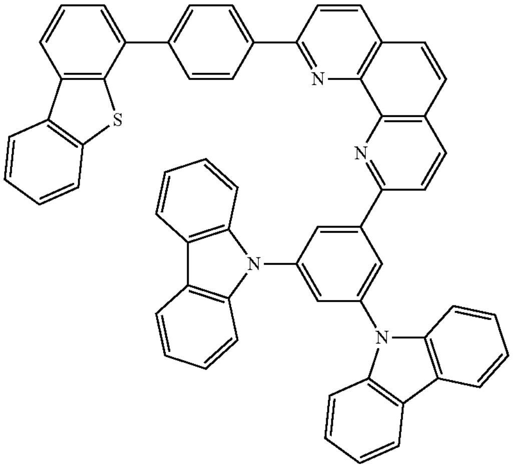
ET268
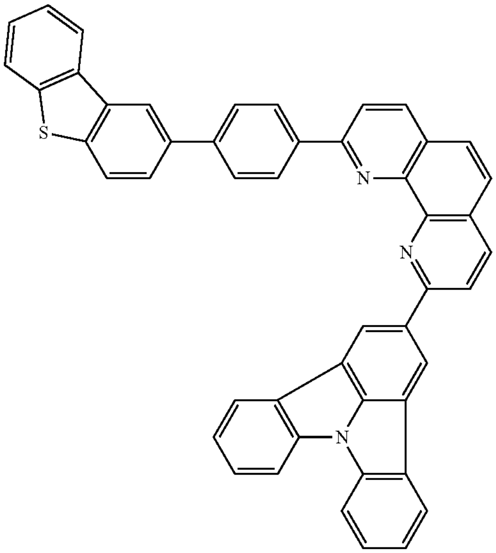
ET269
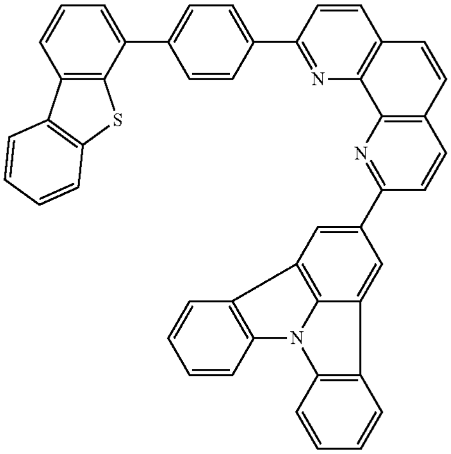
ET270

-continued
ET271
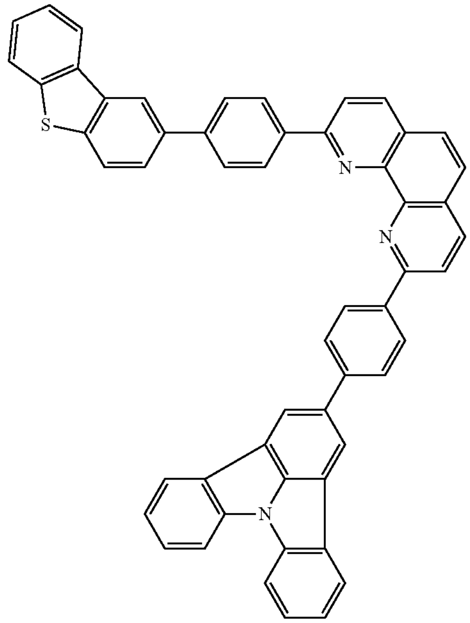
ET272
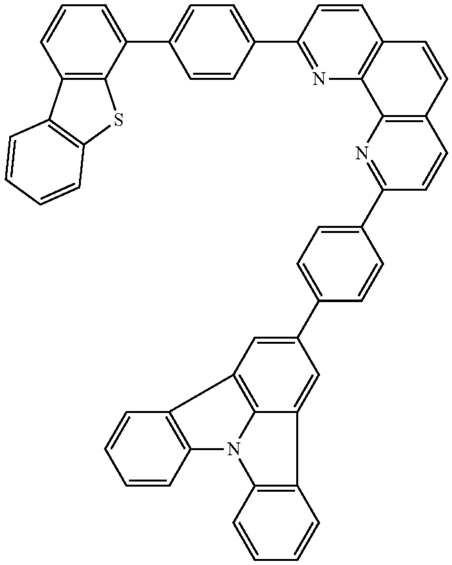
ET273
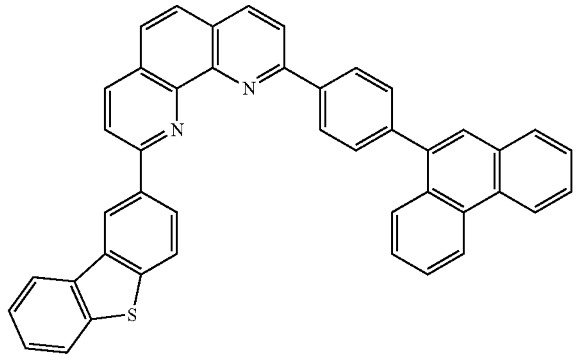
ET274
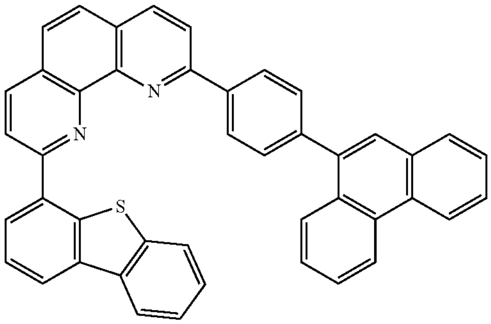
ET275
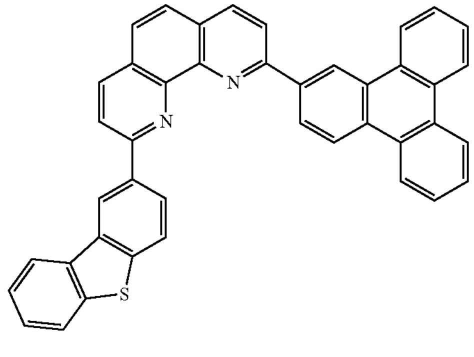
ET276
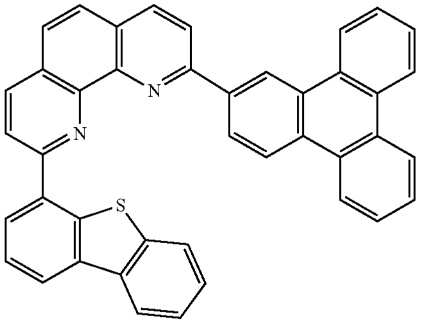

-continued
ET277
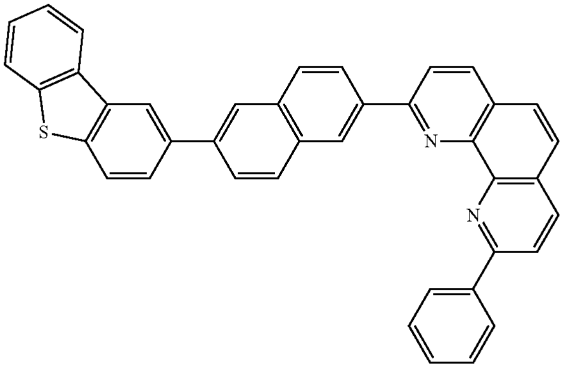
ET278
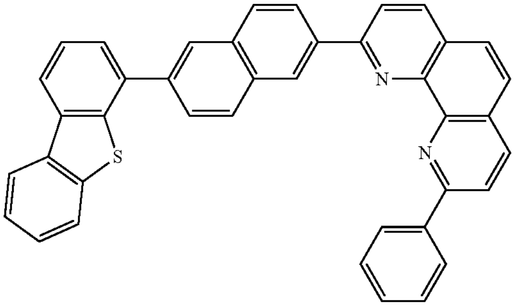
ET279
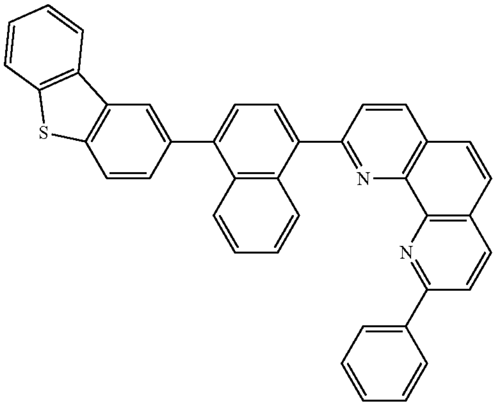
ET280
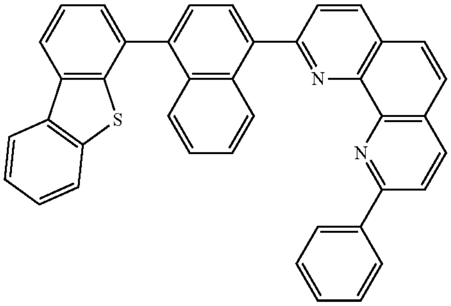
ET281
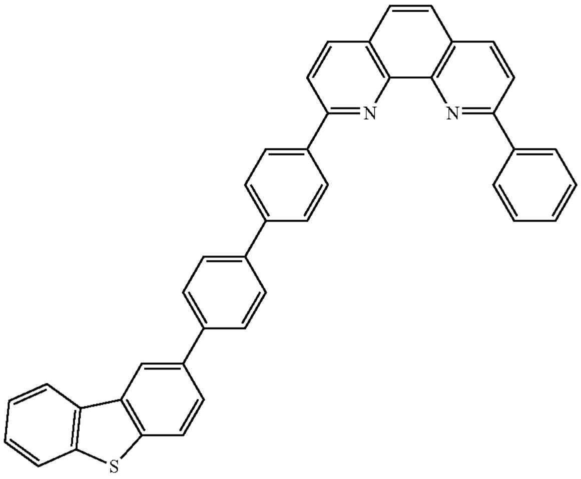
ET282
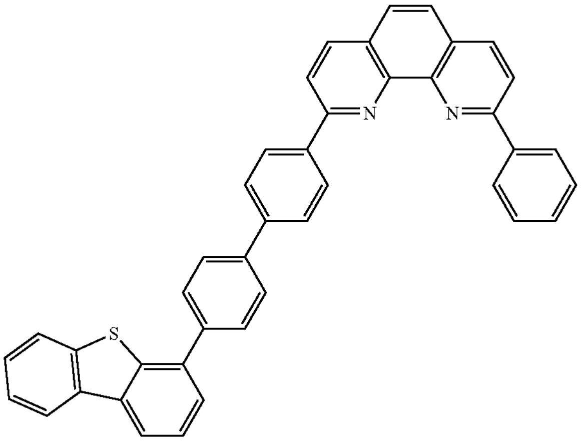

-continued
ET283
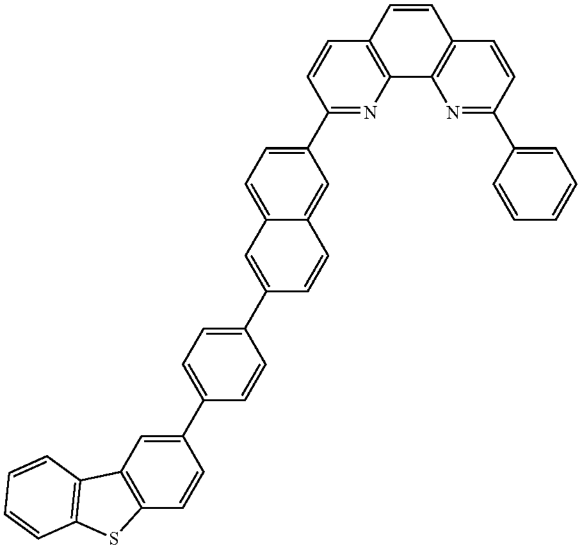
ET284
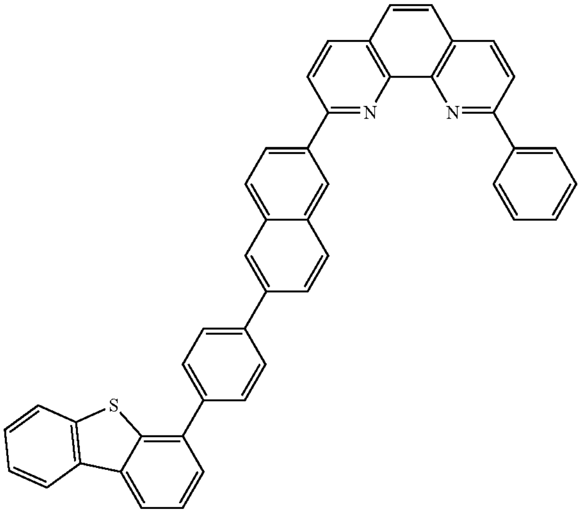
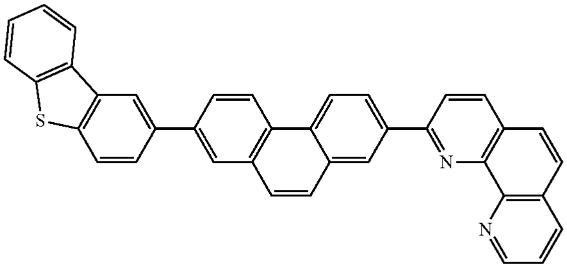
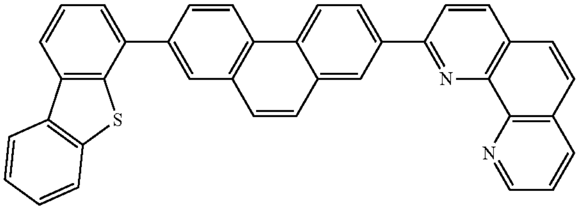
ET287
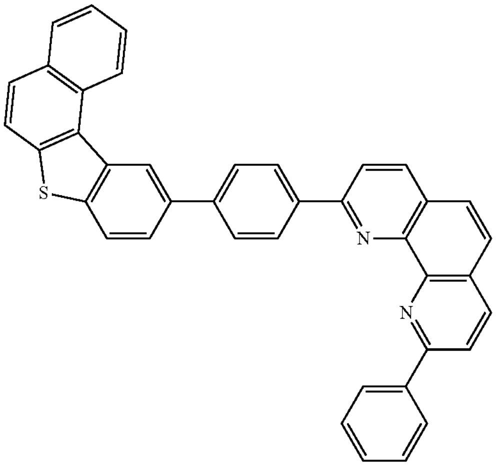
ET288
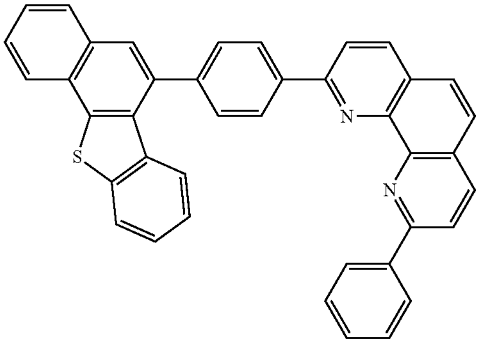

-continued
ET289
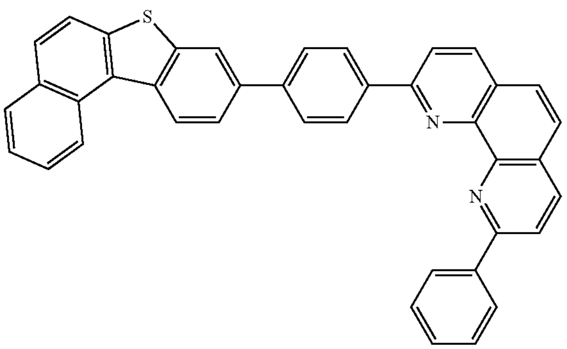
ET290
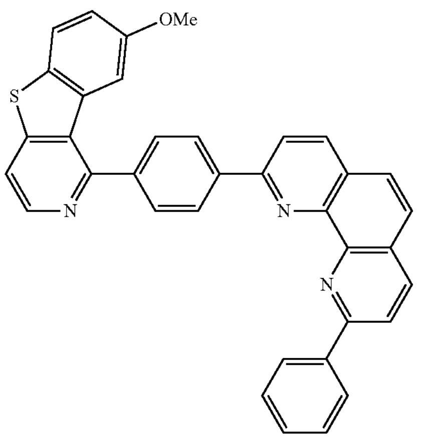
ET291
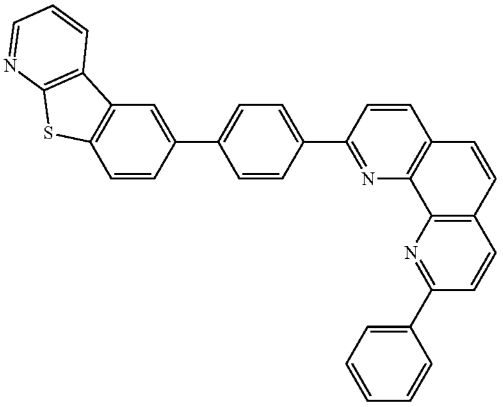
ET292
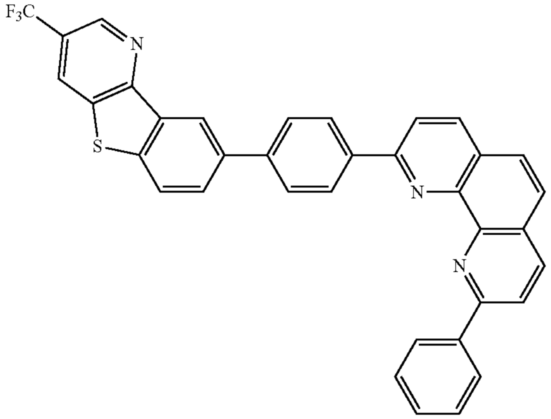
ET293
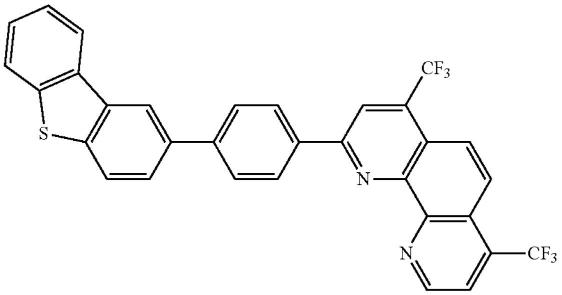
ET294
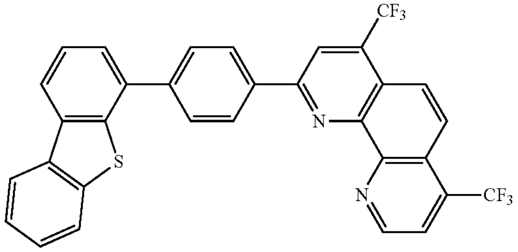
ET295
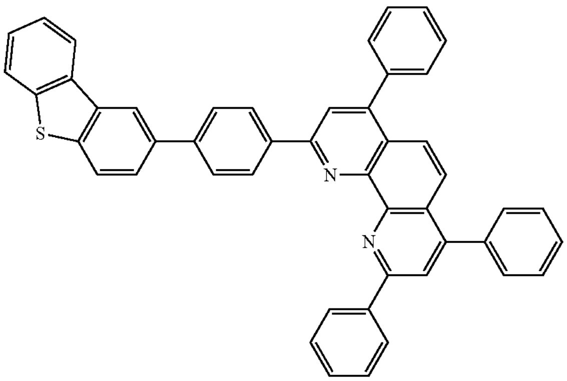
ET296
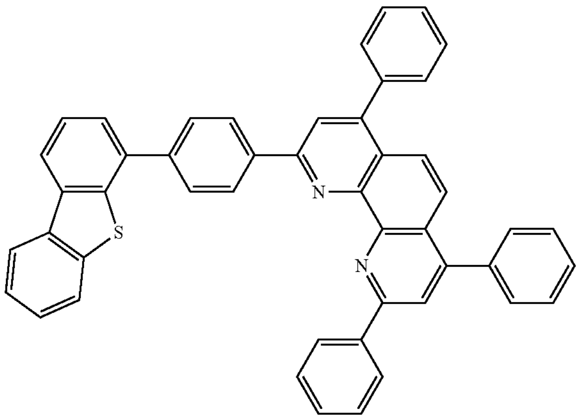

-continued
ET297
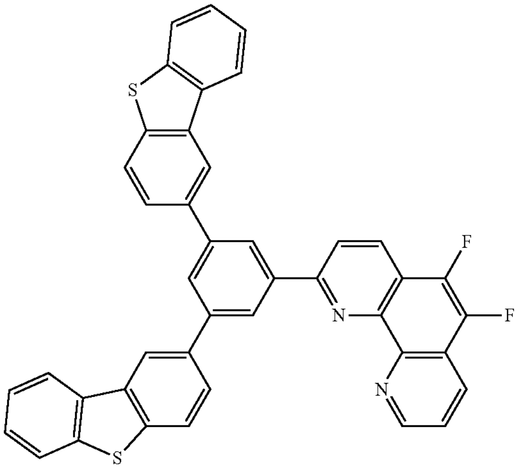
ET298
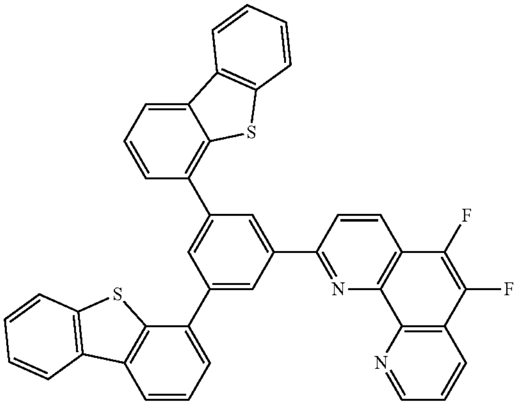
ET299
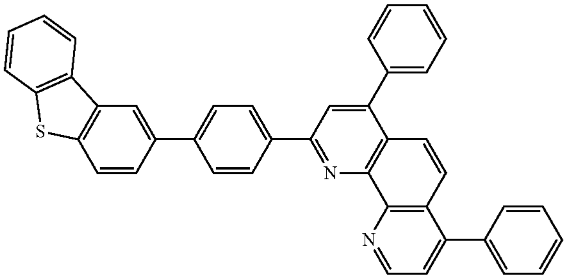
ET300
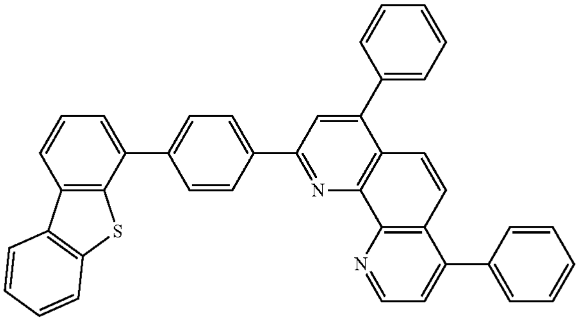
ET301
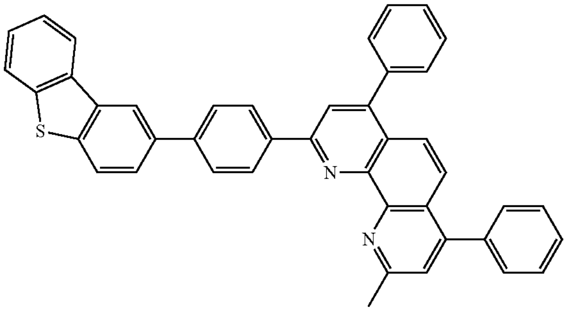
ET302
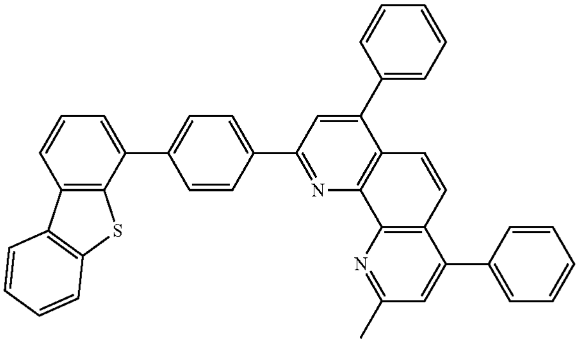
ET303
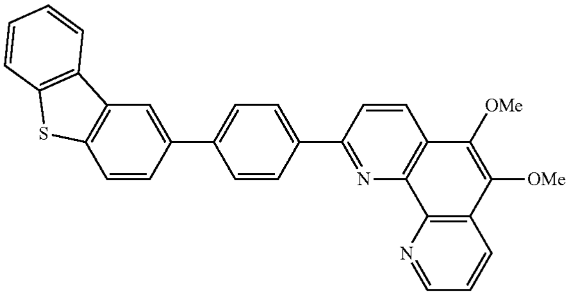
ET304
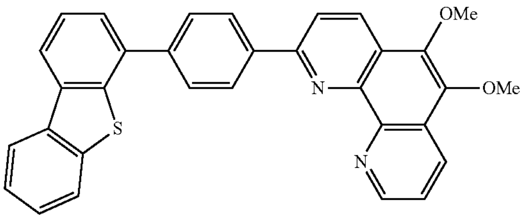

-continued
ET305
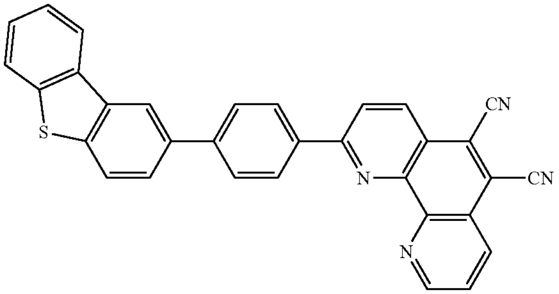
ET306
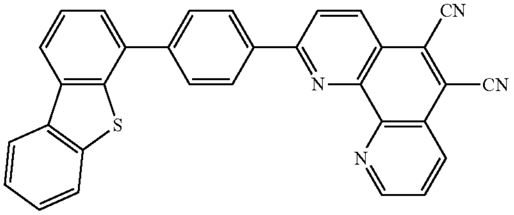
ET307
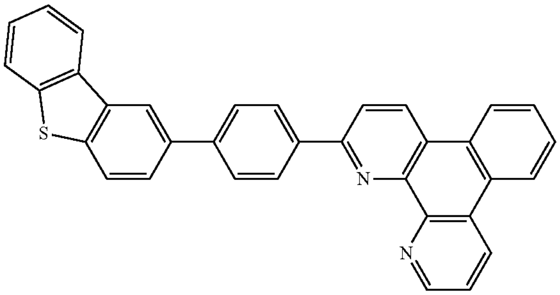
ET308
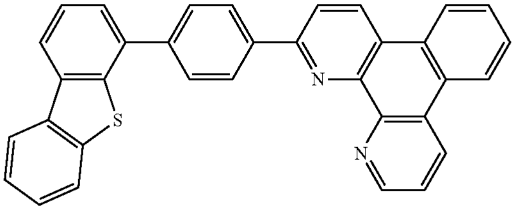
ET309
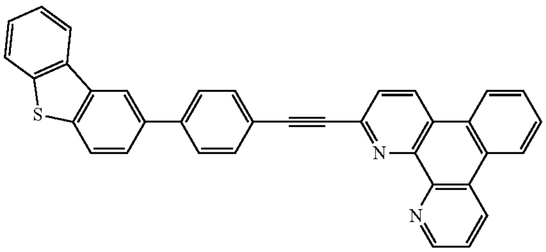
ET310
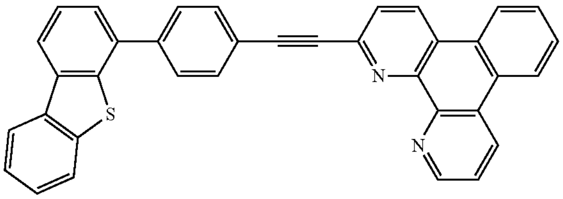
ET311
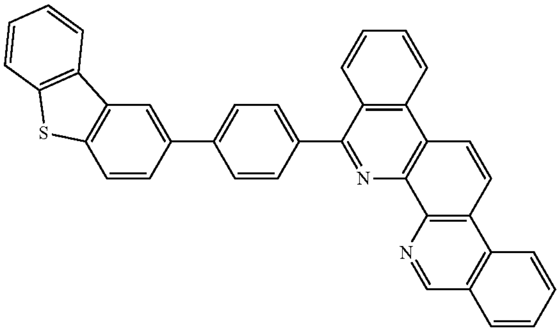
ET312
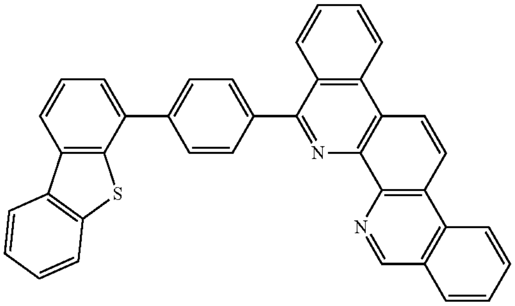
ET313
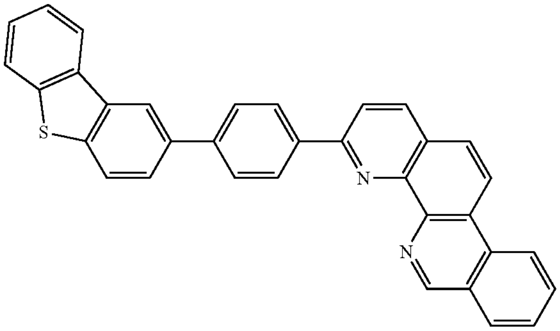
ET314
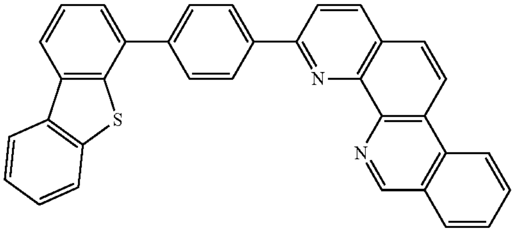

-continued
ET315
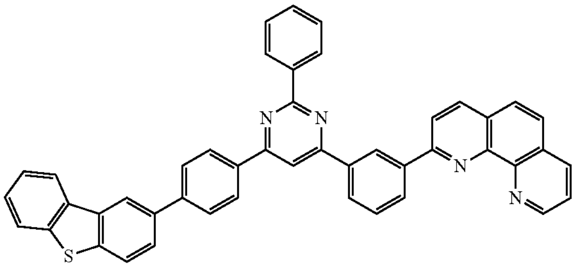
ET316
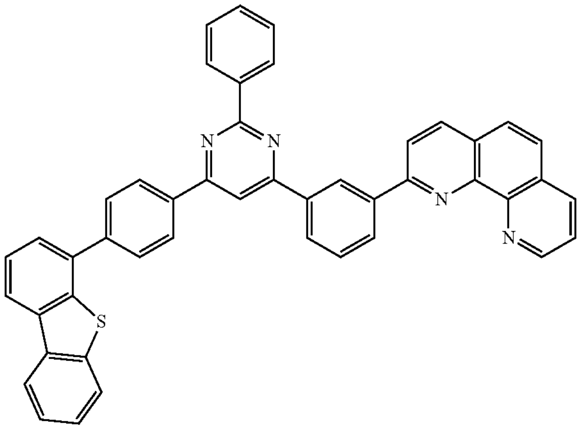
ET317
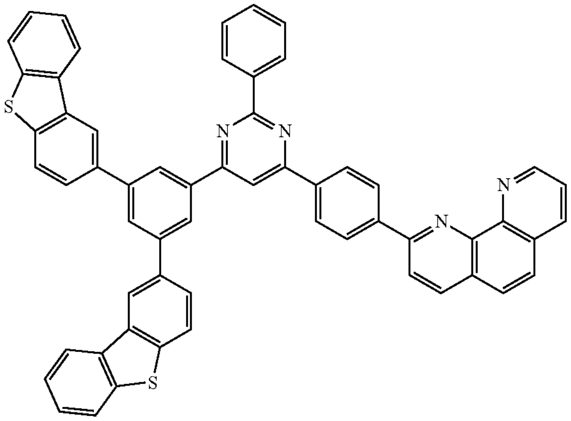
ET318
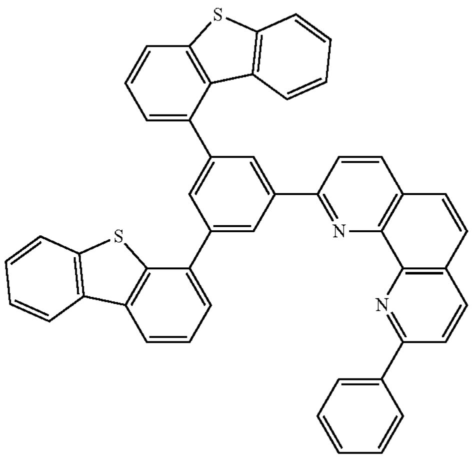
ET319
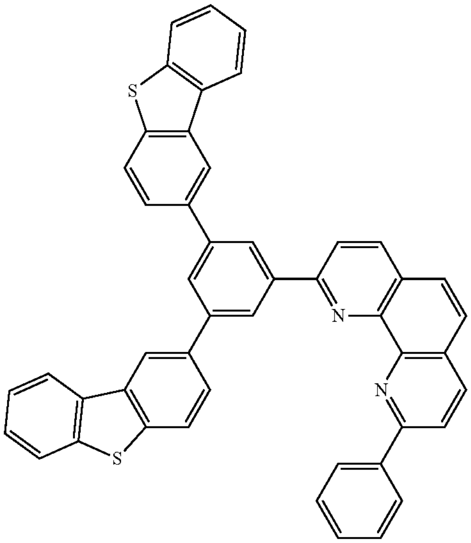
ET320
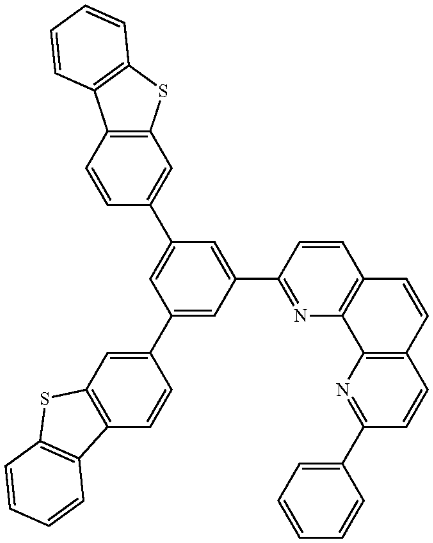

-continued
ET322
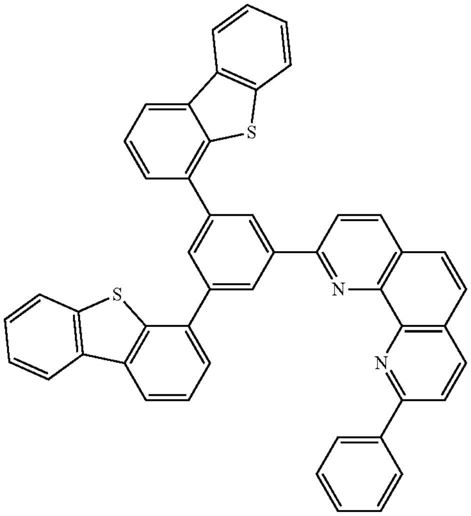
ET321
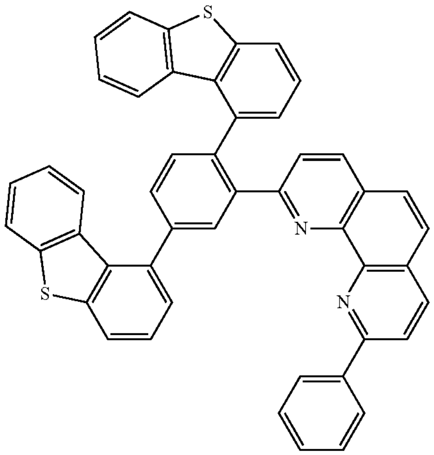
ET323
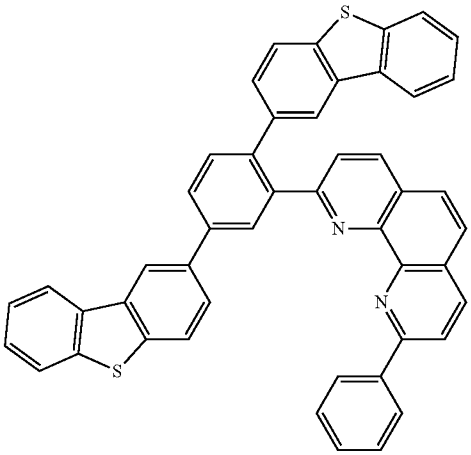
ET324
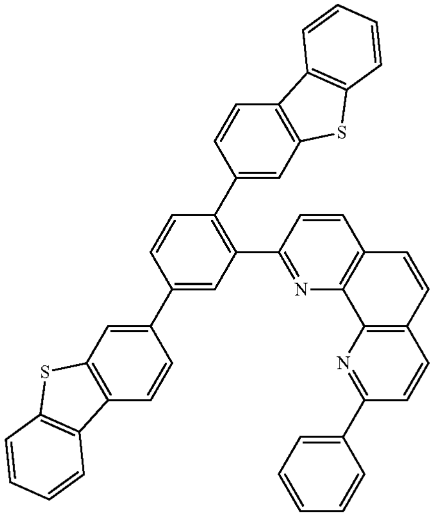
ET325
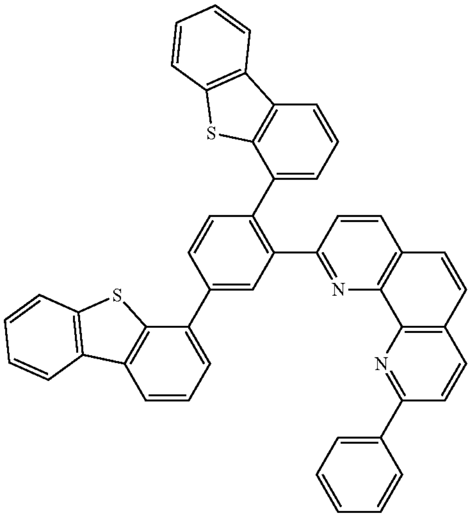
ET326
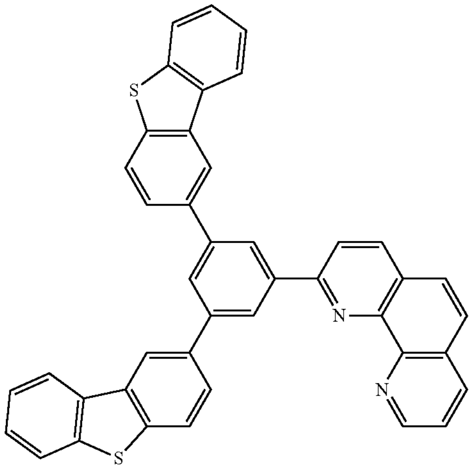

-continued
ET327
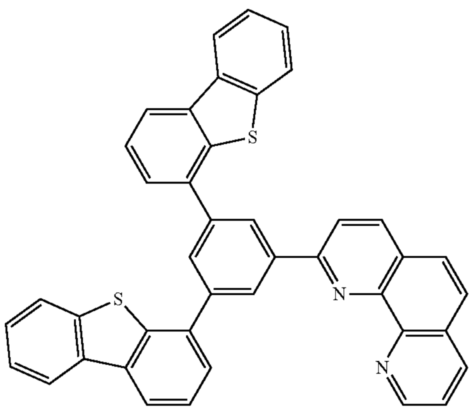
ET328
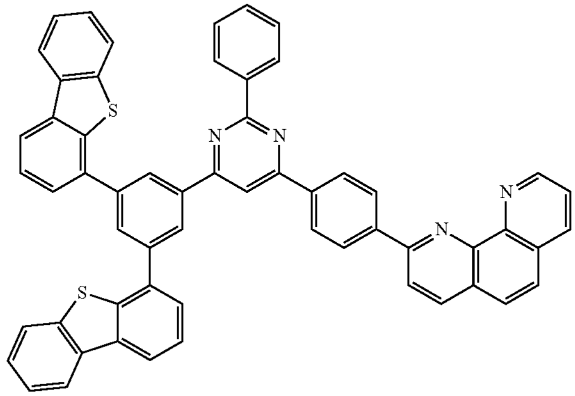
ET329
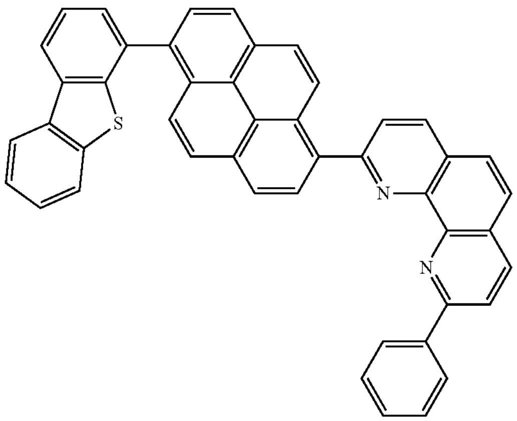
ET330
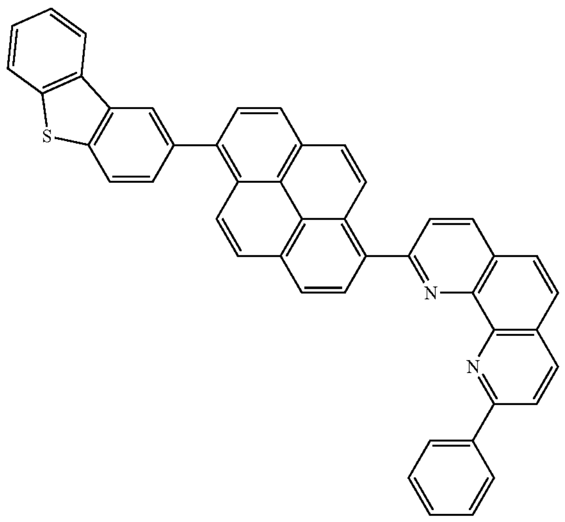
ET331
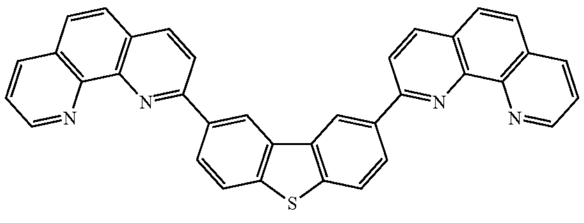
ET332
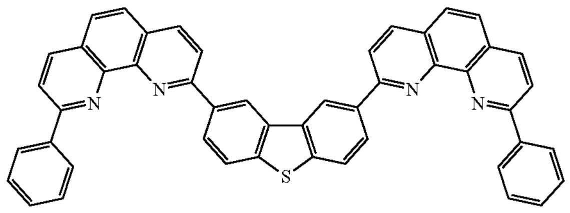
ET333
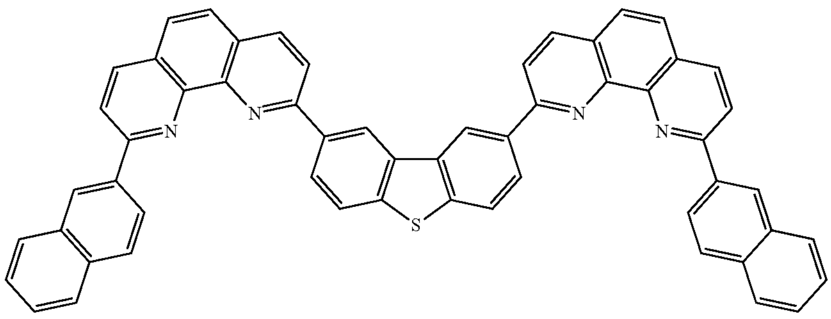

-continued
ET334
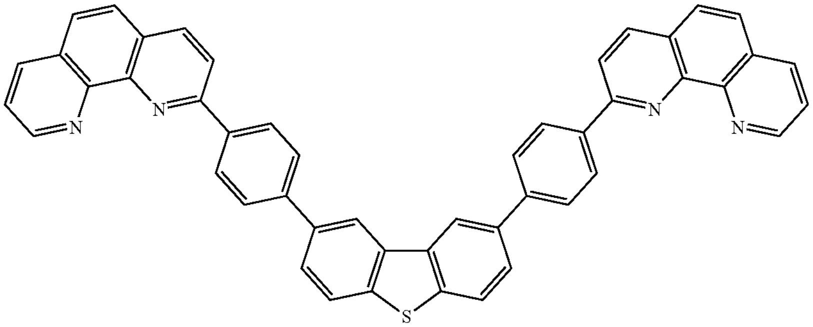
ET335
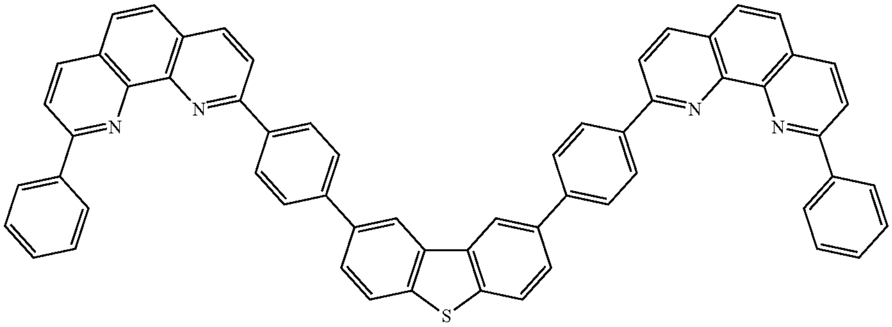
ET336
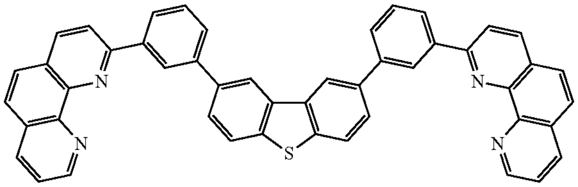
ET337
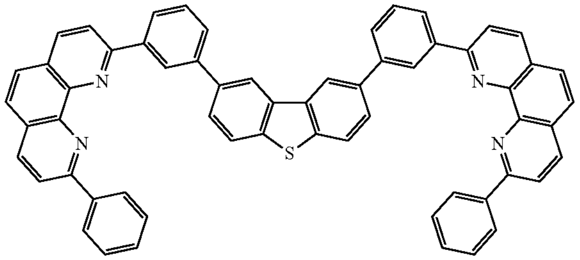
ET338
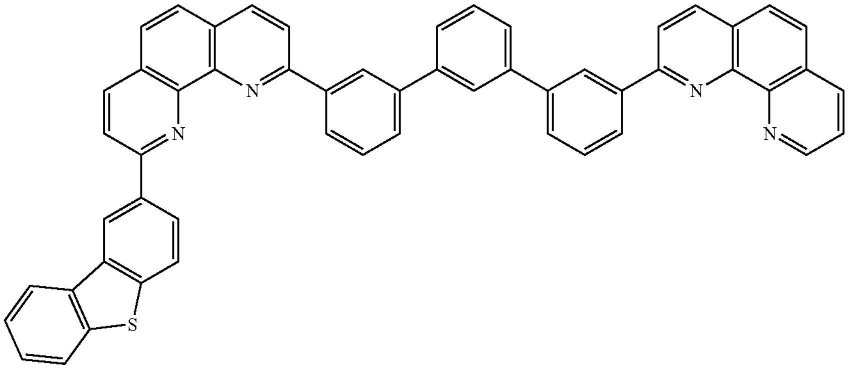
ET339
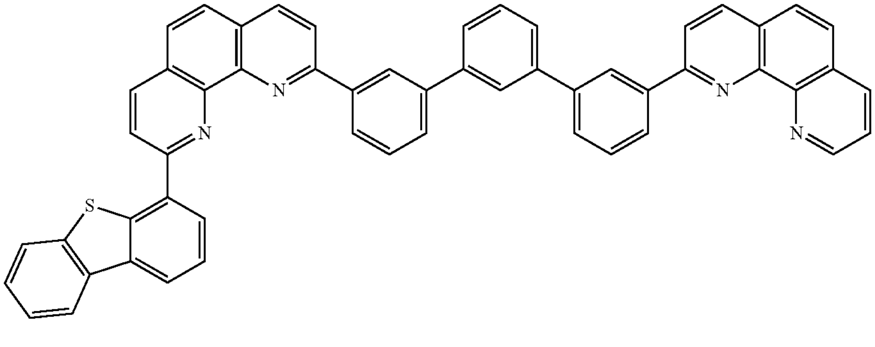

-continued
ET340
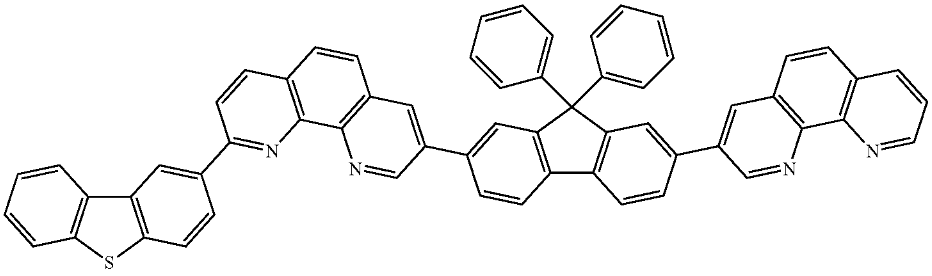
ET341
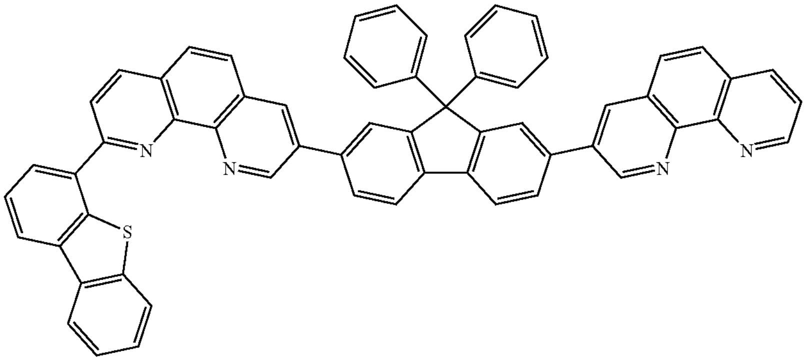
ET1007
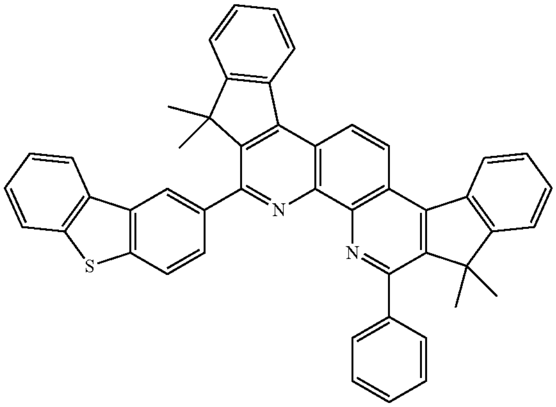
ET1008
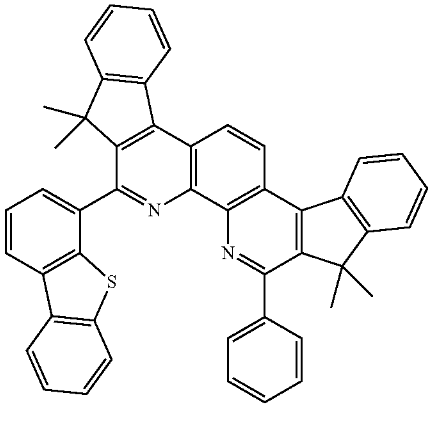
ET1009
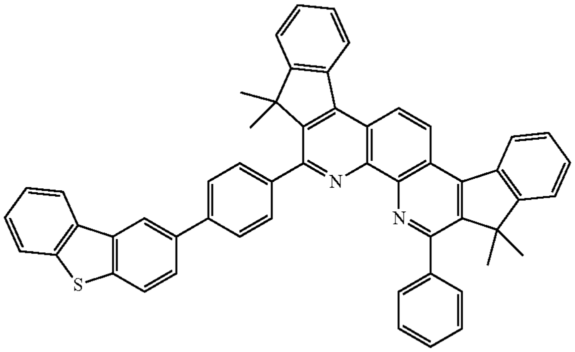
ET1010
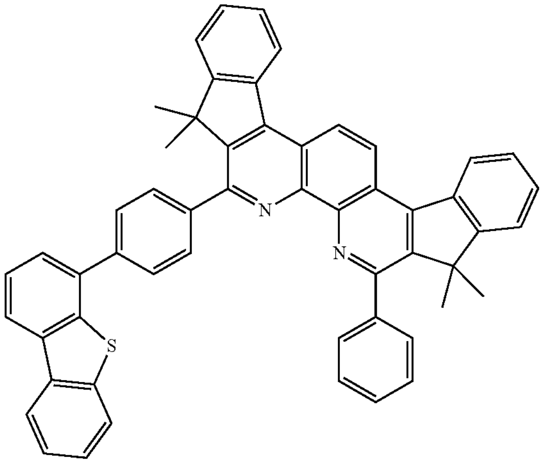

-continued
ET1011
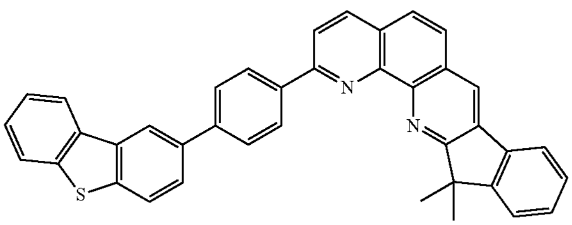
ET1012
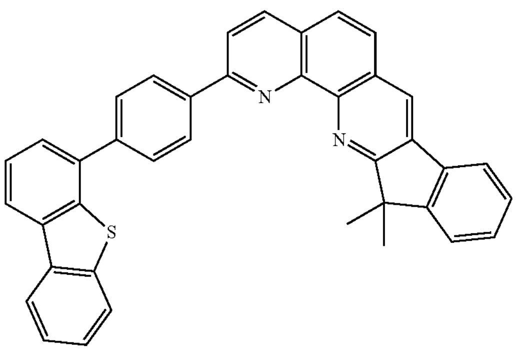
ET342
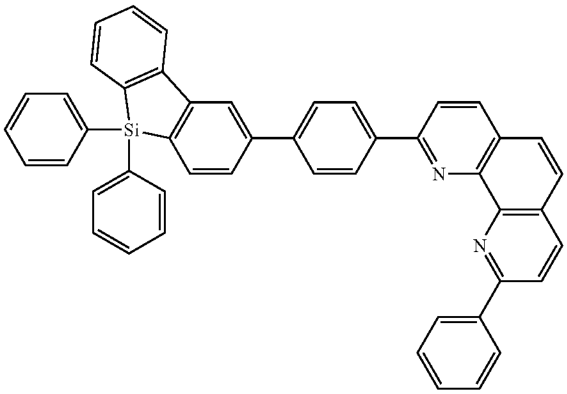
ET343
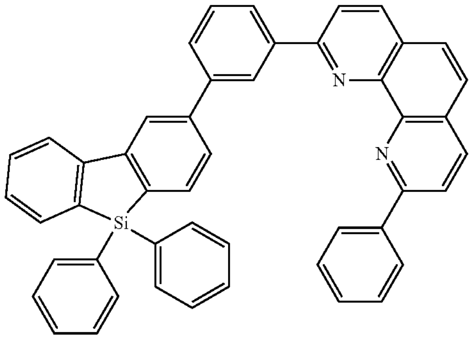
ET344
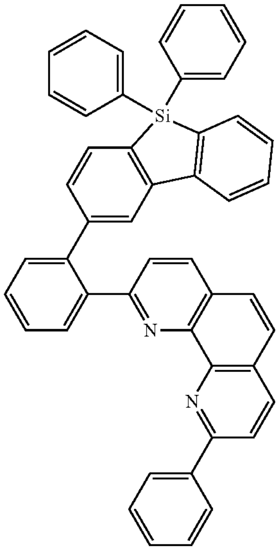
ET345
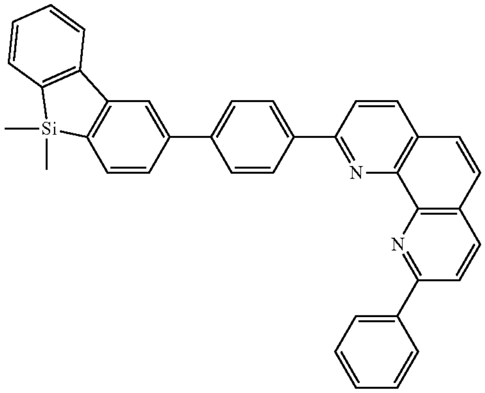

-continued
ET346
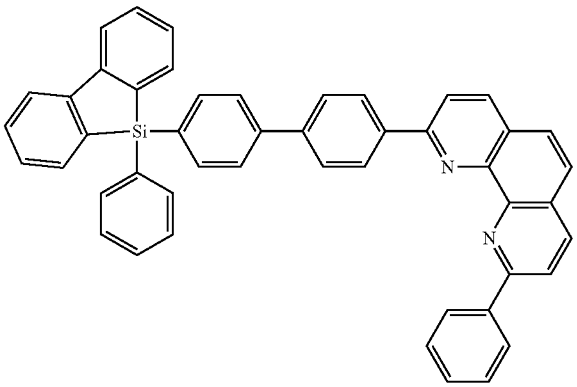
ET347
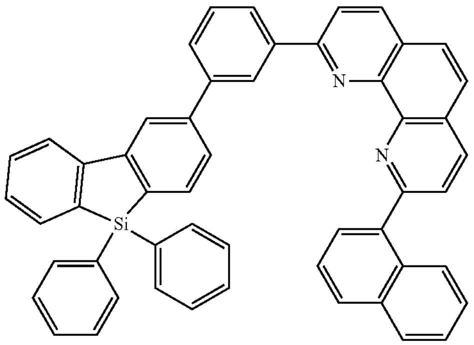
ET348
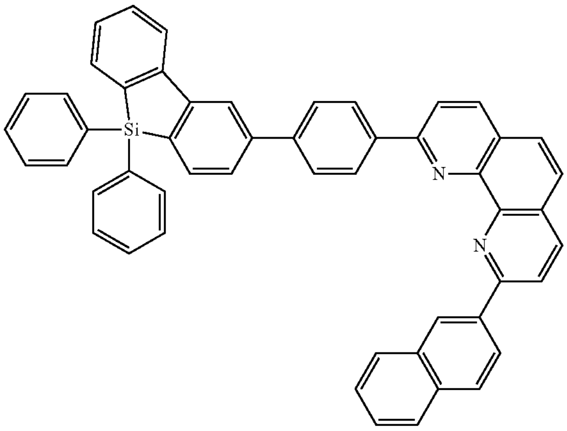
ET349
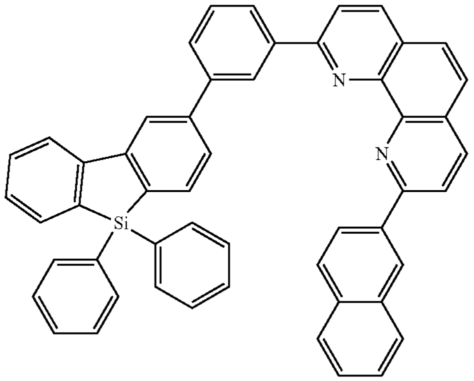
ET350
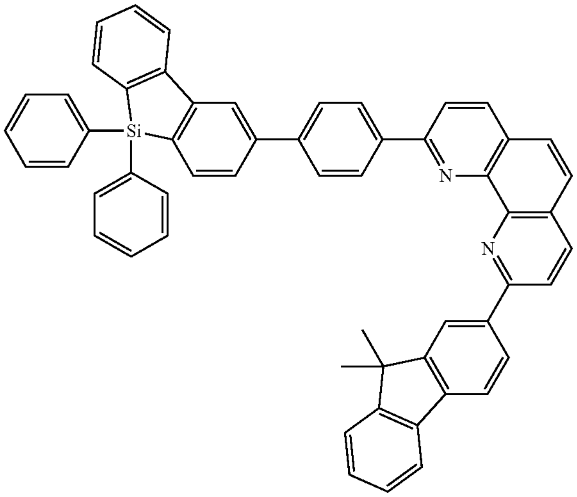
ET351
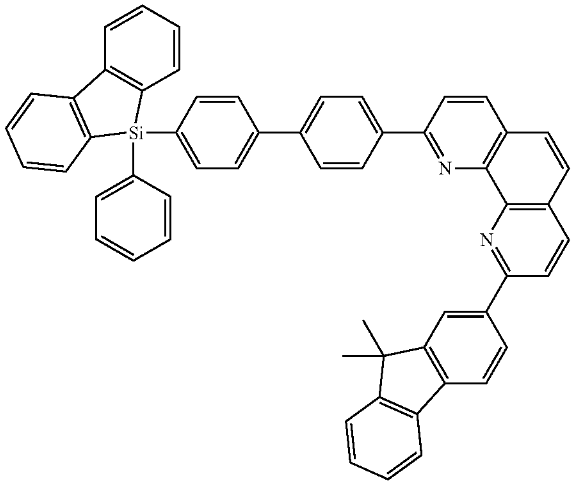

-continued
ET352
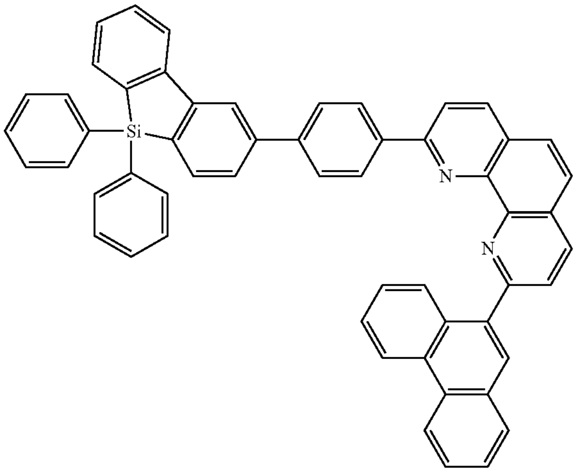
ET353
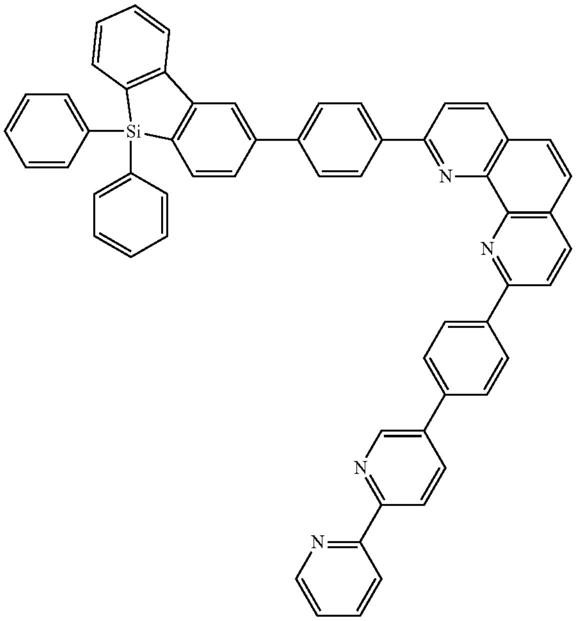
ET354
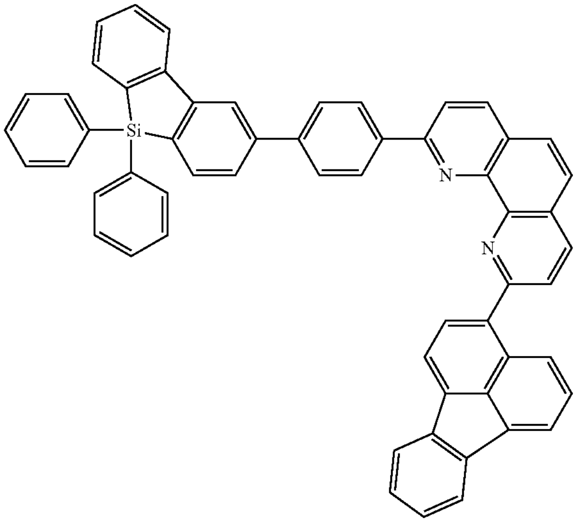
ET355
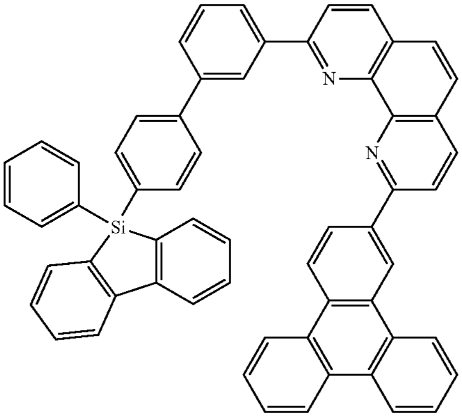

-continued
ET356
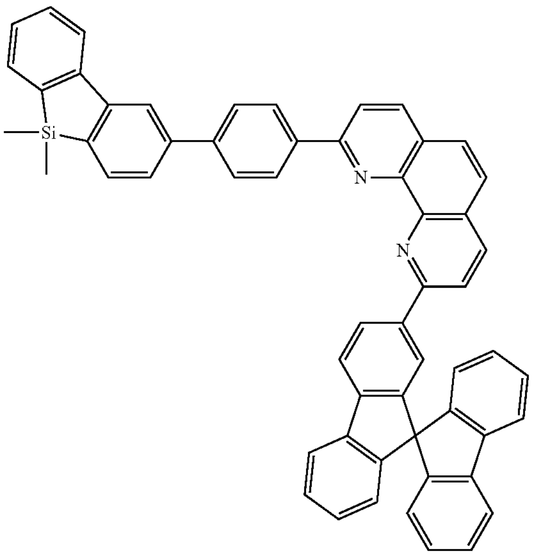
ET357
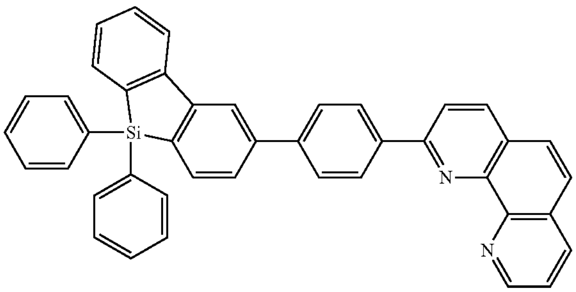
ET358
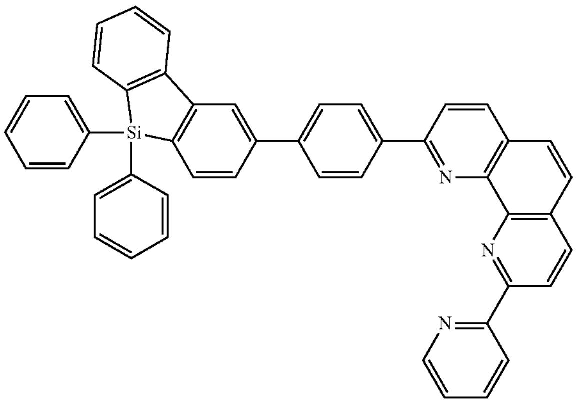
ET359
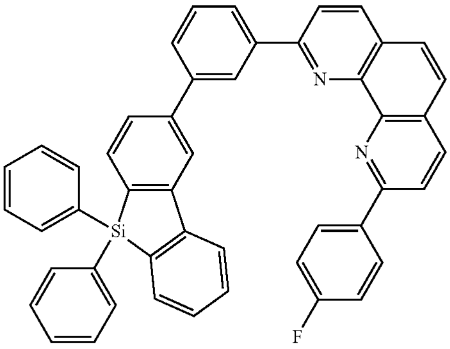
ET360
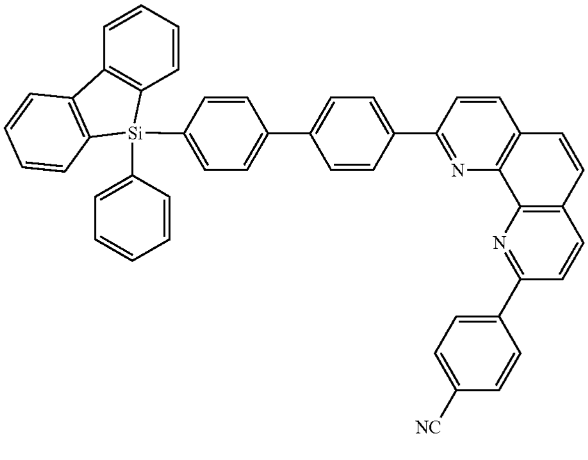
ET361
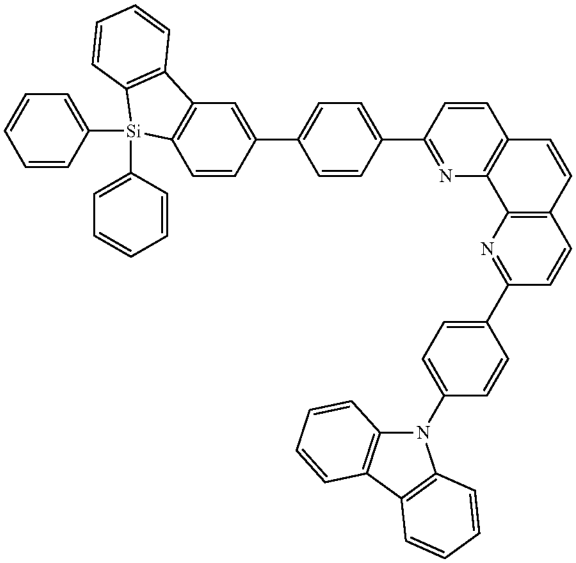

-continued
ET362
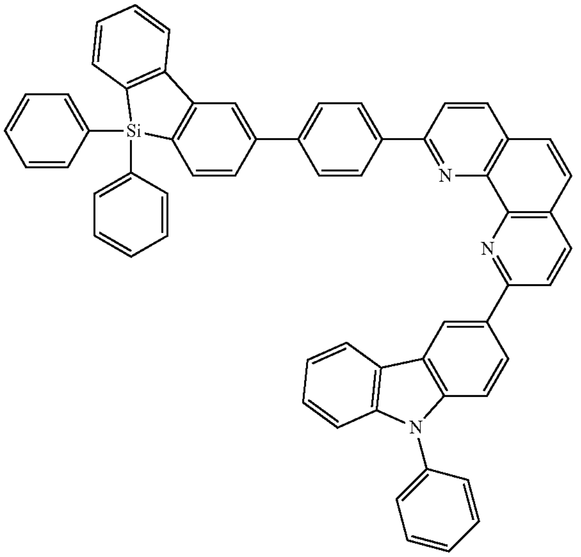
ET363
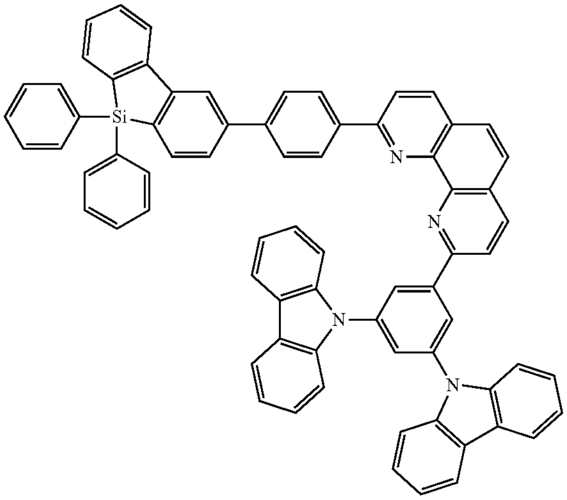
ET364
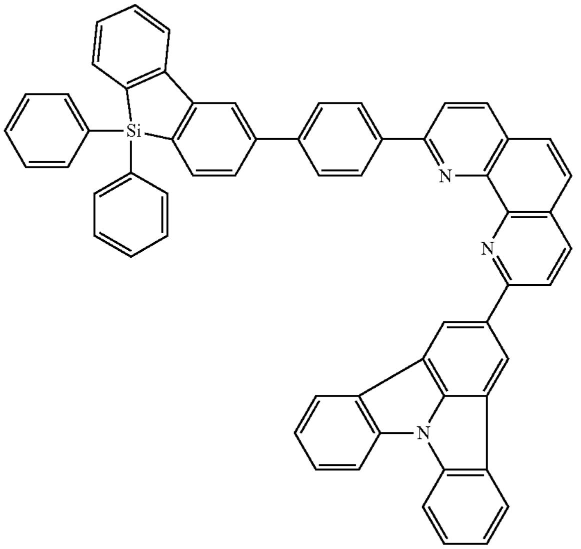
ET365
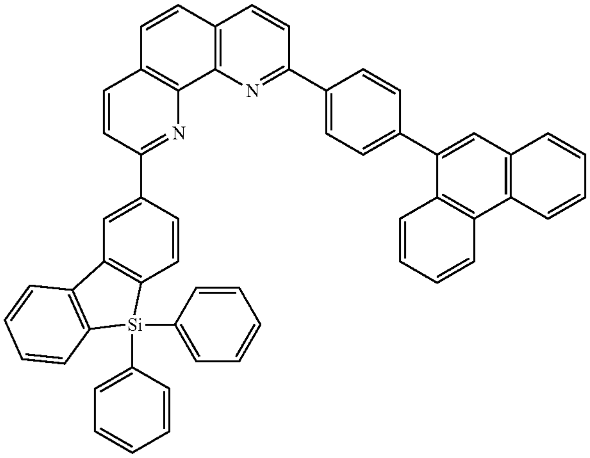
ET366
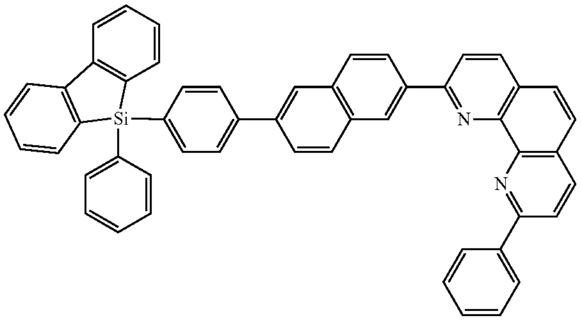
ET367
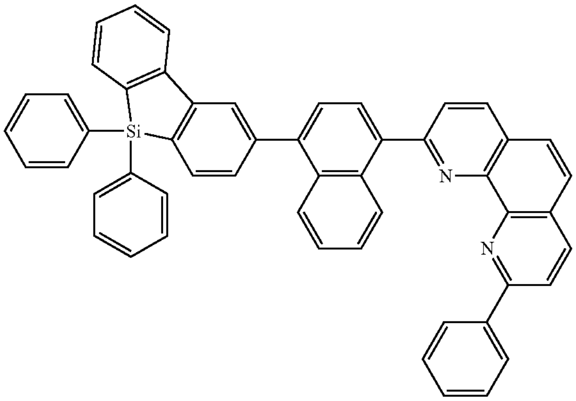

-continued
ET368
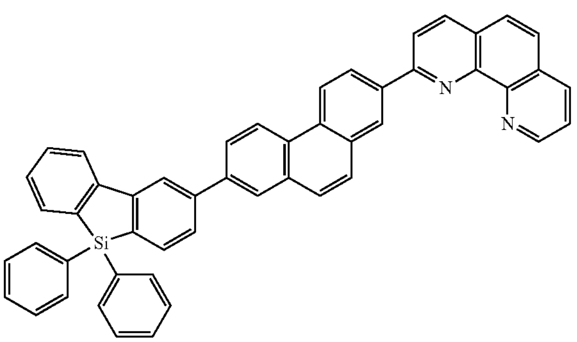
ET369
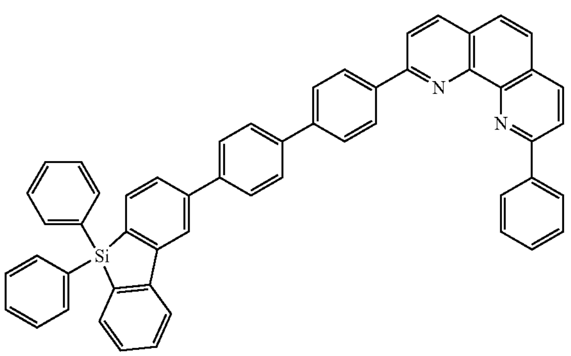
ET370
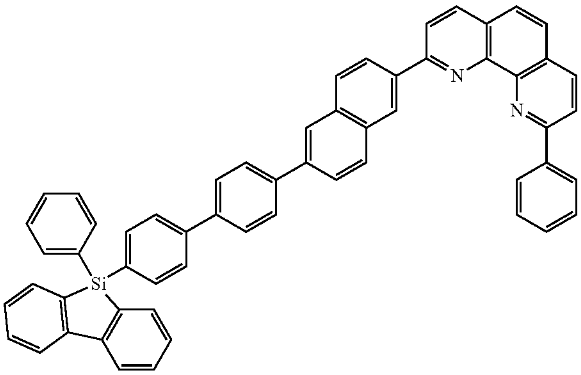
ET371
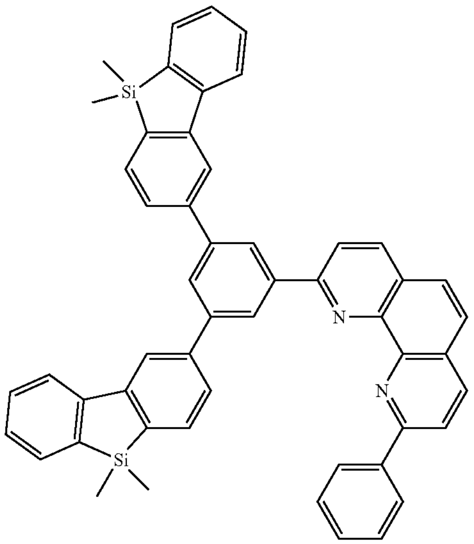
ET372
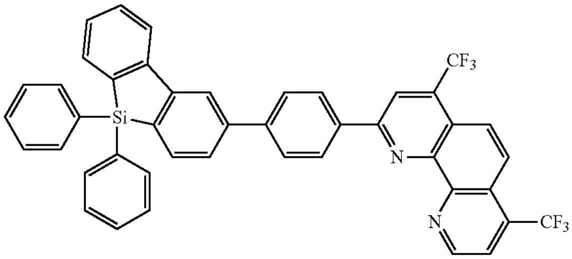
ET373
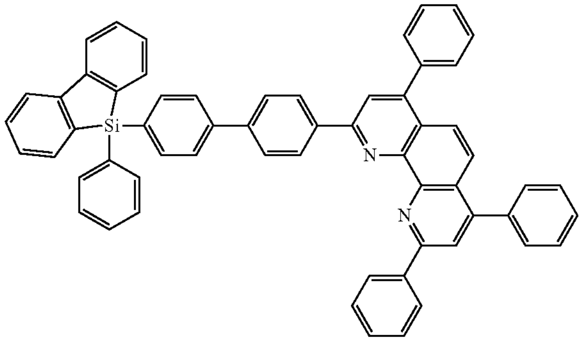
ET374
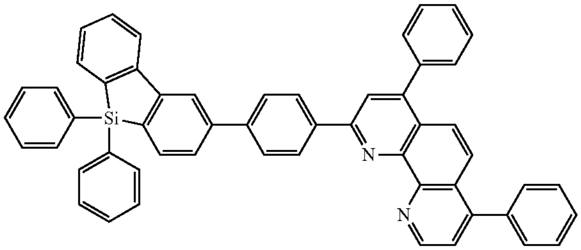
ET375
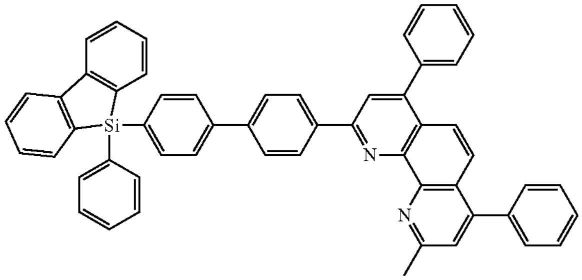

-continued
ET376
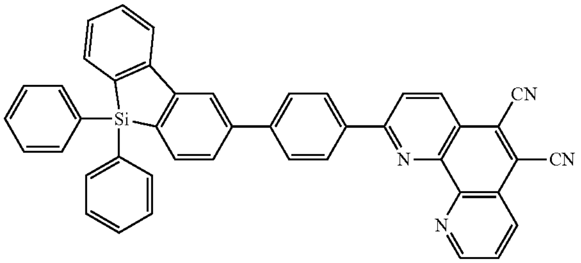
ET377
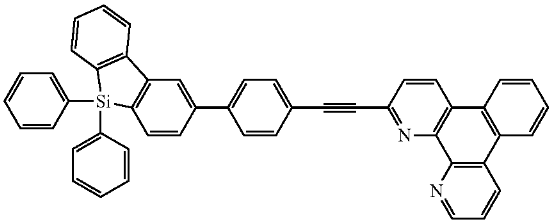
ET378
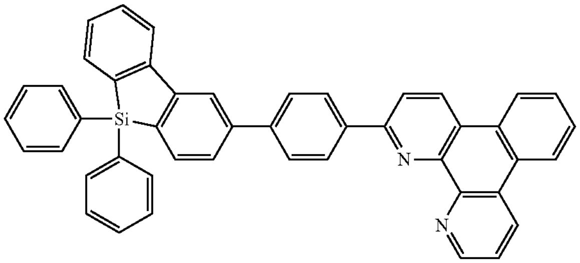
ET379
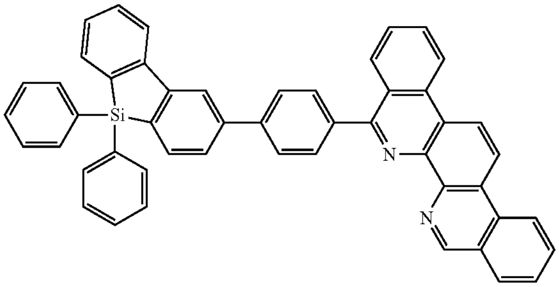
ET380
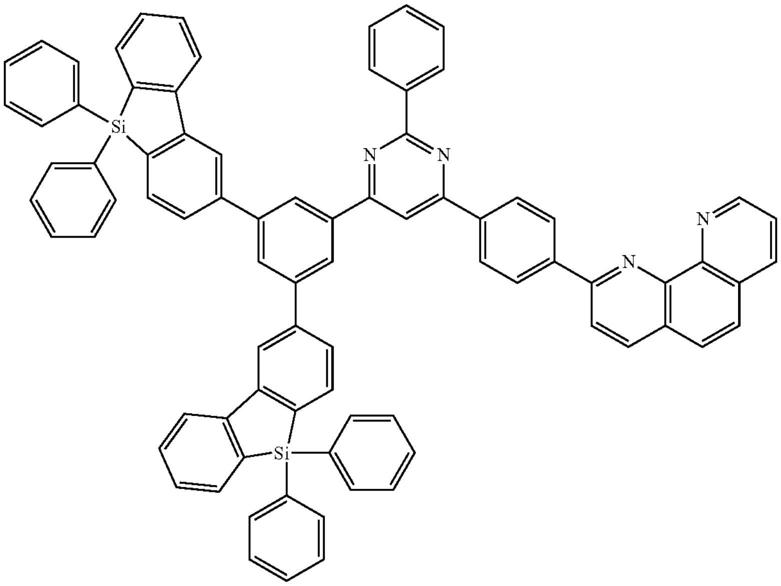
ET381
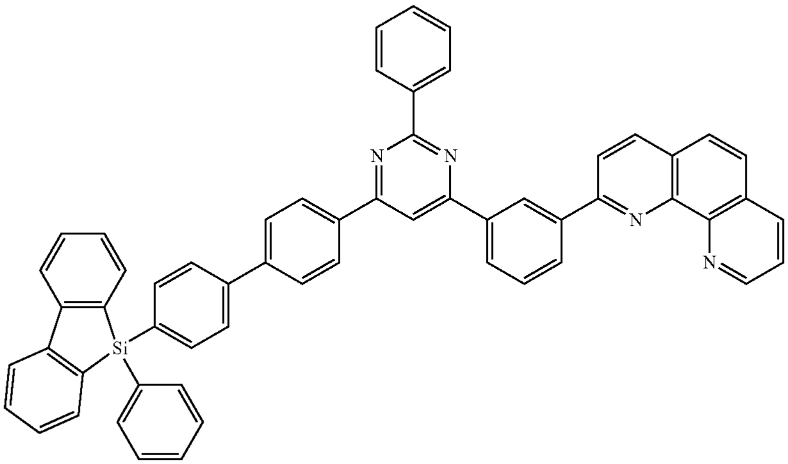

-continued

ET382

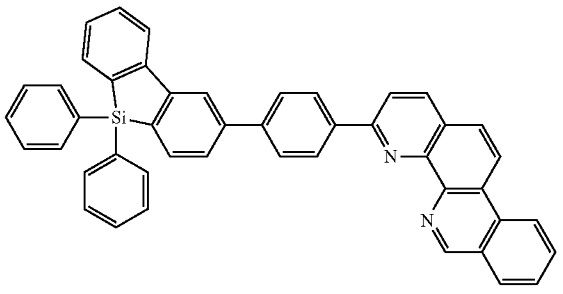

ET383

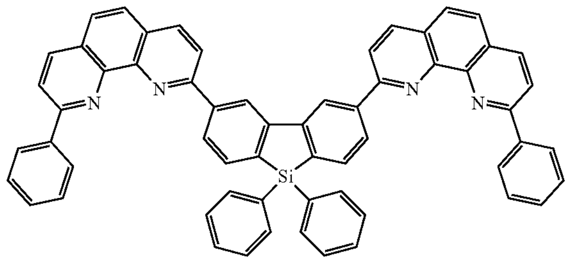

ET385

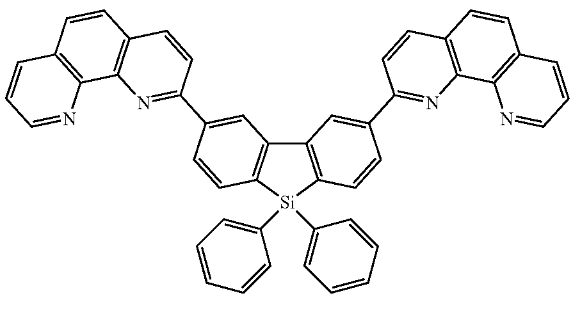

ET1013

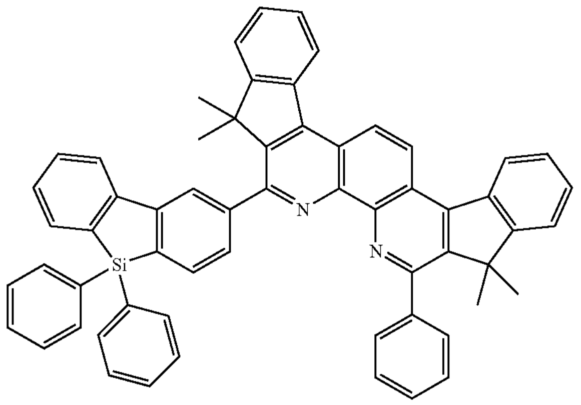

ET1014

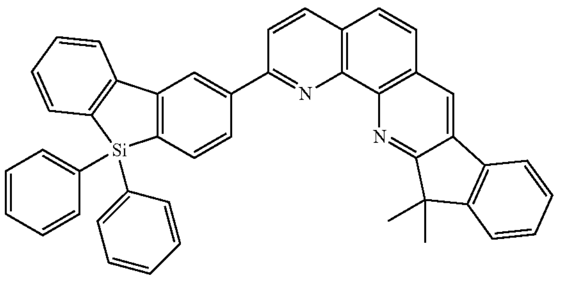

As described in the compounds ET1 to ET156, ET160 to ET385, and ET1001 to ET1014 among the compounds listed as the examples of the compound represented by the formula (1-7), $X^2$ to $X^8$ in the formula (1-7) representing the compound according to the exemplary embodiment are preferably $CR^X$. Further, as described in the compounds ET1 to ET156, ET160 to ET341, and ET1001 to ET1012, it is preferable that $X^2$ to $X^8$ are $CR^X$ and Z is an oxygen atom or a sulfur atom in the formula (1-7). Moreover, as described in the compounds ET1 to ET156, ET160 to ET172, and ET1001 to ET1006, it is more preferable that $X^2$ to $X^8$ are preferably $CR^X$ and Z is an oxygen atom in the formula (1-7).

Examples of the compound represented by the formula (1-8) are as follows.

ET157
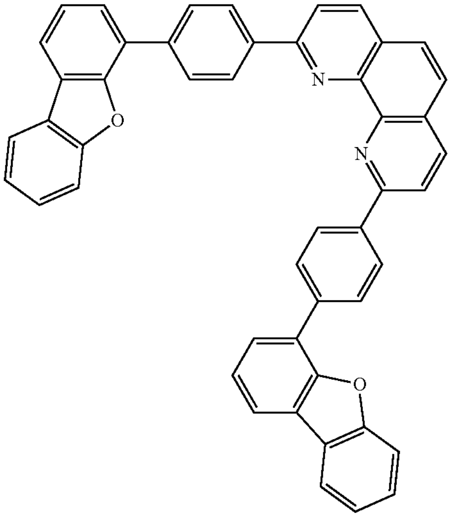
ET158
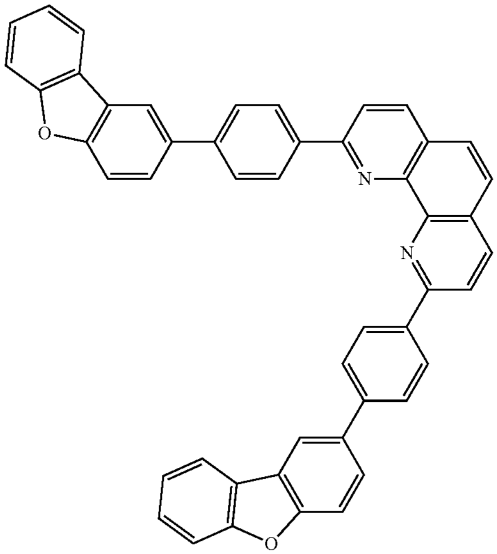
ET159
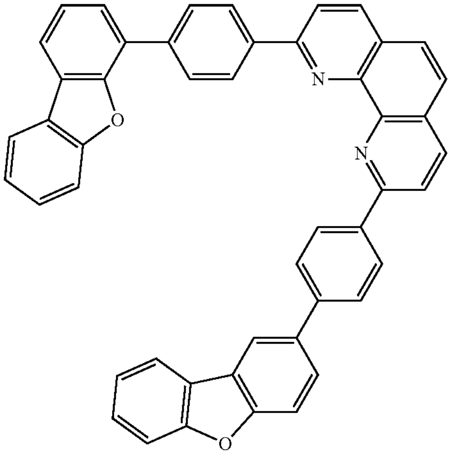
ET387
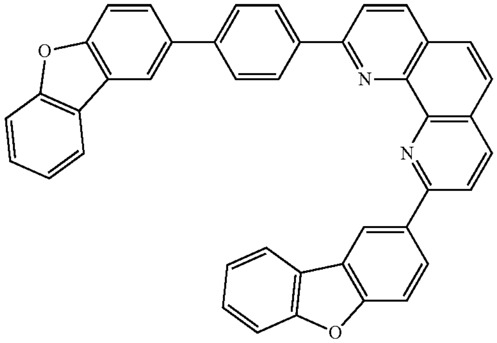
ET388
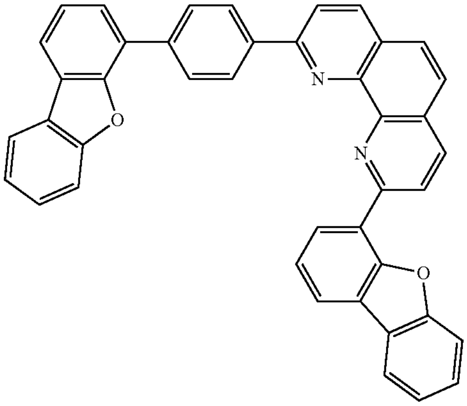
ET389
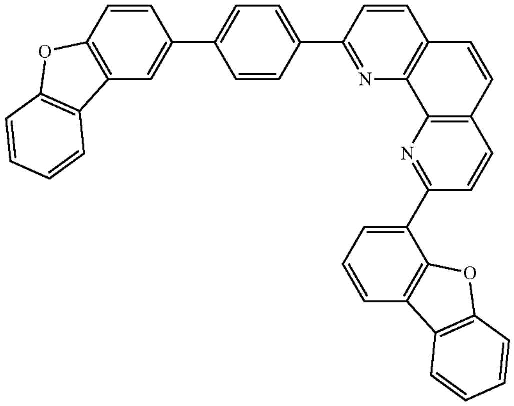

-continued
ET390
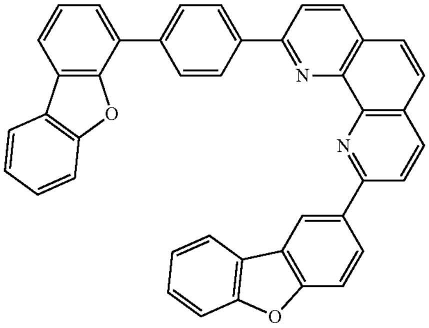
ET391
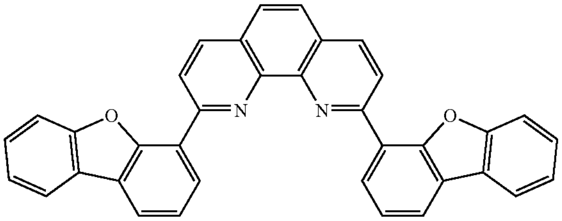
ET392
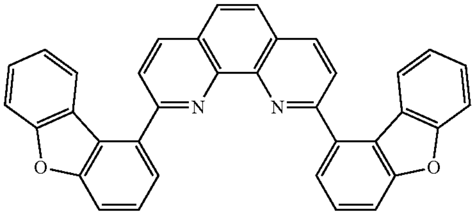
ET393
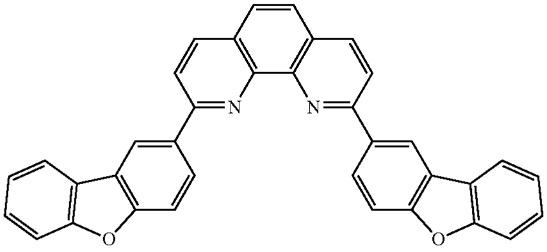
ET394
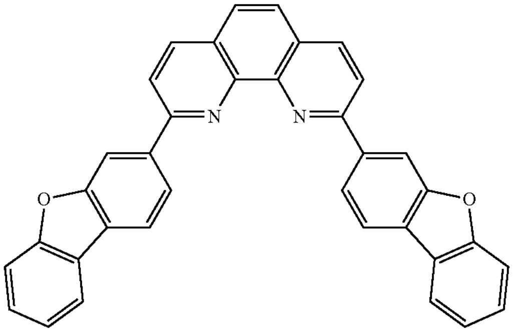
ET395
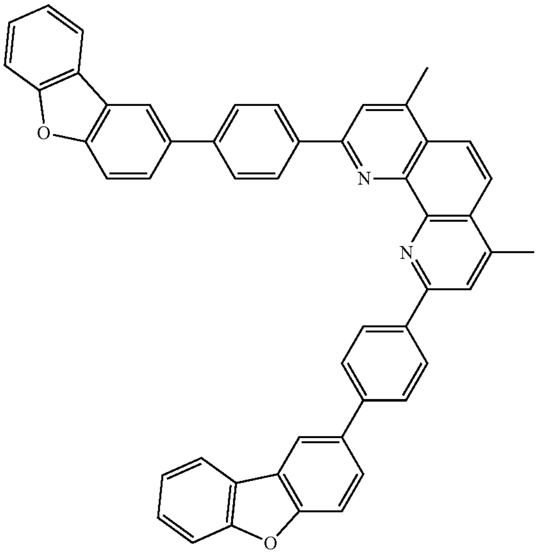

-continued
ET396
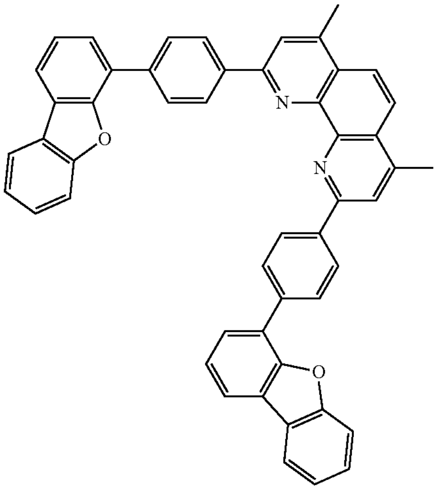
ET397
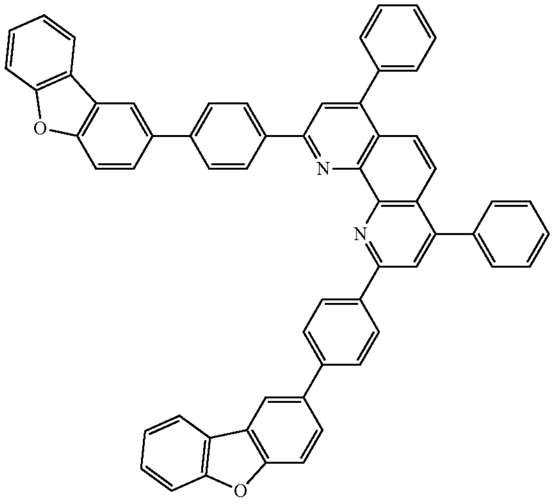
ET398
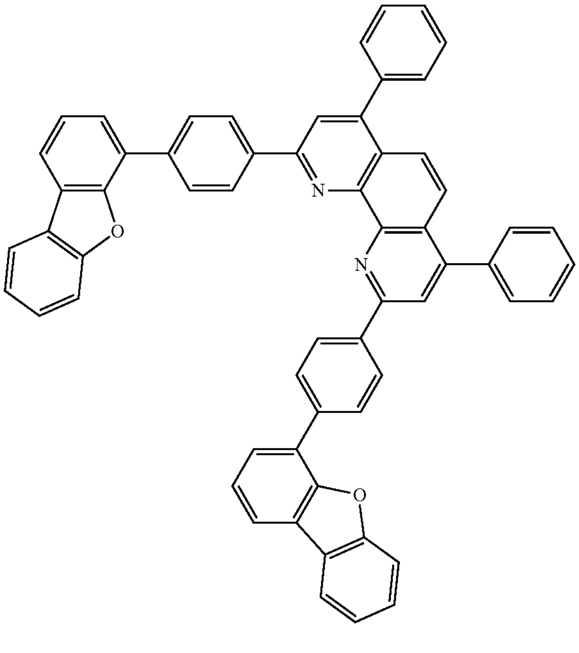

-continued
ET399
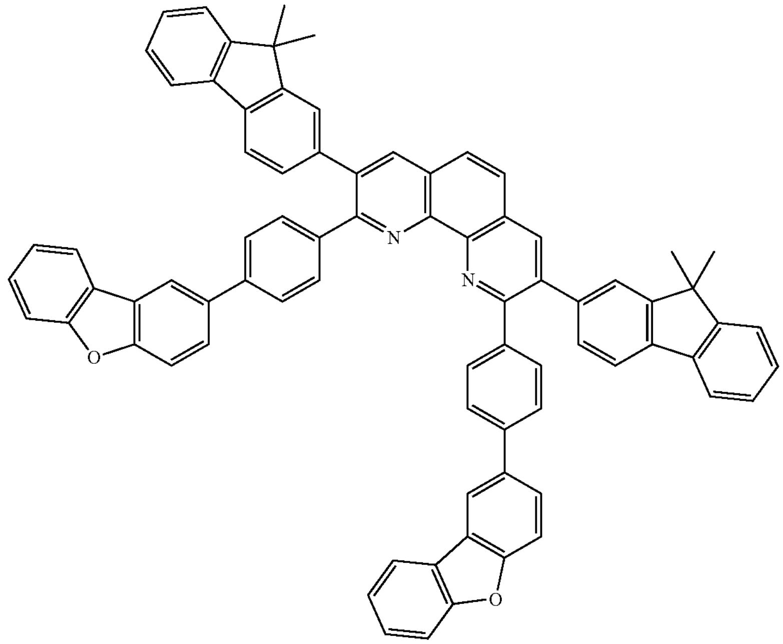
ET400
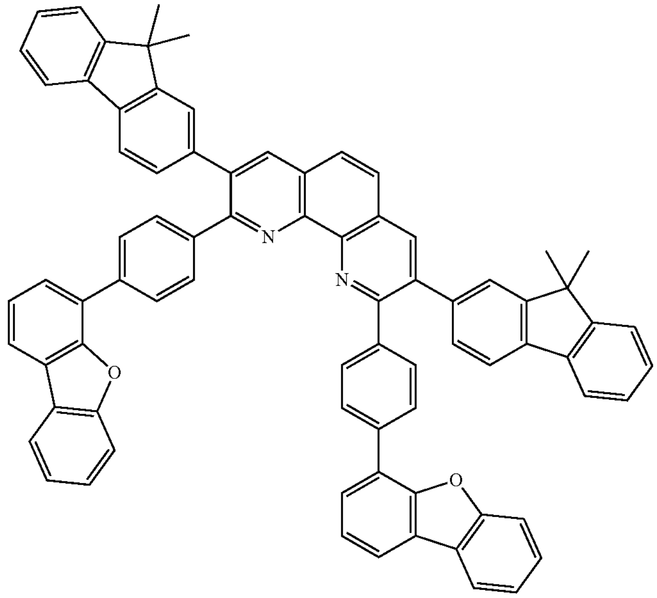

-continued
ET401
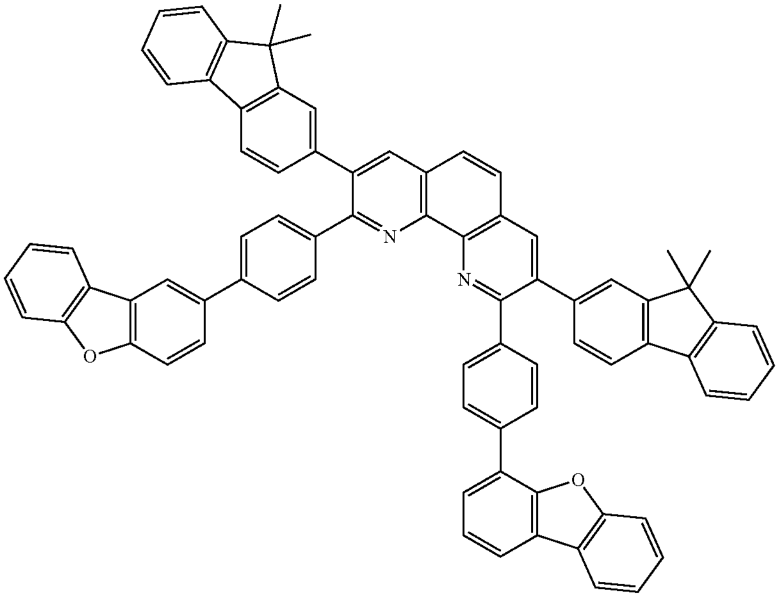
ET402
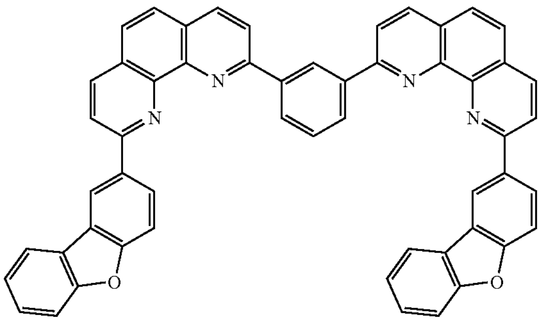
ET403
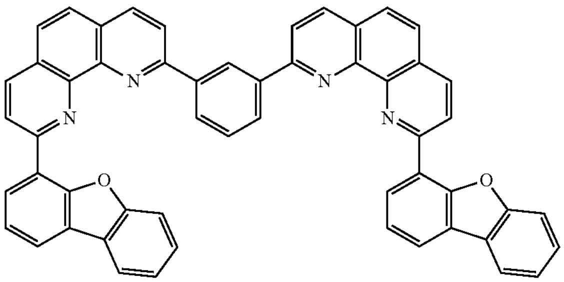
ET404
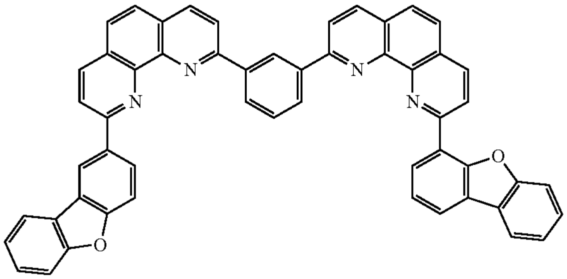
ET405
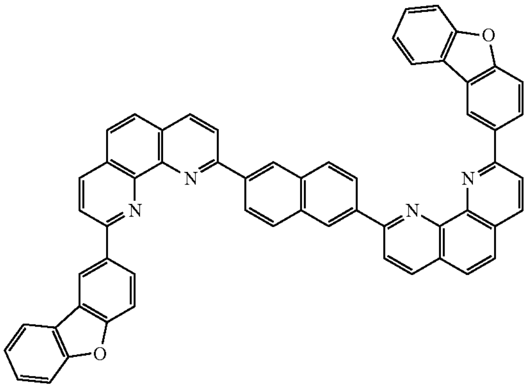

-continued
ET406
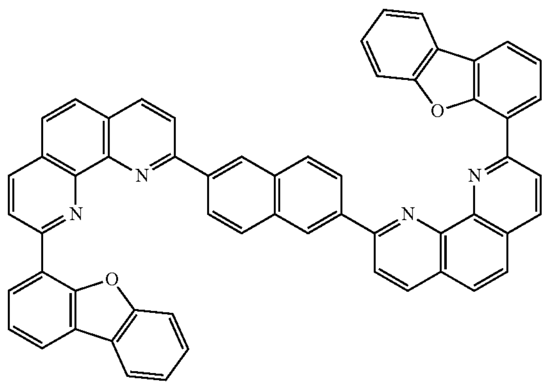
ET407
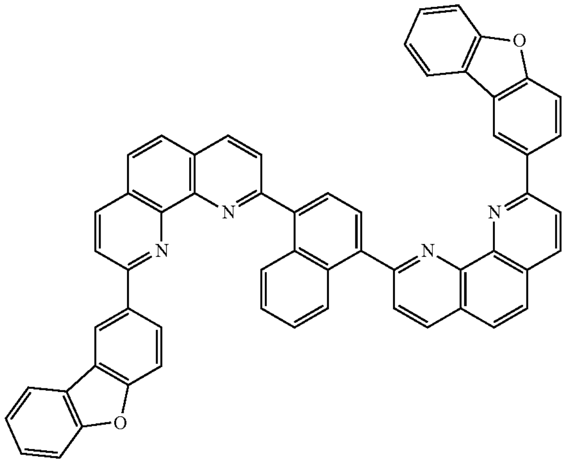
ET408
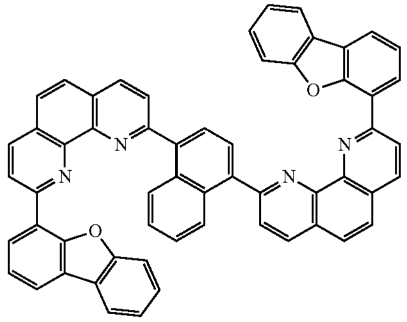
ET409
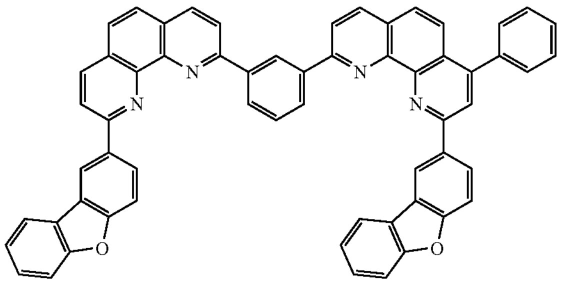
ET410
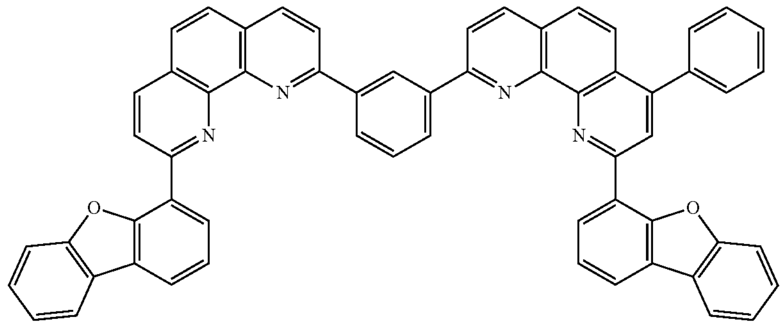
ET411
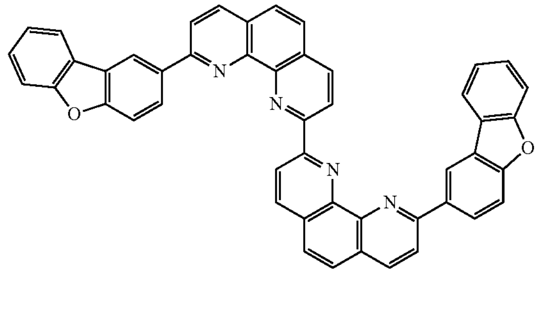
ET412
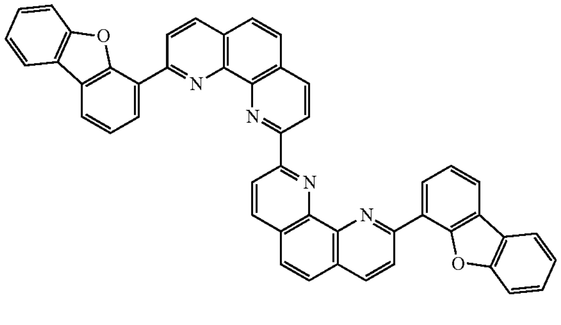

-continued
ET413
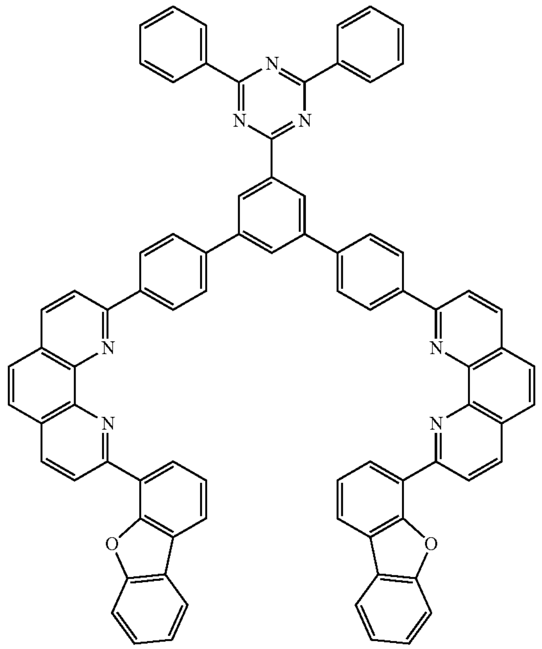
ET414
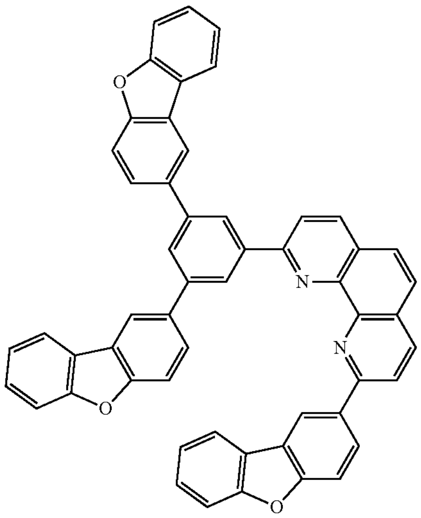
ET415
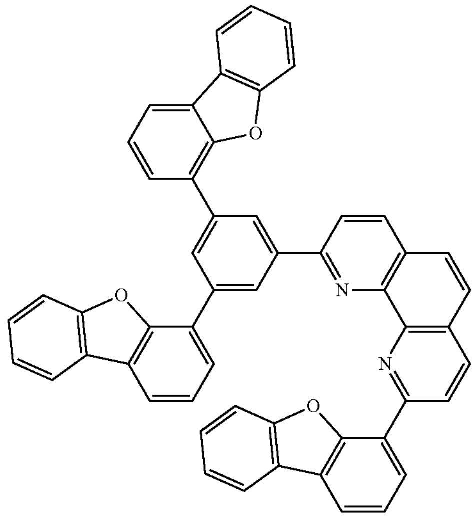
ET416
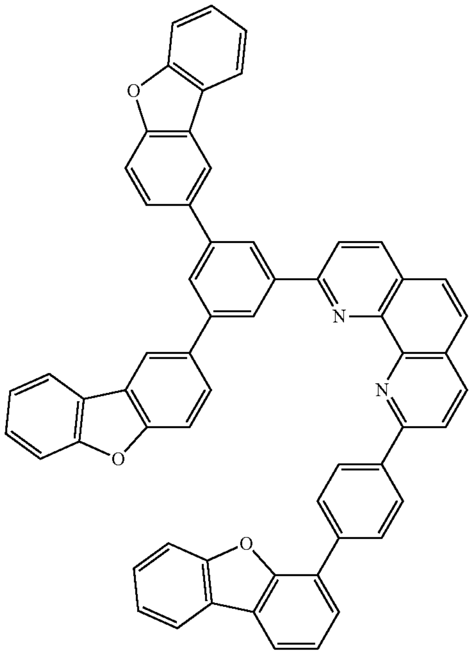

-continued
ET417
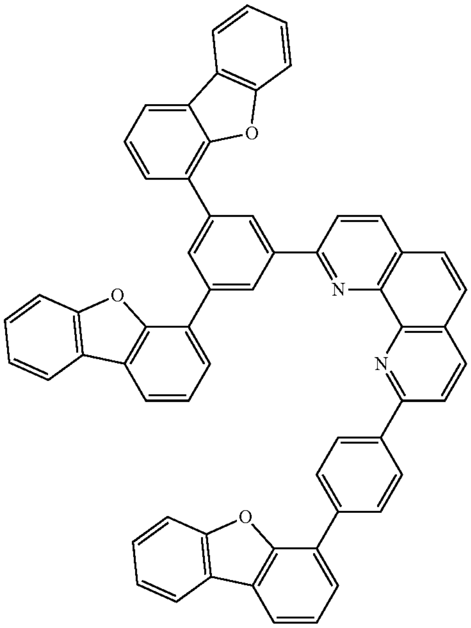
ET418
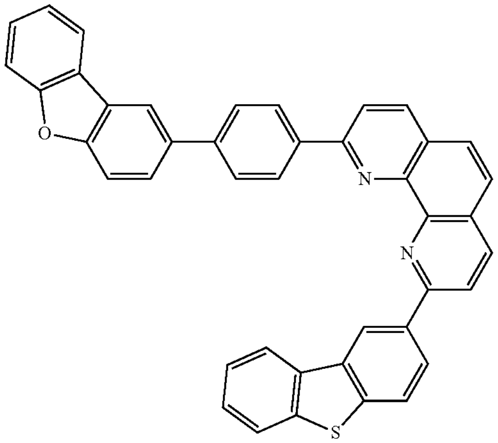
ET419
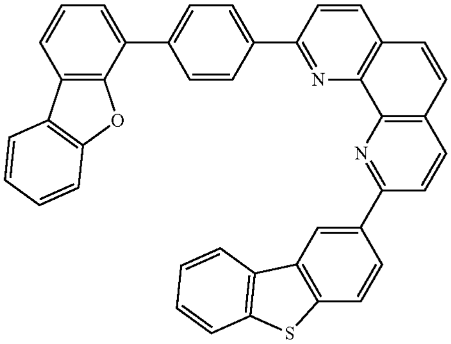
ET420
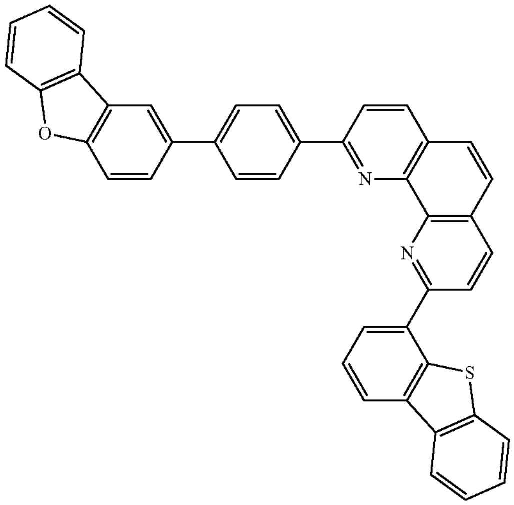
ET421
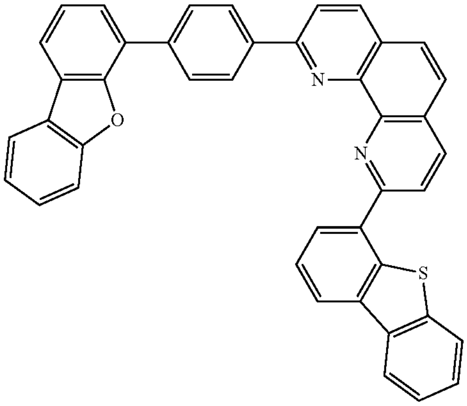
ET422
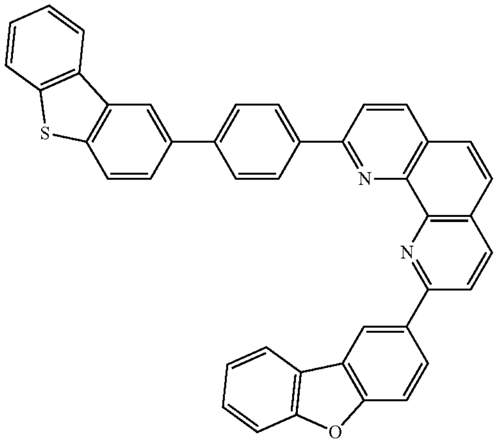

-continued
ET423
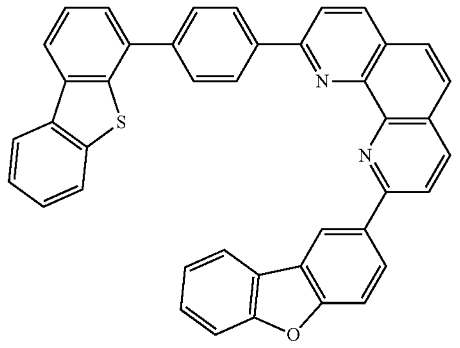
ET424
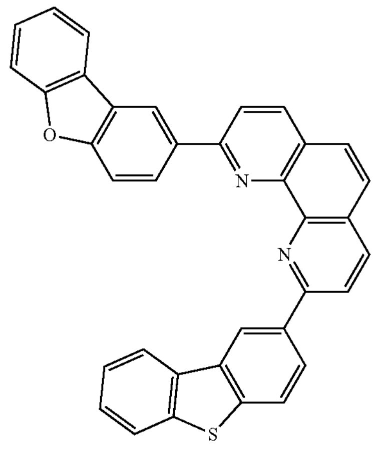
ET425
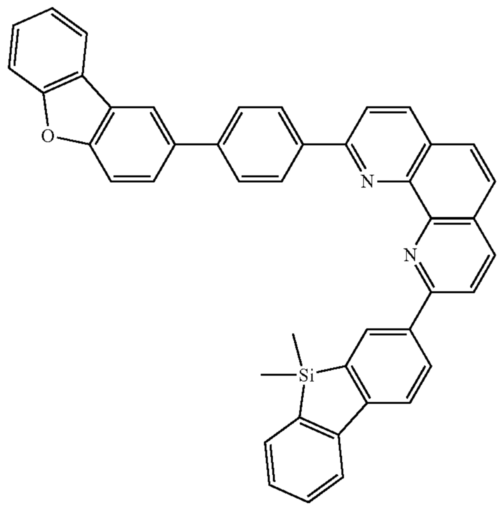
ET426
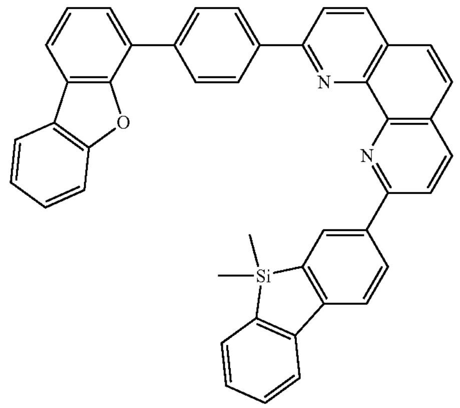
ET427
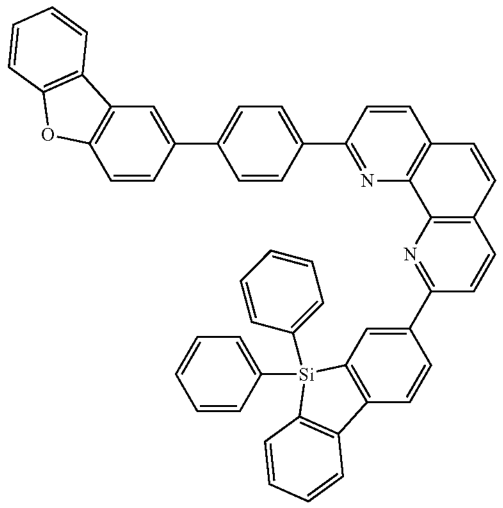
ET428
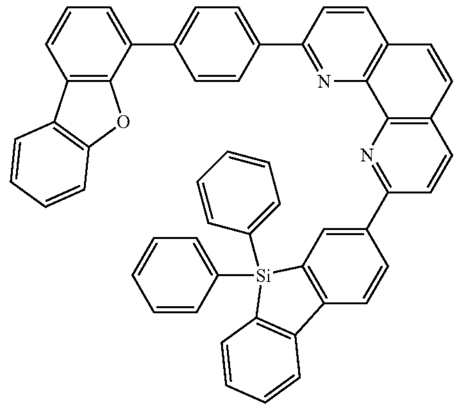

-continued
ET429
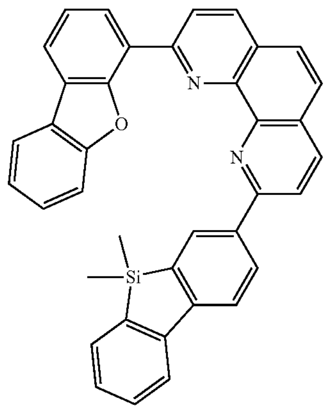
ET430
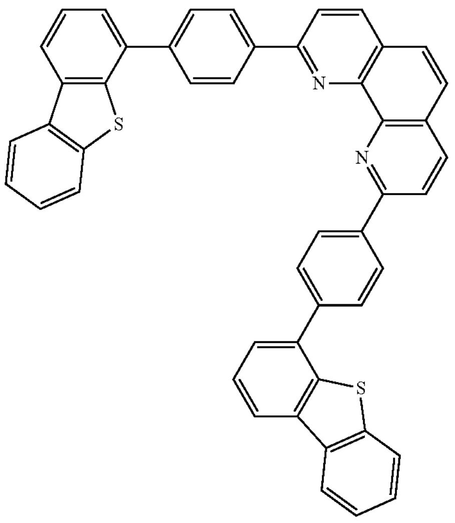
ET431
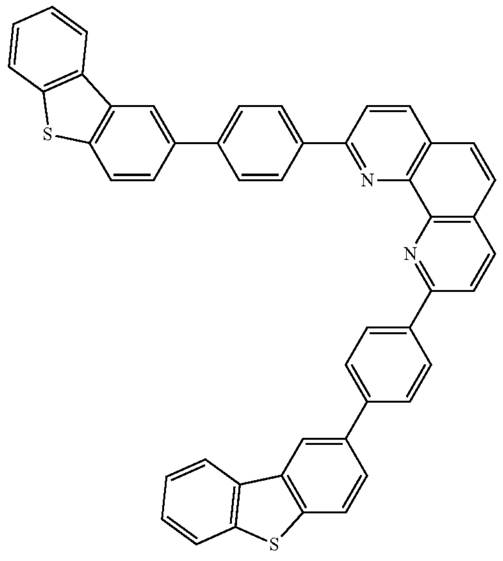
ET432
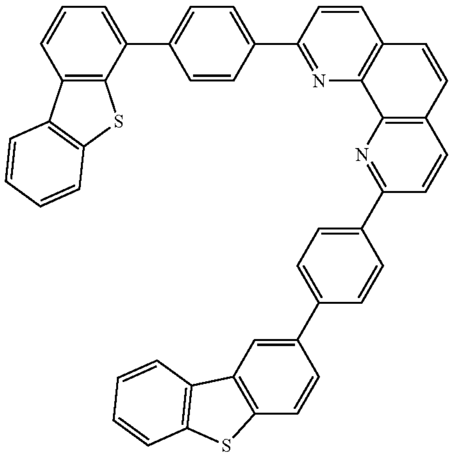
ET433
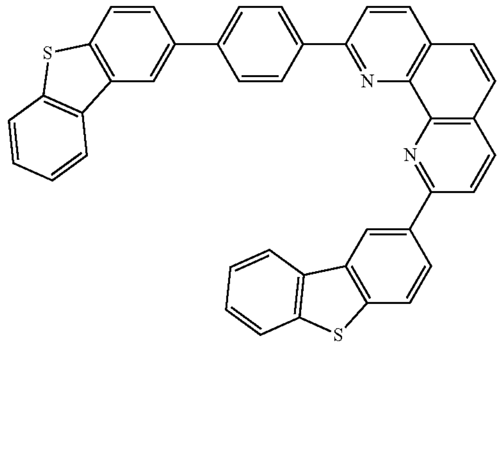
ET434
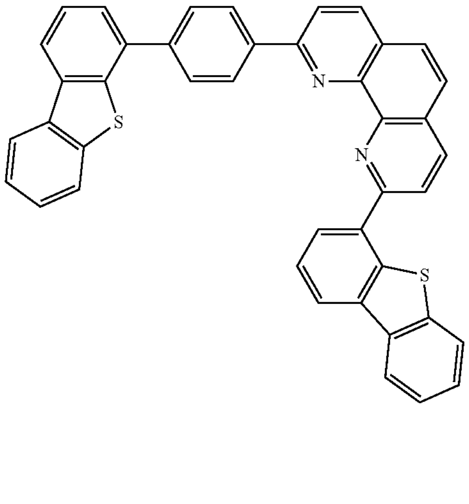

-continued
ET435
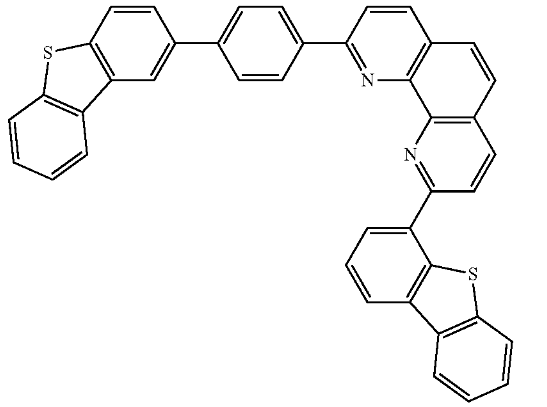
ET436
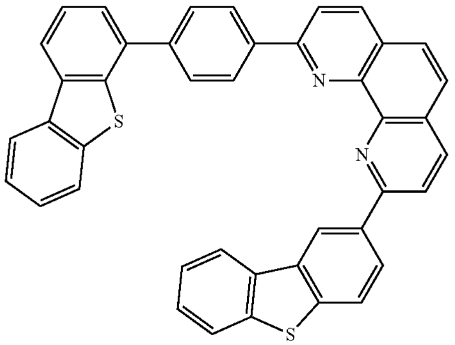
ET437
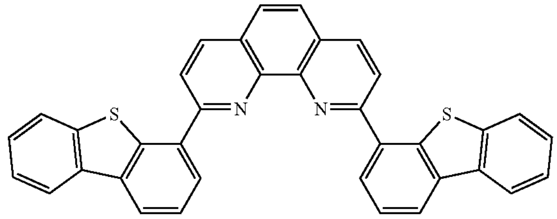
ET438
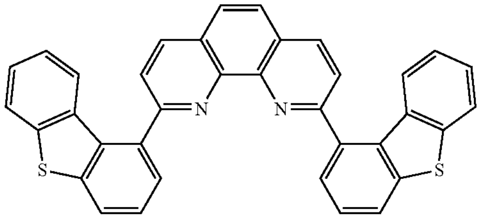
ET439
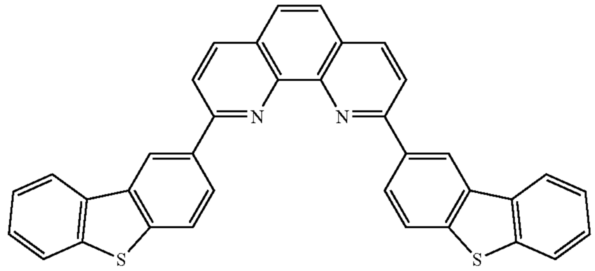
ET440
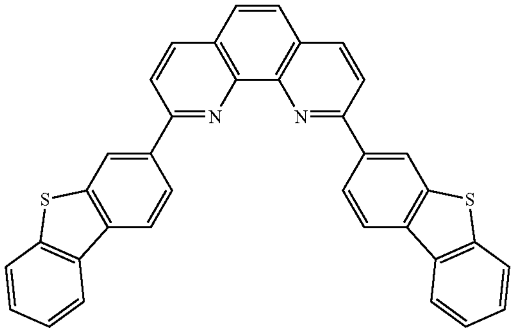
ET441
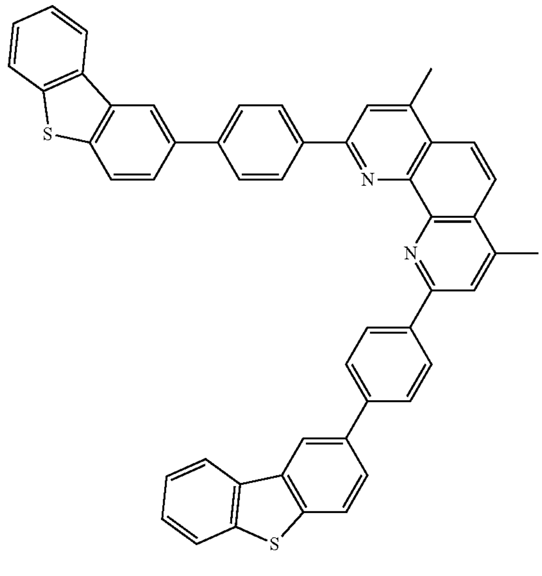
ET442
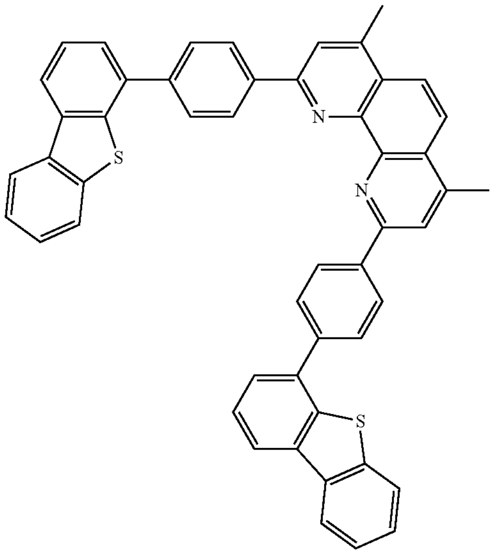

-continued
ET443
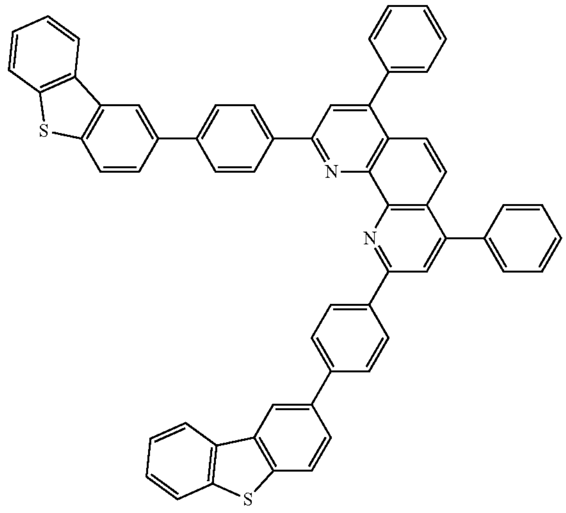
ET444
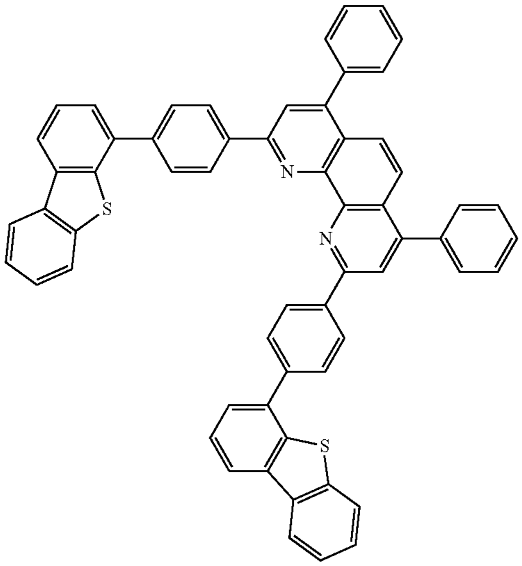
ET445
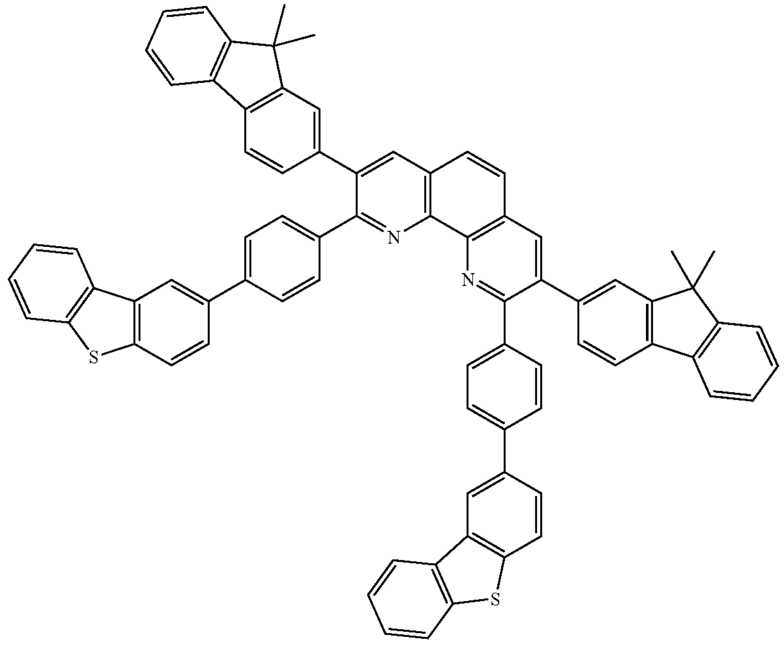

-continued
ET446
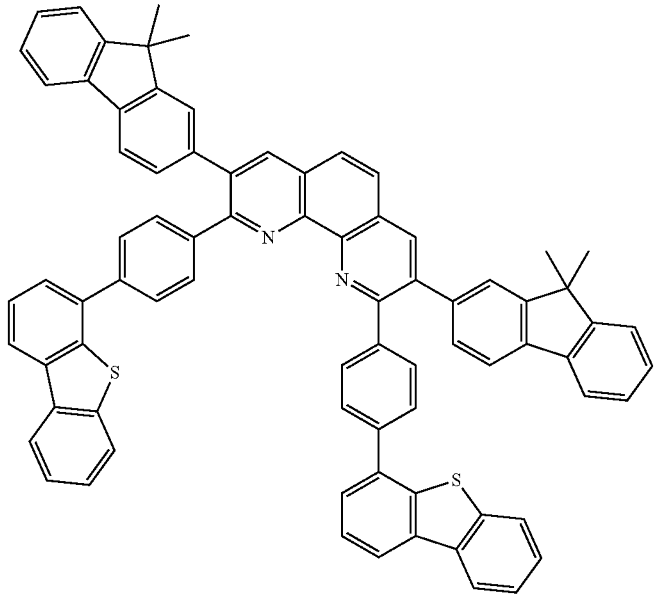
ET447
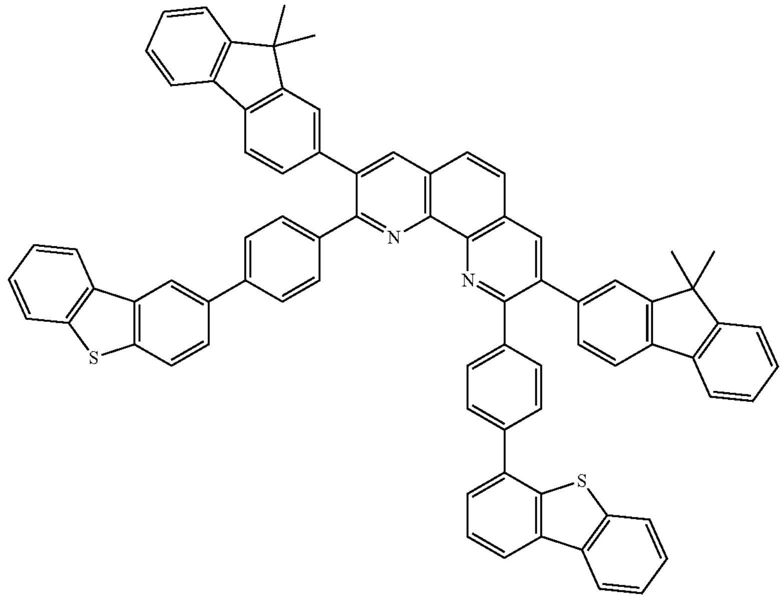
ET448
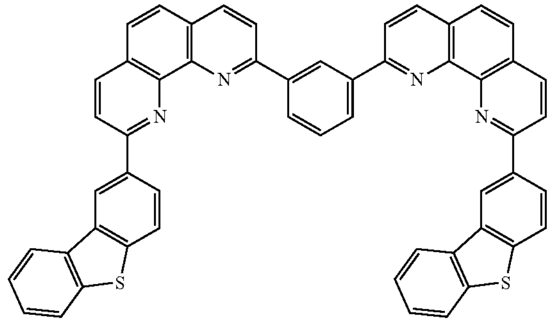
ET449
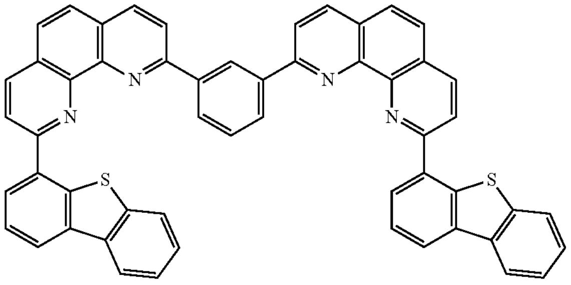

-continued
ET450
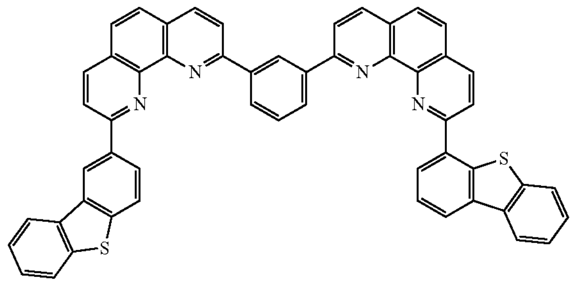
ET451
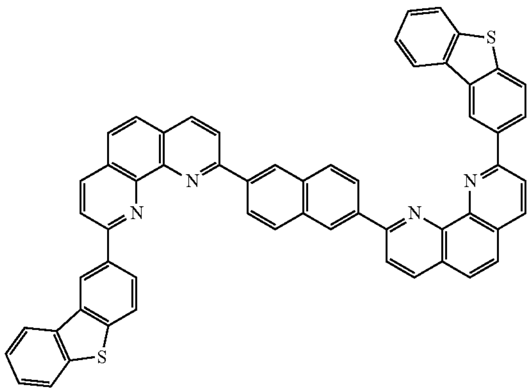
ET452
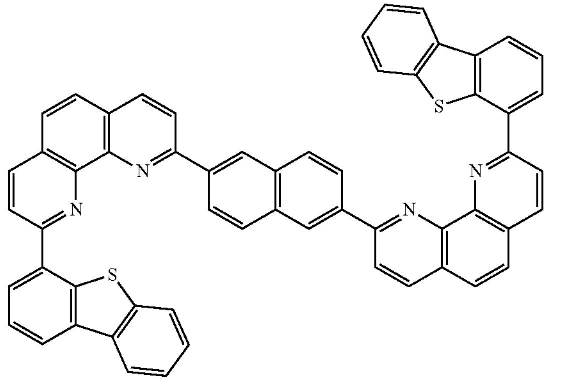
ET453
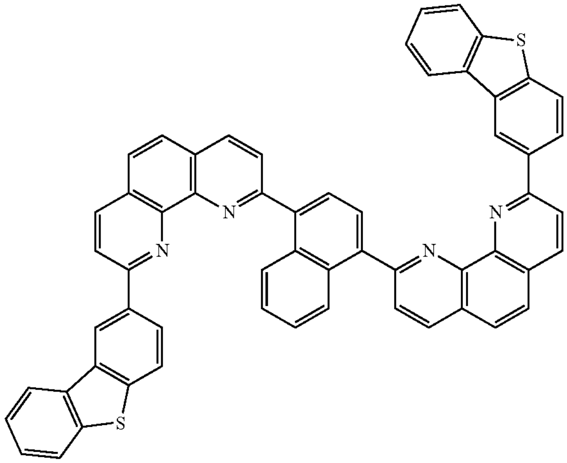
ET454
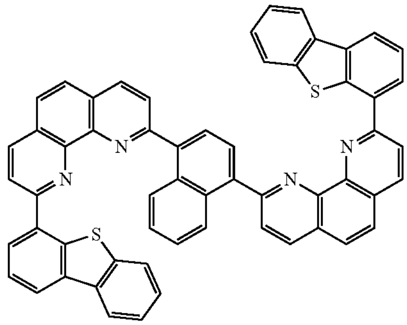
ET455
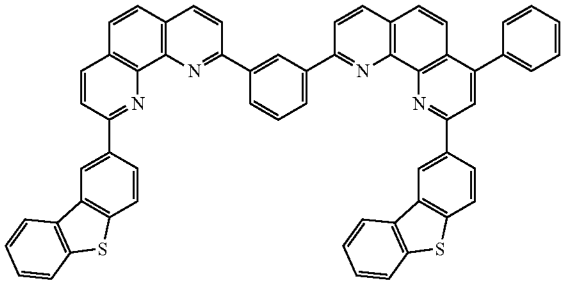
ET456
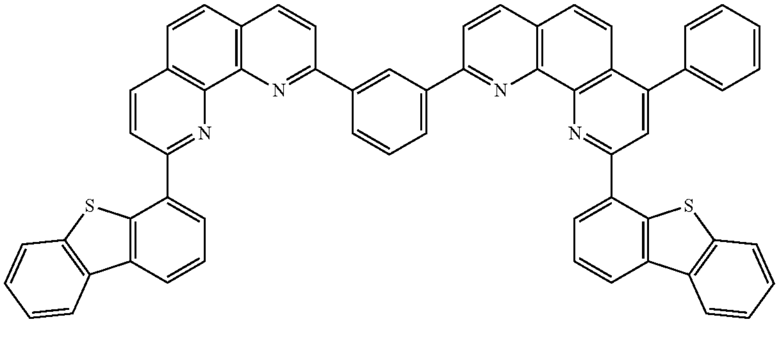

-continued
ET457
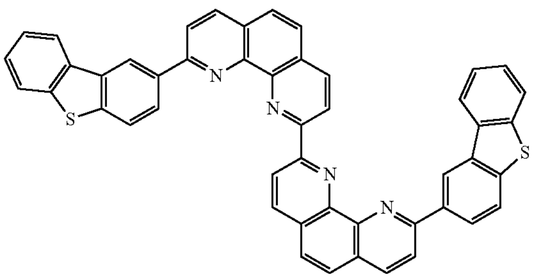
ET458
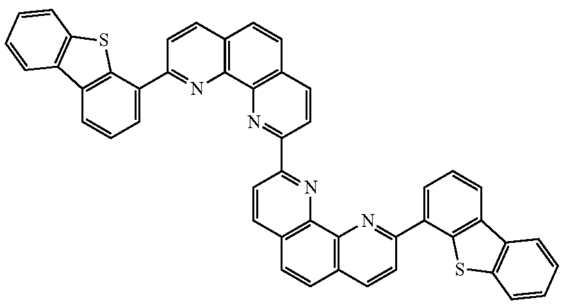
ET459
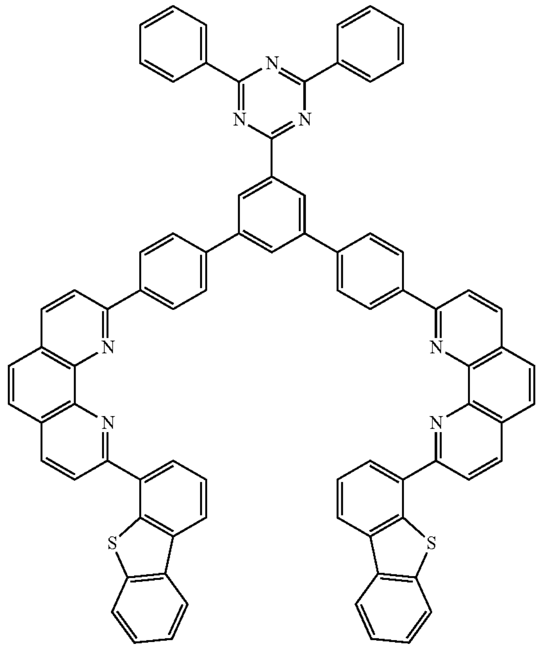
ET460
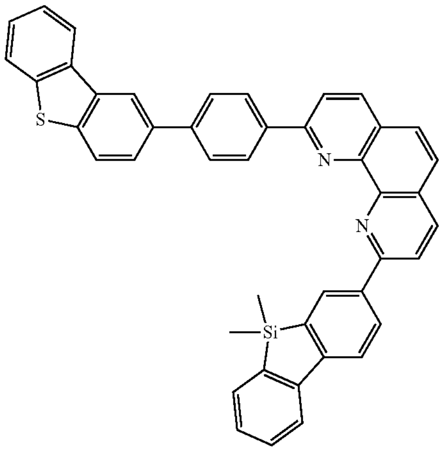
ET461
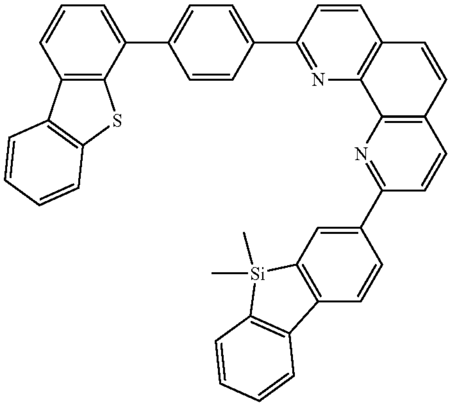
ET462
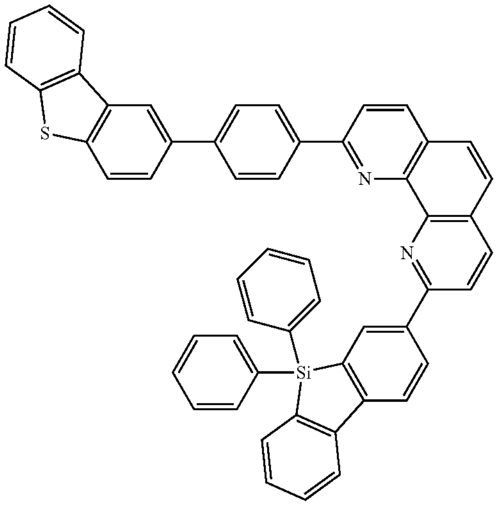

-continued
ET463
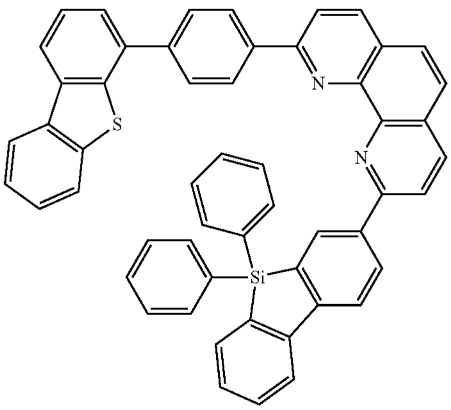
ET464
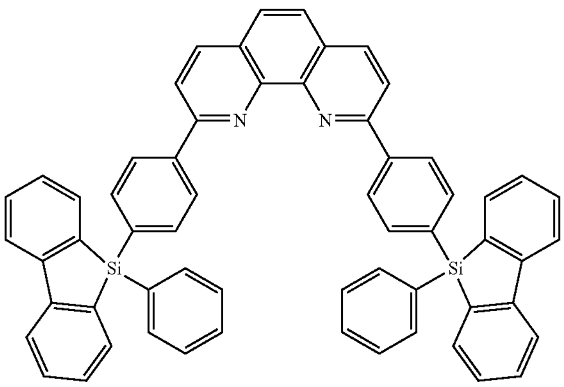
ET465
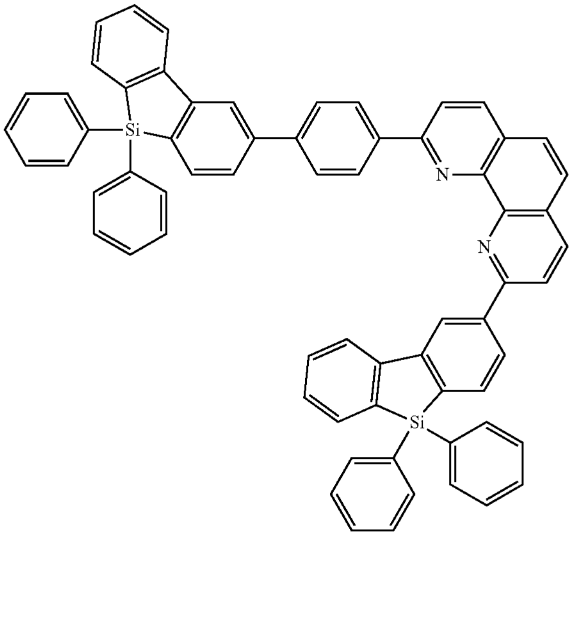
ET466
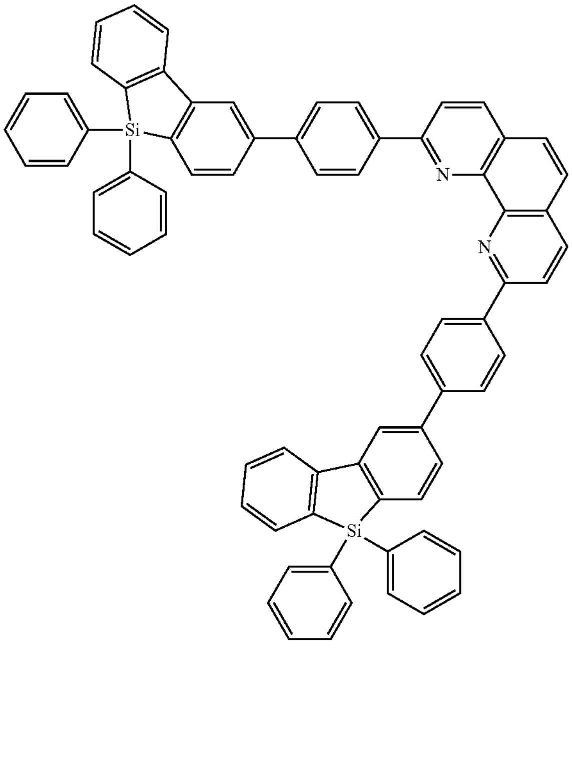

-continued
ET467
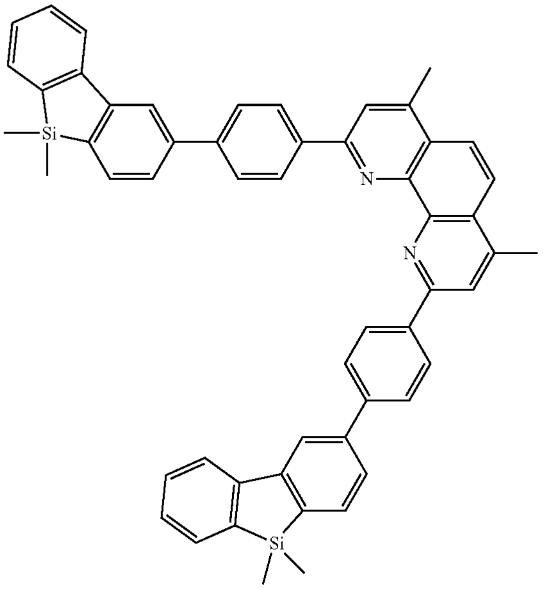
ET468
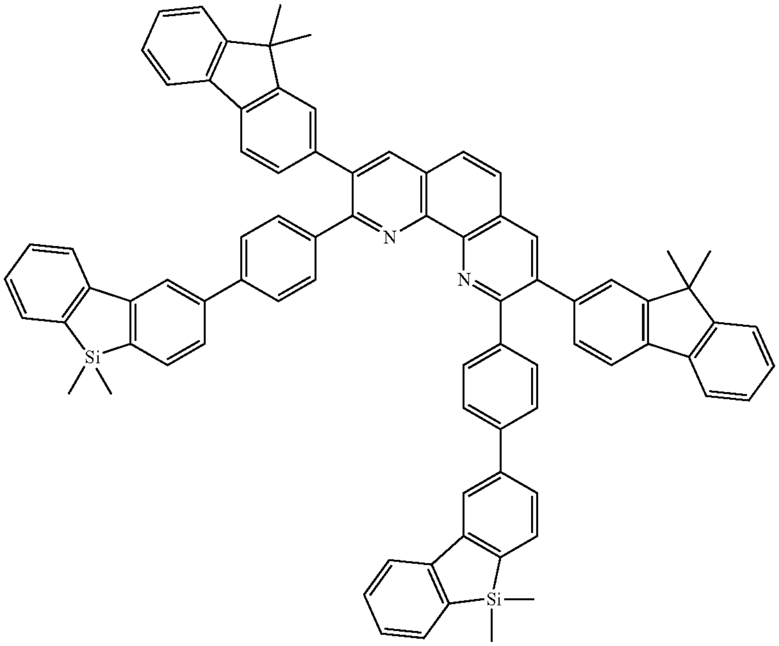
ET469
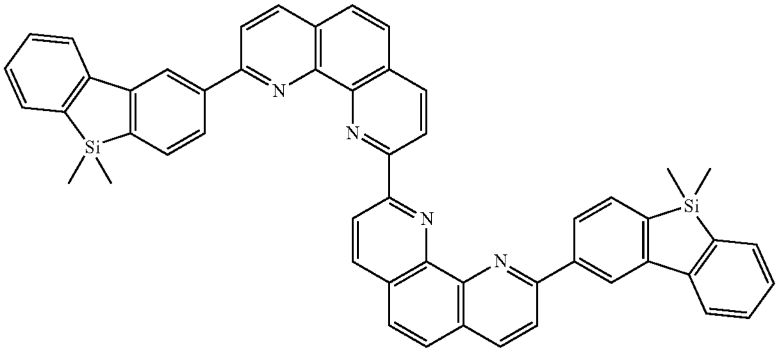

-continued

ET470

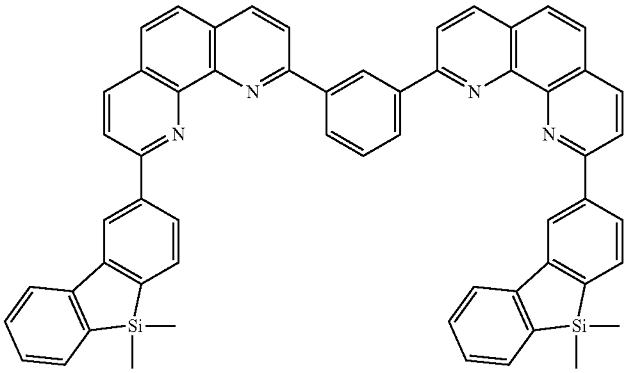

As described in the compounds ET157 to ET159 and ET387 to ET470 among the compounds listed as the examples of the compound represented by the formula (1-8), $X^2$ to $X^7$ in the formula (1-8) representing the compound according to the exemplary embodiment are preferably $CR^X$. Further, as described in the compounds ET157 to ET159, ET387 to ET424, and ET430 to ET459, it is preferable that $X^2$ to $X^7$ are $CR^X$ and Z is an oxygen atom or a sulfur atom in the formula (1-8). Moreover, as described in the compounds ET157 to ET159 and ET387 to ET417, it is more preferable that $X^2$ to $X^7$ are preferably $CR^X$ and Z is an oxygen atom in the formula (1-7).

Examples of the compound represented by the formula (1-9) are as follows.

ET471

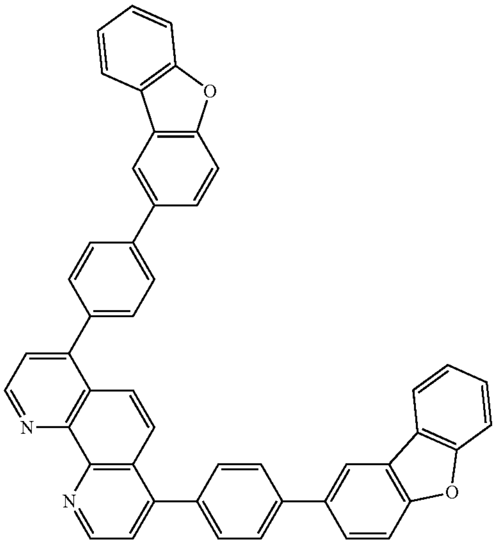

-continued

ET472

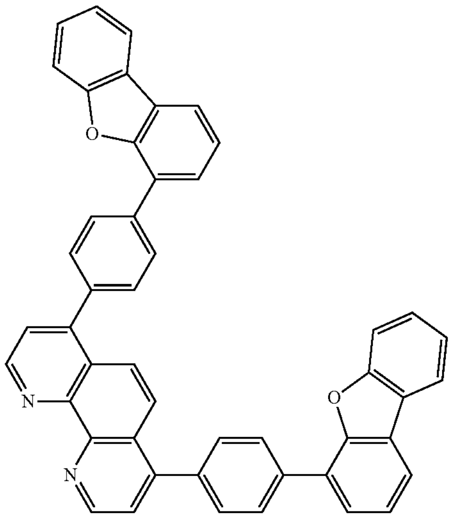

ET473

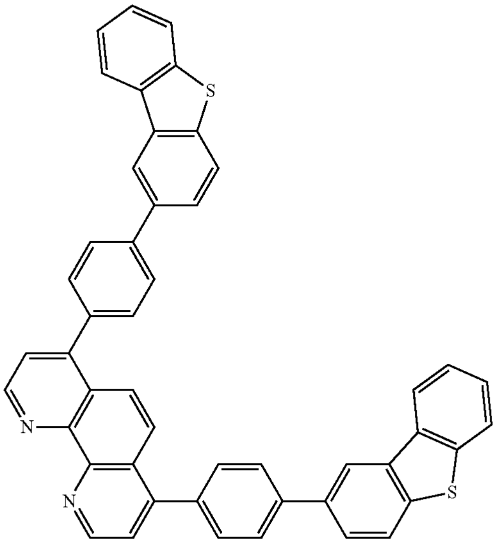

-continued

ET474

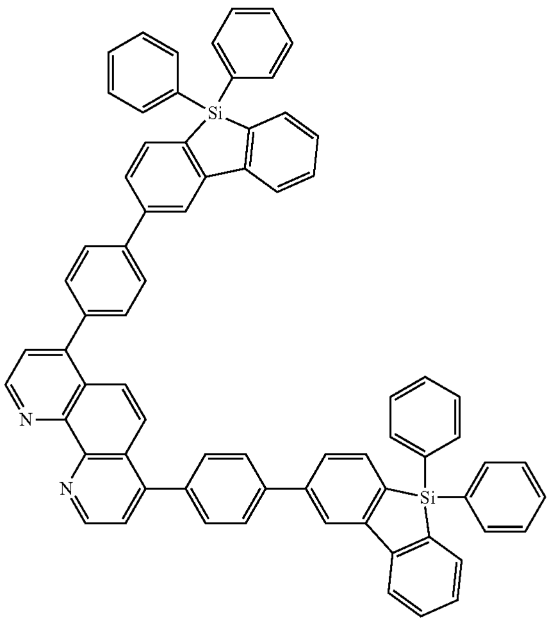

As described in the compounds ET471 to ET474 among the compounds listed as the examples of the compound represented by the formula (1-9), $X^1$, $X^2$, $X^4$, $X^5$, $X^7$ and $X^8$ in the formula (1-9) representing the compound according to the exemplary embodiment are preferably $CR^X$. Further, as described in the compounds ET471 to ET473, it is preferable that $X^1$, $X^2$, $X^4$, $X^5$, $X^7$ and $X^8$ are $CR^X$ and Z is an oxygen atom or a sulfur atom in the formula (1-9). Moreover, as described in the compounds ET471 to ET472, it is more preferable that $X^1$, $X^2$, $X^4$, $X^5$, $X^7$ and $X^8$ are $CR^X$ and Z is an oxygen atom in the formula (1-9).

Examples of the compound represented by the formula (1-10) are as follows.

ET475

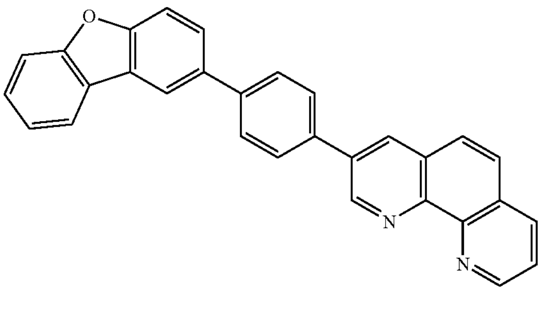

-continued

ET476

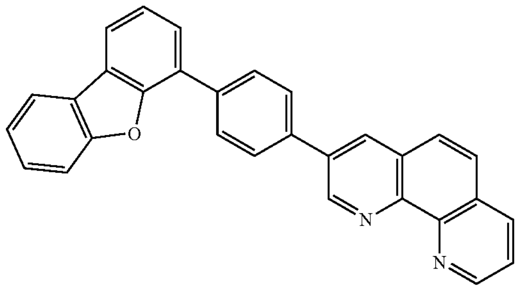

ET477

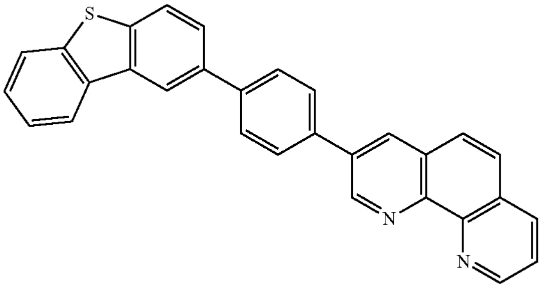

ET478

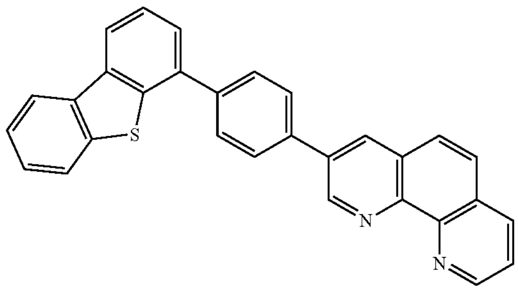

ET479

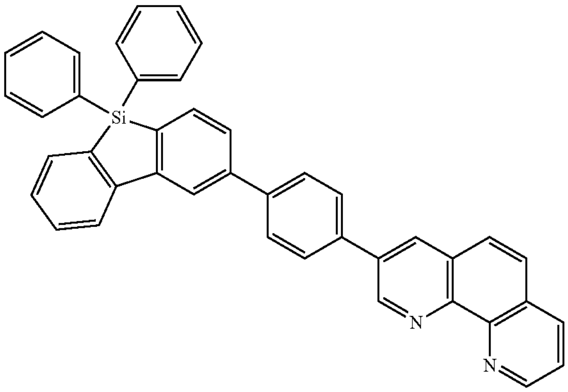

As described in the compounds ET475 to ET479 among the compounds listed as the examples of the compound represented by the formula (1-10), $X^1$ and $X^3$ to $X^8$ in the formula (1-10) representing the compound according to the exemplary embodiment are preferably $CR^X$. Further, as described in the compounds ET475 to ET478, it is preferable that $X^1$and $X^3$ to $X^8$ are $CR^X$ and Z is an oxygen atom or a sulfur atom in the formula (1-10).Moreover, as described in the compounds ET475 to ET476, it is more preferable that $X^1$ and $X^3$ to $X^8$ are $CR^X$ and Z is an oxygen atom in the formula (1-10).

Examples of the compound represented by the formula (1-11) are as follows.
ET480
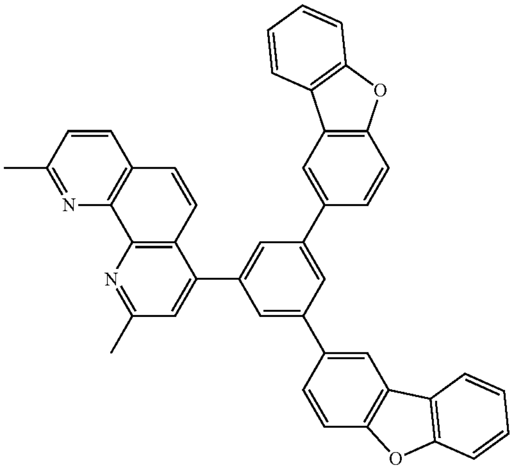
ET481
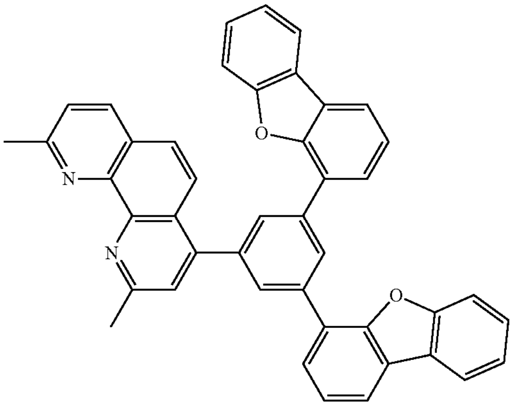
ET482
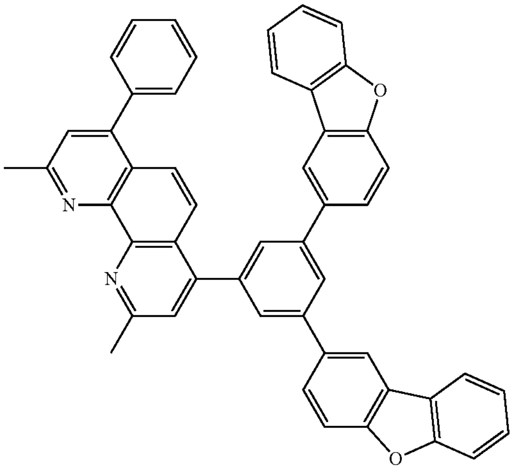
ET483
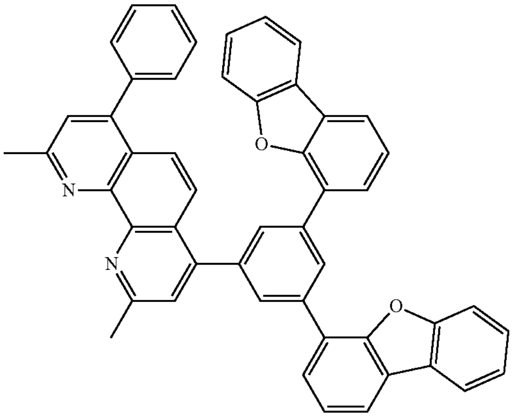
ET484
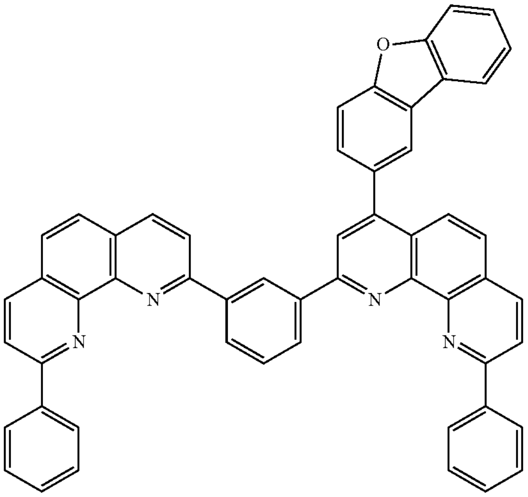
ET485
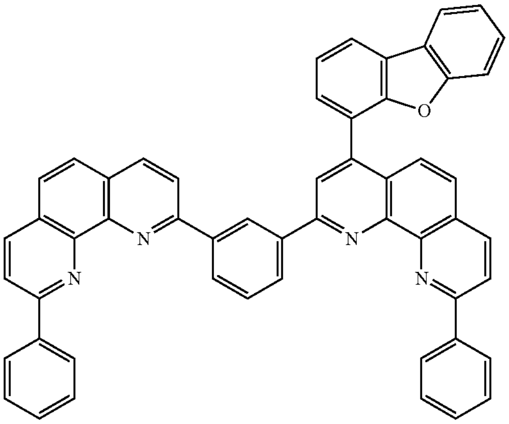

-continued
ET486
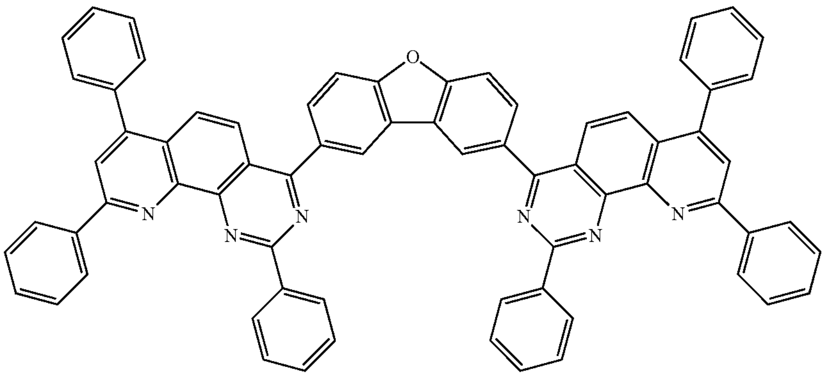
ET487
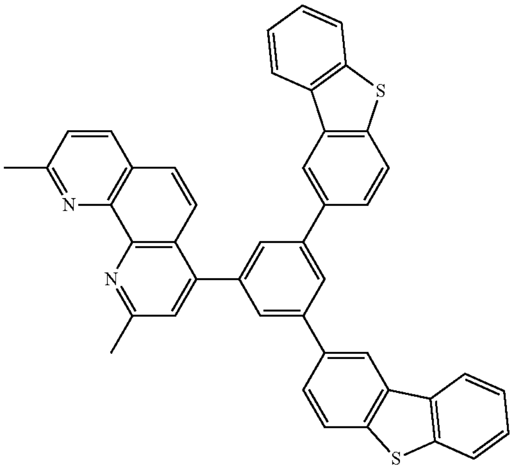
ET488
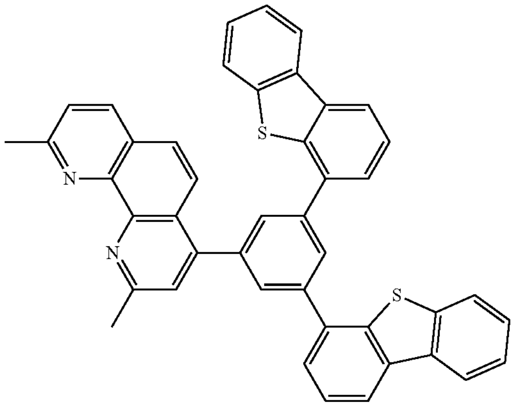
ET489
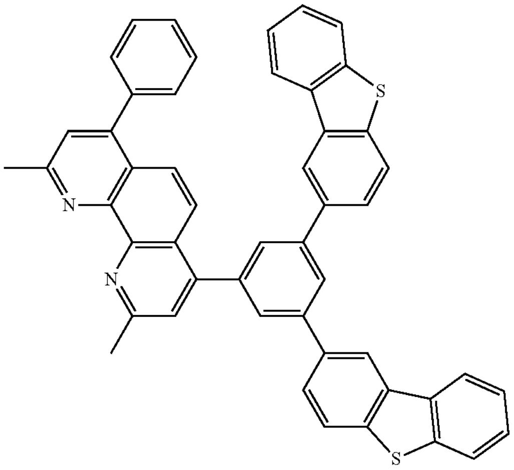
ET490
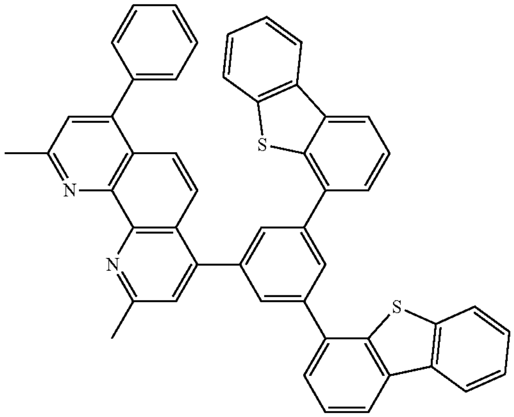

-continued

ET491

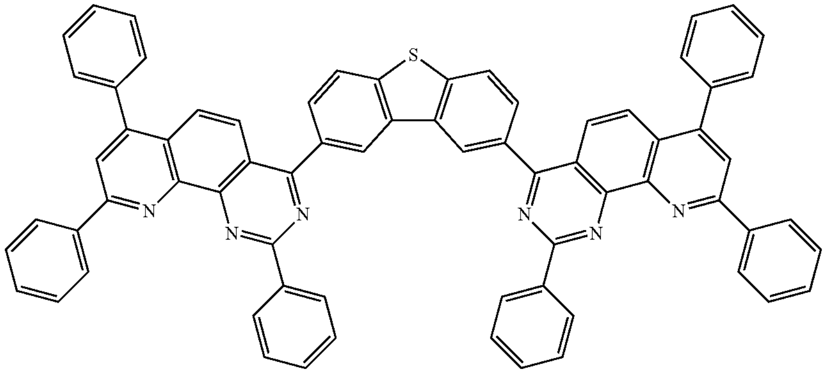

ET492

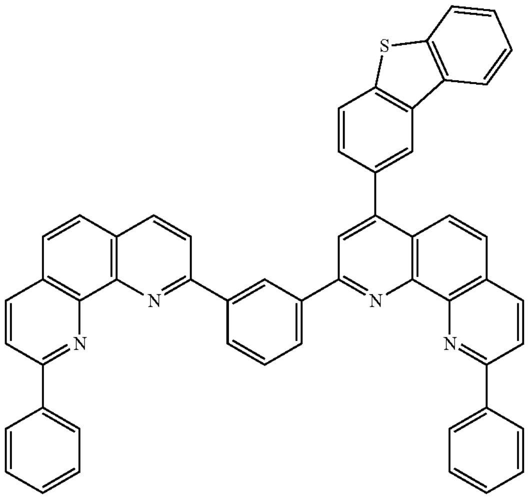

ET493

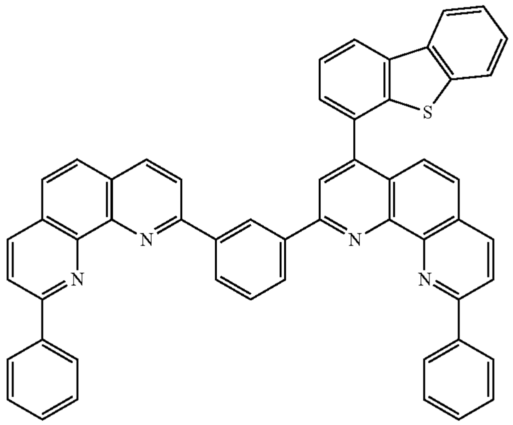

ET494

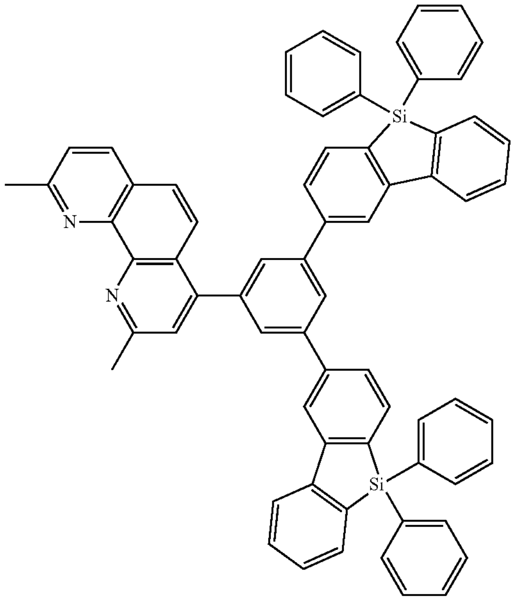

ET495

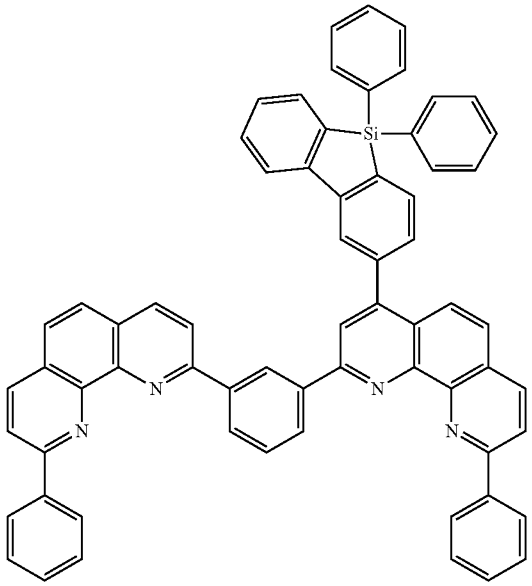

As described in the compounds ET480 to ET485, ET487 to ET490 and ET492 to ET495 among the compounds listed as the examples of the compound represented by the formula (1-11), $X^1$, $X^2$ and $X^4$ to $X^8$ in the formula (1-11) representing the compound according to the exemplary embodiment are preferably $CR^X$. Further, as described in the compounds ET480 to ET485, ET487 to ET490 and ET492 to ET493, it is preferable that $X^1$, $X^2$ and $X^4$ to $X^8$ are $CR^X$ and Z is an oxygen atom or a sulfur atom in the formula (1-11). Moreover, as described in the compounds ET480 to ET485, it is more preferable that $X^1$, $X^2$ and $X^4$ to $X^8$ are $CR^X$ and Z is an oxygen atom in the formula (1-11),
Examples of the compound represented by the formula (1-12) are as follows.
ET496
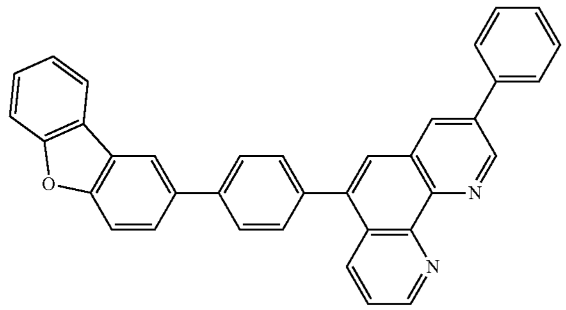
ET497
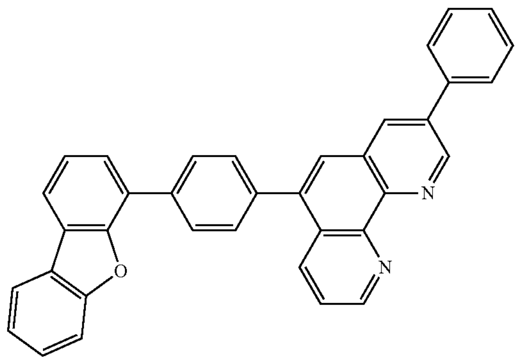
ET498
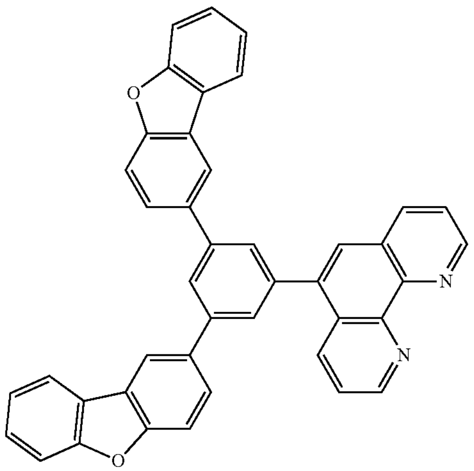
-continued
ET499
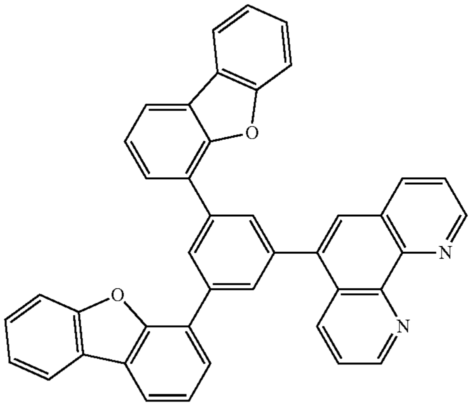
ET500
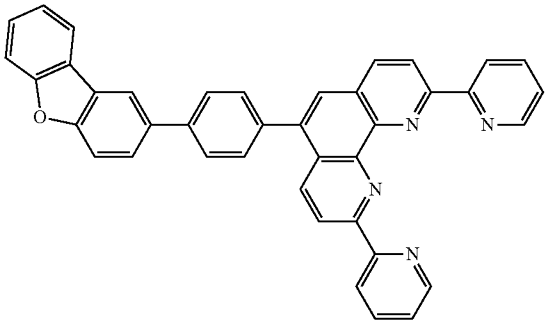
ET501
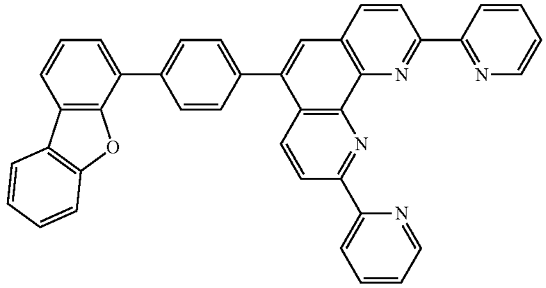
ET502
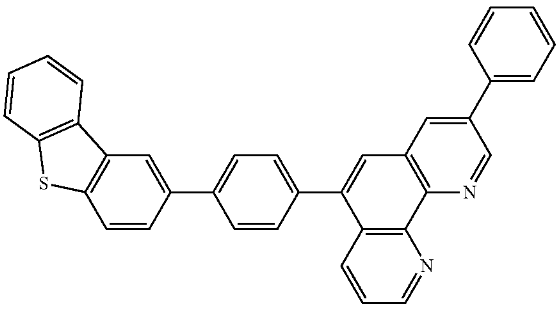

-continued

ET503

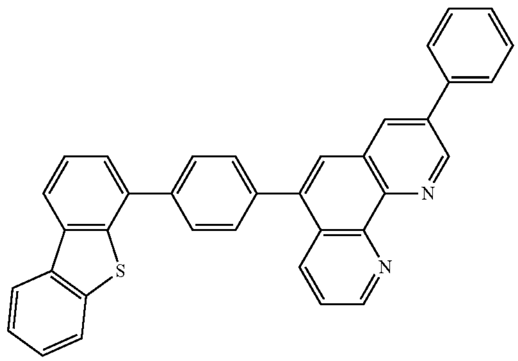

ET504

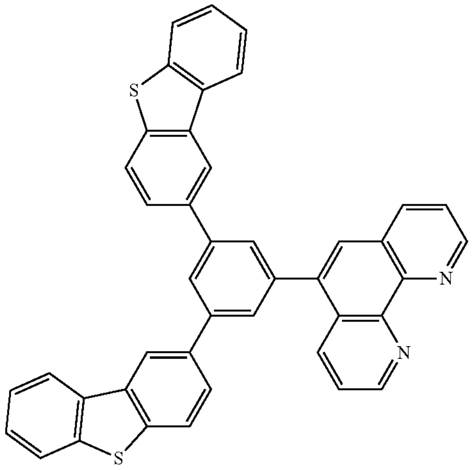

ET505

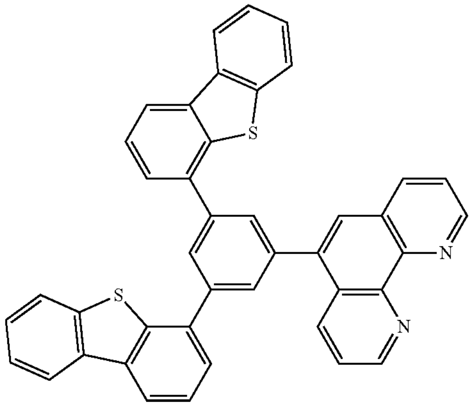

ET506

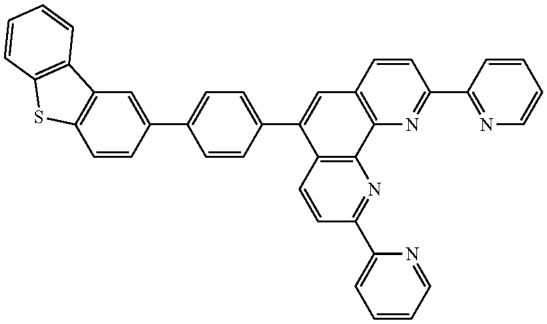

-continued

ET507

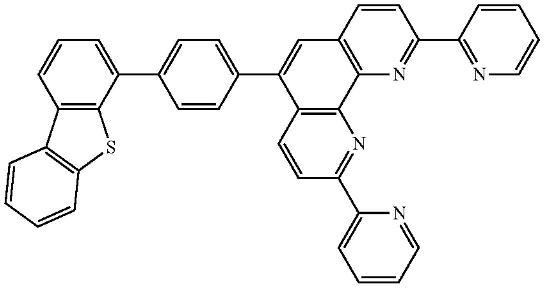

ET508

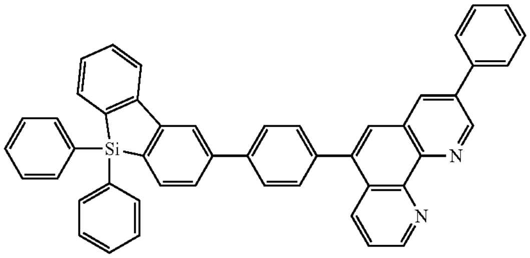

ET509

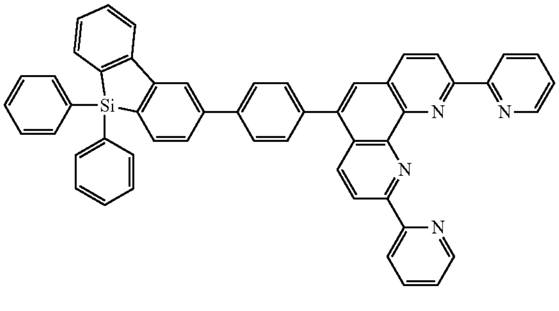

As described in the compounds ET496 to ET509 among the compounds listed as the examples of the compound represented by the formula (1-12), $X^1$ to $X^3$ and $X^5$ to $X^8$ in the formula (1-12) representing the compound according to the exemplary embodiment are preferably $CR^X$. Further, as described in the compounds ET496 to ET507, it is preferable that $X^1$ to $X^3$ and $X^5$ to $X^8$ are $CR^X$ and Z is an oxygen atom or a sulfur atom in the formula (1-12). Moreover, as described in the compounds ET496 to ET501, it is more preferable that $X^1$ to $X^3$ and $X^5$ to $X^8$ are $CR^X$ and Z is an oxygen atom in the formula (1-12).

Examples of the compound represented by the formula (1-13) are as follows.

ET510

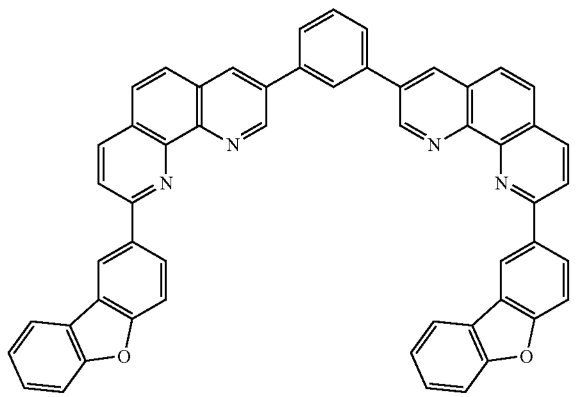

ET511

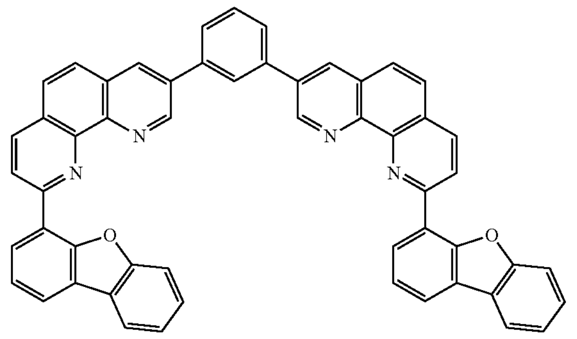

ET512

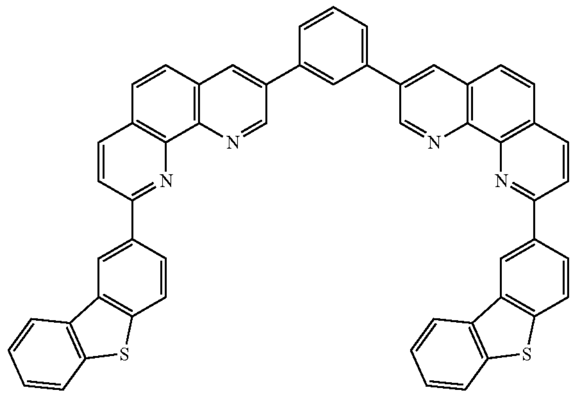

ET513

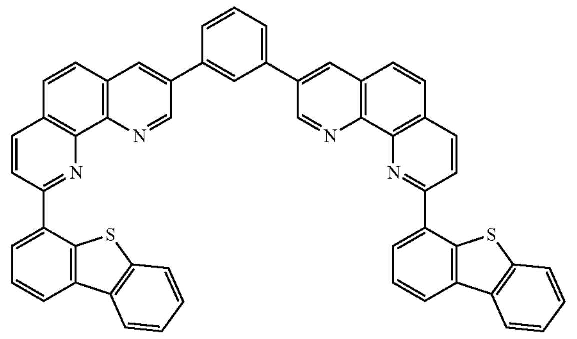

As described in the compounds ET510 to ET513 among the compounds listed as the examples of the compound represented by the formula (1-13), $X^2$ to $X^6$ and $X^8$ in the formula (1-13) representing the compound according to the exemplary embodiment are preferably $CR^X$. Further, as described in the compounds ET510 to ET513, it is preferable that $X^2$ to $X^6$ and $X^8$ are $CR^X$ and Z is an oxygen atom or a sulfur atom in the formula (1-13). Moreover, as described in the compounds ET510 to ET511, it is more preferable that $X^2$ to $X^6$ and $X^8$ are $CR^X$ and Z is an oxygen atom in the formula (1-13).

Examples of the compound represented by the formula (1-14) are as follows.

ET514

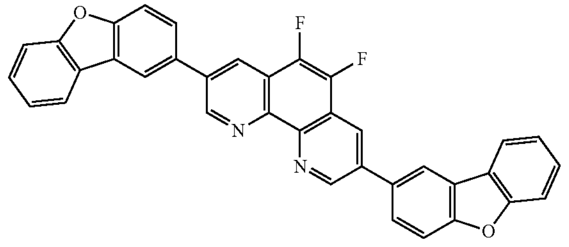

ET515

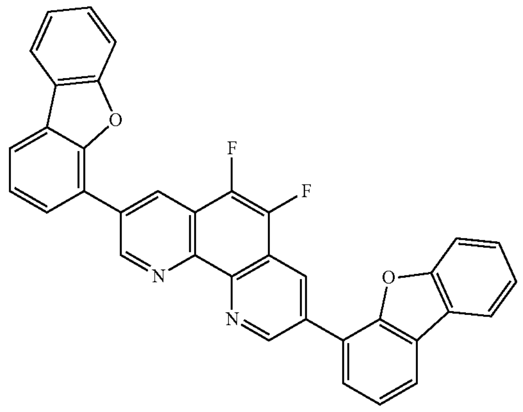

ET516

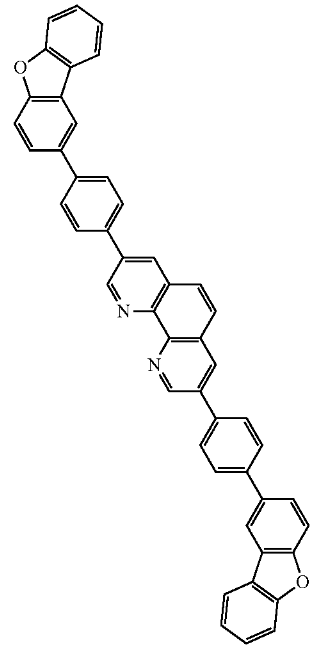

-continued
ET517
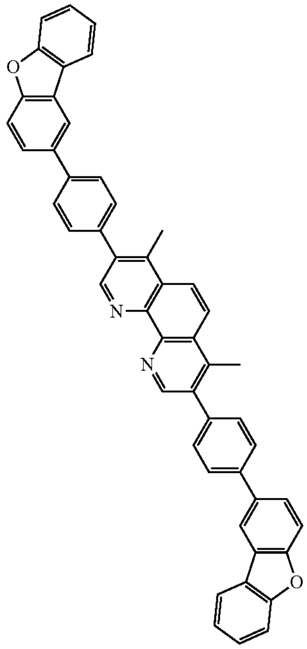
ET518
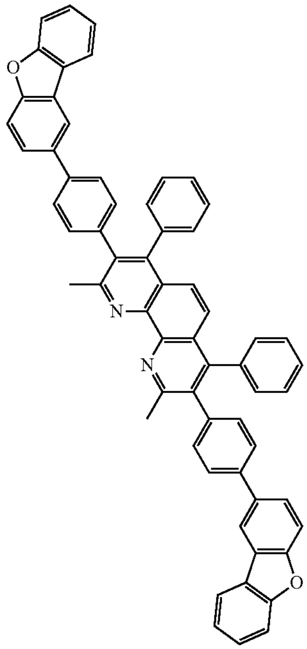
-continued
ET519
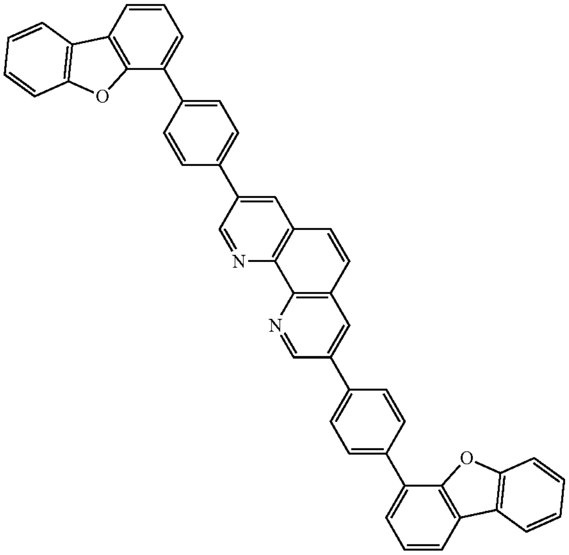
ET520
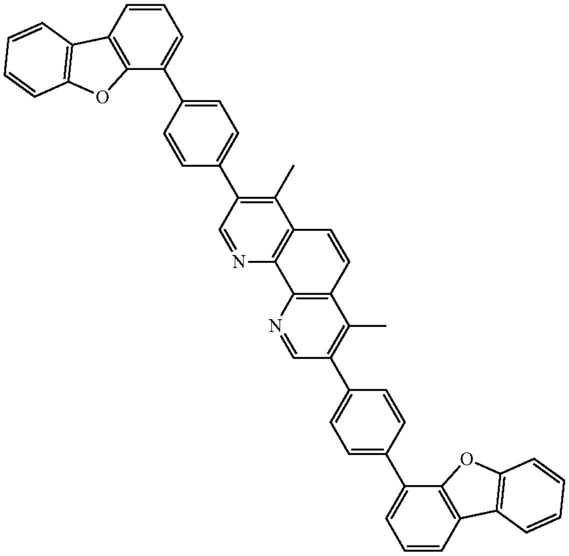

-continued
ET521
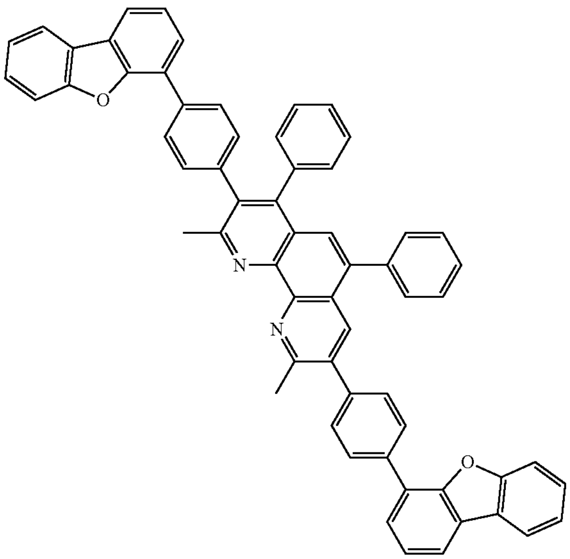
ET522
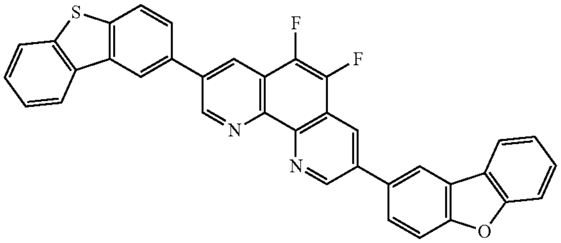
ET523
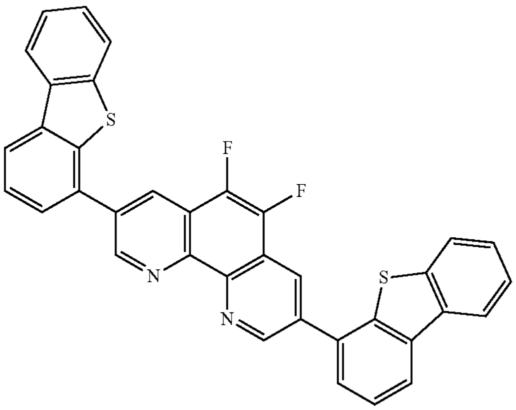
-continued
ET524
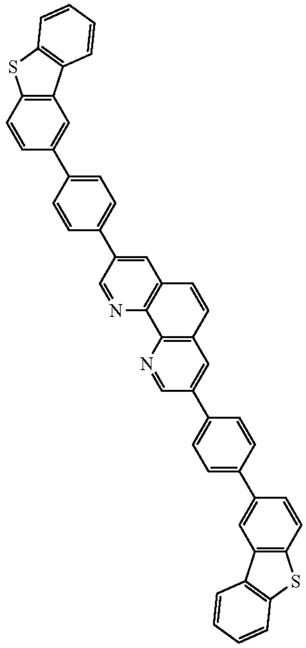
ET525
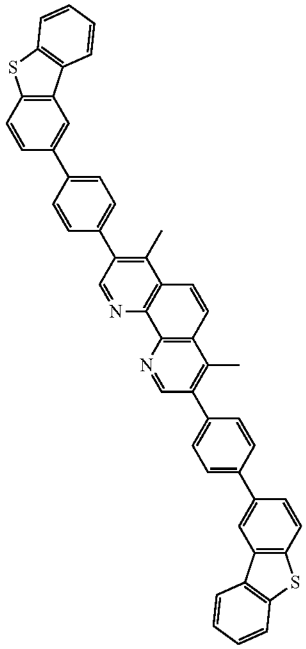

-continued

ET526

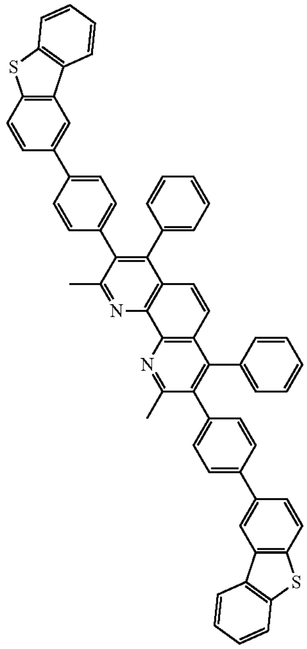

ET527

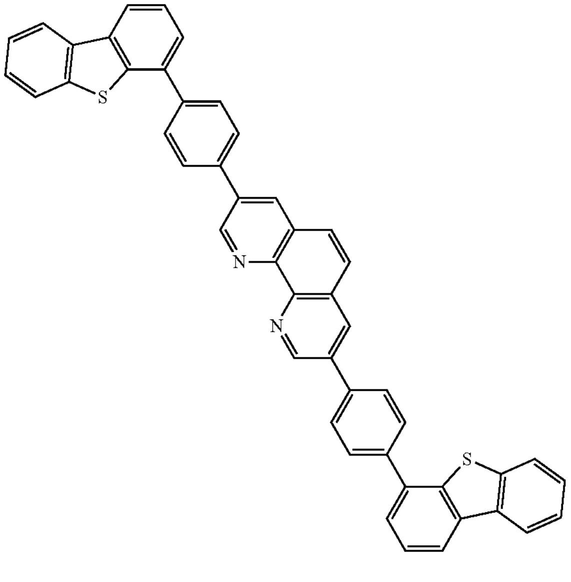

-continued

ET528

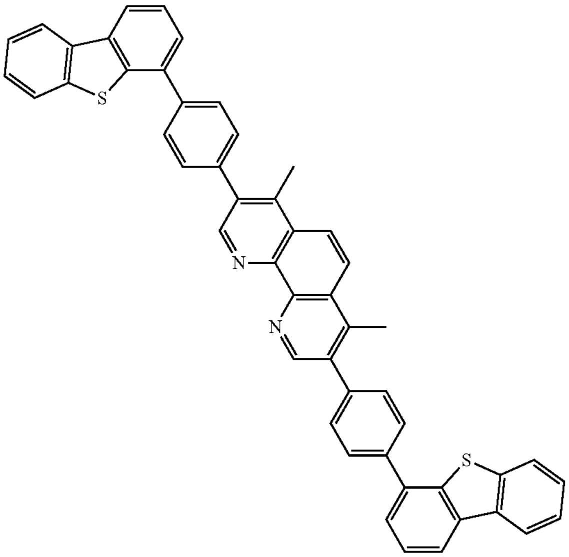

ET529

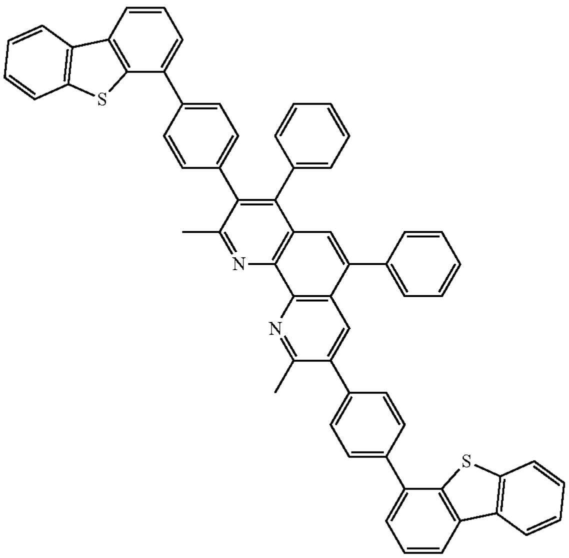

ET530

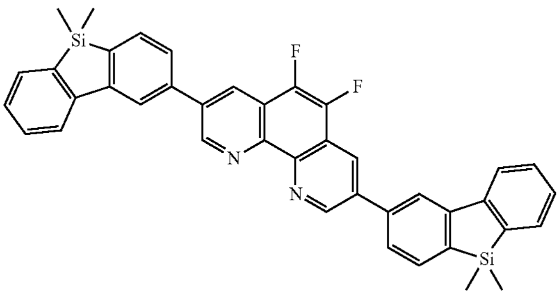

As described in the compounds ET514 to ET530 among the compounds listed as the examples of the compound represented by the formula (1-14), $X^1$, $X^3$ to $X^6$ and $X^8$ in the formula (1-14) representing the compound according to the exemplary embodiment are preferably $CR^X$. Further, as described in the compounds ET514 to ET529, it is preferable that $X^1$, $X^3$ to $X^6$ and $X^8$ are $CR^X$ and Z is an oxygen atom or a sulfur atom in the formula (1-14). Moreover, as described in the compounds ET514 to ET521, it is more preferable that $X^1$, $X^3$ to $X^6$ and $X^8$ are $CR^X$ and Z is an oxygen atom in the formula (1-14).

Examples of the compound represented by the formula (1-15) are as follows.

ET531

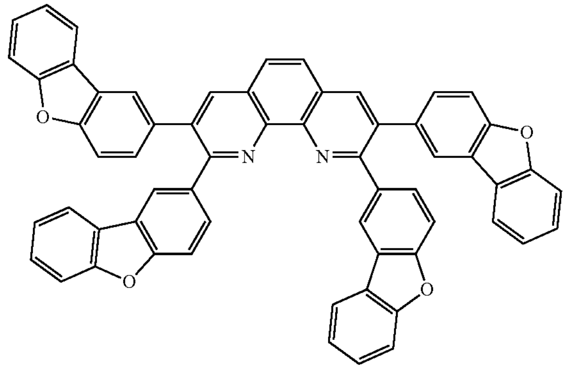

ET532

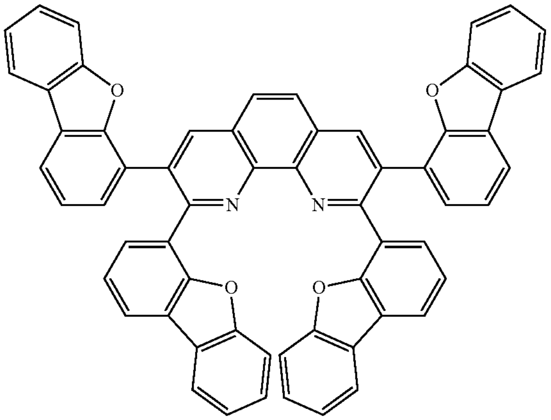

ET533

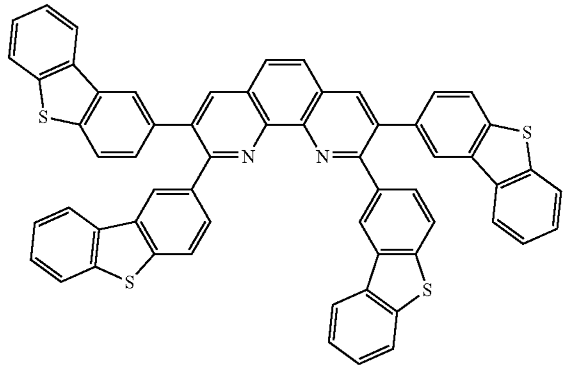

-continued

ET534

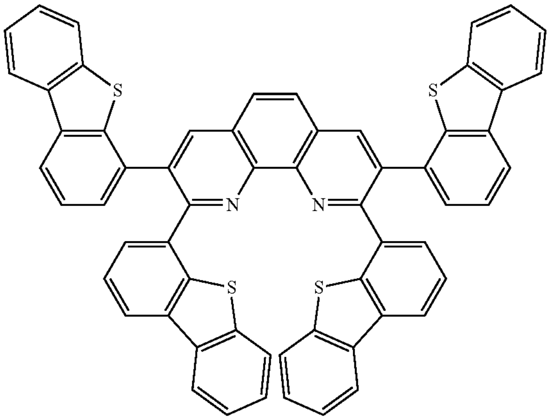

As described in the compounds ET531 to ET534 among the compounds listed as the examples of the compound represented by the formula (1-15), $X^3$ to $X^6$ in the formula (1-15) representing the compound according to the exemplary embodiment are preferably $CR^X$. Further, as described in the compounds ET531 to ET534, it is preferable that $X^3$ to $X^6$ are $CR^X$ and Z is an oxygen atom or a sulfur atom in the formula (1-15). Moreover, as described in the compounds ET531 to ET532, it is more preferable that $X^3$ to $X^6$ are $CR^X$ and Z is an oxygen atom in the formula (1-15).

Examples of the compound represented by the formula (1-16) are as follows.

ET535

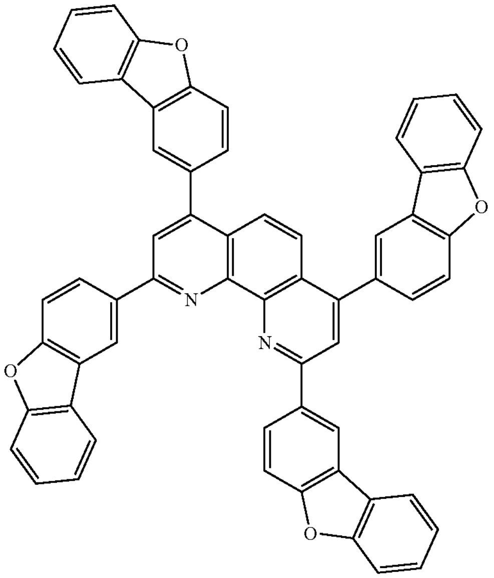

-continued
ET536
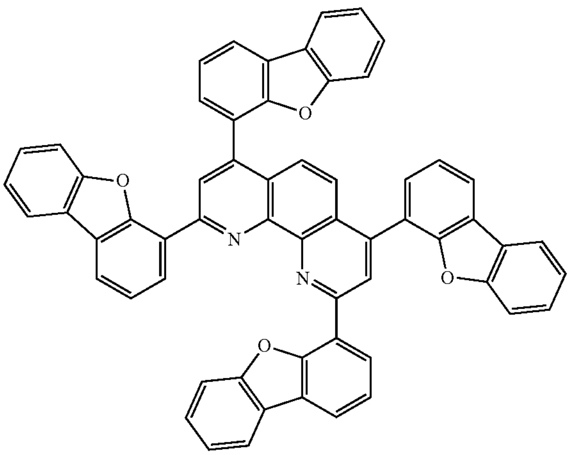
ET537
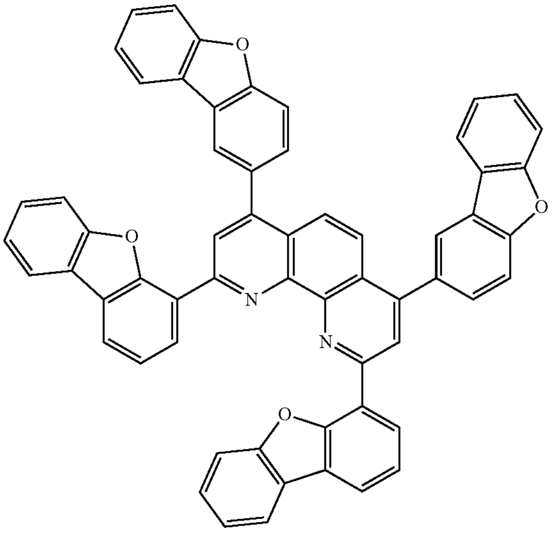
-continued
ET538
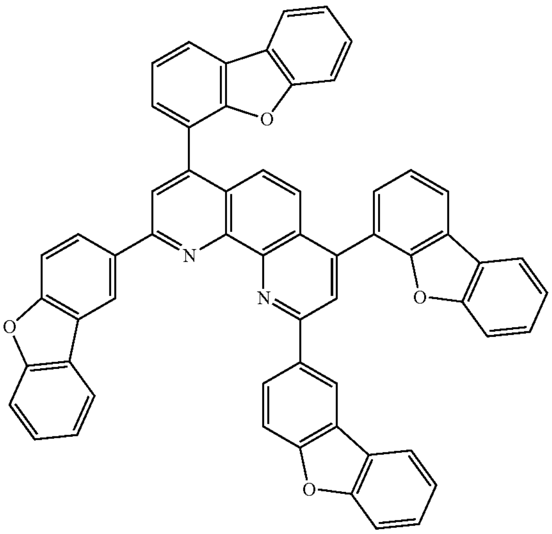
ET539
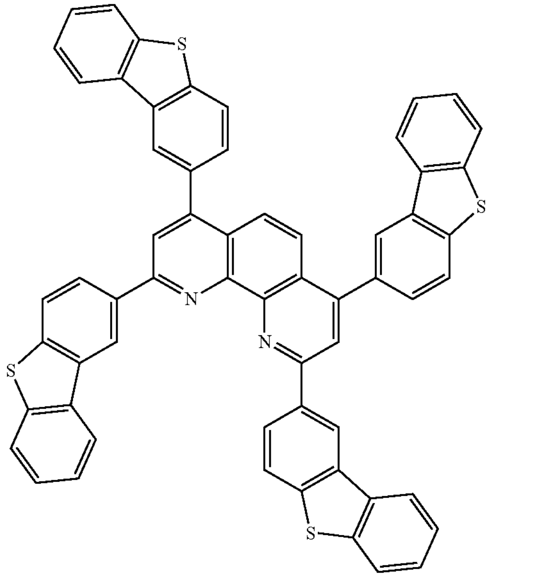

-continued

ET540

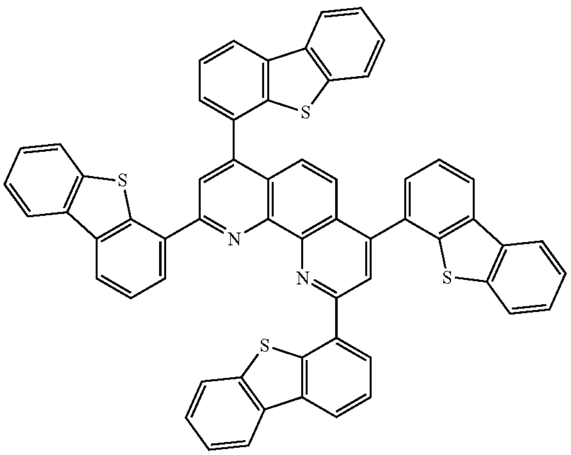

ET541

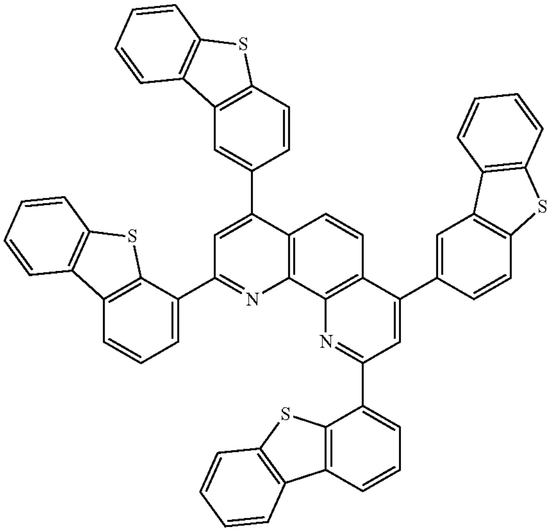

-continued

ET542

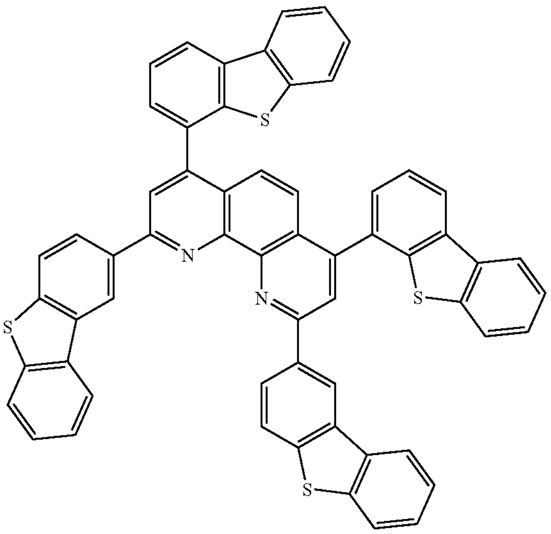

ET543

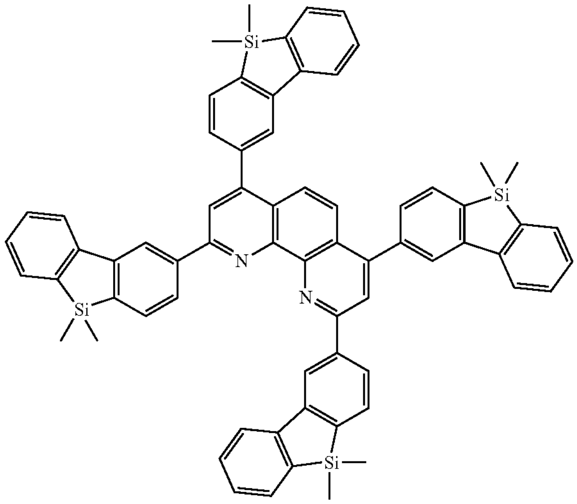

As described in the compounds ET535 to ET543 among the compounds listed as the examples of the compound represented by the formula (1-16), $X^2$, $X^4$, $X^5$ and $X^7$ in the formula (1-16) representing the compound according to the exemplary embodiment are preferably $CR^X$. Further, as described in the compounds ET535 to ET542, it is preferable that $X^2$, $X^4$, $X^5$ and $X^7$ are $CR^X$ and Z is an oxygen atom or a sulfur atom in the formula (1-16). Moreover, as described in the compounds ET535 to ET538, it is more preferable that $X^2$, $X^4$, $X^5$ and $X^7$ are $CR^X$ and Z is an oxygen atom in the formula (1-16).

Specific examples of the compound represented by the formula (1) are shown below, but the invention is not limited to the examples.

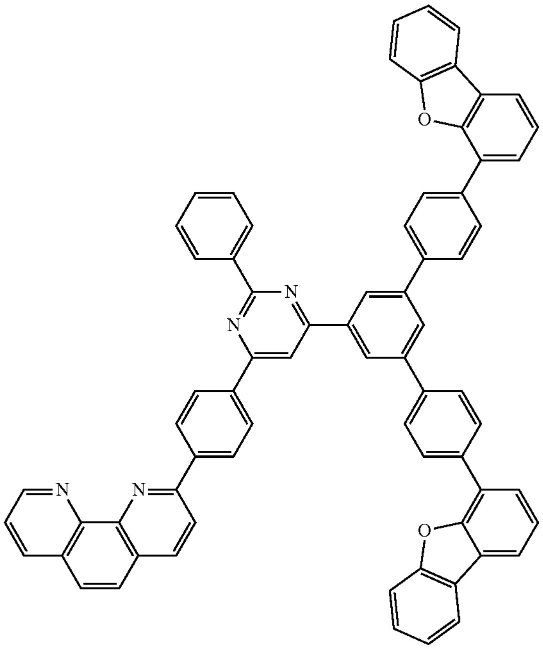
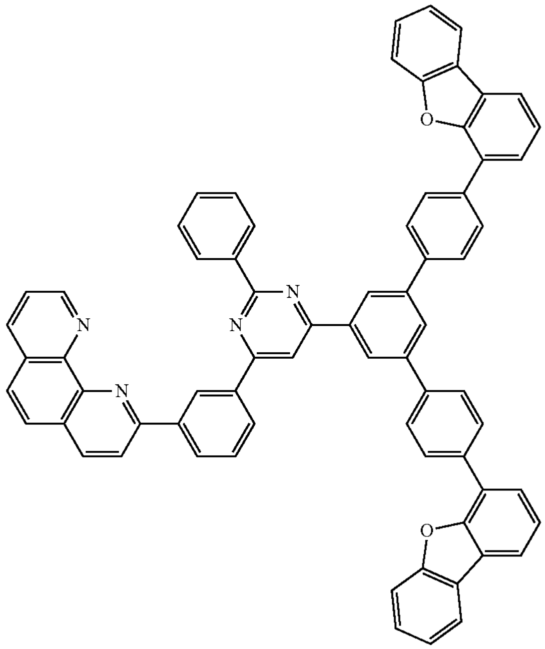
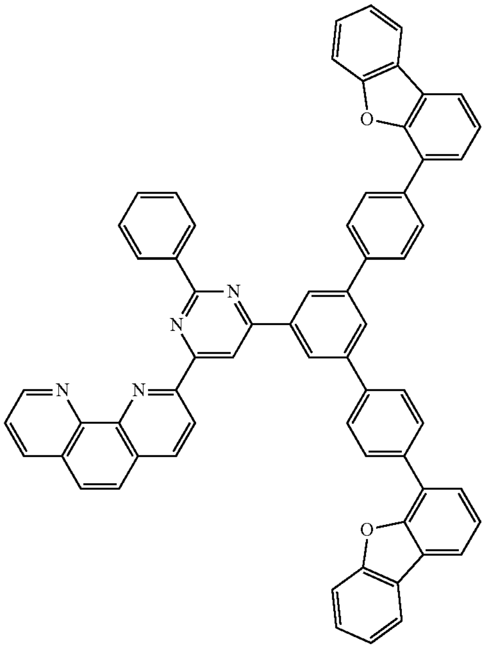

-continued
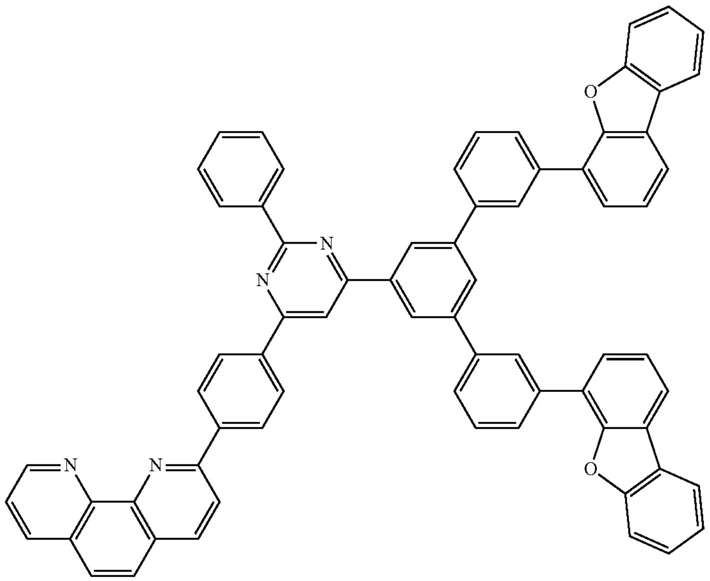
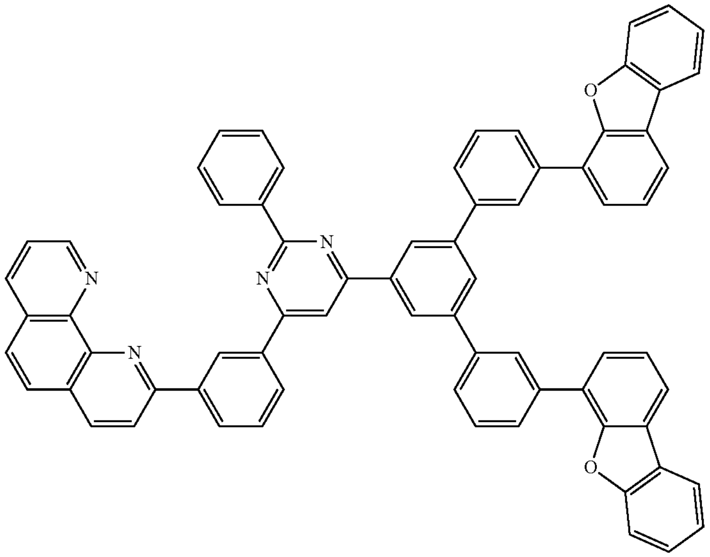
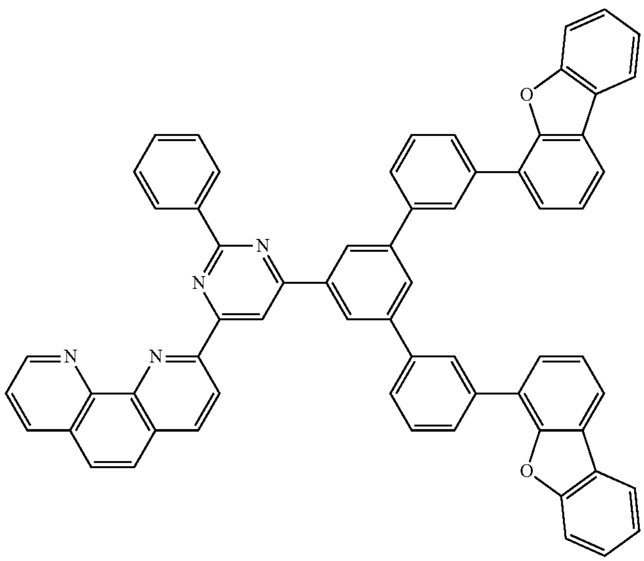

-continued
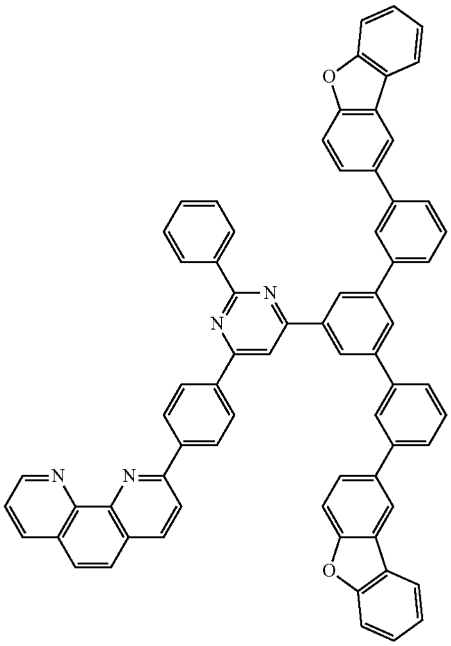
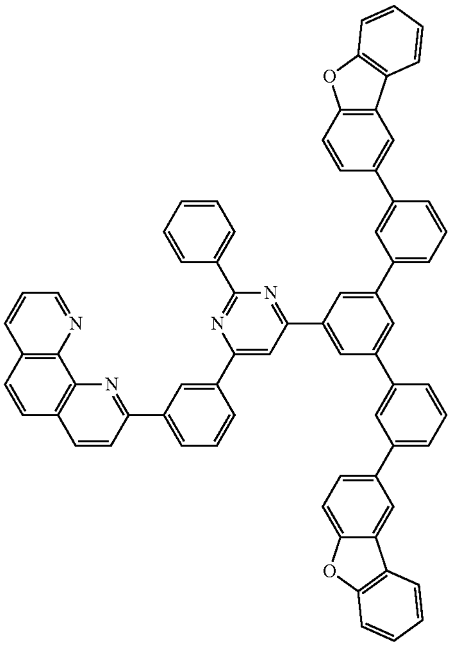
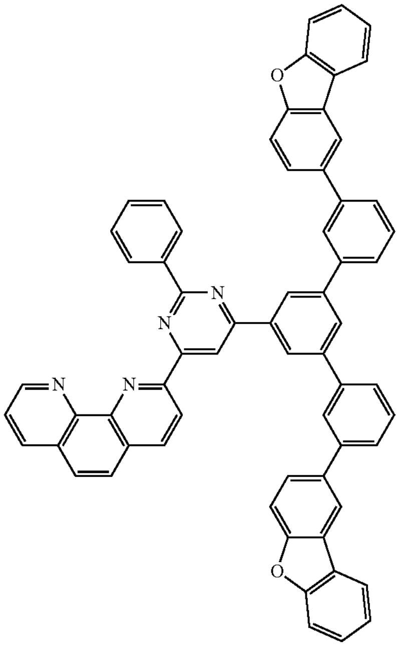

-continued
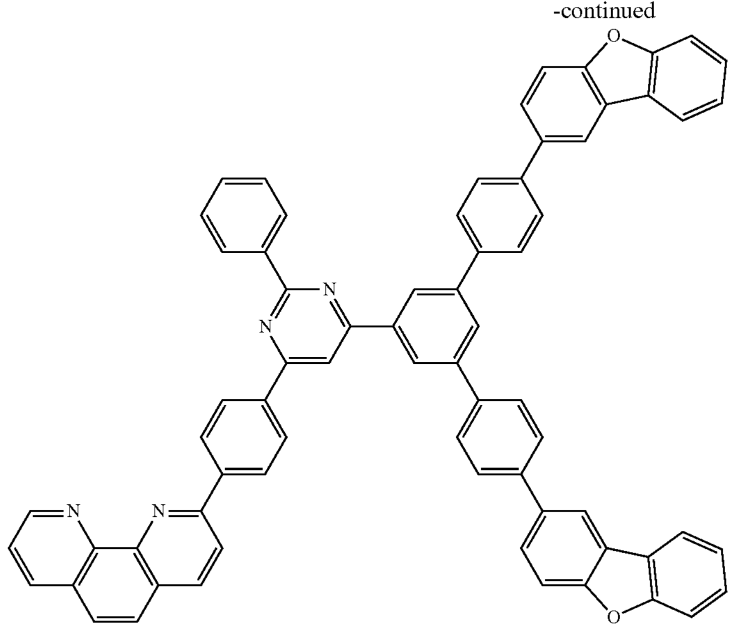
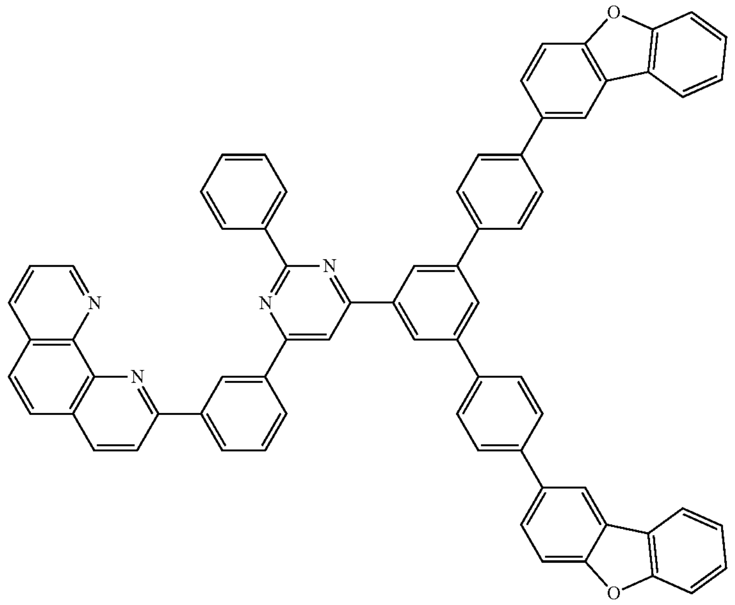

-continued
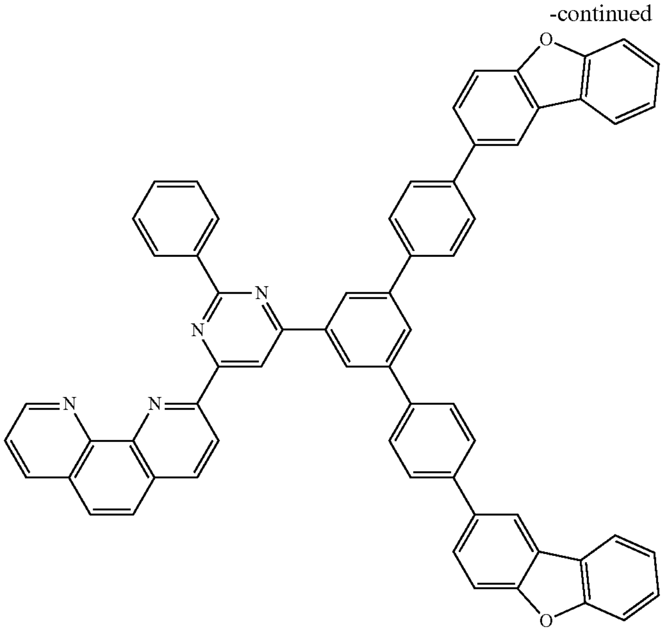
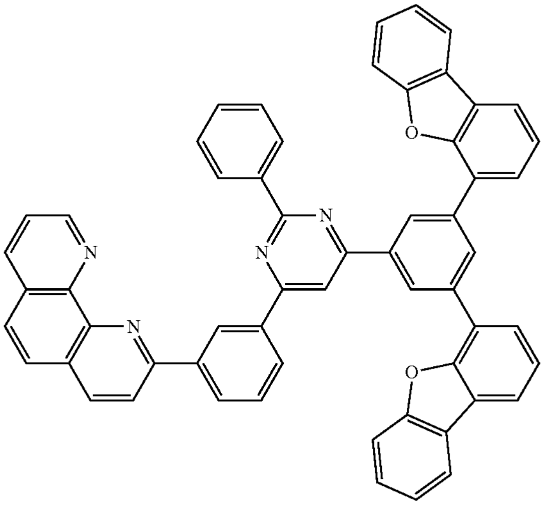
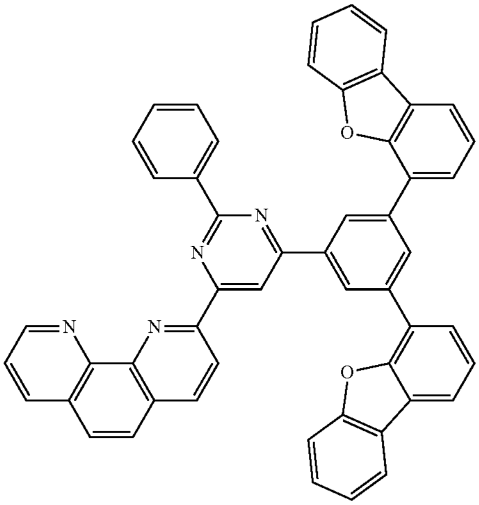
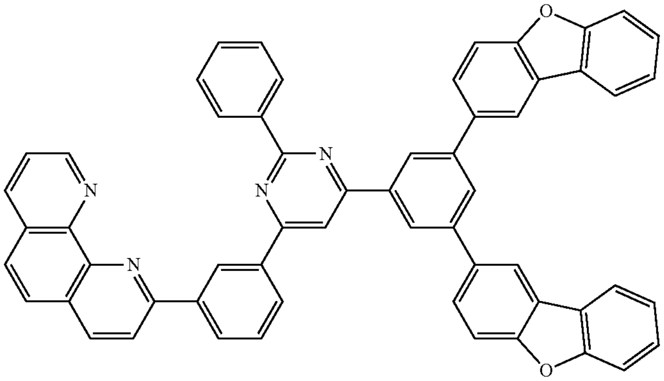

-continued
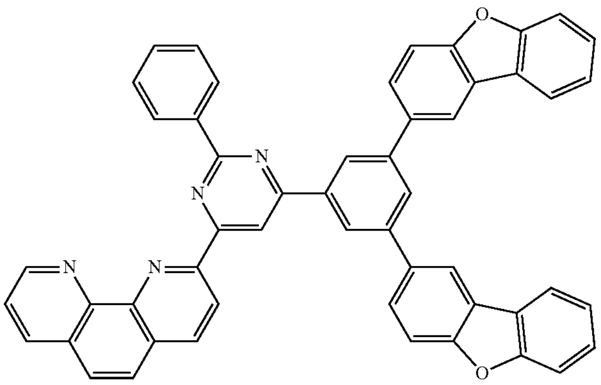
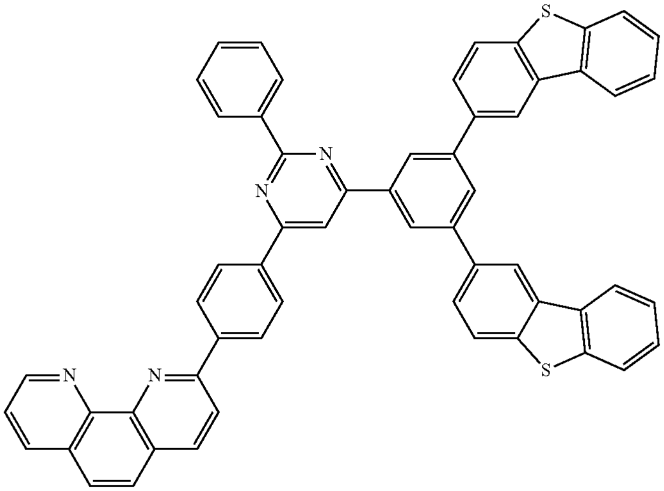
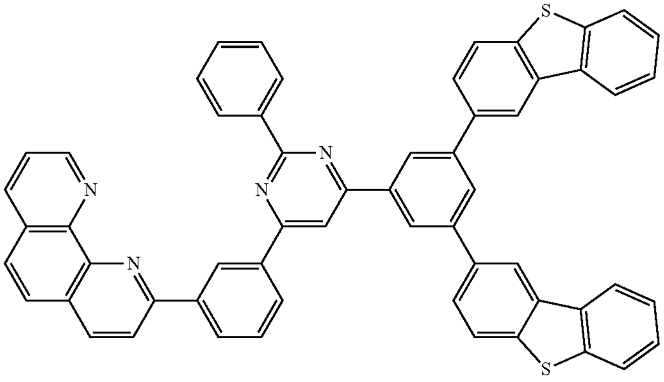
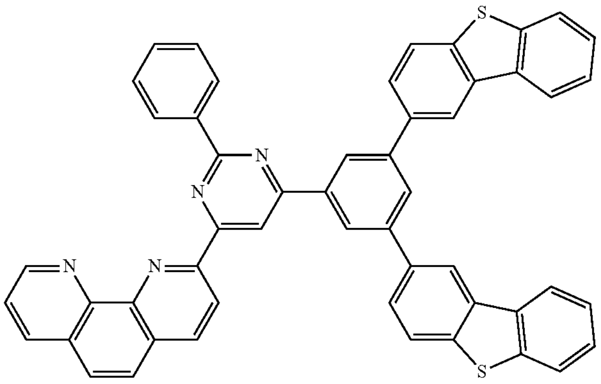

-continued
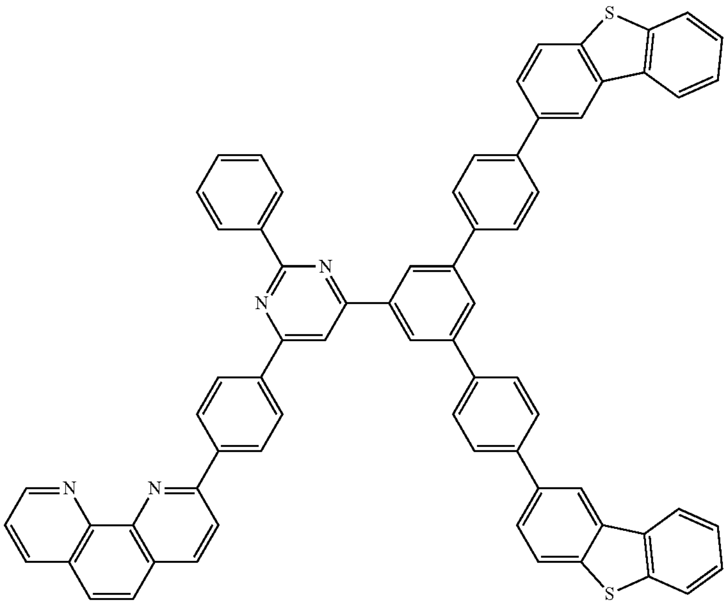
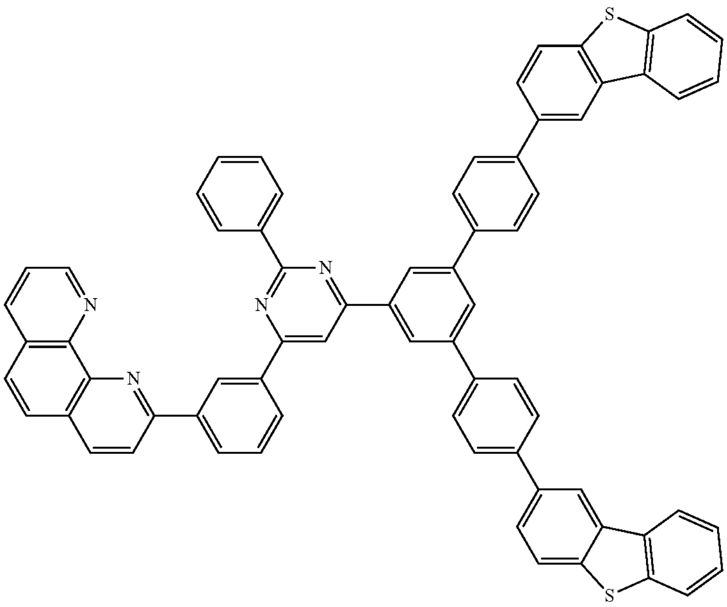

-continued
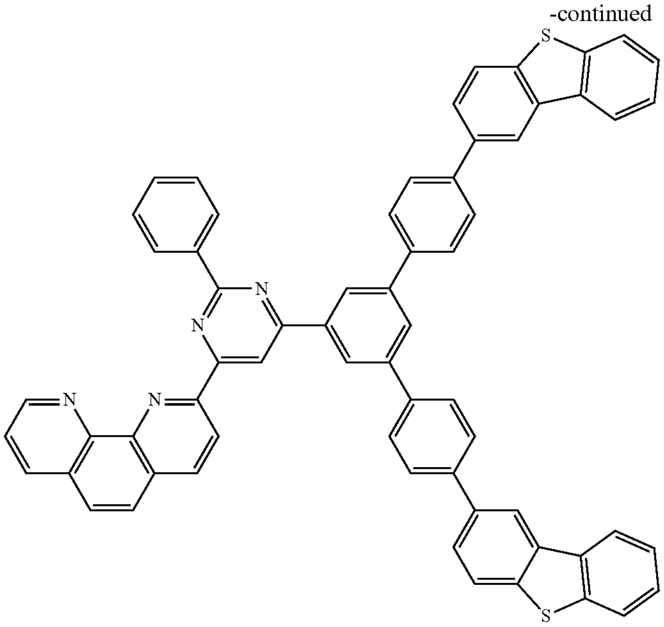
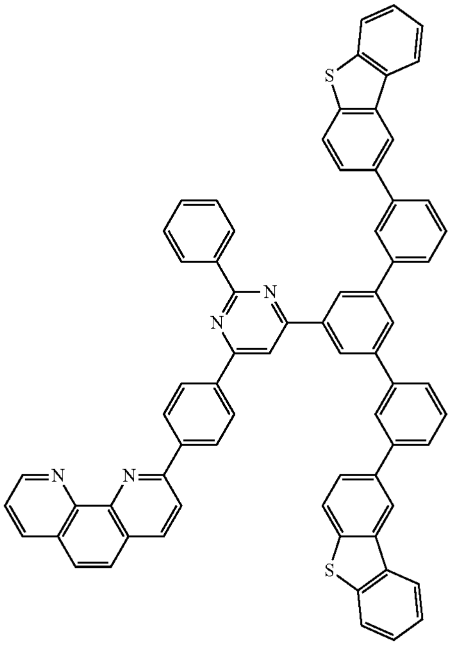
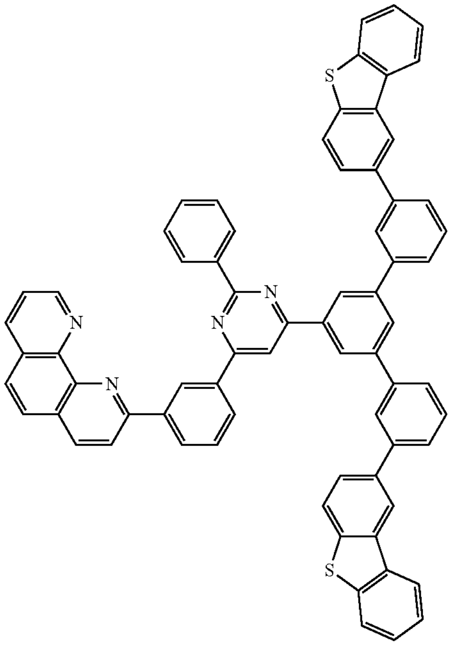

-continued
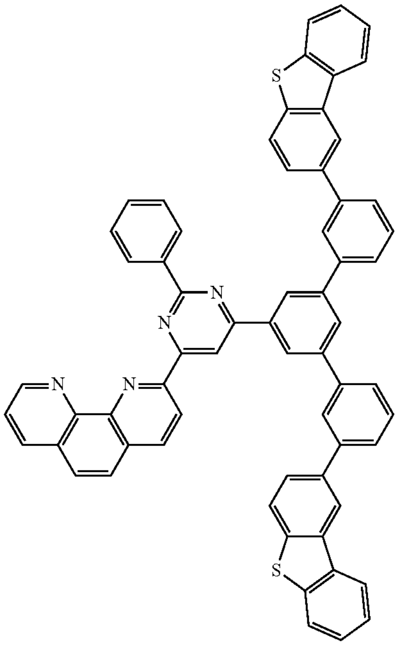
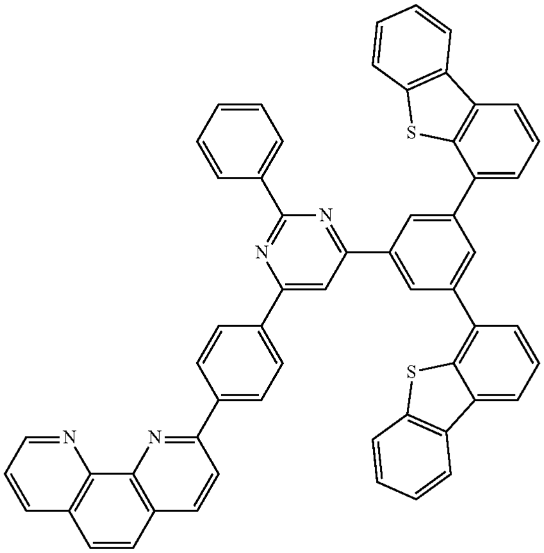
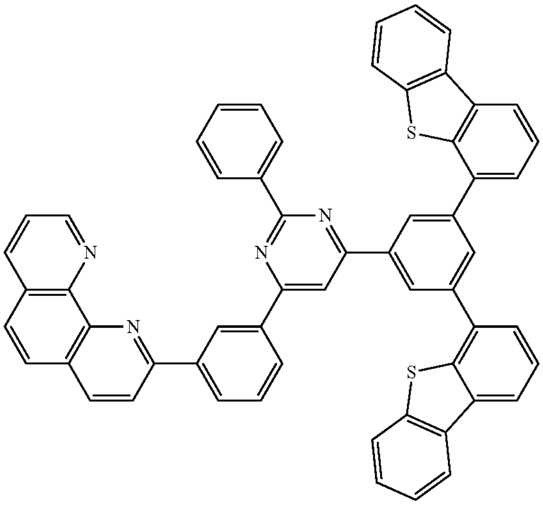
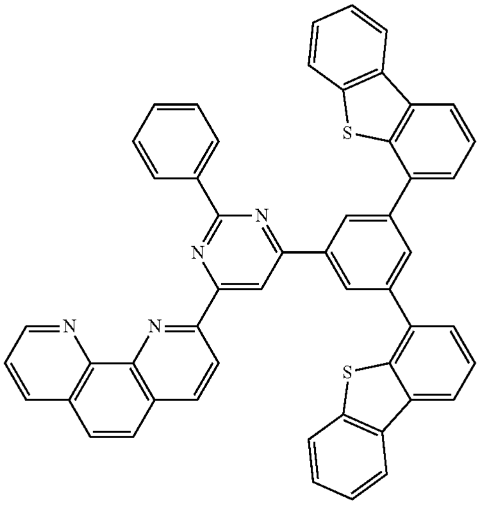

-continued
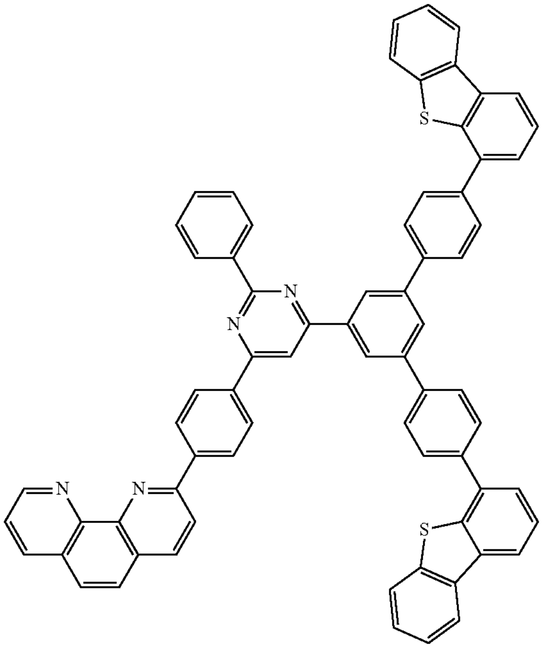
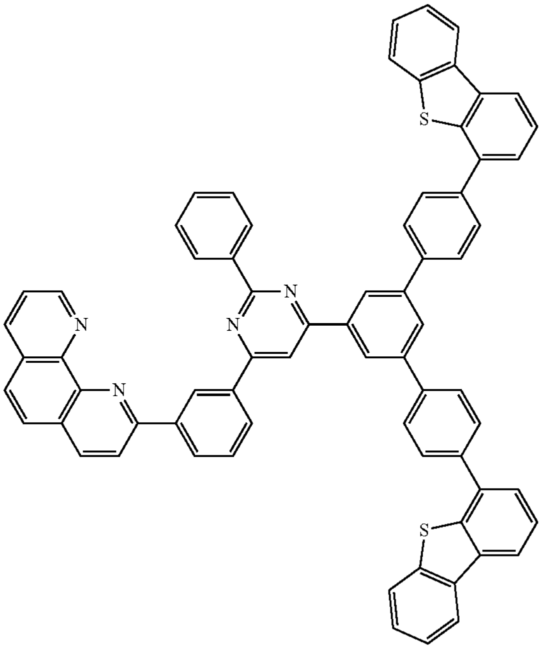
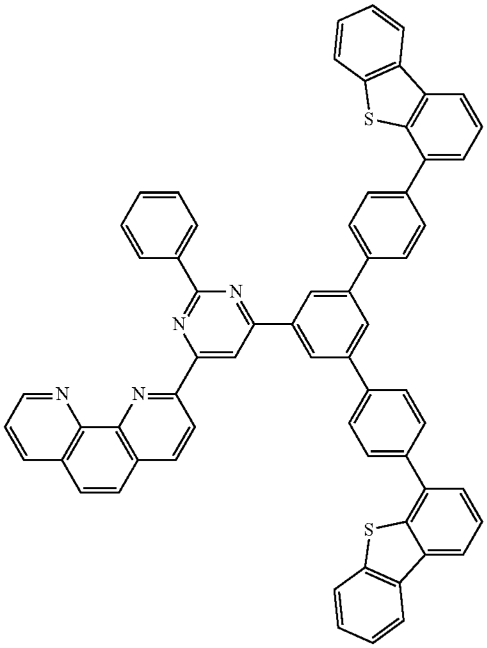

-continued
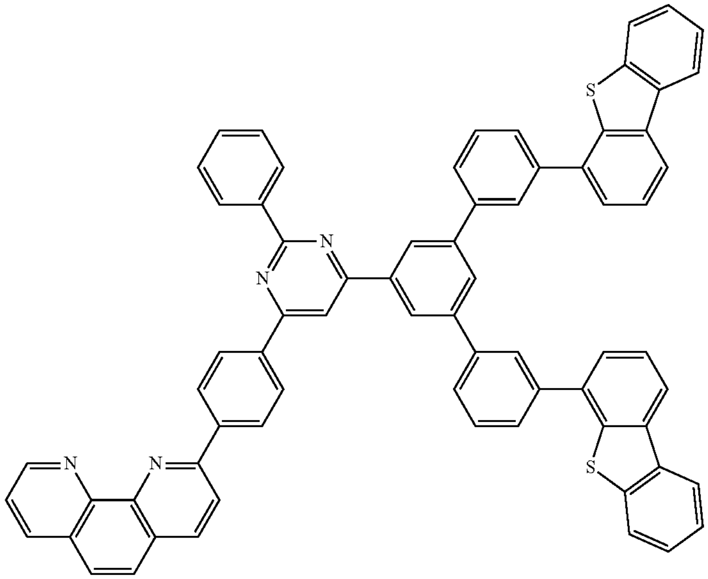
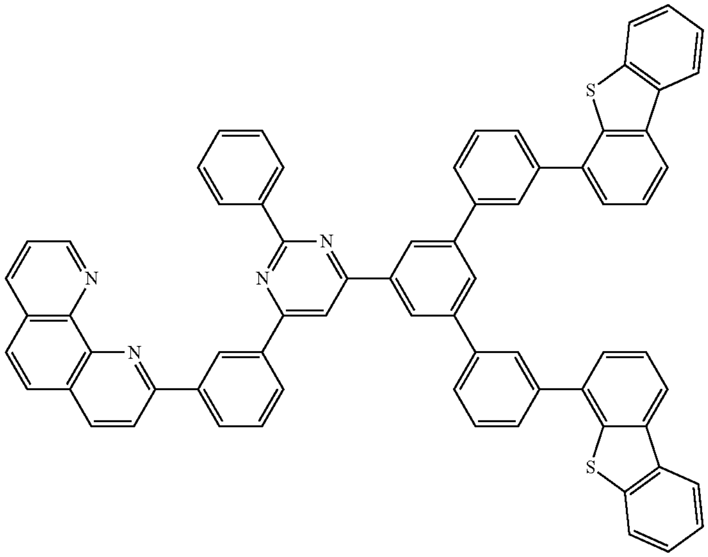
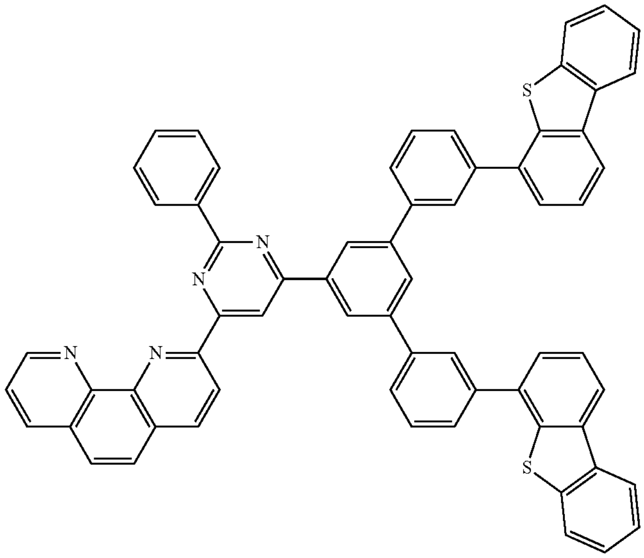
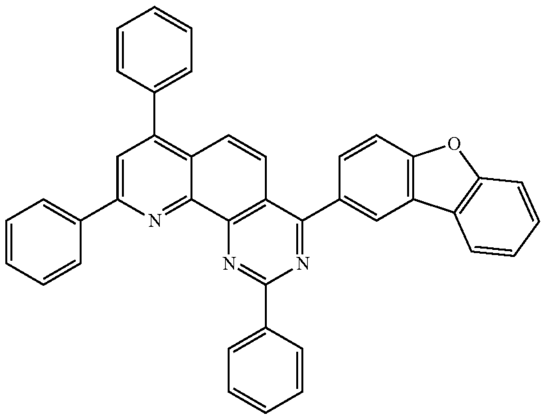

-continued
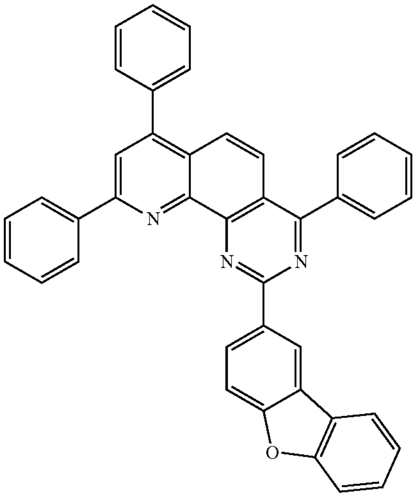
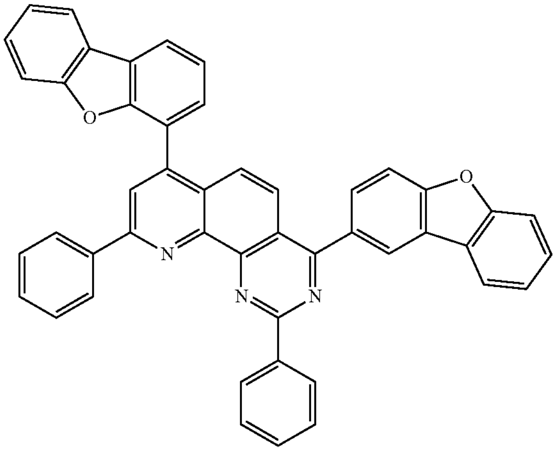
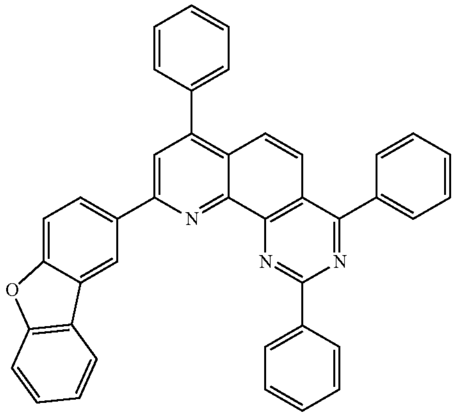
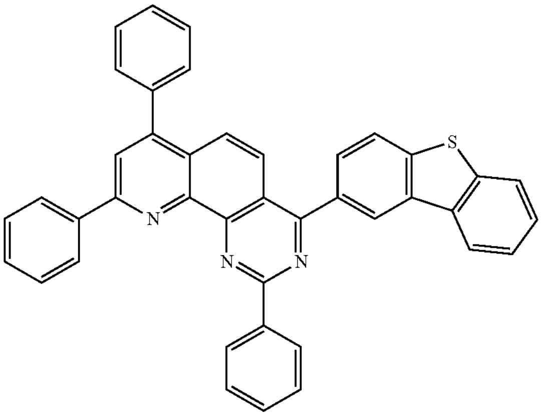
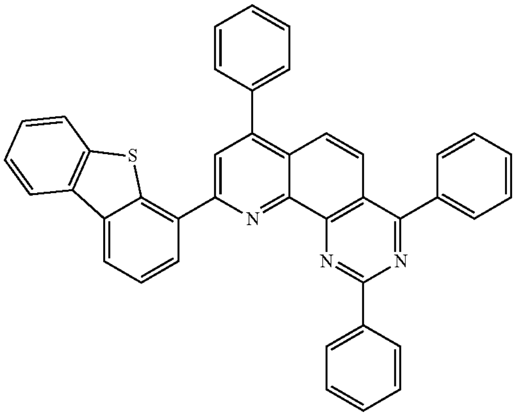
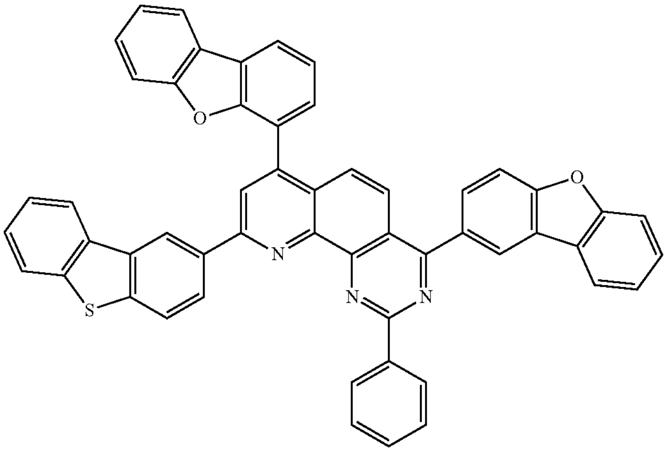

-continued
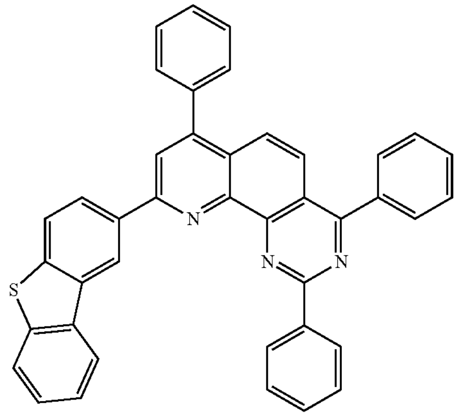
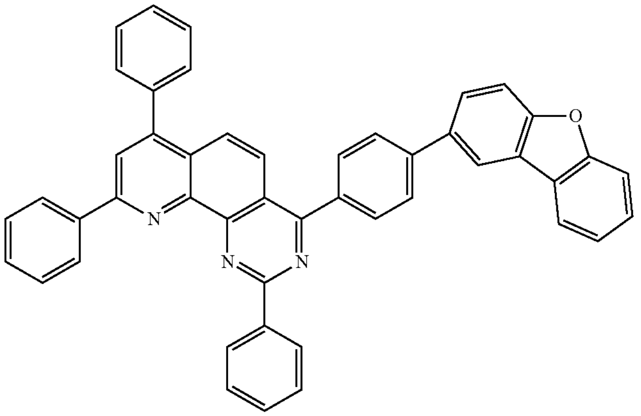
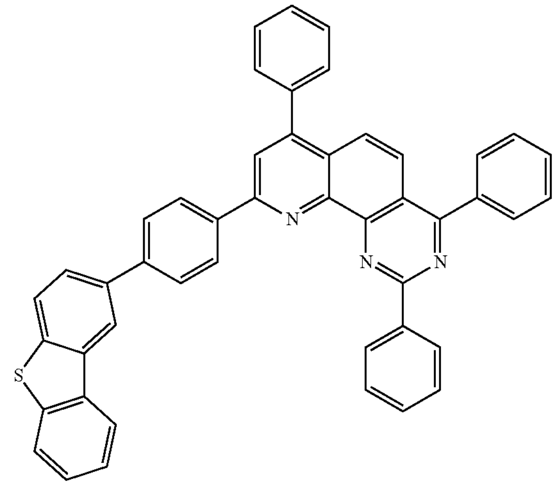
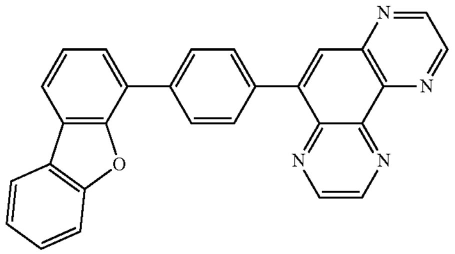
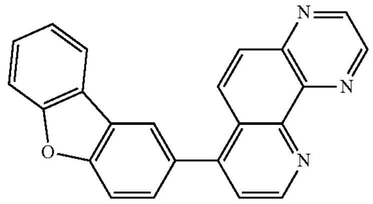
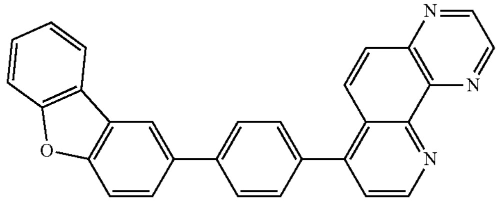
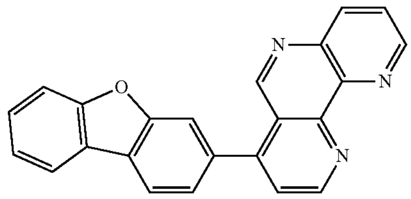
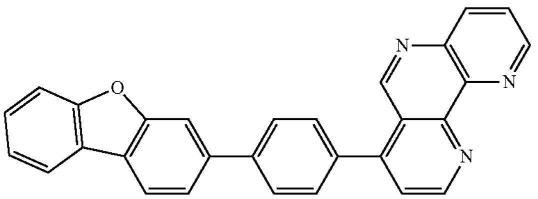
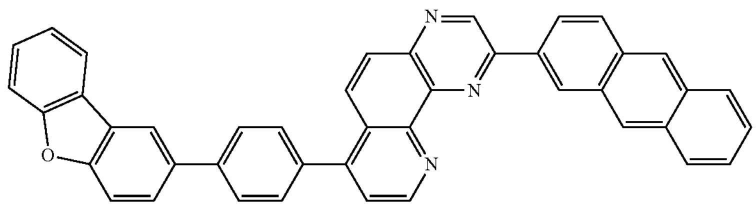

-continued

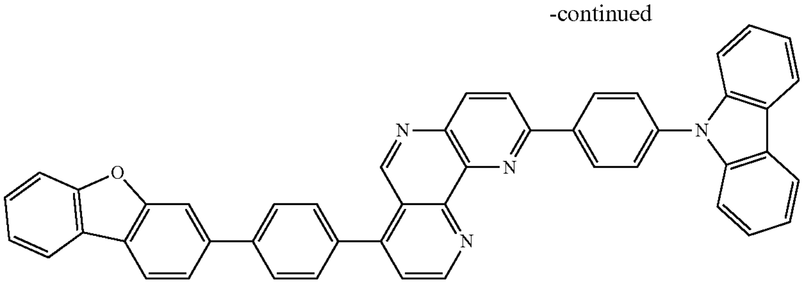

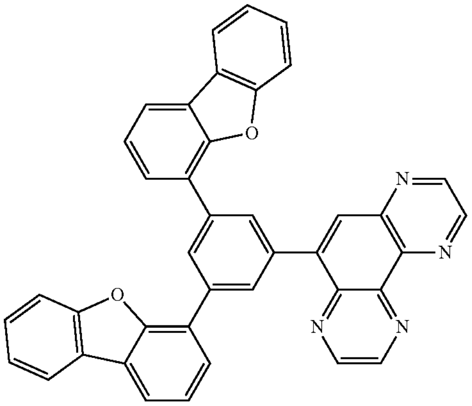

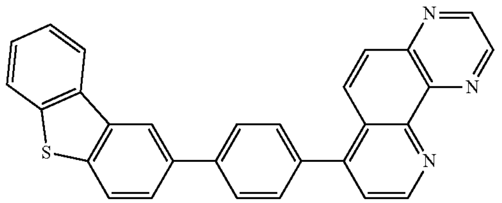

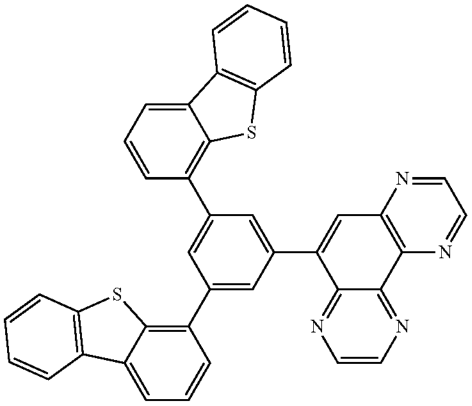

The compound according to the exemplary embodiment is preferably contained in an organic compound layer interposed between the anode and the cathode of an organic EL device. Moreover, in the organic EL device including an emitting layer and an electron transporting layer between the anode and the cathode, the compound according to the exemplary embodiment is more preferably contained in the electron transporting layer. Organic-Electroluminescence-Device Material An organic-EL-device material preferably includes the compound according to the exemplary embodiment. The organic-EL-device material may singularly include the compound represented by the formula (1) or may include other compounds in addition to the compound represented by the formula (1). The organic-EL-device material according to the exemplary embodiment is usable for forming the organic compound layer of the organic EL device.

The organic-EL-device material according to the exemplary embodiment is preferably used for the organic compound layer provided between the anode and the cathode of the organic EL device, more preferably used for the electron transporting layer in the organic EL device that includes the emitting layer and the electron transporting layer between the anode and the cathode.

Organic EL Device

Typical device arrangements of an organic EL device include the following arrangements (a) to (e) and the like:

(a) anode/emitting layer/cathode;

(b) anode/hole injecting•transporting layer/emitting layer/cathode;

(c) anode/emitting layer/electron injecting•transporting layer/cathode;

(d) anode/hole injecting•transporting layer/emitting layer/electron injecting•transporting layer/cathode; and (e) anode/hole injecting•transporting layer/emitting layer/blocking layer/electron injecting•transporting layer/cathode.

While the arrangements (d) and (e) are preferably used among the above arrangements, the arrangement of the invention is not limited to the above arrangements.

It should be noted that the aforementioned "emitting layer" is an organic layer having an emission function and, when a doping system is applied, including a host material and a dopant material. Herein, the host material has a function of mainly promoting recombination of electrons and holes and trapping excitons in the emitting layer while the dopant material has a function of making the excitons obtained in the recombination efficiently emit. In a phosphorescent device, the host material has a function of trapping the excitons, which are generated mainly in the dopant, within the emitting layer.

The "hole injecting/transporting layer" (or hole injecting•transporting layer) means "at least one of a hole injecting layer and a hole transporting layer" while the "electron injecting/transporting layer" (or electron injecting•transporting layer) means "at least one of an electron injecting layer and an electron transporting layer," Herein, when the hole injecting layer and the hole transporting layer are provided, the hole injecting layer is preferably adjacent to the anode. When the electron injecting layer and the electron transporting layer are provided, the electron injecting layer is preferably adjacent to the cathode.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, in the phosphorescent organic EL device, a blocking layer having an electron mobility that is not always high may be provided as shown in the arrangement (e) between the emitting layer and the electron transporting layer in order to prevent diffusion of exciton energy generated in the emitting layer. Thus, the organic layer adjacent to the emitting layer does not always correspond to the electron transporting layer.

In an exemplary embodiment of the invention, an organic EL device includes: a cathode; an anode; and an organic compound layer provided between the cathode and the anode. The organic compound layer at least includes an emitting layer and an electron transporting layer. The organic compound layer may include layers applied for an organic EL device such as a hole injecting layer, a hole transporting layer, an electron injecting layer, a hole blocking layer and an electron blocking layer. The organic compound layer may include an inorganic compound.

The aforementioned organic-EL-device material according to the exemplary embodiment is contained in the organic compound layer. When the organic compound layer is provided by a plurality of layers, the organic-EL-device material according to the exemplary embodiment is contained singularly or as a component of a mixture in at least one of the layers. The electron transporting layer preferably includes the organic-EL-device material according to the exemplary embodiment.

The organic EL device according to the exemplary embodiment includes a light-transmissive substrate, the anode, the cathode, and the organic compound layer provided between the anode and the cathode.

The organic compound layer includes the hole injecting layer, the hole transporting layer, the emitting layer, the hole blocking layer, the electron transporting layer and the electron injecting layer in this sequence from the anode.

Electron Transporting Layer

The electron transporting layer of the organic EL device according to the exemplary embodiment includes a compound represented by the following formula (10).

(10)

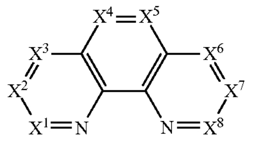

In the formula (10), $X^1$ to $X^8$ each independently represent a carbon atom to be bonded to a group represented by the following formula (20), $CR^X$ or a nitrogen atom. At least one of $X^1$ to $X^8$ is a carbon atom to be bonded to the group represented by the following formula (20).

$R^X$ is each independently selected from the group consisting of a hydrogen atom, halogen atom, hydroxyl group, cyano group, nitro group, carboxyl group, sulfonyl group, boryl group, phosphino group, mercapto group, acyl group, substituted or unsubstituted amino group, substituted or unsubstituted silyl group, substituted or unsubstituted alkyl group having 1 to 30 carbon atom, substituted or unsubstituted alkenyl group having 2 to 30 carbon atoms, substituted or unsubstituted alkynyl group having 2 to 30 carbon atoms, substituted or unsubstituted aralkyl group having 6 to 30 carbon atoms, substituted or unsubstituted aryl group having 6 to 40 ring carbon atoms, and substituted or unsubstituted heteroaryl group having 5 to 40 ring atoms.

Among $X^1$ to $X^8$ in the formula (10), adjacent $R^X$ of $CR^X$ are bonded to each other to form a cyclic structure, or are not bonded to each other.

(20)

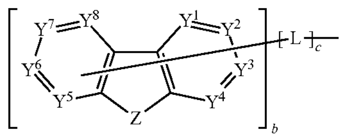

In the formula (20), b is an integer of 1 to 5. In the formula (20), c is an integer of 1 to 8.

In the formula (20), Z is an oxygen atom, a sulfur atom or a silicon atom. When b is 2 to 5, Z are mutually the same or different. When Z is a silicon atom, $R^9$ and $R^{10}$ are bonded to the silicon atom. $R^9$ and $R^{10}$ each independently represent the same as $R^X$ in the formula (10). $R^9$ and $R^{10}$ may be bonded to the structure represented by the formula (10).

In the formula (20), L is selected from a single bond or a linking group. The linking group represents a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, and a substituted or unsubstituted polyvalent heteroaryl group having 5 to 40 ring atoms. The polyvalent heteroaryl group having 5 to 40 ring atoms for L in the formula (20) includes a substituted or unsubstituted polyvalent group derived from a phenanthroline ring represented by the formula (10). When c is 2 to 8, L are mutually the same or different.

In the formula (20), $Y^1$ to $Y^8$ each independently represent a nitrogen atom, $CR^Y$ or a carbon atom bonded to L.

$R^Y$ in the formula (20) represents the same as $R^X$ in the formula (10). The heteroaryl group having 5 to 40 ring atoms for $R^Y$ includes a substituted or unsubstituted phenanthrolyl group derived from the phenanthroline ring represented by the formula (10). In the formula (20), adjacent $R^Y$ are bonded to each other to form a cyclic structure, or are not bonded to each other.

$X^1$ to $X^8$ in the formula (10) represent the same as $X^1$ to $X^8$ in the formula (1).

$Y^1$ to $Y^8$, L, Z, b and c in the formula (20) each represent the same as $Y^1$ to $Y^8$, L, Z, b and c in the formula (2).

The substituents in the formulae (10) and (20) also represent the same as the substituents in the formulae (1), (1-1) to (1-16), (2), (2-1), (1-x), (1-xx-1) and (1-xx-2).

For instance, the following formula (20-1) represents a case where a substituted or unsubstituted polyvalent group derived from the phenanthroline ring represented by the formula (10) is contained in L in the formula (20). In the following formula (20-1), A1 schematically shows the structure represented by the formula (10).

(20-1)

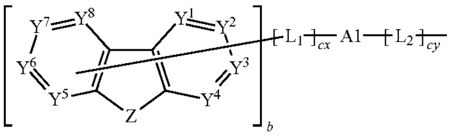

In the formula (20-1), cx is an integer of 0 to 7, cy is an integer of 0 to 7, and $0 \leq cx+cy \leq 7$. In the formula (20-1), $Y^1$ to $Y^8$, Z, L, b and $X^1$ to $X^8$ in A1 each represent the same as $X^1$ to $X^8$, $Y^1$ to $Y^8$, Z, L and b in the formulae (10) and (20).

For instance, the following formula (10-1) represents a case where $R^Y$ of $CR^Y$ in the formula (20) is a substituted or unsubstituted phenanthrolyl group derived from the phenanthroline ring represented by the formula (10). In the following formula (10-1), A2 and A3 schematically show the structure represented by the formula (10).

(10-1)

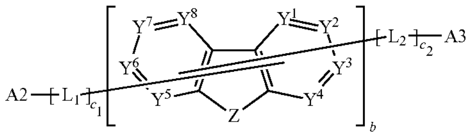

In the formula (10-1), $c_1$ is an integer of 1 to 8 and $c_2$ is an integer of 1 to 8. In the formula (10-1), $L_1$ and $L_2$ each independently represent the same as L in the formula (20). In the formula (10-1), $Y^1$ to $Y^8$, Z, b and $X^1$ to $X^8$ in A2 and A3 each represent the same as $X^1$ to $X^8$, $Y^1$ to $Y^8$, Z and b in the formulae (10) and (20).

For instance the following formula (10-2) shows a case where a substituted or unsubstituted polyvalent group derived from the phenanthroline ring represented by the formula (10) is included in L of the formula (20), and $R^Y$ of $CR^Y$ in the formula (20) is a substituted or unsubstituted phenanthrolyl group derived from the phenanthroline ring represented by the formula (10). In the following formula (10-2), A1, A2 and A3 schematically show the structure represented by the formula (10).

(10-2)

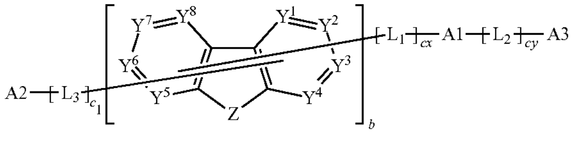

In the formula (10-2), $Y^1$ to $Y^8$, Z, $L_1$ to $L_3$, b, cx, cy, $c_1$ and $X^1$ to $X^8$ in A1, A2 and A3 each represent the same as $X^1$ to $X^8$, $Y^1$ to $Y^8$, Z, $L_1$ to $L_3$, b, cx, cy and $c_1$ in the formulae (10), (20), (10-1) and (20-1).

In the organic EL device according to the exemplary embodiment, $X^1$ or $X^8$ in the formula (10) is preferably a carbon atom to be bonded to a group represented by the formula (20).

In the organic EL device according to the exemplary embodiment, $X^1$ and $X^8$ in the formula (10) are preferably carbon atoms to be bonded to the group represented by the formula (20).

In the organic EL device according to the exemplary embodiment, $X^3$ and $X^6$ in the formula (10) are preferably carbon atoms to be bonded to the group represented by the formula (20).

In the organic EL device according to the exemplary embodiment, $X^2$ and $X^7$ in the formula (10) are preferably carbon atoms to be bonded to the group represented by the formula (20).

In the organic EL device according to the exemplary embodiment, $X^3$ or $X^6$ in the formula (10) is preferably a carbon atom to be bonded to the group represented by the formula (20).

In the organic EL device according to the exemplary embodiment, $X^4$ or $X^5$ in the formula (10) is preferably a carbon atom to be bonded to the group represented by the formula (20).

In the organic EL device according to the exemplary embodiment, $X^1$ and $X^7$ in the formula (10) are preferably carbon atoms to be bonded to the group represented by the formula (20).

In the organic EL device according to the exemplary embodiment, $X^2$ and $X^7$ in the formula (10) are preferably carbon atoms to be bonded to the group represented by the formula (20).

In the organic EL device according to the exemplary embodiment, $X^1$, $X^2$, $X^7$ and $X^8$ in the formula (10) are preferably carbon atoms to be bonded to the group represented by the formula (20).

In the organic EL device according to the exemplary embodiment, $X^1$, $X^3$, $X^6$ and $X^8$ in the formula (10) are preferably carbon atoms to be bonded to the group represented by the formula (20).

In the organic EL device according to the exemplary embodiment, a compound in which $X^1$ or $X^8$ in the formula (10) is a carbon atom to be bonded to a group represented by the formula (20) while $X^1$ and $X^8$ in the formula (10) are carbon atoms to be bonded to a group represented by the formula (20) is preferably used.

In the organic EL device according to the exemplary embodiment, in the formulae (10) and (10-1) to (10-2), other than $X^1$ to $X^8$ being a carbon atom bonded to the group represented by the formula (20), $X^1$ to $X^8$ are preferably $CR^X$, in which $R^X$ is preferably any one of a hydrogen atom, an alkyl group and an aryl group, more preferably a hydrogen atom or a phenyl group.

Moreover, in the organic EL device according to the exemplary embodiment, Z in the formula (20) is preferably an oxygen atom or a sulfur atom, more preferably an oxygen atom.

The organic EL device according to this exemplary embodiment preferably includes at least one of an electron-donating dopant and an organic metal complex in the electron transporting layer. The content of the electron-donating dopant or the organic metal complex in the electron transporting layer is preferably in a range from 1 mass % to 50 mass %.

A material of the electron-donating dopant is preferably at least one selected from the group consisting of an alkali metal, an alkaline-earth metal, a rare-earth metal, an alkali metal oxide, an alkali metal halide, an alkaline-earth metal oxide, an alkaline-earth metal halide, a rare-earth metal oxide and a rare-earth metal halide.

The organic metal complex is preferably at least one selected from the group consisting of an organic metal complex including an alkali metal, an organic metal complex including an alkaline-earth metal, an organic metal complex including a rare-earth metal and the like.

The electron-donating dopant and the organic metal complex will be described in detail later.

According to the organic EL device of the exemplary embodiment, since the compound represented by the formula (10) is contained in the electron transporting layer, the drive voltage can be reduced. Moreover, since the compound represented by the formula (10) and at least one of the electron-donating dopant and the organic metal complex are contained in the electron transporting layer, the electron-donating dopant and the organic metal complex contained in the electron transporting layer are easily captured by the phenanthroline skeleton of the formula (10), so that the drive voltage is further reduced.

Moreover, an organic-EL-device material including the compound represented by the formula (10) may be used for the organic EL device of the exemplary embodiment.

The compound represented by the formula (10) includes the compound represented by the formula (1). Specific examples of the compound represented by the formula (10) are the aforementioned specific examples of the compound represented by the formula (1) and the following compounds. However, the invention is not limited to the examples.

ET1100

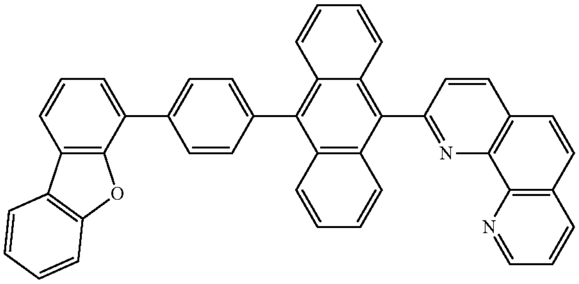

ET1101

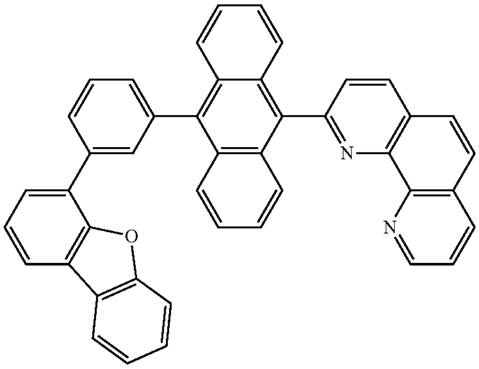

-continued

ET1102

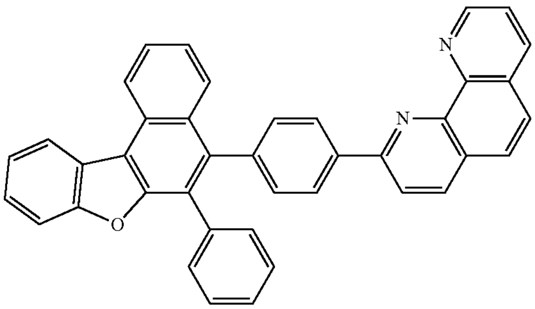

ET1103

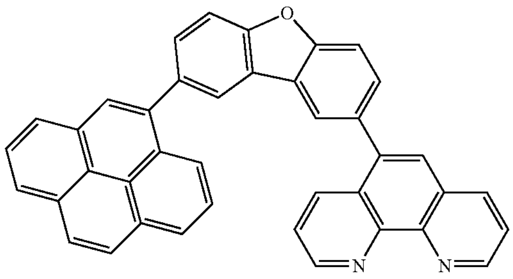

ET1104

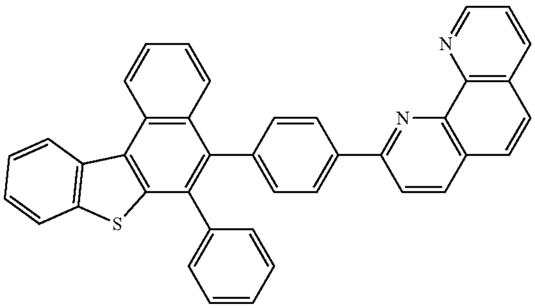

ET1105

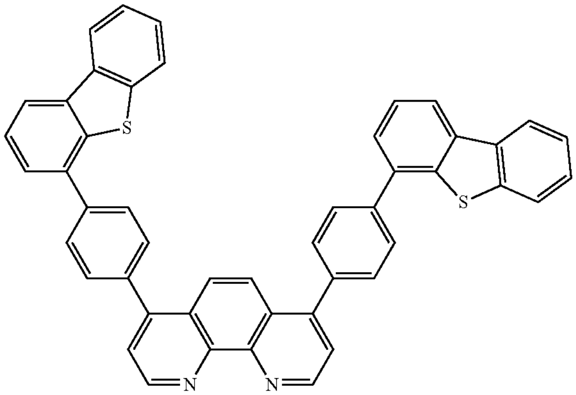

ET1106

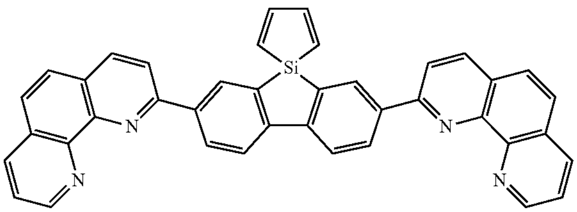

-continued

ET1107

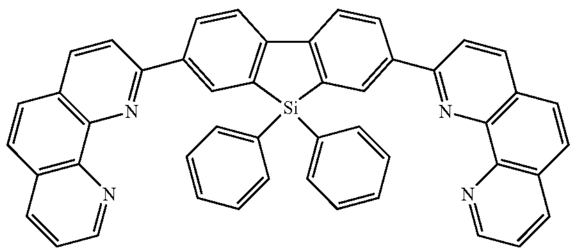

ET1108

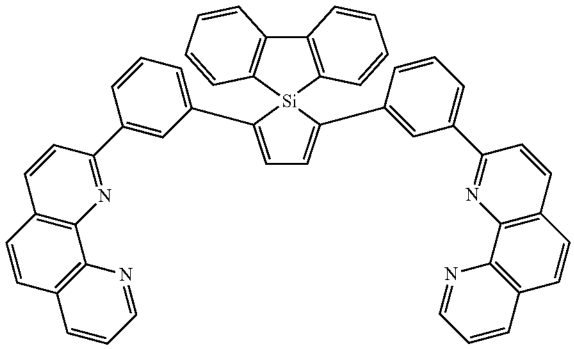

ET1109

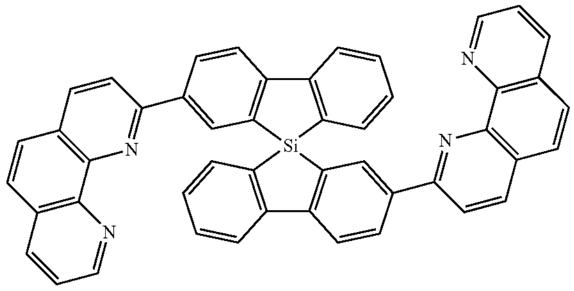

Substrate

The organic EL device of the exemplary embodiment is formed on a light-transmissive substrate. The light-transmissive plate, which supports the organic EL device, is preferably a smoothly-shaped substrate that transmits 50% or more of light in a visible region of 400 nm to 700 nm. Specifically, a glass plate, a polymer plate, and the like are preferable.

Anode and Cathode

The anode of the organic EL device is used for injecting holes into the hole injecting layer, the hole transporting layer or the emitting layer. It is effective that the anode has a work function of 4.5 eV or more. Specific examples of a material for the anode are alloys of indium-tin oxide (ITO), tin oxide (NESA), indium zinc oxide, gold, silver, platinum and copper.

The cathode is preferably formed of a material with smaller work function in order to inject electrons into the electron injecting layer, the electron transporting layer and the emitting layer. Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Emitting Layer

The emitting layer of the organic EL device has a function for providing conditions for recombination of the electrons and the holes to emit light. The emitting layer is preferably a molecular deposit film. The molecular deposit film means a thin film formed by depositing a material compound in gas phase or a film formed by solidifying a material compound in a solution state or in liquid phase. The molecular deposit film is typically distinguished from a thin film (molecular accumulation film) formed by the LB (Langmuir Blodgett) method by differences in aggregation structures, higher order structures and functional differences arising therefrom.

Dopant Material

A dopant material is selected from a known fluorescent material exhibiting fluorescent emission or a known phosphorescent material exhibiting phosphorescent emission.

Host Material

A host material, which is applicable to the organic EL device, is exemplified by an amine derivative, azine derivative and fused polycyclic aromatic derivative.

Examples of the amine derivative are a monoamine compound, diamine compound, triamine compound, tetramine compound and amine compound substituted by a carbazole group.

Examples of the azine derivative are a monoazine derivative, diazine derivative and triazine derivative.

The fused polycyclic aromatic derivative is preferably a fused polycyclic aryl having no heterocyclic skeleton, examples of which include a fused polycyclic aryl such as naphthalene, anthracene, phenanthrene, chrysene, fluoranthene and triphenylene, or derivatives thereof.

Hole Injecting/Transporting Layer

The hole injecting/transporting layer helps injection of holes to the emitting layer and transports the holes to an emitting region. The hole injecting/transporting layer exhibits a large hole mobility and a small ionization energy.

A material for forming the hole injecting layer and the hole transporting layer is preferably a material for transporting the holes to the emitting layer at a lower electric field intensity. For instance, an aromatic amine compound is preferably used. A material for the hole injecting layer is preferably a porphyrin compound, an aromatic tertiary amine compound or a styryl amine compound, particularly preferably the aromatic tertiary amine compound such as hexacyanohexaazatriphenylene (HAT).

Electron Injecting/Transporting Layer

The electron injecting/transporting layer helps injection of the electron to the luminescent layer and has a high electron mobility. The electron injecting layer is provided for adjusting energy level, by which, for instance, sudden changes of the energy level can be reduced.

In the exemplary embodiment, the electron injecting/transporting layer at least includes the electron transporting layer containing the compound represented by the formula (10). In addition, the electron injecting/transporting layer may include an electron injecting layer. Alternatively, the electron injecting/transporting layer may include another electron transporting layer. Moreover, the electron injecting/transporting layer may be provided by layering a first electron transporting layer, a second electron transporting layer and the electron injecting layer on the anode in this sequence. In this arrangement, the compound represented by the formula (10) is preferably contained in the first electron transporting layer. When the organic EL device according to the exemplary embodiment includes a plurality of electron transporting layers, it is only necessary that the compound represented by the formula (10) is contained in at least one of the plurality of electron transporting layers. It is preferable that this compound is contained in the electron transporting layer closer to the emitting layer. Moreover, the electron transporting layer in which the compound represented by the formula (10) is contained may further include an alkali metal as described above. The electron transporting layer may further include the following electron transporting material in addition to the alkali metal.

The organic EL device according to the exemplary embodiment preferably includes the electron injecting layer between the electron transporting layer and the cathode, and the electron injecting layer preferably contains a nitrogen-containing cyclic derivative as a main component. The electron injecting layer may serve as the electron transporting layer. Noted that "as a main component" means that the nitrogen-containing cyclic derivative is contained in the electron injecting layer at a content of 50 mass % or more.

The electron transporting material for forming the electron injecting layer or the electron transporting layer is preferably an aromatic heterocyclic compound having at least one heteroatom in a molecule, particularly preferably a nitrogen-containing cyclic derivative. The nitrogen-containing cyclic derivative is preferably an aromatic ring having a nitrogen-containing six-membered or five-membered ring skeleton, or a condensed aromatic cyclic compound having a nitrogen-containing six-membered or five-membered ring skeleton.

Electron-donating Dopant and Organic Metal Complex

The organic EL device according to the exemplary embodiment preferably includes at least one of the electron-donating dopant and the organic metal complex in the electron transporting layer. With this arrangement, the drive voltage of the organic EL device can be lowered. The electron-donating dopant may be at least one selected from an alkali metal, an alkali metal compound, an alkaline-earth metal, an alkaline-earth metal compound, a rare-earth metal, a rare-earth metal compound and the like.

The organic metal complex may be at least one selected from an organic metal complex including an alkali metal, an organic metal complex including an alkaline-earth metal, an organic metal complex including a rare-earth metal and the like.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), which particularly preferably has a work function of 2.9 eV or less. Among the above, the reductive dopant is preferably K, Rb or Cs, more preferably Rb or Cs, the most preferably Cs.

Examples of the alkaline-earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare-earth metal are scandium (Sc), yttrium (Y), cerium (Ce), terbium (Tb), and ytterbium (Yb), among which a substance having a work function of 2.9 eV or less is particularly preferable.

Since the above preferred metals have particularly high reducibility, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) and potassium oxide ($K_2O$), and an alkali halogenide such as sodium fluoride (NaF), cesium fluoride (CsF) and potassium fluoride (KF), among which lithium fluoride (LiF), lithium oxide ($Li_2O$) and sodium fluoride (NaF) are preferable.

Examples of the alkaline-earth metal compound are barium oxide (BaO), strontium oxide (SrO), calcium oxide (CaO) and a mixture thereof, i.e., barium strontium oxide ($Ba_xSr_{1-x}O$) (0<x<1), barium calcium oxide ($Ba_xCa_{1-x}O$) (0<x<1), among which BaO, SrO and CaO are preferable.

Examples of the rare earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), among which $YbF_3$, $ScF_3$, and $TbF_3$ are preferable.

The organic metal complex is not specifically limited as long as containing at least one metal ion of an alkali metal ion, an alkaline-earth metal ion and a rare earth metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The electron-donating dopant and the organic metal complex are preferably added by a method of dispersing at least one of the electron-donating dopant and the organic metal complex in the electron transporting layer while co-depositing the at least one of the electron-donating dopant and the organic metal complex with the compound represented by the formula (1) by resistance heating evaporation. Dispersion concentration represented by a film-thickness ratio (the compound represented by the formula (1) to the electron-donating dopant or the organic metal complex) is 1000:1 to 1:1000, preferably 100:1 to 1:1.

When the at least one of the electron-donating dopant and the organic metal complex forms a layer, the compound represented by the formula (1) is initially layered, and then, the at least one of the electron-donating dopant and the organic metal complex is singularly deposited thereon by resistance heating evaporation to preferably form a 0.1 nm- to 15 nm-thick layer.

When the at least one of the electron-donating dopant and the organic metal complex is formed in an island, the compound represented by the formula (1) is initially formed in an island, and then, the at least one of the electron-donating dopant and the organic metal complex is singularly deposited thereon by resistance heating evaporation to preferably form a 0.05 nm- to 1 nm-thick an island.

A ratio of the at least one of the electron-donating dopant and the organic metal complex in the organic EL device according to the exemplary embodiment is preferably a film-thick ratio (a main component to the electron-donating dopant or the organic metal complex) of 100:1 to 1:1, more preferably 50:1 to 4:1.

Blocking Layer

The organic EL device preferably includes a blocking layer such as an electron blocking layer, hole blocking layer or triplet blocking layer at a part adjacent to the emitting layer. Herein, the electron blocking layer prevents electrons from leaking from the emitting layer into the hole transporting layer while the hole blocking layer prevents holes from leaking from the emitting layer into the electron transporting layer. In organic EL device according to the exemplary embodiment, as described above, the hole blocking layer is provided between the electron transporting layer and the emitting layer. The triplet blocking layer has a function of preventing triplet excitons generated in the emitting layer from diffusing into neighboring layers to trap the triplet excitons within the emitting layer, thereby suppressing energy deactivation of the triplet excitons on molecules other than the emitting dopant in the electron transporting layer.

Formation Method of Each Layer of Organic EL Device

A method of forming each of the layers in the organic EL device according to the exemplary embodiment is not particularly limited. Conventionally-known methods such as vacuum deposition and spin coating may be employed for forming the layers. The organic layer used in the organic EL device according to this exemplary embodiment can be formed by a well-known coating method such as vacuum deposition method, molecular beam epitaxy (MBE) method or a coating method with a solution by a dipping method, spin coating method, casting method, bar coating method, or roll coating method.

Film Thickness of Each Layer of Organic EL Device

A film thickness of the emitting layer is preferably in a range of 5 nm to 50 nm, more preferably in a range of 7 nm to 50 nm and most preferably in a range of 10 nm to 50 nm. By forming the emitting layer at the film thickness of 5 nm or more, the emitting layer is easily formable and chromaticity is easily adjustable. By forming the emitting layer at the film thickness of 50 nm or less, increase in the drive voltage is suppressible.

A film thickness of the organic layer other than the emitting layer is not particularly limited, but is preferably in a typical range of several nm to 1 μm. When the film thickness is provided in the above range, defects such as pin holes caused by an excessively thinned film can be avoided while increase in the drive voltage caused by an excessively thickened film is suppressible.

According to an exemplary embodiment of the invention, a compound and an organic electroluminescence device which are capable of reducing a drive voltage can be provided.

Modifications of Embodiment(s)

It should be noted that the invention is not limited to the above exemplary embodiment but may include any modification and improvement as long as such modification and improvement are compatible with the invention.

In the exemplary embodiment, the organic EL device including the hole blocking layer between the emitting layer and the electron transporting layer containing the compound according to the exemplary embodiment is exemplarily explained. However, the arrangement of the organic EL device is not limited thereto.

For instance, an organic EL device including the emitting layer and the electron transporting layer containing the compound according to the exemplary embodiment adjacent to the emitting layer is preferable.

The emitting layer is not limited to a single layer, but may be provided by laminating a plurality of emitting layers. When the organic EL device includes the plurality of emitting layers, the plurality of emitting layers may be each independently a fluorescent emitting layer or a phosphorescent emitting layer.

Moreover, when the organic EL device includes the plurality of emitting layers, the plurality of emitting layers may be adjacent to each other, or the organic EL device may be provided in a tandem type in which a plurality of emitting units are laminated on each other via an intermediate layer.

In the organic EL device, at least one of the electron-donating dopant and the organic metal complex is preferably contained in an interfacial region between the cathode and the organic compound layer. With this arrangement, the organic EL device can emit light with enhanced luminance intensity and have a longer lifetime. The same as described above can be used as the electron-donating dopant and an organic metal complex.

The electron-donating dopant and the organic metal complex are added to preferably form a layer or an island in the interfacial region. The electron-donating dopant and the organic metal complex are preferably added by a method of depositing an organic substance (luminescent material or electron injecting material) for forming the interfacial region while simultaneously depositing at least one of the electron-donating dopant and the organic metal complex by resistance heating deposition, and dispersing the at least one of the electron-donating dopant and the organic metal complex in the organic substance.

In the invention, the emitting layer may also preferably contain an assistance material for assisting injection of charges. When the emitting layer is formed of a host material that exhibits a wide energy gap, a difference in ionization potential (Ip) between the host material and the hole injecting/transporting layer etc. becomes so large that injection of the holes into the emitting layer becomes difficult, which may cause a rise in a drive voltage required for providing sufficient luminance. In the above instance, introducing a hole-injectable or hole-transportable assistance material for assisting injection of charges into the emitting layer can contribute to facilitation of the injection of the holes into the emitting layer and to reduction of the drive voltage.

As the assistance substance for assisting the injection of charges, for instance, a general hole injecting/transporting material or the like can be used.

Specific examples of the assistance material for assisting the injection of charges are a triazole derivative, oxadiazole derivative, imidazole derivative, polyarylalkane derivative, pyrazoline derivative, pyrazolone derivative, phenylenediamine derivative, arylamine derivative, amino-substituted chalcone derivative, oxazole derivative, fluorenone derivative, hydrazone derivative, stilbene derivative, silazane derivative, polysilane copolymer, aniline copolymer, and conductive polymer oligomer (particularly, a thiophene oligomer).

The hole injecting material is exemplified by the above. The hole injecting material is preferably a porphyrin compound, aromatic tertiary amine compound and styryl amine compound, particularly preferably aromatic tertiary amine compound.

The organice EL device of the invention is suitably usable as a display device of a television set, a mobile phone, a personal computer and the like, or as an electronic device such as an illumination unit or a light-emitting device of a vehicle light.

EXAMPLES

Next, the invention will be described in further detail by exemplifying Example(s) and Comparative(s). However, the invention is not limited by the description of Example(s).

Synthesis Examples

Synthesis Example 1

Synthesis of Compound 5

A synthesis scheme of the following compound 5 is shown below.

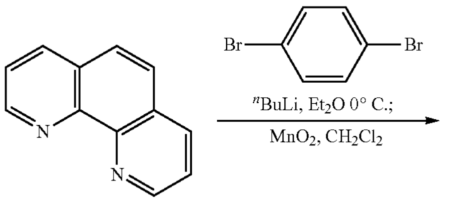

Compound 1

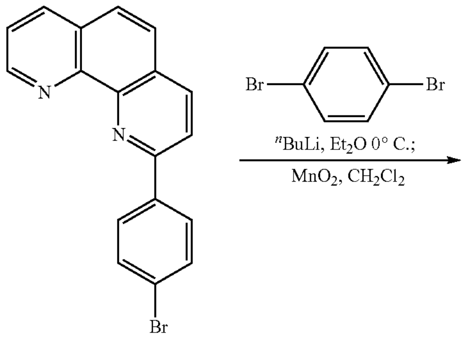

Compound 2

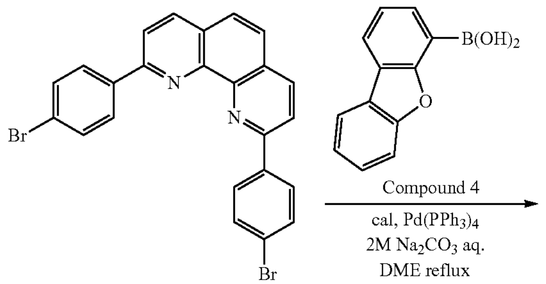

Compound 4

Compound 3

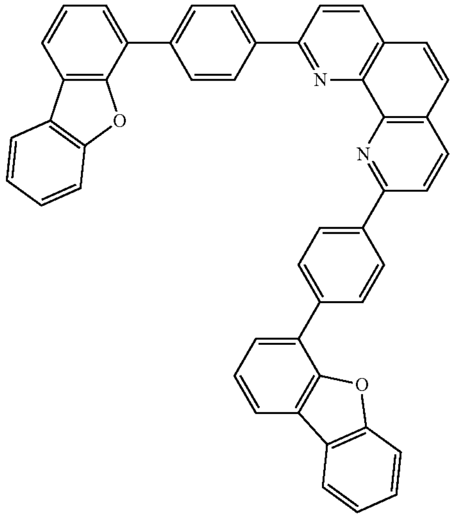

Compound 5

(1-1) Synthesis of Compound 2

In order to synthesize the compound 5, a compound 2 was initially synthesized.

Under an argon gas atmosphere, 1,4-dibromobenzene (50 g, 211 mmol) was dissolved in diethylether (350 mL). The obtained solution was cooled down to 0 degree C., into which n-butyllithium (2.69M hexane solution) (72 mL, 194 mmol) was dropped for 30 minutes and was stirred for another 30 minutes. The prepared p-bromophenyllithium was dropped into a suspension of diethylether (350 mL) of 1,10-phenanthroline (15 g, 85 mmol) (compound 1) at 0 degree C. for 45 minutes and was further stirred for five hours. After the completion of the reaction, water was dropped into the reaction solution at 0 degree C. for 30 minutes. The reaction solution was extracted by dichloromethane. A solvent was distilled off under reduced pressure while leaving 200 mL of dichloromethane. Manganese dioxide (150 g) was added to the obtained solution and stirred for 4.5 hours at the room temperature. Subsequently, the solution was added with magnesium sulfate and separated by filtration. The solvent was distilled off under reduced pressure. A residue was refined by silica-gel column chromatography (dichloromethane/hexane/methanol). The obtained solid was washed with methanol and then was dried under reduced pressure to provide the compound 2 (23 g, a yield of 81%) as a white solid. As a result of FD-MS (Field Desorption Mass Spectrometry) analysis, the reactant was identified as the compound 2.

(1-2) Synthesis of Compound 3

A compound 3 (18 g, a yield of 55%) was obtained as a white solid in the same synthesizing method as in the above (1-1) synthesis of the compound 2 except for replacing the compound 1 with the compound 2 (23 g, 68 mmol). As a result of FD-MS (Field Desorption Mass Spectrometry) analysis, the reactant was identified as the compound 3.

(1-3) Synthesis of Compound 5

Tetrakis(triphenylphosphine)palladium (0) (0.7 g, 0.61 mmol) and an aqueous solution of 2M sodium carbonate (37 mL) were added to a suspension of 1,2-dimethoxyethane (200 mL) of the compound 3 (6.9 g, 12 mmol) and a compound 4 (5.7 g, 27 mmol), and heated to reflux for seven hours. After the completion of the reaction, water was added and the obtained solid was separated by filtration. Then, the obtained solid was washed with water and methanol and was dried under reduced pressure. The obtained crude product was refined by silica-gel column chromatography (dichloromethane). The obtained solid was washed with methanol and then was dried under reduced pressure to provide a compound 5 (7.2 g, a yield of 88%) as a white solid. As a result of FD-MS (Field Desorption Mass Spectrometry) analysis, the reactant was identified as the compound 5.

(2) Synthesis Example 2

Synthesis of Compound 9

A synthesis scheme of the following compound 9 is shown below.

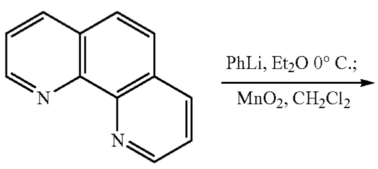

Compound 1

-continued

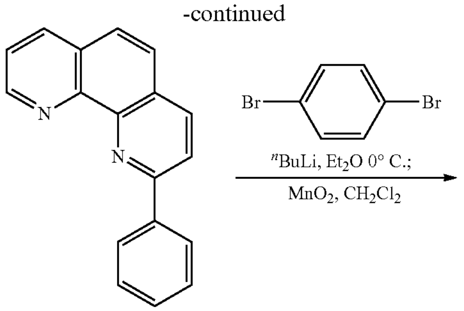

Compound 6

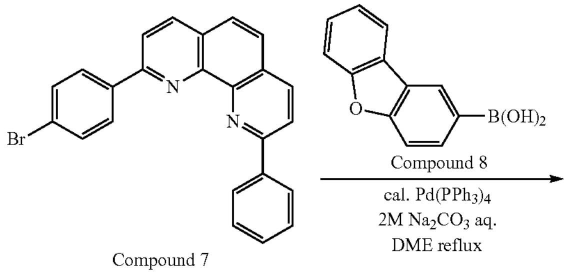

Compound 7

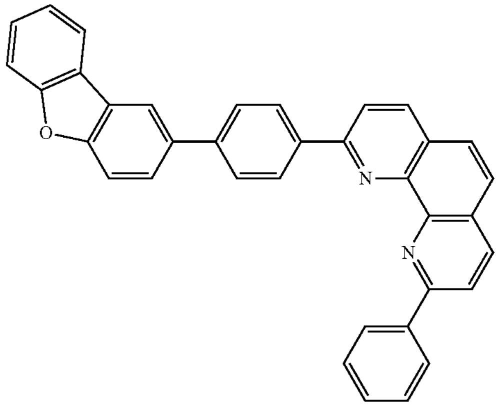

Compound 9

(2-1) Synthesis of Compound 6

A compound 6 (24 g, a yield of 83%) was obtained as a yellow solid in the same synthesizing method as in the above (1-1) synthesis of the compound 2 except for replacing p-bromophenyllithium with phenyllithium (1.6M butylether solution) (139 mL, 222 mmol) and using a 2-mol equivalent of phenyllithim relative to 1,10-phenanthroline. As a result of FD-MS (Field Desorption Mass Spectrometry) analysis, the reactant was identified as the compound 6.

(2-2) Synthesis of Compound 7

A compound 7 (12 g, a yield of 76%) was obtained as a yellow solid in the same synthesizing method as in the above (1-1) synthesis of the compound 2 except for replacing the compound 1 with the compound 2 (10 g, 39 mmol). As a result of FD-MS (Field Desorption Mass Spectrometry) analysis, the reactant was identified as the compound 7.

(2-3) Synthesis of Compound 9

A compound 9 (1.7 g, a yield of 23%) was obtained as a white solid in the same synthesizing method as in the above (1-3) synthesis of the compound 5 except for replacing the compound 3 with the compound 7 (6.0 g, 15 mmol) and replacing the compound 4 with the compound 8 (3.4 g, 16 mmol). As a result of FD-MS (Field Desorption Mass Spectrometry) analysis, the reactant was identified as the compound 9.

(3) Synthesis Example 3

Synthesis of Compound 10

A synthesis scheme of the following compound 10 is shown below.

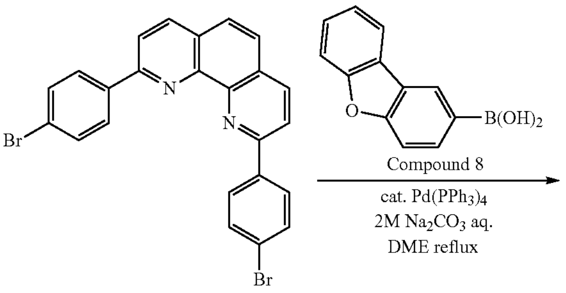

Compound 3

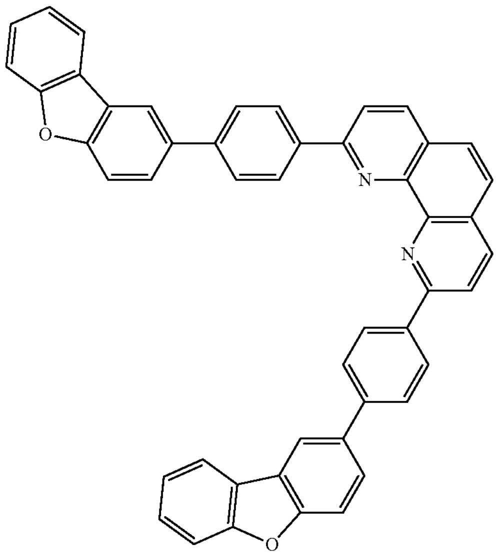

Compound 10

(3-1) Synthesis of Compound 10

A compound 10 (7.2 g, a yield of 80%) was obtained as a white solid in the same synthesizing method as in the above (1-3) synthesis of the compound 5 except for replacing the compound 4 with the compound 8 (6.3 g, 30 mmol). As a result of FD-MS (Field Desorption Mass Spectrometry) analysis, the reactant was identified as the compound 10.

(4) Synthesis Example 4

Synthesis of Compound 13

A synthesis scheme of the following compound 13 is shown below.

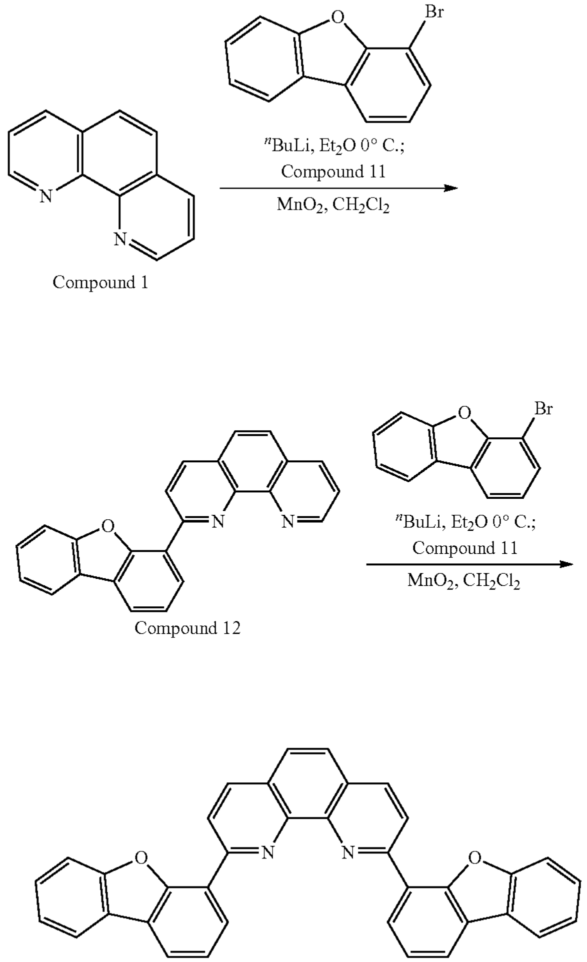

Compound 1

Compound 12

Compound 13

(4-1) Synthesis of Compound 12

A compound 12 (6.5 g, a yield of 67%) was obtained as a yellow solid in the same synthesizing method as in the above (1-1) synthesis of the compound 2 except for replacing 1,4-dibromobenzene with the compound 11 (17 g, 69 mmol). As a result of FD-MS (Field Desorption Mass Spectrometry) analysis, the reactant was identified as the compound 12.

(4-2) Synthesis of Compound 13

A compound 13 (2.1 g, a yield of 22%) was obtained as a light yellow solid in the same synthesizing method as in the above (1-1) synthesis of the compound 2 except for replacing the compound 1 with the compound 12 (6.5 g, 19 mmol) and replacing 1,4-dibromobenzene with the compound 11 (12 g, 47 mmol). As a result of FD-MS (Field Desorption Mass Spectrometry) analysis, the reactant was identified as the compound 13.

(4A) Synthesis Example 4A

Synthesis of Compound 1C

A synthesis scheme of the following compound 1 is shown below.

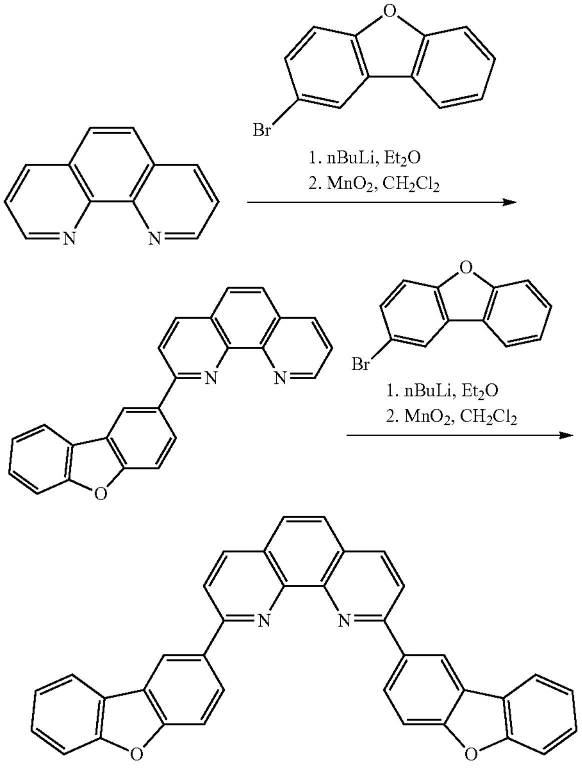

1C

A compound 1C was synthesized according to the above scheme by the same method as in synthesis of the compound 13 except for replacing the compound 11 with 2-dibromobenzofuran.

(4B) Synthesis Example 4B

Synthesis of Compound 1D

A synthesis scheme of the following compound 1 is shown below.

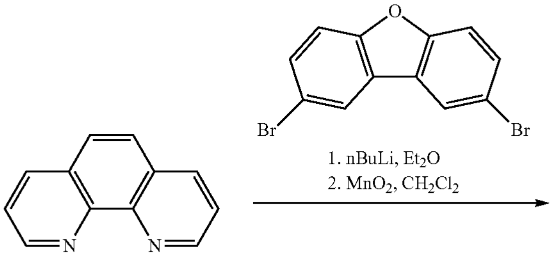

-continued

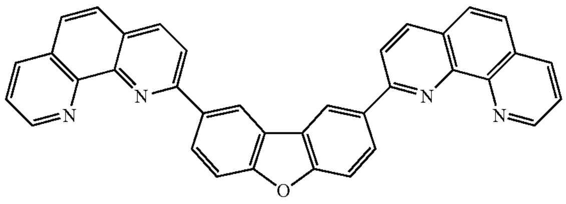

1D

A compound 1D was synthesized according to the above scheme by the same method as in synthesis of the compound 13 except for replacing the compound 11 with 2,8-dibromodibenzofuran.

(5) Synthesis Example 5

Synthesis of Compound 16

A synthesis scheme of the following compound 16 is shown below.

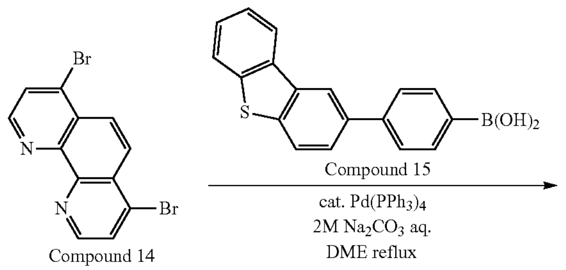

Compound 14

-continued

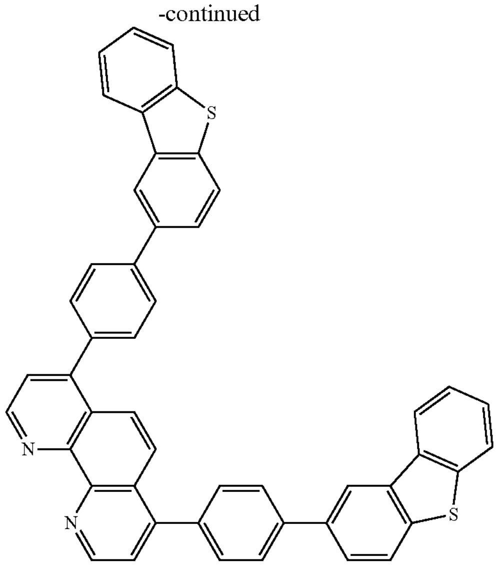

Compound 16

A compound 16 (8.6 g, a yield of 83%) was obtained as a white solid in the same synthesizing method as in the above (1-3) synthesis of the compound 5 except for replacing the compound 3 with the compound 14 (5.0 g, 15 mmol) and replacing the compound 4 with the compound 15 (9.9 g, 33 mmol). As a result of FD-MS (Field Desorption Mass Spectrometry) analysis, the reactant was identified as the compound 16.

(6) Synthesis Example 6

Synthesis of Compound 19

A synthesis scheme of the following compound 19 is shown below.

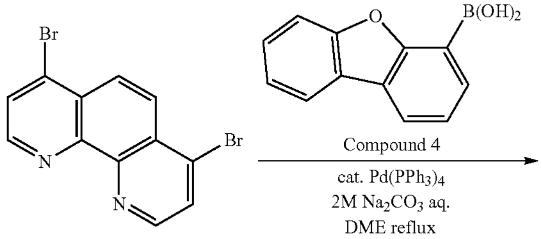

Compound 14

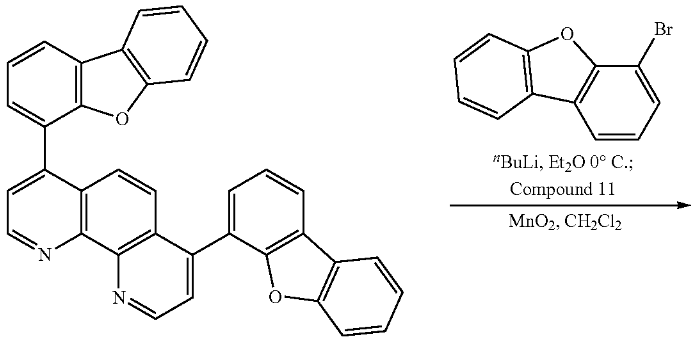

Compound 17

-continued

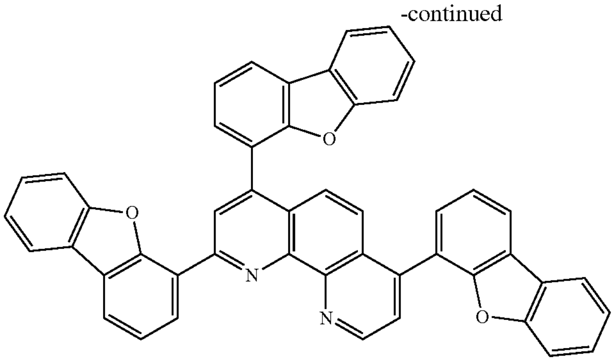

Compoupnd 18

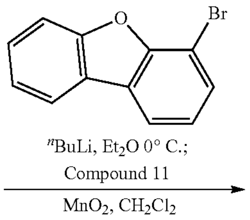

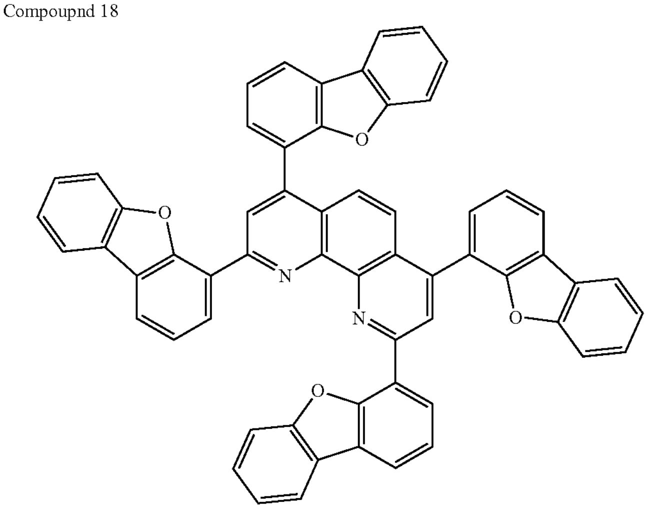

Compound 19

(6-1) Synthesis of Compound 17

A compound 17 (13 g, a yield of 86%) was obtained as a white solid in the same synthesizing method as in the above (1-3) synthesis of the compound 5 except for replacing the compound 3 with the compound 14 (10 g, 30 mmol). As a result of FD-MS (Field Desorption Mass Spectrometry) analysis, the reactant was identified as the compound 17.

(6-2) Synthesis of Compound 18

A compound 18 (9.6 g, a yield of 56%) was obtained as a yellow solid in the same synthesizing method as in the above (1-1) synthesis of the compound 2 except for replacing the compound 1 with the compound 17 (13 g, 25 mmol) and replacing 1,4-dibromobenzene with the compound 11 (16 g, 6 3mmol). As a result of FD-MS (Field Desorption Mass Spectrometry) analysis, the reactant was identified as the compound 18.

(6-3) Synthesis of Compound 19

A compound 19 (3.2 g, a yield of 27%) was obtained as a light yellow solid in the same synthesizing method as in the above (1-1) synthesis of the compound 2 except for replacing the compound 1 with the compound 18 (9.6 g, 14 mmol) and replacing 1,4-dibromobenzene with the compound 11 (8.7 g, 35 mmol). As a result of FD-MS (Field Desorption Mass Spectrometry) analysis, the reactant was identified as the compound 19.

(7) Synthesis Example 7

Synthesis of Compound 22

A synthesis scheme of the following compound 22 is shown below.

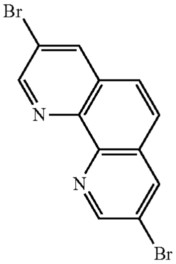

Compound 20

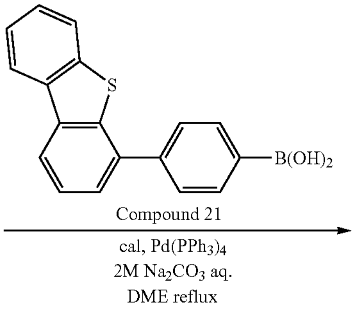

-continued

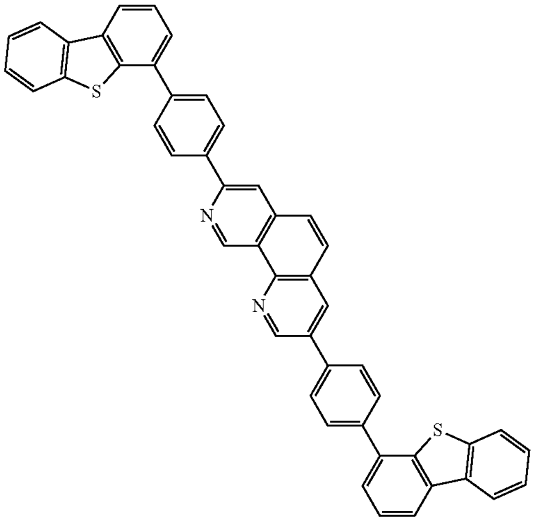

Compound 22

(7-1) Synthesis of Compound 22

A compound 22 (6.5 g, a yield of 63%) was obtained as a white solid in the same synthesizing method as in the above (1-3) synthesis of the compound 5 except for replacing the compound 3 with the compound 20 (5.0 g, 15 mmol) and replacing the compound 4 with the compound 21 (9.9 g, 33 mmol). As a result of FD-MS (Field Desorption Mass Spectrometry) analysis, the reactant was identified as the compound 22.

(8) Synthesis Example 8

Synthesis of Compound 26

A synthesis scheme of the following compound 26 is shown below.

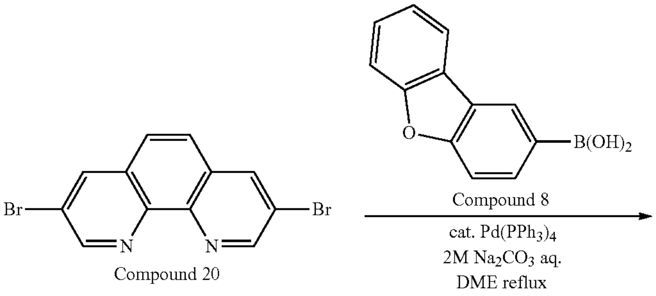

Compound 20

Compound 8

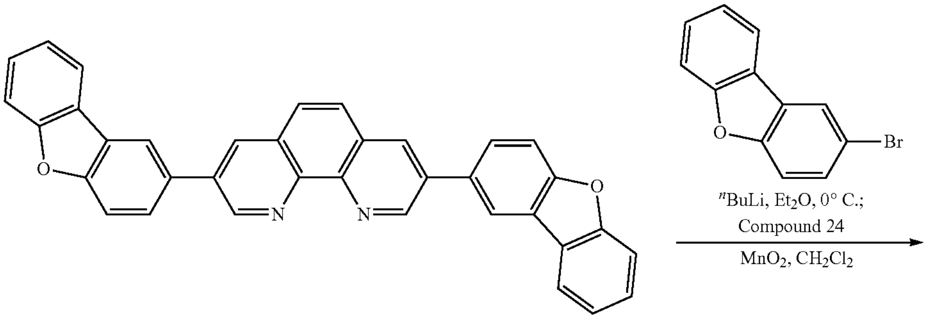

Compound 23

-continued

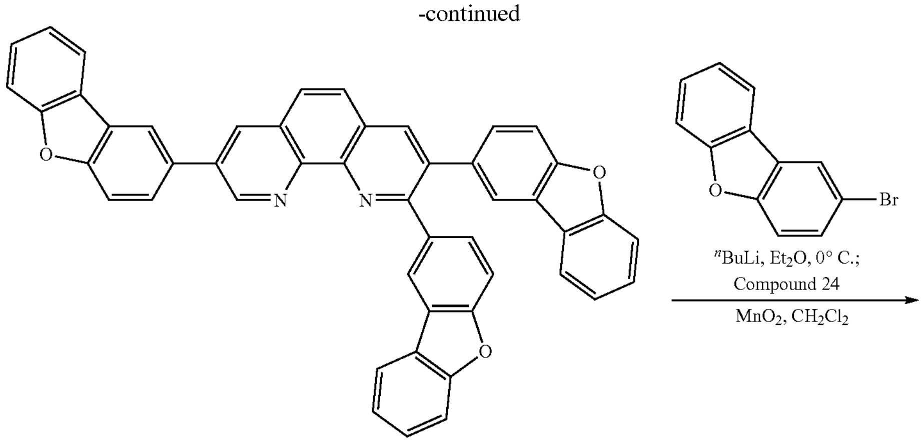

Compound 25

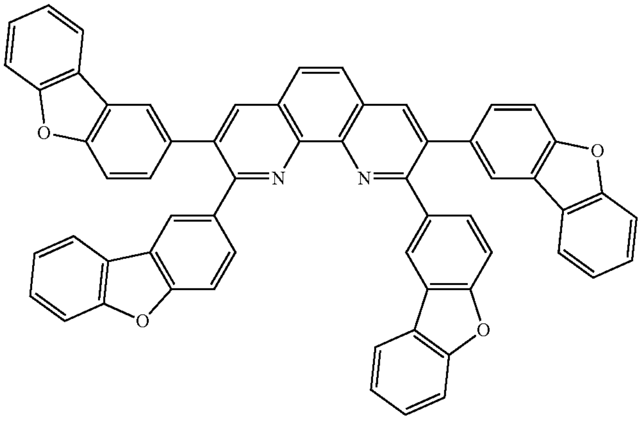

Compound 26

(8-1) Synthesis of Compound 23

A compound 23 (13 g, a yield of 89%) was obtained as a white solid in the same synthesizing method as in the above (1-3) synthesis of the compound 5 except for replacing the compound 3 with the compound 20 (10 g, 30 mmol) and replacing the compound 4 with the compound 8 (16 g, 65 mmol). As a result of FD-MS (Field Desorption Mass Spectrometry) analysis, the reactant was identified as the compound 23.

(8-2) Synthesis of Compound 25

A compound 25 (6.2 g, a yield of 36%) was obtained as a yellow solid in the same synthesizing method as in the above (1-1) synthesis of the compound 2 except for replacing the compound 1 with the compound 23 (13 g, 25 mmol) and replacing 1,4-dibromobenzene with the compound 24 (16 g, 6 3 mmol). As a result of FD-MS (Field Desorption Mass Spectrometry) analysis, the reactant was identified as the compound 25.

(8-3) Synthesis of Compound 26

A compound 26 (2.1 g, a yield of 27%) was obtained as a light yellow solid in the same synthesizing method as in the above (1-1) synthesis of the compound 2 except for replacing the compound 1 with the compound 25 (6.2 g, 9.1 mmol) and replacing 1,4-dibromobenzene with the compound 24 (5.6 g, 23 mmol). As a result of FD-MS (Field Desorption Mass Spectrometry) analysis, the reactant was identified as the compound 26.

(9) Synthesis Example 9

Synthesis of Compound 29

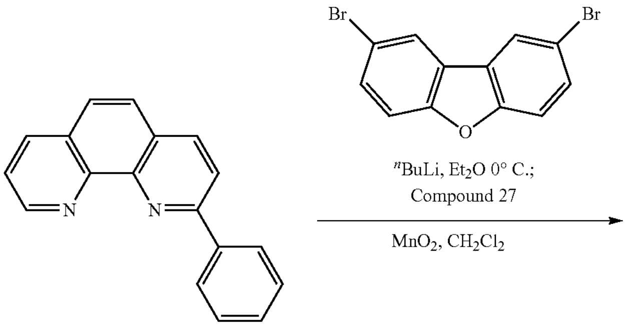

Compound 6

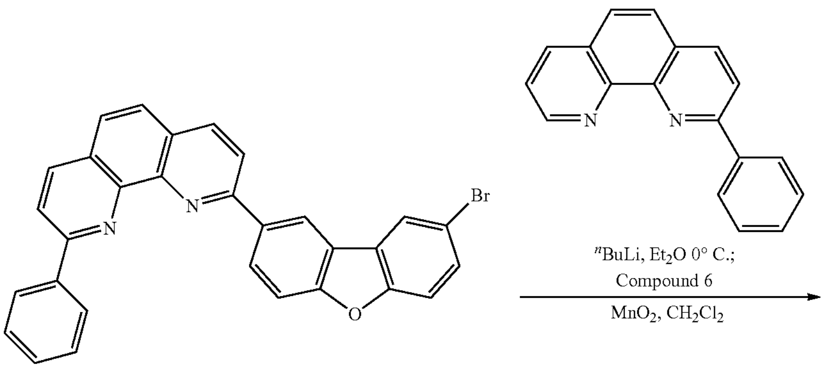

Compound 28

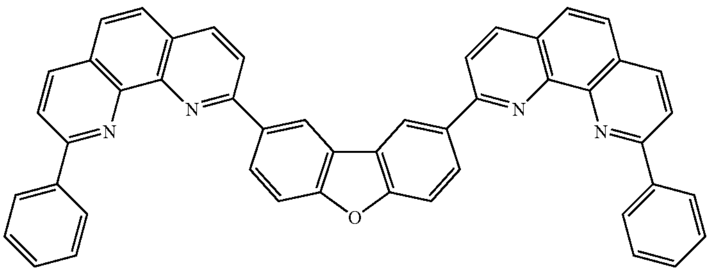

Compound 29

(9-1) Synthesis of Compound 28

A compound 28 (7.6 g, a yield of 98%) was obtained as a brown oily product in the same synthesizing method as in the above (1-1) synthesis of the compound 2 except for replacing the compound 1 with the compound 6 (4.0 g, 16 mmol) and replacing 1,4-dibromobenzene with the compound 27 (10 g, 31 mmol). As a result of FD-MS (Field Desorption Mass Spectrometry) analysis, the reactant was identified as the compound 28.

(9-2) Synthesis of Compound 29

A compound 29 (4.9 g, a yield of 48%) was obtained as a light yellow solid in the same synthesizing method as in the above (1-1) synthesis of the compound 2 except for replacing the compound 1 with the compound 6 (4.7 g, 18 mmol) and replacing 1,4-dibromobenzene with the compound 28 (7.6 g, 15 mmol). As a result of FD-MS (Field Desorption Mass Spectrometry) analysis, the reactant was identified as the compound 29.

(9A) Synthesis Example 9A
Synthesis of Compound 1A
A synthesis scheme of the following compound 1A is shown below.
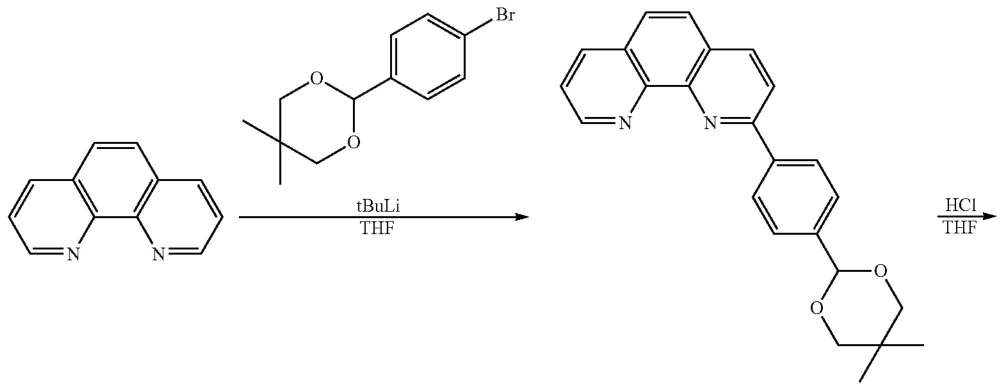
T1
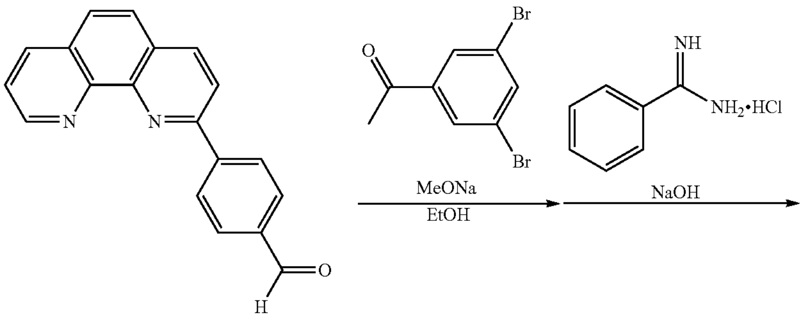
T2
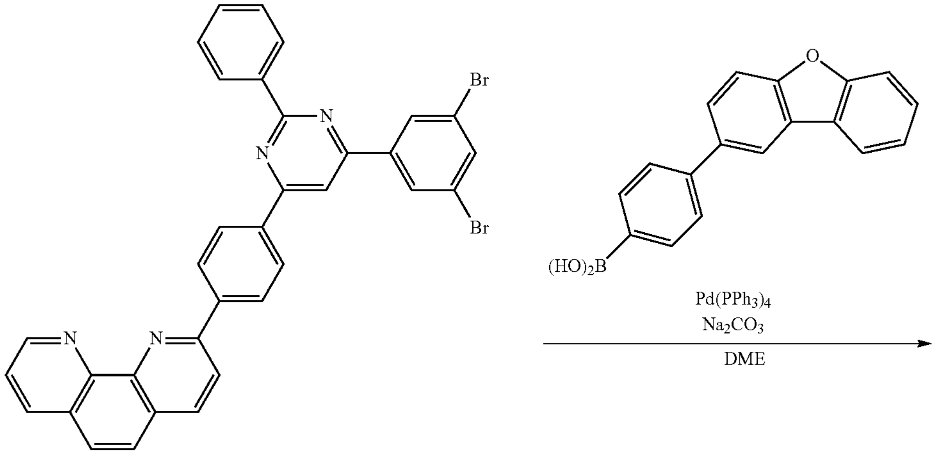

-continued

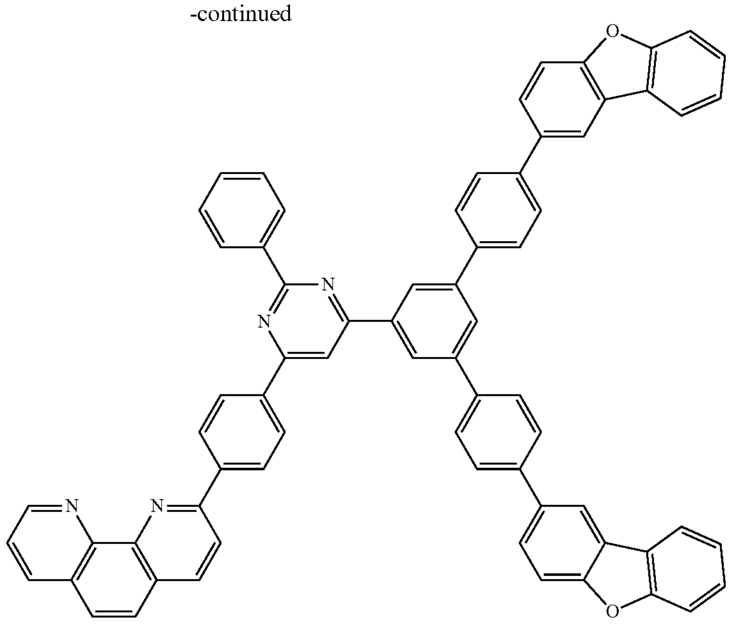

1A (9A-1) Synthesis of Compound T1

Under an argon gas atmosphere, p-(5,5-dimethyl-1,3-dioxane-2-yl)bromobenzene (15.4 g, 56.8 mmol) was dissolved in tetrahydrofuran (100 mL). The obtained solution was cooled down to −78 degrees C., into which t-butyllithium (1.3M hexane solution) (45.9 mL, 59.6 mmol) was dropped for 20 minutes and was further stirred for two hours. Subsequently, the solution was heated up to 0 degree C., to which a solution provided by dissolving 1,10-phenanthroline (10.2 g, 56.8 mmol) in tetrahydrofuran (50 mL) was added and stirred for eight hours at the room temperature. After the completion of the reaction, water (80 mL) was added at 0 degree C. The reaction solution was extracted by dichloromethane. The obtained solution was added with manganese dioxide (60 g) and stirred for four hours at the room temperature. Subsequently, the solution was dried with magnesium sulfate to distill the solvent under reduced pressure. A residue was refined by silica-gel column chromatography to obtain a compound T1 (8.41 g, a yield of 40%).

(9A-2) Synthesis of Compound T2

The compound T1 (8.30 g, 22.4 mmol) was dissolved in tetrahydrofuran (500 mL), to which hydrochloric acid (5% aqueous solution) (125 mL, 200 mmol) was added and stirred for 15 hours at 50 degrees C. Subsequently, the solid formed after the reaction was dissolved in a mixture of water and dichloromethane and neutralized by an aqueous solution of sodium acid carbonate. The obtained solution was extracted by dichloromethane and then was dried with magnesium sulfate. The solvent was distilled under reduced pressure to obtain a compound T2 (5.99 g, a yield of 94%).

(1-3) Synthesis of Compound T3

Under an argon gas atmosphere, ethanol (50 mL) was added to the compound T2 (5.80 g, 20.4 mmol), 3,5-dibromo-4-hydroxyacetophenone (5.67 g, 20.4 mmol), sodium methoxide (110 mg, 2.04 mmol). The obtained solution was stirred for two hours at the room temperature and for three hours at a reflux temperature. Subsequently, benzamidine hydrochloride (3.29 g, 21.0 mmol) and sodium hydroxide were added and stirred for three hours at the reflux temperature. After the completion of the reaction, a precipitated substance was separated by filtration and washed with water and methanol to obtain a compound T3 (7.75 g, a yield of 38%).

(1-4) Synthesis of Compound 1A

Under an argon gas atmosphere, 4-(2-dibenzofuranyl)phenylboronic acid (4.92 g, 17.1 mmol), the compound T3 (5.00 g, 7.76 mmol), tetrakis(triphenylphosphine)palladium (896 mg, 0.776 mmol), 1,2-dimethoxyethane (100 mL), an aqueous solution of sodium carbonate (2M, 100 mL) were mixed and stirred for six hours while being heated to reflux. After the reaction solution was cooled down to the room temperature, the reaction solution was extracted with toluene. After an aqueous phase was removed, an organic layer was washed with saturated saline. After the organic phase was dried with magnesium sulfate and concentrated, the obtained residue was refined by silica-gel column chromatography to obtain the compound 1A (3.77 g, a yield of 50%). As a result of mass analysis, the obtained compound was a target object, and that m/e was equal to 970 while a molecular weight was 971.13.

(2) Synthesis of Compound 1B
A synthesis scheme of the following compound 1B is shown below.
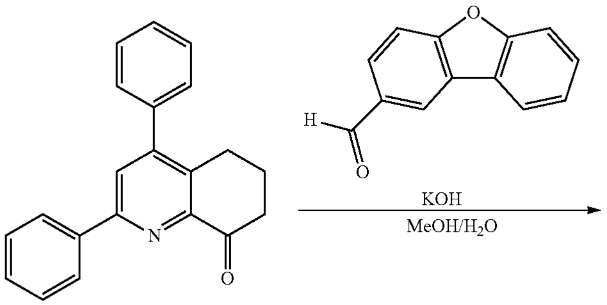
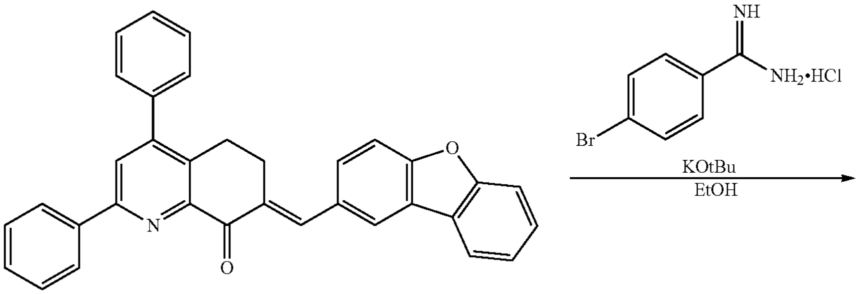
S1
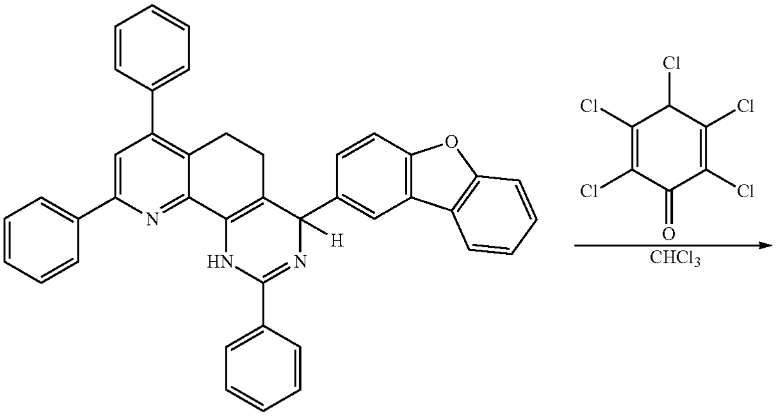
S1
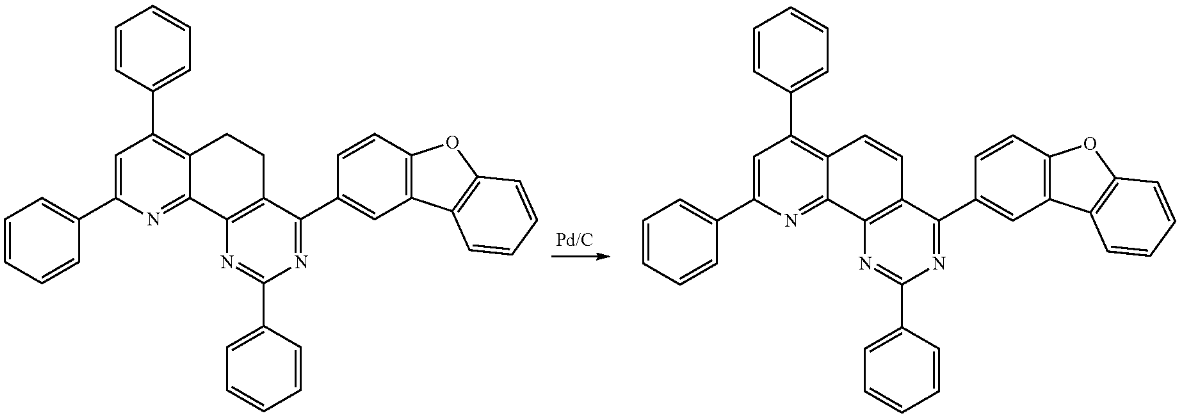
S1 1B Synthesis according to this scheme was conducted with reference to Examples described in Japanese Patent No. 5113571. As a result of mass analysis, the obtained compound was a target object, and that m/e was equal to 575 while a molecular weight was 575.67.

Example 1

(1) Manufacture of Organic EL Device

A glass substrate (size: 25 mm×75 mm×0.7 mm thick, manufactured by Geomatec Co., Ltd.) having an ITO transparent electrode (anode) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum evaporation apparatus. Initially, the following compound HT-1 was evaporated so as to cover the transparent electrode line, thereby forming a 50-nm thick HT-1 film of the following compound HT-1. The HT-1 film serves as a hole injecting layer. Subsequently, the following compound HT-2 was evaporated on the HT-1 film to form a 45-nm thick HT-2 film on the HT-1 film. The HT-2 film serves as a hole transporting layer.

The following compound BH-1 (host material) and the following compound BD-1 (dopant material) were co-evaporated on the HT-2 film at a film thickness ratio of the compound BD-1 being 3 mass %, thereby forming a 20-nm thick organic layer. The organic layer serves as an emitting layer. The compound 5 and lithium (Li) were evaporated on the emitting layer at the film thickness ratio of Li being 2 mass %, thereby forming a 30-nm thick electron transporting layer on the emitting layer. Metal (A1) was evaporated on the electron transporting layer to form an 80-nm thick metal cathode, thereby providing the organic EL device.

HT-1

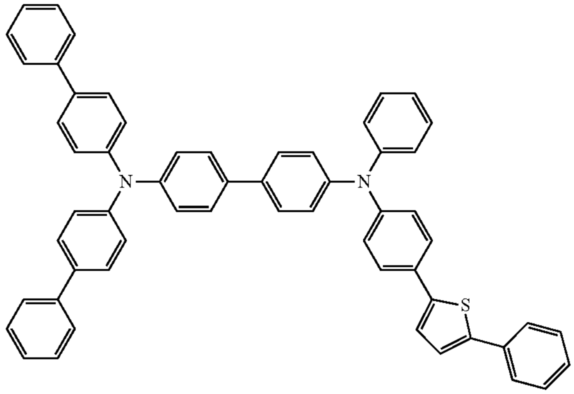

-continued

HT-2

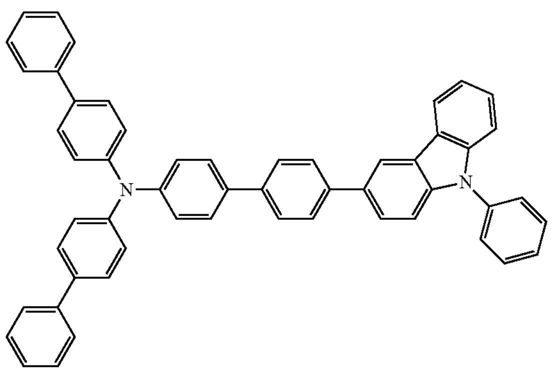

BH-1

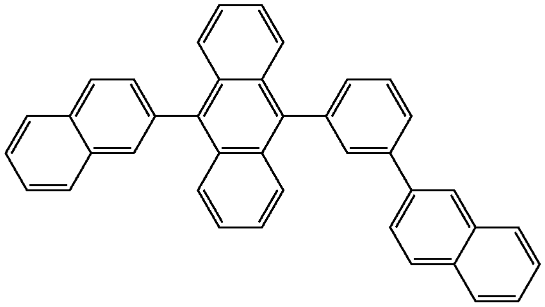

BD-1

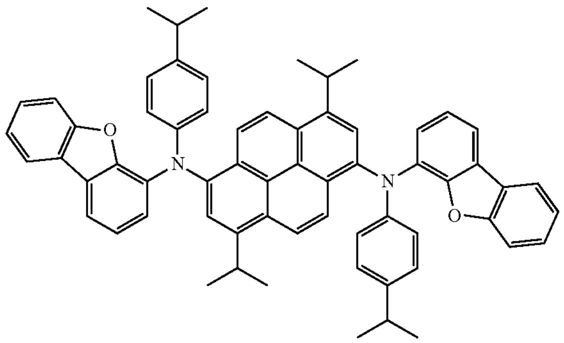

(2) Evaluation of Organic EL Device

A voltage was applied on the organic EL devices such that a current density was 10 $mA/cm^2$, where a value (V) of the voltage was measured. The results are shown in Table 1.

Examples 2 to 3 and Comparative 1

Organic EL devices were manufactured by the same method as in Example 1 except for replacing the compound 5 with the compound 9 (Example 2), the compound 10 (Example 3) and the following compound ET-1 (Comparative 1) to form the respective electron transporting layers, and were evaluated. The results are shown in Table 1.

ET-1

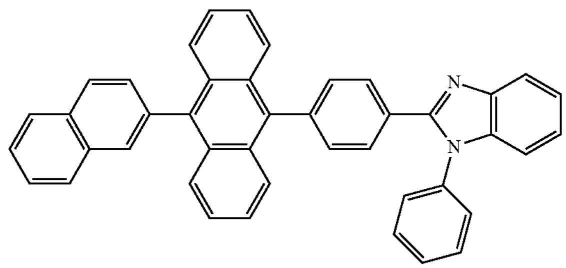

TABLE 1

| | Electron transporting layer | Drive voltage (V) |
|---|---|---|
| Example 1 | Compound 5 | 3.4 |
| Example 2 | Compound 9 | 3.2 |
| Example 3 | Compound 10 | 3.5 |
| Comparative 1 | Compound ET-1 | 3.7 |

Examples 4 to 8 and Comparative 2

An organic EL device in Example 4 was manufactured by the same method as in Example 1 except for changing the amount of lithium doped when forming the electron transporting layer to 5 mass %.

Organic EL devices of Example 5 to 8 and Comparative 2 were manufactured by the same method as in Example 1 except for changing the amount of lithium doped when forming the electron transporting layer to 5 mass % and replacing the compound 5 used for the electron transporting layer with the compound 9 (Example 5), the compound 13 (Example 6), the compound 1C (Example 7), the compound 1D (Example 8) and the following compound ET-2 (Comparative 2).

The manufactured organic EL devices were driven by direct-current electricity (50 $mA/cm^2$) at the room temperature to emit light, and time elapsed until luminance was reduced to 80% was measured, whereby lifetime (80% LT) was evaluated. The results are shown in Table 2

Voltage was applied on each of the manufactured organic EL devices such that a current density was 10 $mA/cm^2$, where spectral radiance spectrum was measured by a spectroradiometer CS-1000 (manufactured by Konica Minolta, Inc.). The external quantum efficiency EQE (unit: %) was calculated based on the obtained spectral-radiance spectra, assuming that the spectra was provided under a Lambertian radiation. The results are shown in Table 2.

ET-2

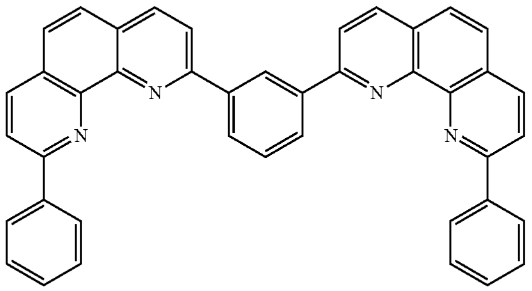

TABLE 2

| | Electron transporting layer | Lifetime (80% LT) (hr) | External quantum efficiency (%) | Emission color |
|---|---|---|---|---|
| Example 4 | Compound 5 | 350 | 7.41 | blue |
| Example 5 | Compound 9 | 290 | 7.10 | blue |
| Example 6 | Compound 13 | 230 | 7.51 | blue |
| Example 7 | Compound 1C | 320 | 7.09 | blue |
| Example 8 | Compound 1D | 310 | 7.52 | blue |
| Comparative 2 | Compound ET-2 | 220 | 7.21 | blue |

Table 2 shows that lifetime of the organic EL devices can be prolonged by using the compounds of the invention. In comparison with the compound (ET-2) used in Comparative 2, the organice EL devices using the derivative in which phenanthroline is combined with dibenzofuran or dibenzothiophene operate for a longer lifetime. Moreover, in comparison between the organic EL devices in Example 8 and Comparative 2, the organice EL device using the derivative in which phenanthroline is combined with dibenzofuran operates for a longer lifetime at a higher efficiency.

Further, as understood from comparison between the organic EL devices in Examples 6 and 7, the organic EL device using phenanthroline having dibenzofuran substituted at the position 4 (compound 13) exhibits a higher efficiency and the organic EL device using phenanthroline having dibenzofuran substituted at the position 2 (compound 1C) operates for a longer lifetime.

What is claimed is:

1. An organic electroluminescence device comprising:

an anode;

a cathode opposed to the anode; and an organic compound layer provided between the anode and the cathode, the organic compound layer comprising a compound according to formula (1):

(1)

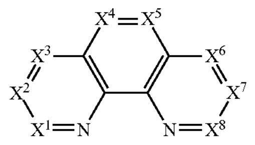

where:

one of $X^1$ to $X^8$ is a carbon atom bonded to a group according to formula (2);

the rest of $X^1$ to $X^8$ are $CR^x$ or a nitrogen atom;

$R^x$ is not the group according to formula (2); and each $R^x$ is independently selected from the group consisting of:

a hydrogen atom, a halogen atom, a cyano group, a nitro group, a substituted or unsubstituted hydroxyl group, a substituted or unsubstituted carboxyl group, a substituted or unsubstituted sulfonyl group, a substituted or unsubstituted boryl group, a substituted or unsubstituted phosphino group, a substituted or unsubstituted mercapto group, a substituted or unsubstituted acyl group, a substituted or unsubstituted amino group, a substituted or unsubstituted silyl group, a substituted or unsubstituted alkyl group having 1 to 30 carbon atoms,
a substituted or unsubstituted alkenyl group having 2 to 30 carbon atoms,
a substituted or unsubstituted alkynyl group having 2 to 30 carbon atoms,
a substituted or unsubstituted aralkyl group having 6 to 30 carbon atoms,
a substituted or unsubstituted aryl group having 6 to 40 ring carbon atoms, and
a substituted or unsubstituted heteroaryl group having 5 to 40 ring atoms; and among $X^1$ to $X^8$, adjacent $R^x$ of $CR^x$ are not bonded to each other;

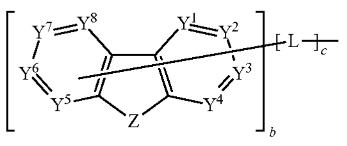

(2)

where:

b is an integer of 1 to 5;
c is an integer of 1 to 8;
Z is an oxygen atom, a sulfur atom, or a silicon atom;
when b is 2 to 5, Z are the same or different;
when Z is a silicon atom, $R^9$ and $R^{10}$ are bonded to the silicon atom, $R^9$ and $R^{10}$ each independently represent $R^x$ as defined in formula (1), and $R^9$ and $R^{10}$ are optionally bonded to the structure according to formula (1);
when Z is a silicon atom, $R^9$ and $R^{10}$ are not bonded to each other to form a cyclic structure;
L is a single bond or a linking group;
the linking group is a substituted or unsubstituted, linear, branched or cyclic polyvalent aliphatic hydrocarbon group having 1 to 30 carbon atoms, a substituted or unsubstituted polyvalent aryl group having 6 to 40 ring carbon atoms, or a substituted or unsubstituted polyvalent heteroaryl group having 5 to 40 ring atoms;
the polyvalent heteroaryl group having 5 to 40 ring atoms for L comprises a substituted or unsubstituted polyvalent group derived from a phenanthroline ring according to formula (1);
when c is 2 to 8, plural L are the same or different;
one of $Y^1$ to $Y^8$ is a carbon atom bonded to L and a remainder of $Y^1$ to $Y^8$ are each independently $CR^Y$;
at least one $R^Y$ is not a hydrogen atom;
each $R^Y$ is independently selected from the group consisting of:

a hydrogen atom,
a halogen atom,
a cyano group,
a nitro group,
a substituted or unsubstituted hydroxyl group,
a substituted or unsubstituted carboxyl group,
a substituted or unsubstituted sulfonyl group,
a substituted or unsubstituted boryl group,
a substituted or unsubstituted phosphino group,
a substituted or unsubstituted mercapto group,
a substituted or unsubstituted acyl group,
a substituted or unsubstituted amino group,
a substituted or unsubstituted silyl group,
a substituted or unsubstituted alkyl group having 1 to 30 carbon atoms,
a substituted or unsubstituted alkenyl group having 2 to 30 carbon atoms,
a substituted or unsubstituted alkynyl group having 2 to 30 carbon atoms,
a substituted or unsubstituted aralkyl group having 6 to 30 carbon atoms,
a substituted or unsubstituted aryl group having 6 to 40 ring carbon atoms, and
a substituted or unsubstituted heteroaryl group having 5 to 40 ring atoms;

the substituted or unsubstituted aryl group having 6 to 40 ring carbon atoms for $R^Y$ is a group selected from a phenyl group, naphthyl group, anthryl group, phenanthryl group, biphenyl group, terphenyl group, quaterphenyl group, fluoranthenyl group, triphenylenyl group, phenanthrenyl group, fluorenyl group, 9,9-dimethylfluorenyl group, spirofluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group;
the heteroaryl group having 5 to 40 ring atoms for $R^Y$ comprises a substituted or unsubstituted phenanthrolyl group derived from the phenanthroline ring of formula (1);
adjacent $R^Y$ are bonded to each other to form a cyclic structure, or are not bonded to each other;
when $X^1$ or $X^8$ is a carbon atom bonded to the group according to formula (2), b is 1, Z is an oxygen atom, $Y^4$ or $Y^5$ is a carbon atom bonded to L, and c is 2, the L closer to the phenanthroline ring of formula (1) among two Ls is a divalent group other than an anthracene group;
when $X^1$ or $X^8$ is a carbon atom bonded to the group according to formula (2), b and c are 1, Z is an oxygen atom or a sulfur atom, $Y^3$ is a carbon atom bonded to L, and L is a p-phenylene group, $R^Y$ for $Y^4$ is a group other than a phenyl group;
when $X^1$ or $X^8$ is a carbon atom bonded to the group according to formula (2), b and c are 1, Z is an oxygen atom or a sulfur atom, $Y^6$ is a carbon atom bonded to L, and L is a p-phenylene group, $R^Y$ for $Y^5$ is a group other than a phenyl group;
when $X^1$ is a carbon atom bonded to the group according to formula (2), Z is a silicon atom, $Y^3$ is a carbon atom bonded to L, L is a single bond, $R^Y$ for $Y^6$ is bonded to the phenanthrolyl group as a heteroaryl group having 5 to 40 ring atoms with a single bond, the phenanthrolyl group is bonded to $R^Y$ for $Y^6$ at a position other than position 2;
when $X^4$ or $X^5$ is a carbon atom bonded to the group according to formula (2), $Y^2$ is a carbon atom bonded to L, L is a single bond, and Z is an oxygen atom, $R^Y$ for $Y^7$ is a group other than a pyrenyl group; and
when $X^4$ or $X^5$ is a carbon atom bonded to the group according to formula (2), $Y^7$ is a carbon atom bonded to L, L is a single bond, and Z is an oxygen atom, $R^Y$ for $Y^2$ is a group other than a pyrenyl group.

2. The organic electroluminescence device according to claim 1, wherein L in formula (2) is selected from a single bond or a linking group, the linking group being a phenyl group, a biphenyl group, or a naphthyl group.

3. The organic electroluminescence device according to claim 1, wherein $X^1$ or $X^8$ in formula (1) is a carbon atom bonded to the group according to formula (2).

4. The organic electroluminescence device according to claim 1, wherein Z in formula (2) is an oxygen atom or a sulfur atom.

5. The organic electroluminescence device according to claim 1, wherein adjacent $R^Y$ in formula (2) are not bonded to each other.

6. The organic electroluminescence device according to claim 1, wherein:

$X^1$ or $X^8$ in formula (1) is a carbon atom bonded to the group according to formula (2); and L in formula (2) is selected from a single bond or a linking group, the linking group being a phenyl group, a biphenyl group, or a naphthyl group.

7. The organic electroluminescence device according to claim 1, wherein:

L in formula (2) is selected from a single bond or a linking group, the linking group being a phenyl group, a biphenyl group, or a naphthyl group; and Z in formula (2) is an oxygen atom or a sulfur atom.

8. The organic electroluminescence device according to claim 1, wherein:

L in formula (2) is selected from a single bond or a linking group, the linking group being a phenyl group, a biphenyl group, or a naphthyl group; and adjacent $R^Y$ in formula (2) are not bonded to each other.

9. The organic electroluminescence device according to claim 1, wherein:

$X^1$ or $X^8$ in formula (1) is a carbon atom bonded to the group according to formula (2); and Z in formula (2) is an oxygen atom or a sulfur atom.

10. The organic electroluminescence device according to claim 1, wherein:

$X^1$ or $X^8$ in formula (1) is a carbon atom bonded to the group according to formula (2); and adjacent $R^Y$ in formula (2) are not bonded to each other.

11. The organic electroluminescence device according to claim 1, wherein:

Z in formula (2) is an oxygen atom or a sulfur atom; and adjacent $R^Y$ in formula (2) are not bonded to each other.

12. The organic electroluminescence device according to claim 1, wherein:

$X^1$ or $X^8$ in formula (1) is a carbon atom bonded to the group according to formula (2);

L in formula (2) is selected from a single bond or a linking group, the linking group being a phenyl group, a biphenyl group, or a naphthyl group; and Z in formula (2) is an oxygen atom or a sulfur atom.

13. The organic electroluminescence device according to claim 1, wherein:

$X^1$ or $X^8$ in formula (1) is a carbon atom bonded to the group according to formula (2);

L in formula (2) is selected from a single bond or a linking group, the linking group being a phenyl group, a biphenyl group, or a naphthyl group; and adjacent $R^Y$ in formula (2) are not bonded to each other.

14. The organic electroluminescence device according to claim 1, wherein:

L in formula (2) is selected from a single bond or a linking group, the linking group being a phenyl group, a biphenyl group, or a naphthyl group;

Z in formula (2) is an oxygen atom or a sulfur atom; and adjacent $R^Y$ in formula (2) are not bonded to each other.

15. The organic electroluminescence device according to claim 1, wherein:

$X^1$ or $X^8$ in formula (1) is a carbon atom bonded to the group according to formula (2);

Z in formula (2) is an oxygen atom or a sulfur atom; and adjacent $R^Y$ in formula (2) are not bonded to each other.

16. The organic electroluminescence device according to claim 1, wherein:

$X^1$ or $X^8$ in formula (1) is a carbon atom bonded to the group according to formula (2);

L in formula (2) is selected from a single bond or a linking group, the linking group being a phenyl group, a biphenyl group, or a naphthyl group;

Z in formula (2) is an oxygen atom or a sulfur atom; and adjacent $R^Y$ in formula (2) are not bonded to each other.

17. The organic electroluminescence device according to claim 1, wherein Z in formula (2) is an oxygen atom.

18. The organic electroluminescence device according to claim 1, wherein L in formula (2) is a single bond.

19. The organic electroluminescence device according to claim 1, wherein L in formula (2) is a linking group, the linking group being a phenyl group, a biphenyl group, or a naphthyl group.

20. The organic electroluminescence device according to claim 1, wherein:

one of $X^1$ to $X^8$ in formula (1) is a carbon atom bonded to the group according to formula (2); and the rest of $X^1$ to $X^8$ are $CR^x$.

* * * * *